United States Patent
Durrant et al.

(10) Patent No.: US 10,233,220 B2
(45) Date of Patent: Mar. 19, 2019

(54) ANTI-TUMOUR RESPONSE TO MODIFIED SELF-EPITOPES

(71) Applicant: SCANCELL LIMITED

(72) Inventors: Linda Gillian Durrant, Nottingham (GB); Victoria Anne Brentville, Nottingham (GB); Rachael Louise Metheringham, Nottingham (GB)

(73) Assignee: Scancell Limited, Nottingham, Nottinghams (GB)

(*) Notice: Subject to any disclaimer, the term of this patent is extended or adjusted under 35 U.S.C. 154(b) by 0 days.

(21) Appl. No.: 14/614,964

(22) Filed: Feb. 5, 2015

(65) Prior Publication Data

US 2015/0232525 A1 Aug. 20, 2015

Related U.S. Application Data

(63) Continuation of application No. PCT/GB2013/052109, filed on Aug. 7, 2013.

(30) Foreign Application Priority Data

Aug. 7, 2012 (GB) .................................. 1214007.5

(51) Int. Cl.
| | |
|---|---|
| *A61K 39/00* | (2006.01) |
| *C07K 14/47* | (2006.01) |
| *C07K 7/08* | (2006.01) |
| *C07K 7/06* | (2006.01) |
| *G01N 33/574* | (2006.01) |

(52) U.S. Cl.
CPC ...... *C07K 14/4748* (2013.01); *A61K 39/0011* (2013.01); *C07K 7/06* (2013.01); *C07K 7/08* (2013.01); *G01N 33/57496* (2013.01); *G01N 2333/47* (2013.01); *G01N 2333/978* (2013.01)

(58) Field of Classification Search
None
See application file for complete search history.

(56) References Cited

U.S. PATENT DOCUMENTS

| | | |
|---|---|---|
| 2006/0014225 A1 | 1/2006 | Georges et al. |
| 2007/0248539 A1 | 10/2007 | Glassy et al. |
| 2007/0248628 A1 | 10/2007 | Keller et al. |
| 2009/0148400 A1 | 6/2009 | Singh et al. |
| 2010/0324270 A1* | 12/2010 | Hestir ............... C07K 14/47 530/387.3 |
| 2012/0295292 A1* | 11/2012 | Thompson ........... C12Q 1/34 435/18 |
| 2013/0274125 A1* | 10/2013 | Binder ............. G01N 33/6854 506/9 |

FOREIGN PATENT DOCUMENTS

| | | |
|---|---|---|
| CA | 2614103 A1 | 1/2007 |
| EP | 1541585 A1 | 6/2005 |
| WO | 2007000320 A2 | 1/2007 |
| WO | 2010117694 A2 | 10/2010 |
| WO | 2012095849 A1 | 7/2012 |
| WO | 2012103365 A1 | 8/2012 |
| WO | 2012138294 A1 | 10/2012 |
| WO | 2014023957 A2 | 2/2014 |

OTHER PUBLICATIONS

De Ceuleneer et al, Proteomics, 12:752-760, Mar. 2012.*
Chang et al, BMC Cancer 9:40, 2009.*
Romani et al, Current topics in microbiology and immunology 351:113-138, 2012.*
Alvarez, et al., "Analysis of the HLA class I associated peptide repertoire in a hepatocellular carcinoma cell line reveals tumor-specific peptides as putative targets for immunotherapy," Proteomics Clinical Applications, 1(3):286-298, 2007.
Ordonez, et al., "Increased levels of citrullinated antithrombin in plasma of patients with rheumatoid arthritis and colorectal adenocarcinoma determined by a newly developed ELISA using a specific monoclonal antibody," Thrombosis and Haemostasis, 104(6):1143-1149, 2010.
Chang, et al., "PADI4 and tumourigenesis," Cancer Cell International, 10:7-12, 2010.

* cited by examiner

*Primary Examiner* — Mark Halvorson
(74) *Attorney, Agent, or Firm* — Elmore Patent Law Group, P.C.; Carolyn Elmore; Mahreen Hoda

(57) ABSTRACT

Anti-tumor immune responses to modified self-epitopes. The present invention relates to the use of tumor-associated epitopes in medicine and in particular in the treatment of cancer. The epitopes stimulate an immune reaction against the tumor and have a modification selected from deimination of arginine to citrulline, nitration of tyrosine, oxidation of tryptophan and deamination of glutamine or asparagine. The invention also relates to nucleic acids comprising sequences that encode such epitopes for use in the treatment of cancer.

10 Claims, 63 Drawing Sheets

Specification includes a Sequence Listing.

FIG 2

```
          10         20         30         40         50         60
MSTRSVSSSS YRRMFGGPGT ASRPSSSRSY VTTSTRTYSL GSALRPSTSR SLYASSPGGV
          70         80         90        100        110        120
YATRSSAVRL RSSVPGVRLL QDSVDFSLAD AINTEFKNTR TMEKVELQEL NDRFANYIDK
         130        140        150        160        170        180
VRFLEQQNKI LLAELEQLKG QGKSRLGDIY EEEMRELRRQ VDQLTNDKAR VEVERDNLAE
         190        200        210        220        230        240
DIMRLREKLQ EEMLQREEAE NTLQSFRQDV DNASLARIDL ERKVESLQEE IAFLKKLHEE
         250        260        270        280        290        300
EIQELQAQIQ EQHVQIDVDV SKPDLTAALR DVRQQYESVA ARMLQEAEEM YKSKFADLSE
         310        320        330        340        350        360
AANRMNDALR QAKQESTEYR RQVQSLTCEV DALKGTNESL ERQMREMEEN FAVEAANYQD
         370        380        390        400        410        420
TIGRLQDEIQ NMKEEMARHL REYQDLLNVK MALDIELATY RKLLEGEESR ISLPLPNFSS
         430        440        450        460
LNLRETNLDS LPLVDTHSKR TLLIKTVETR DGQVINETSQ HHDDLE
```

FIG 8
(i)
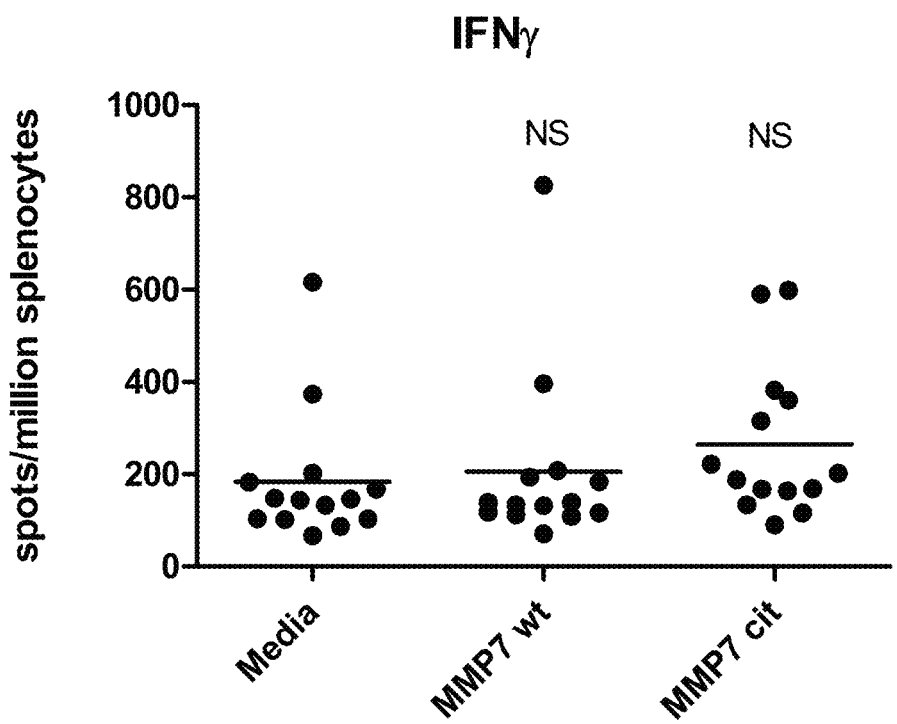
(ii)
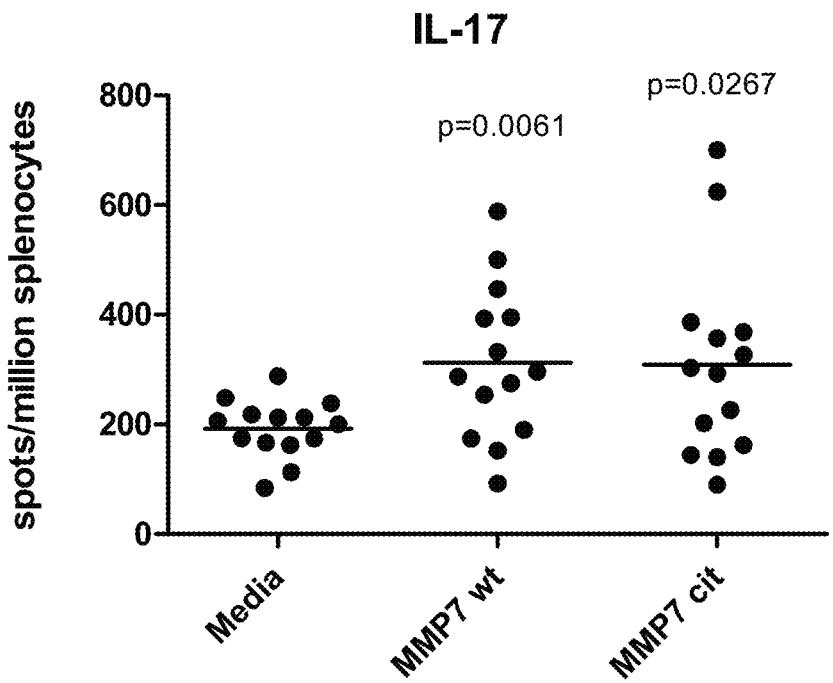

FIG 9
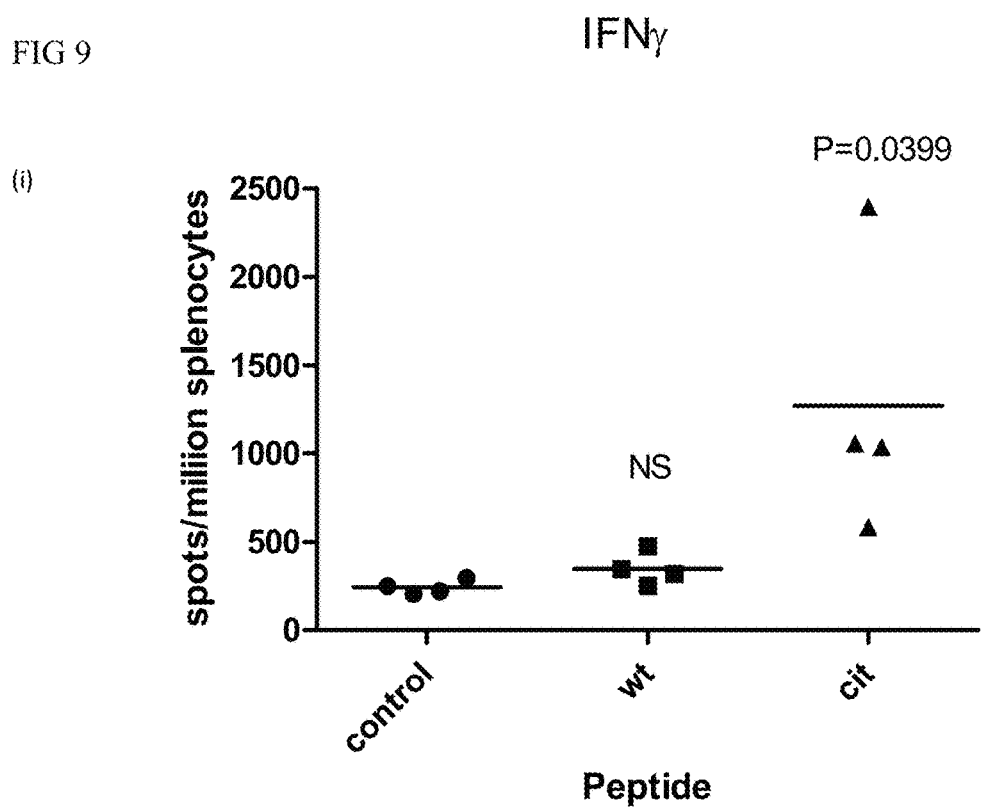
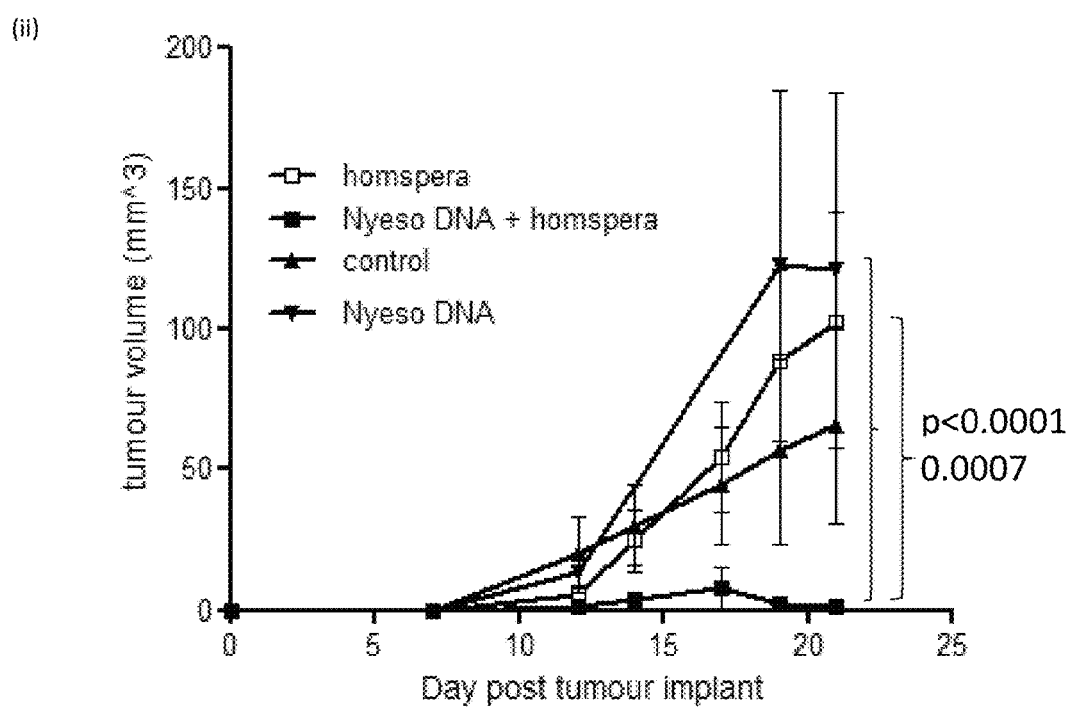

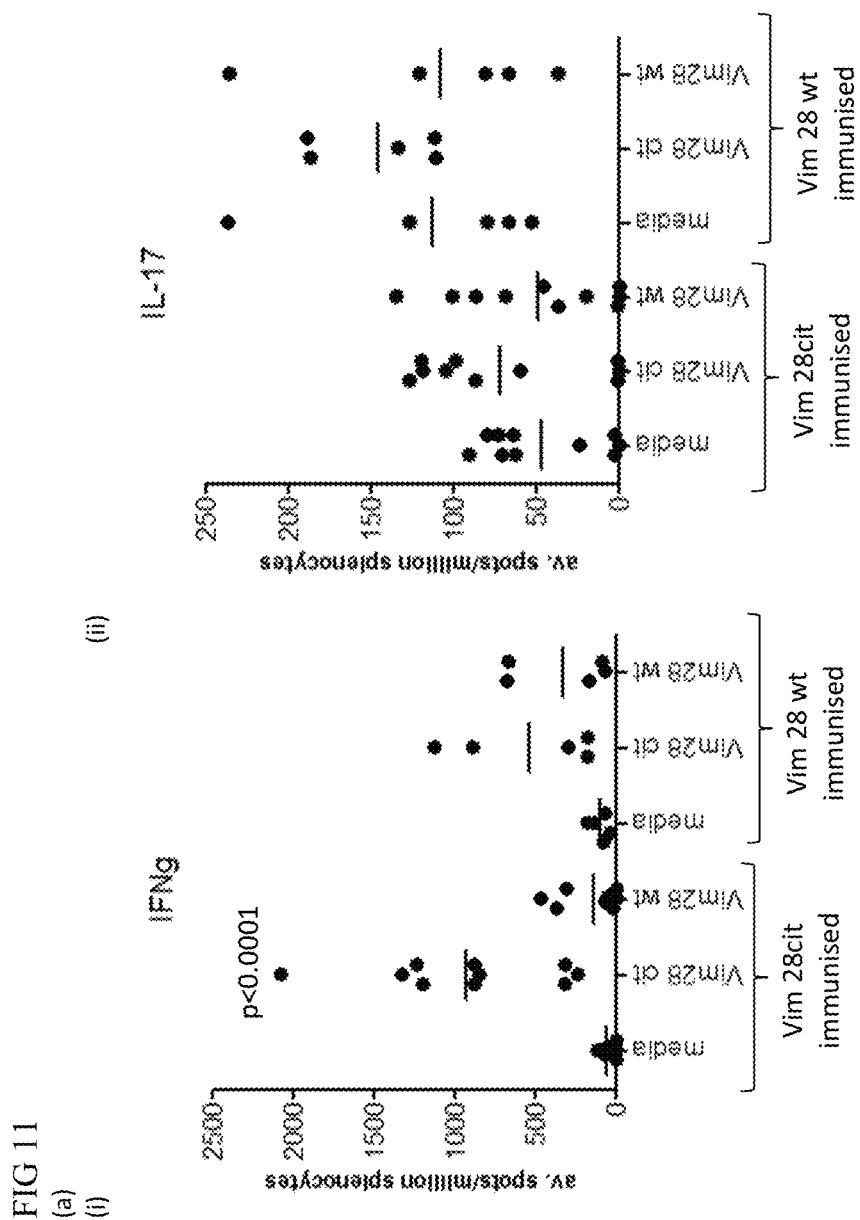
FIG 11 (a) (i), (ii)

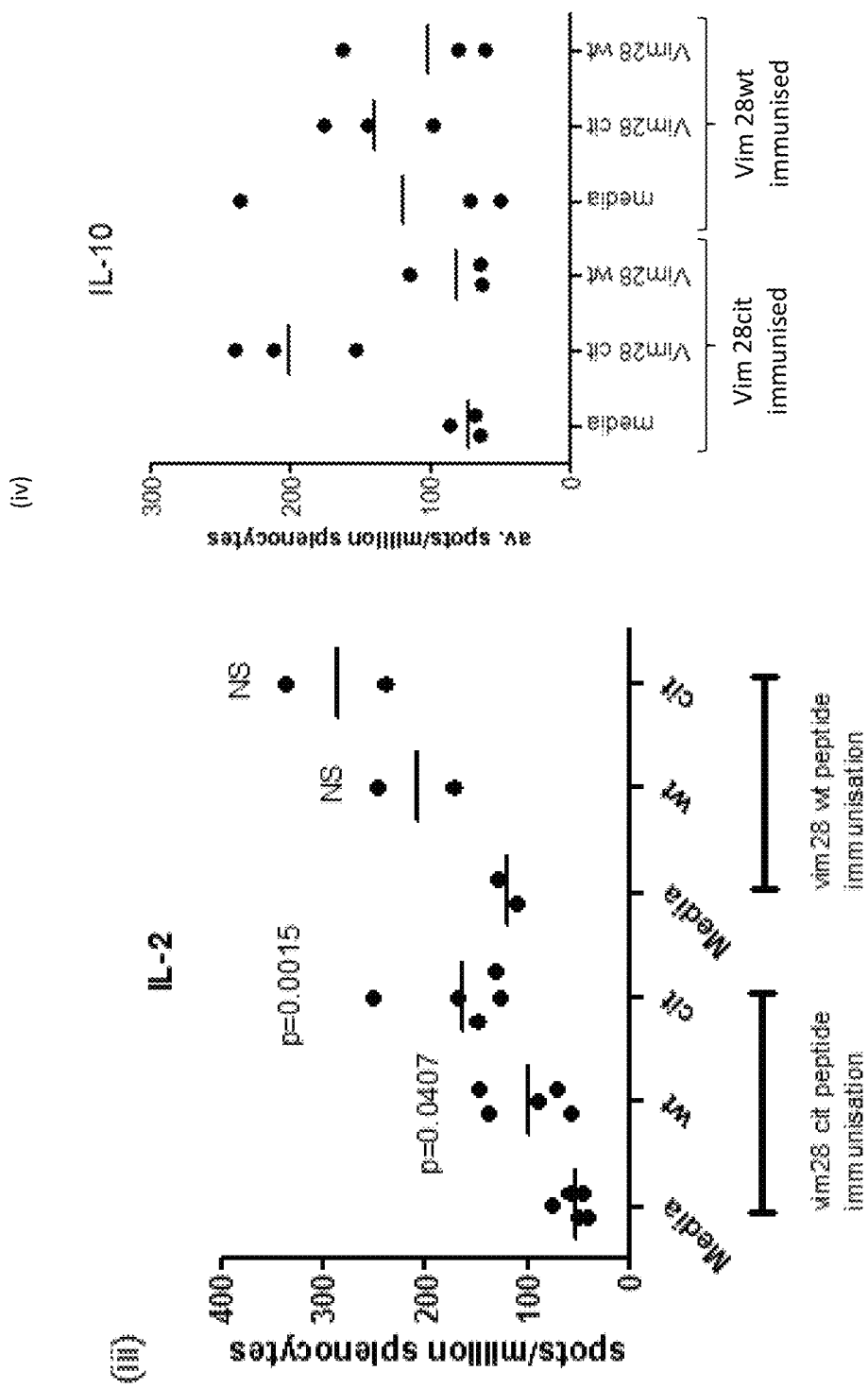
FIG 11 contd

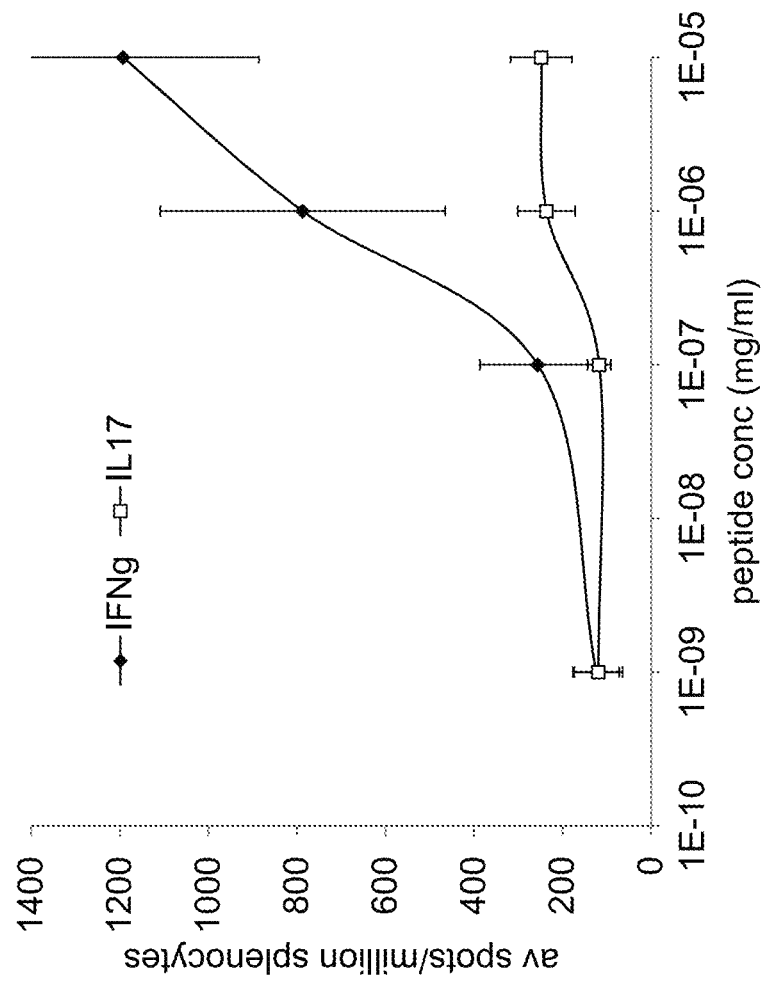
FIG 11 contd (b)

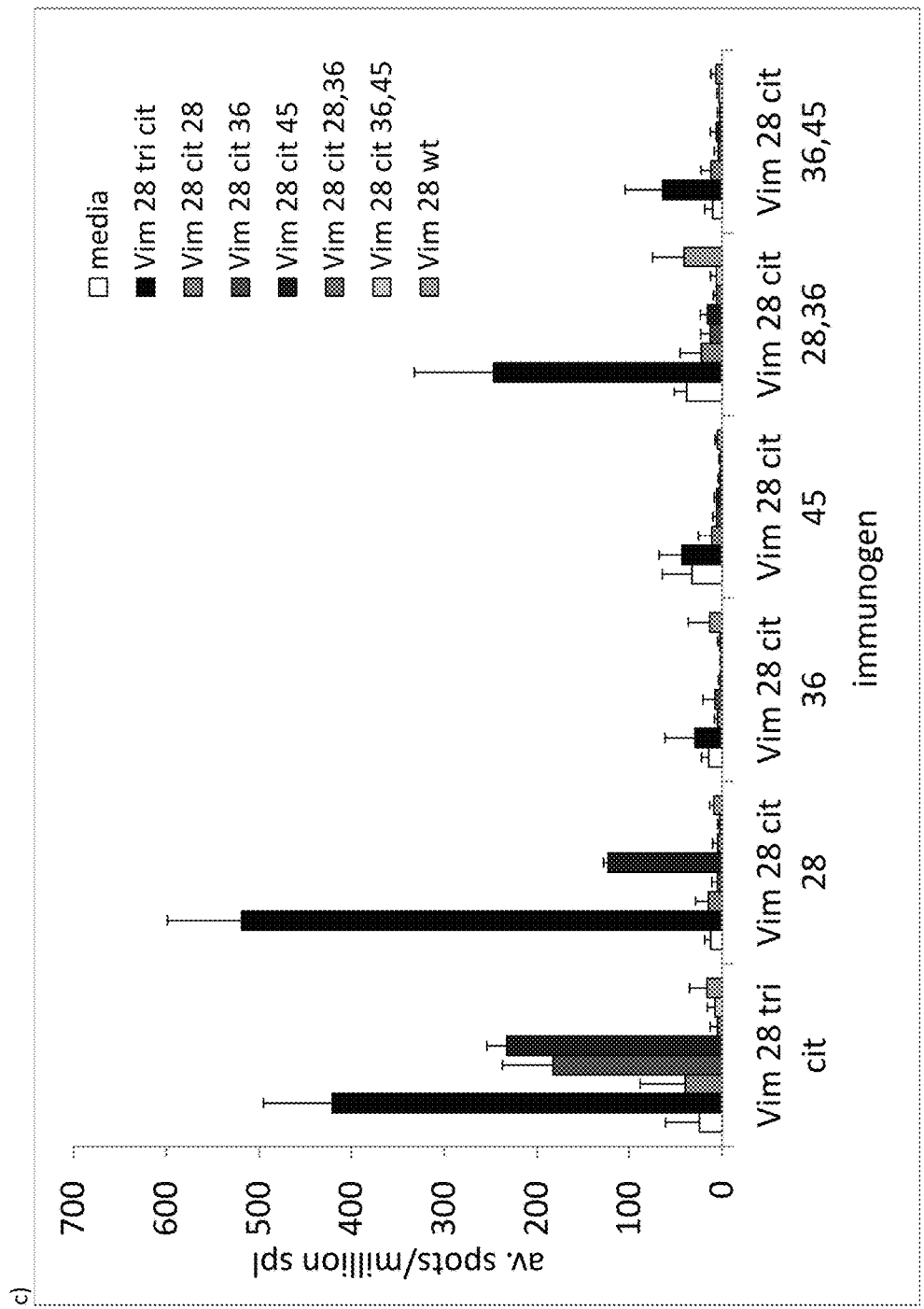
FIG 11 contd

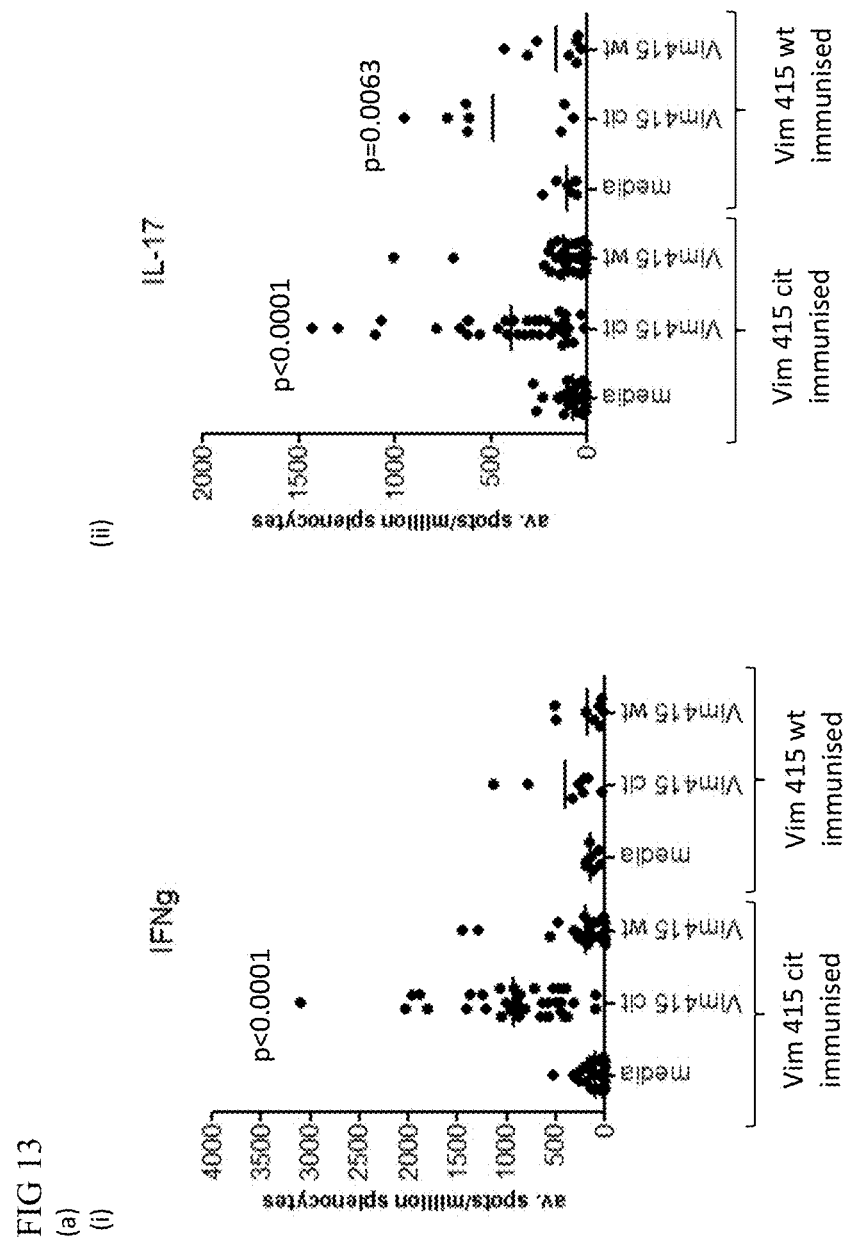
FIG 13 (a) (i)

FIG 13 contd
(a)
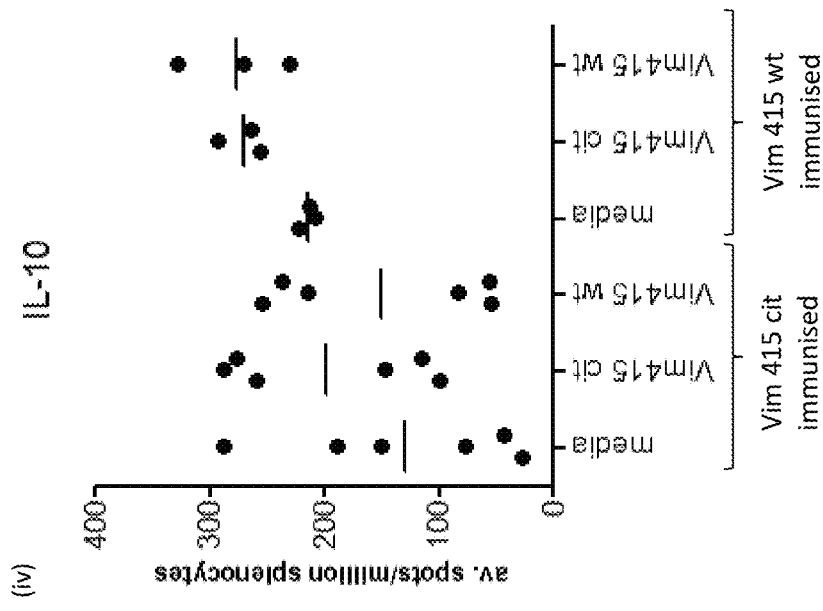
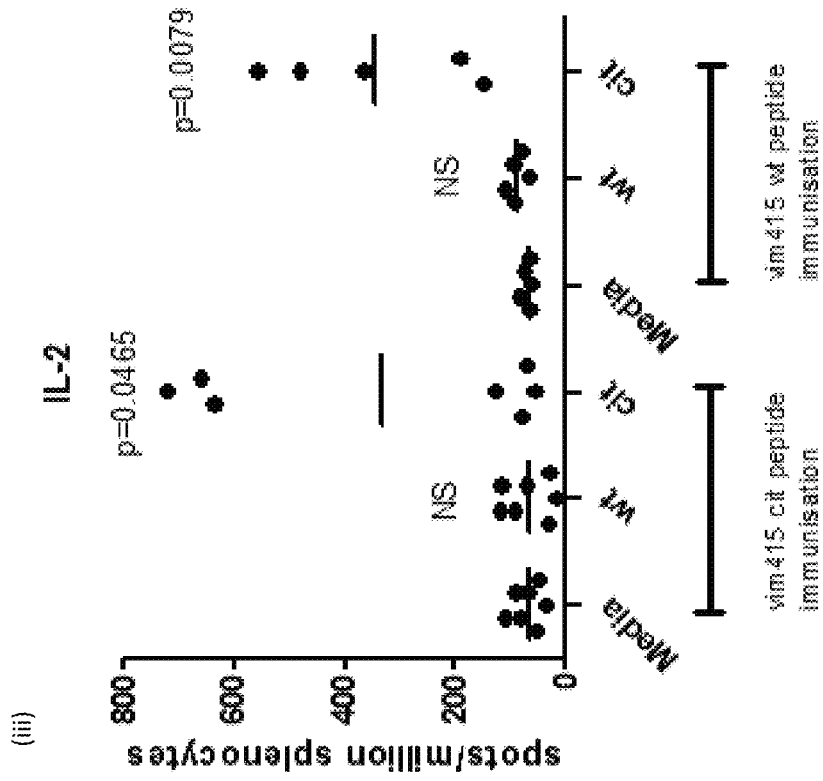

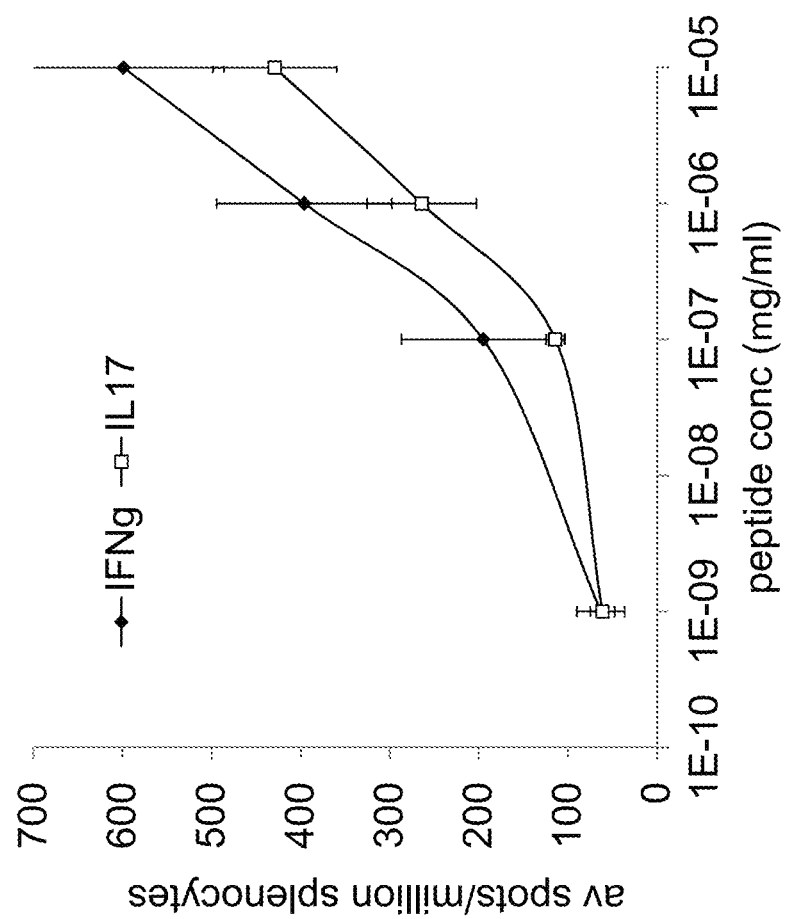
FIG 13 contd
(b)

FIG 14
(i)
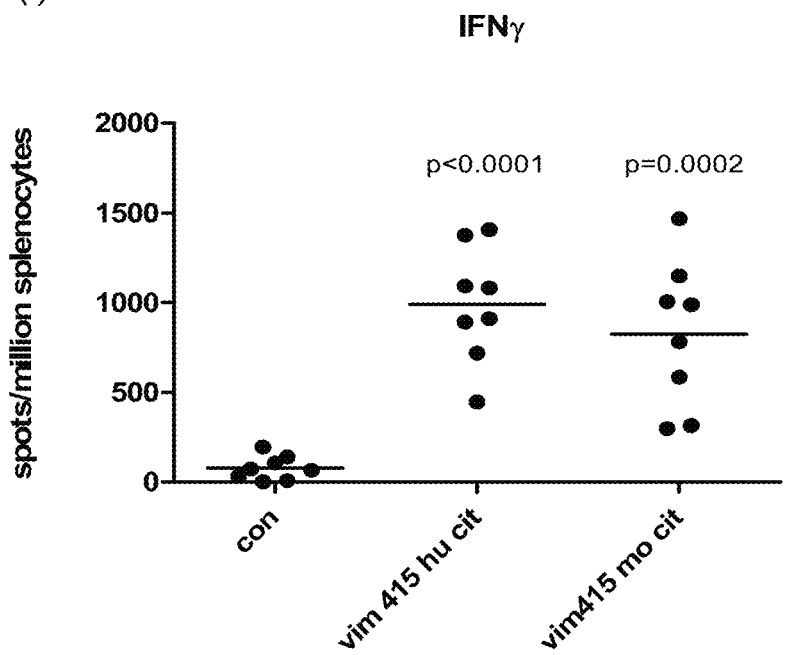
(ii)
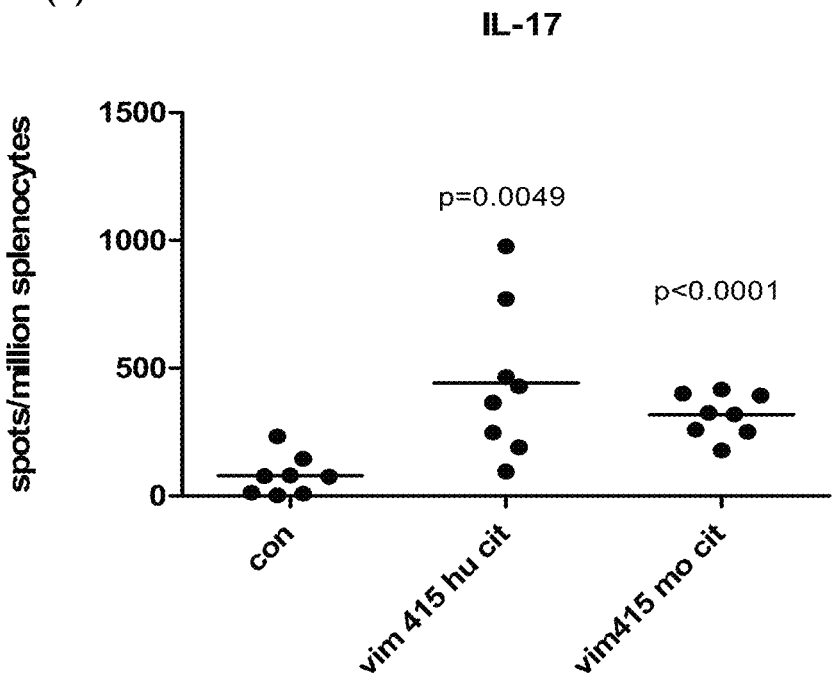

FIG 15
a)
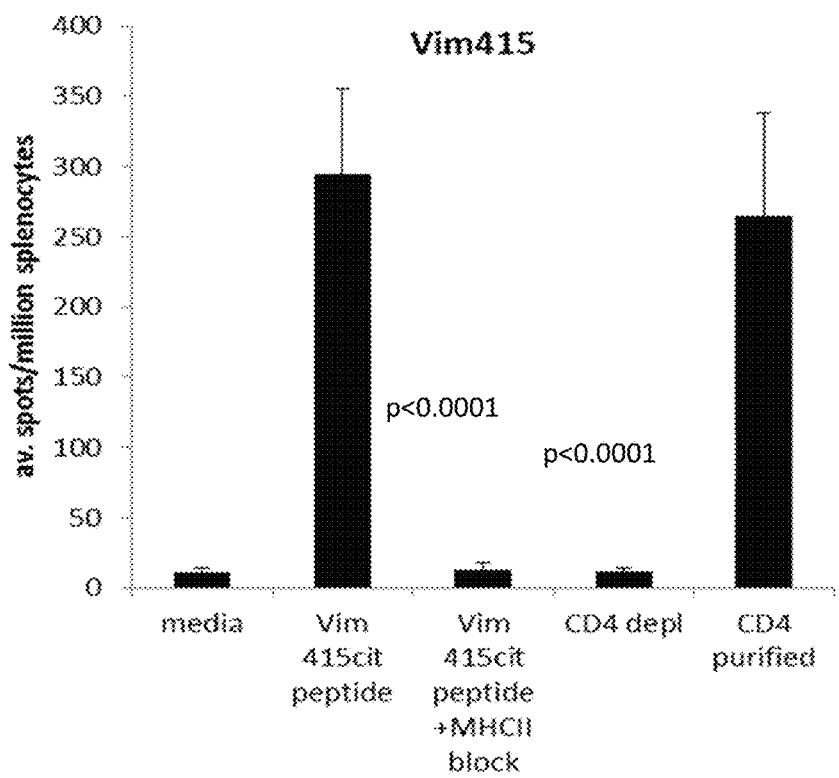
b)
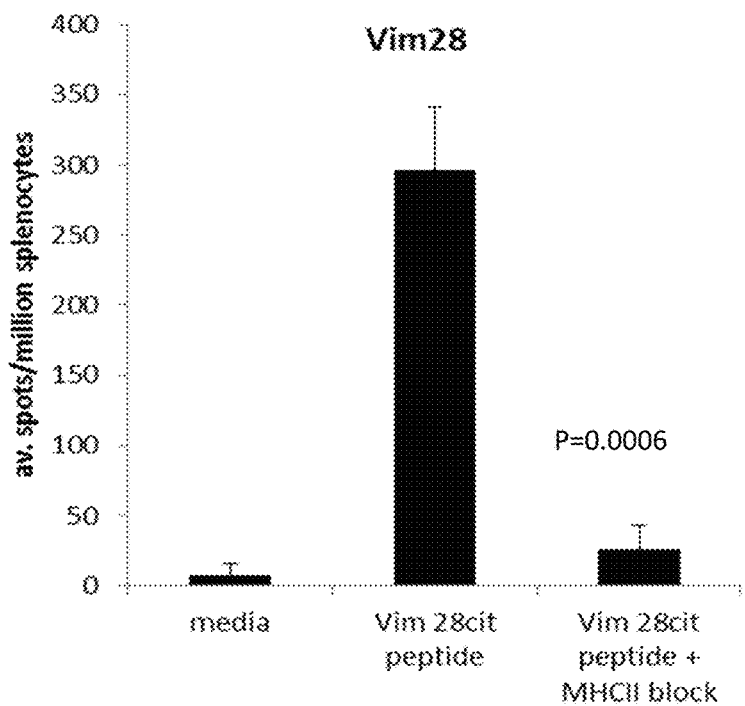

FIG 16
a)
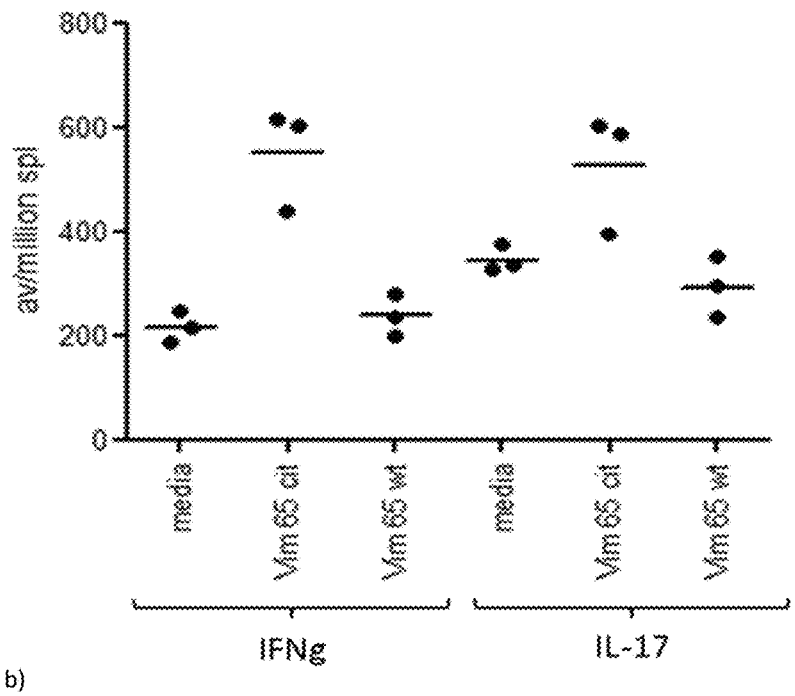
b)
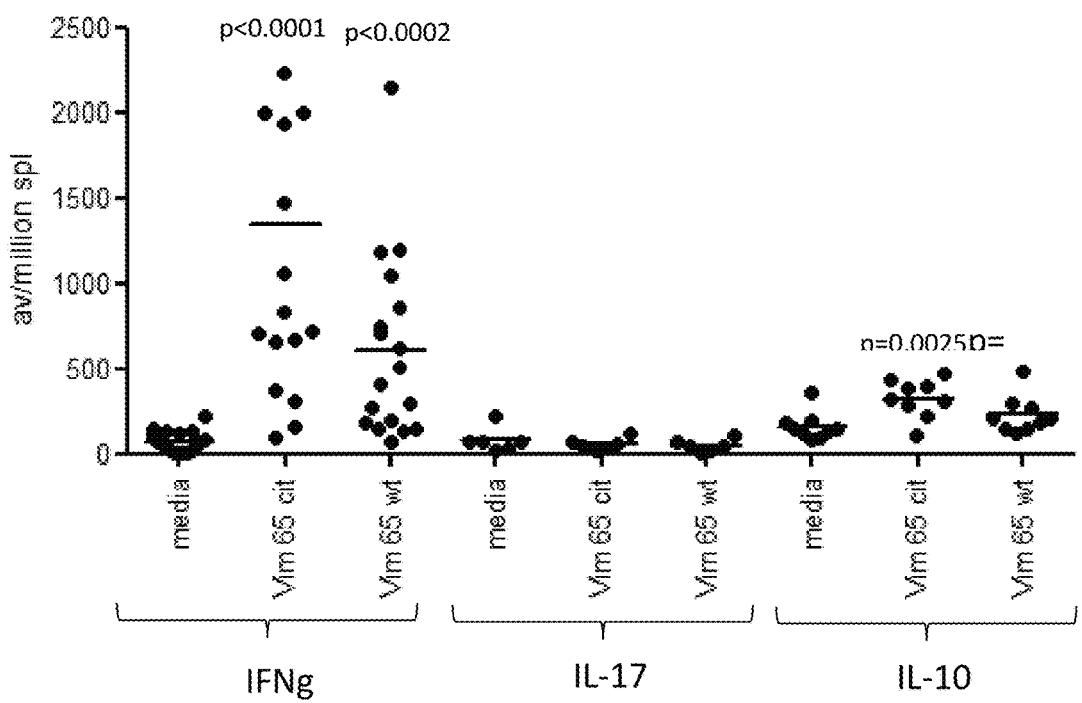

FIG 16 contd
c)
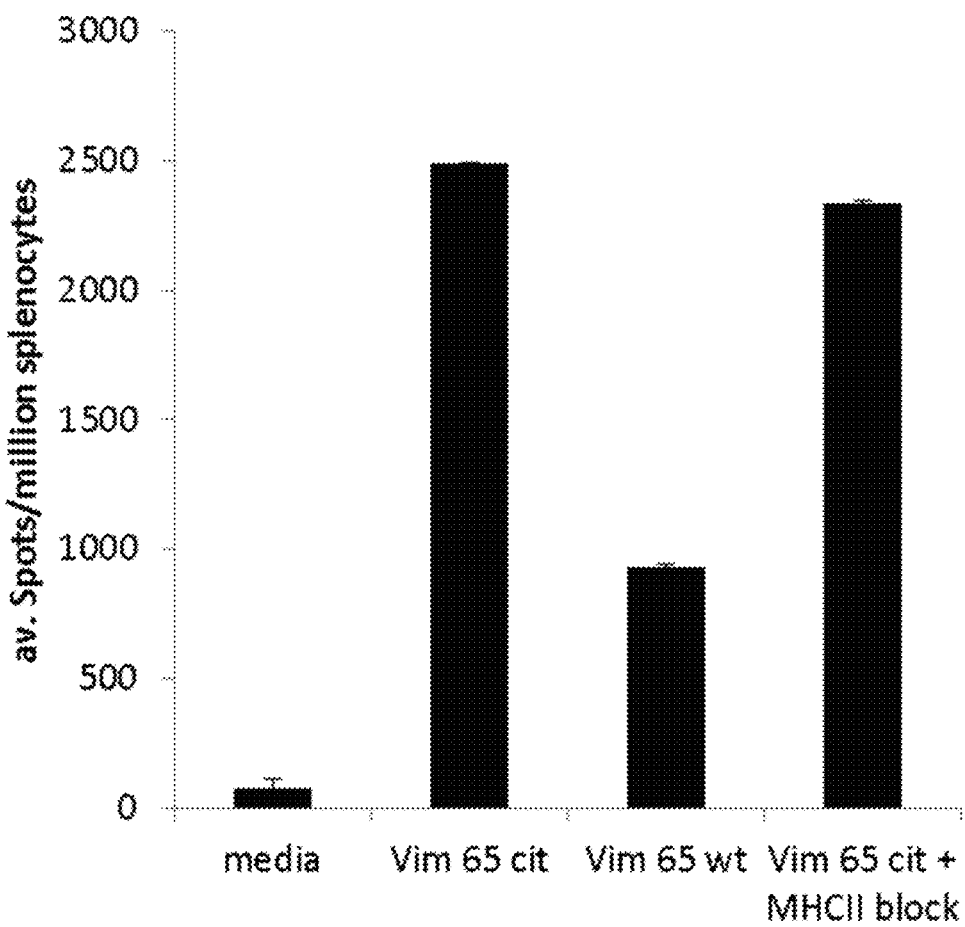

FIG 16 contd
d)
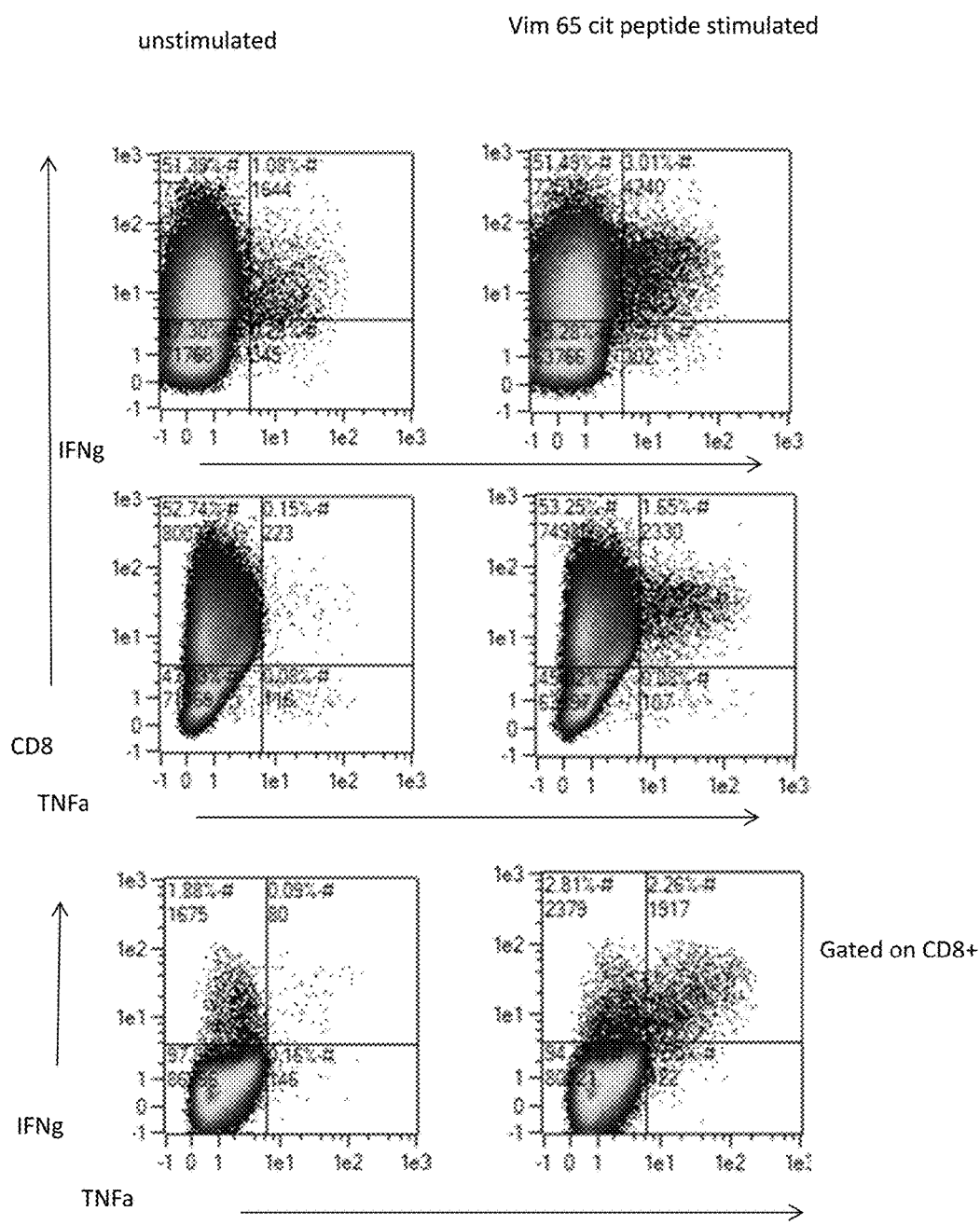

FIG 16 contd
e)
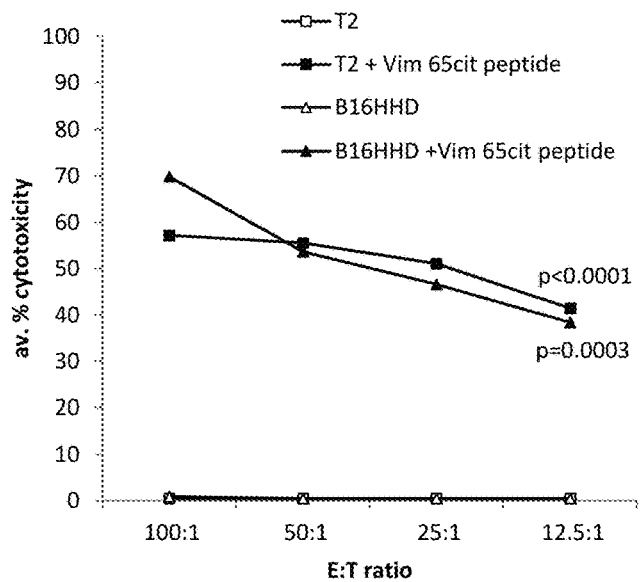
f)
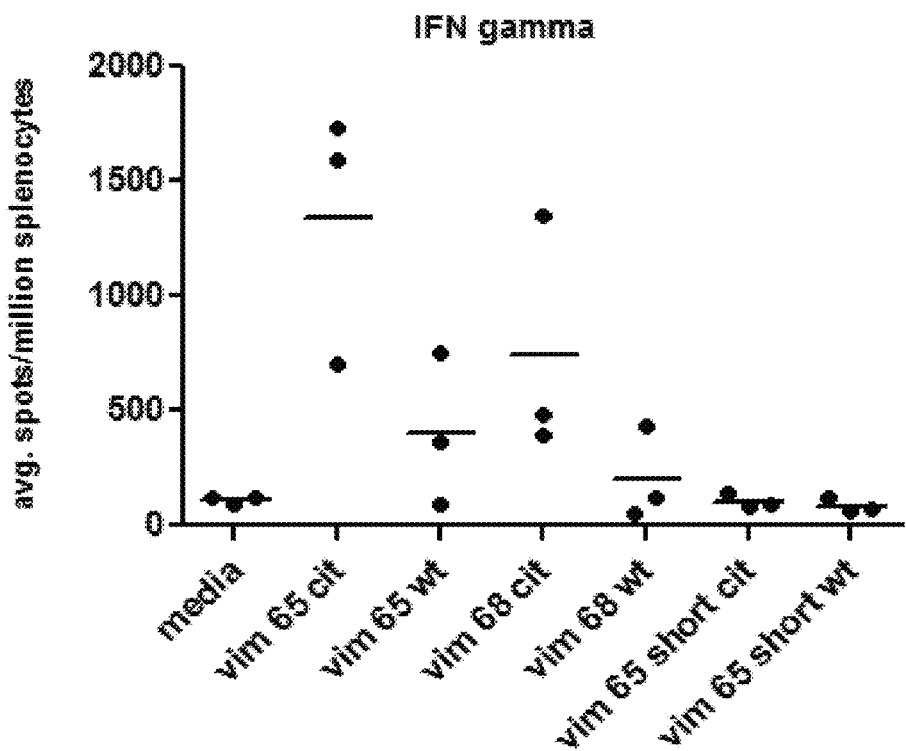

FIG 16 contd
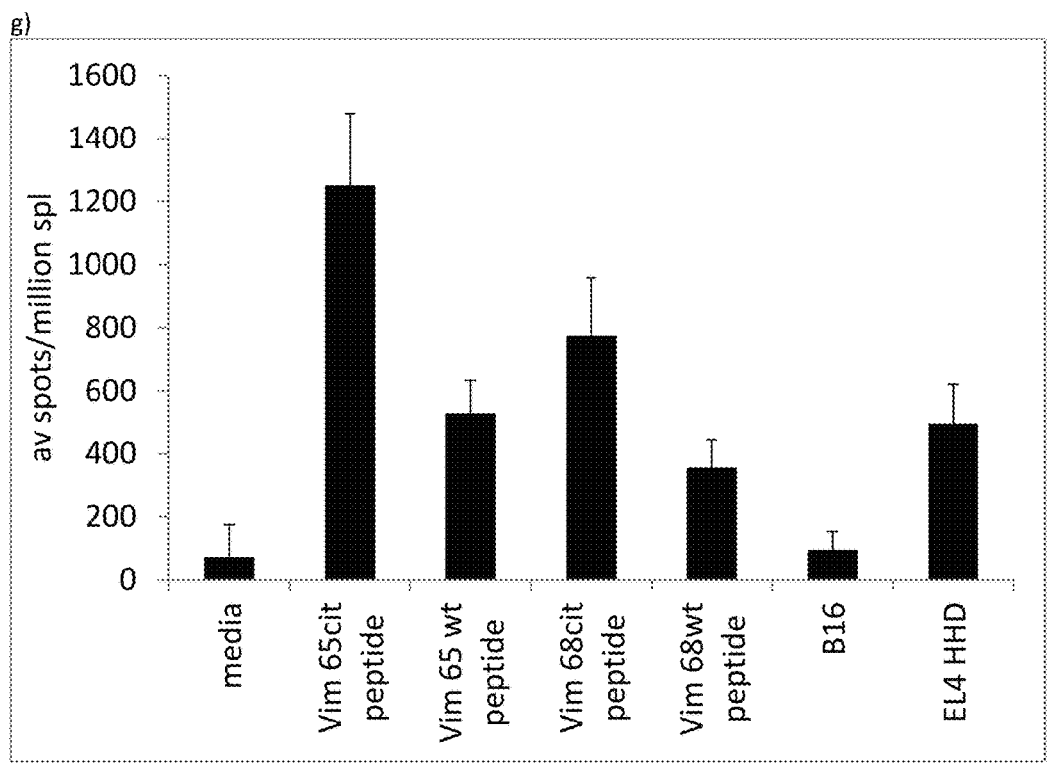
FIG 17
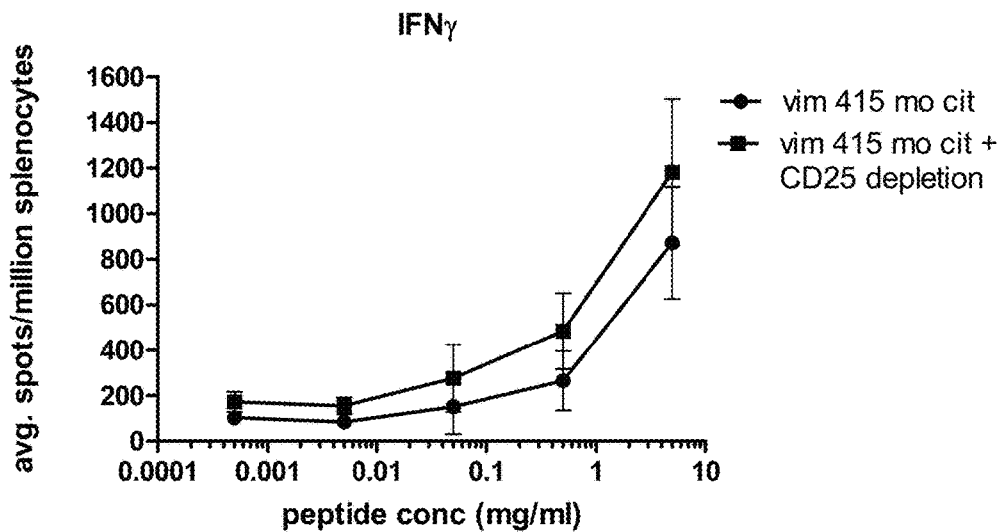

*p<0.05, p<0.001, *p<0.0001

(i)

Figure 18:
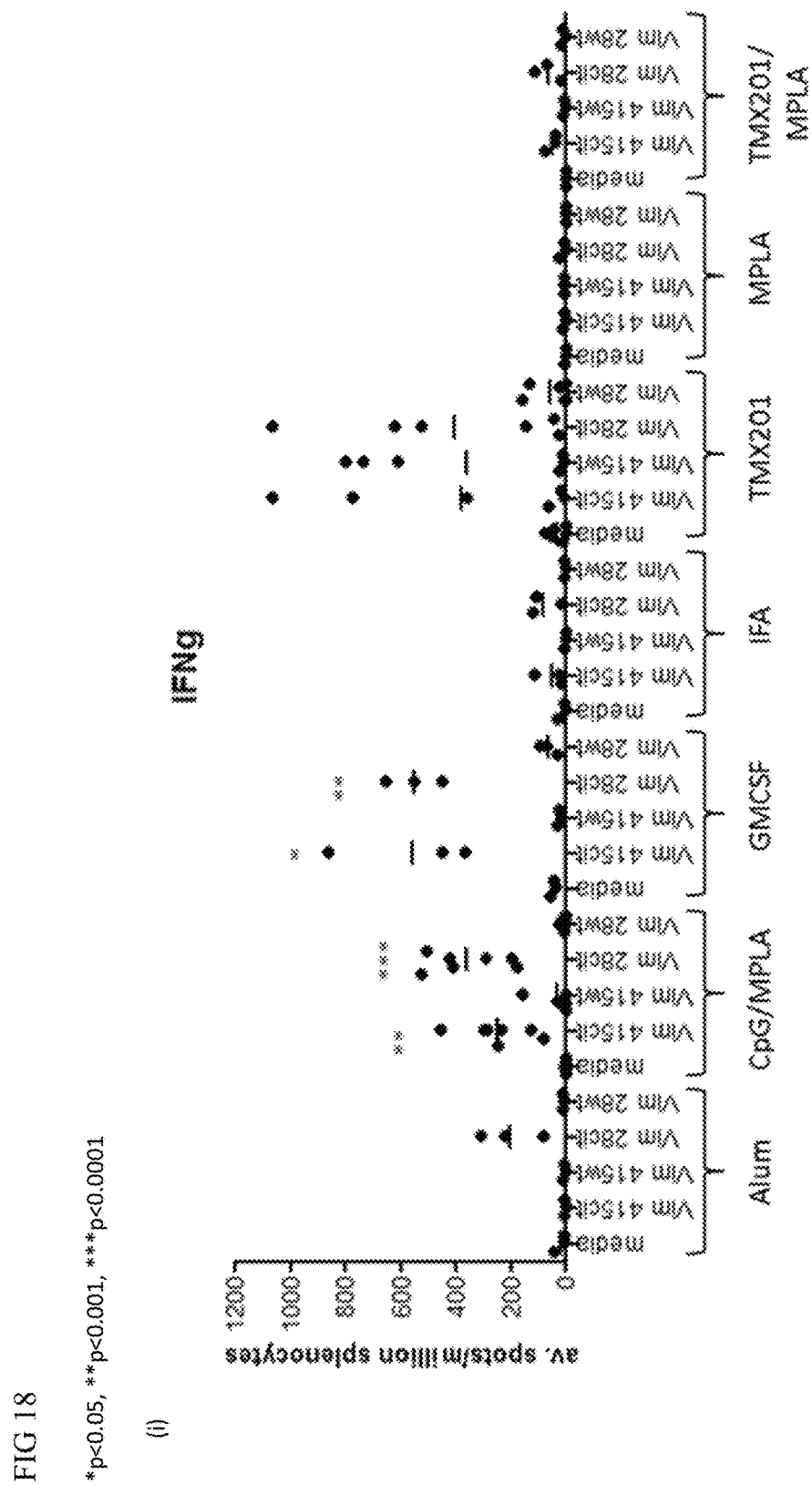

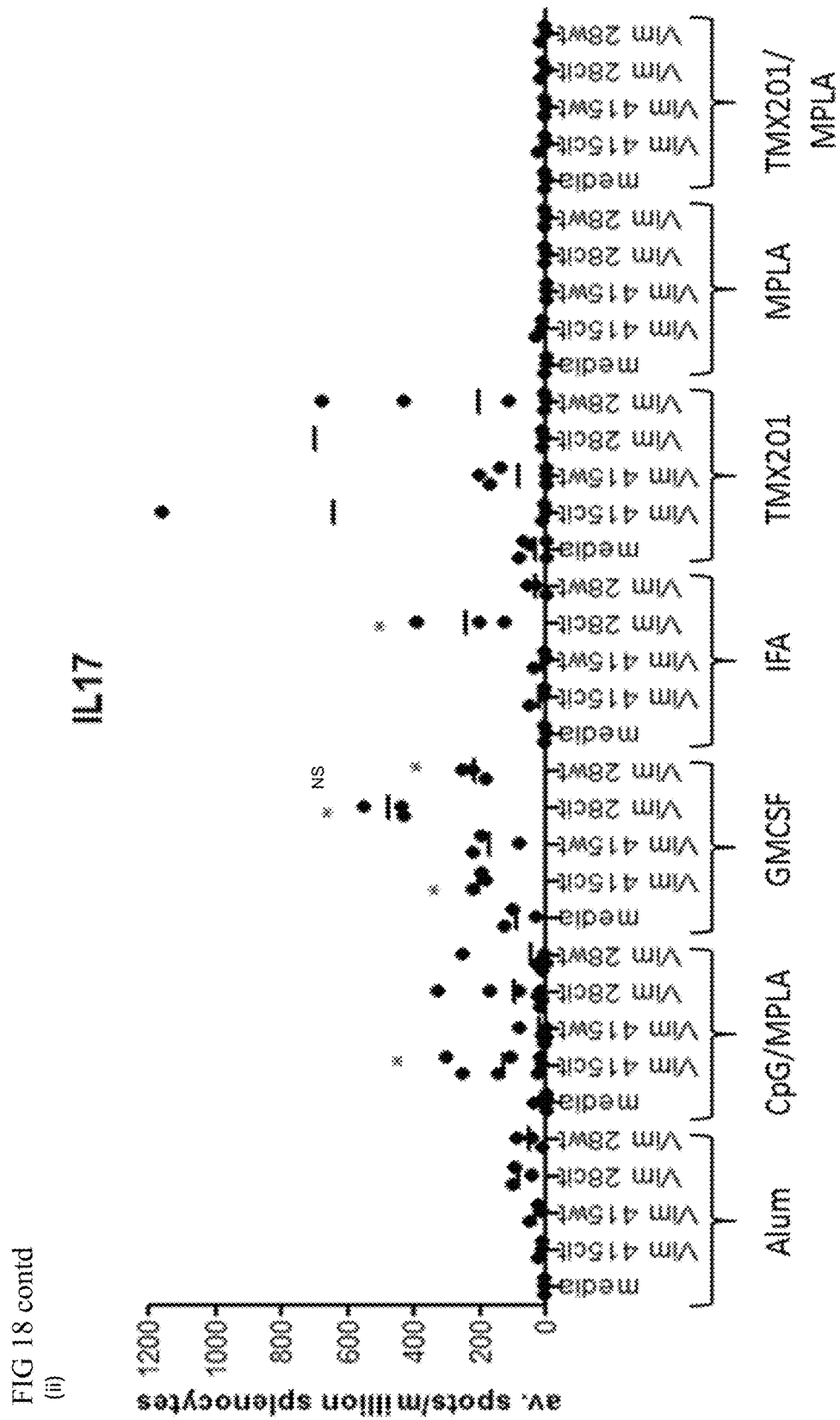
FIG 18 contd (ii)

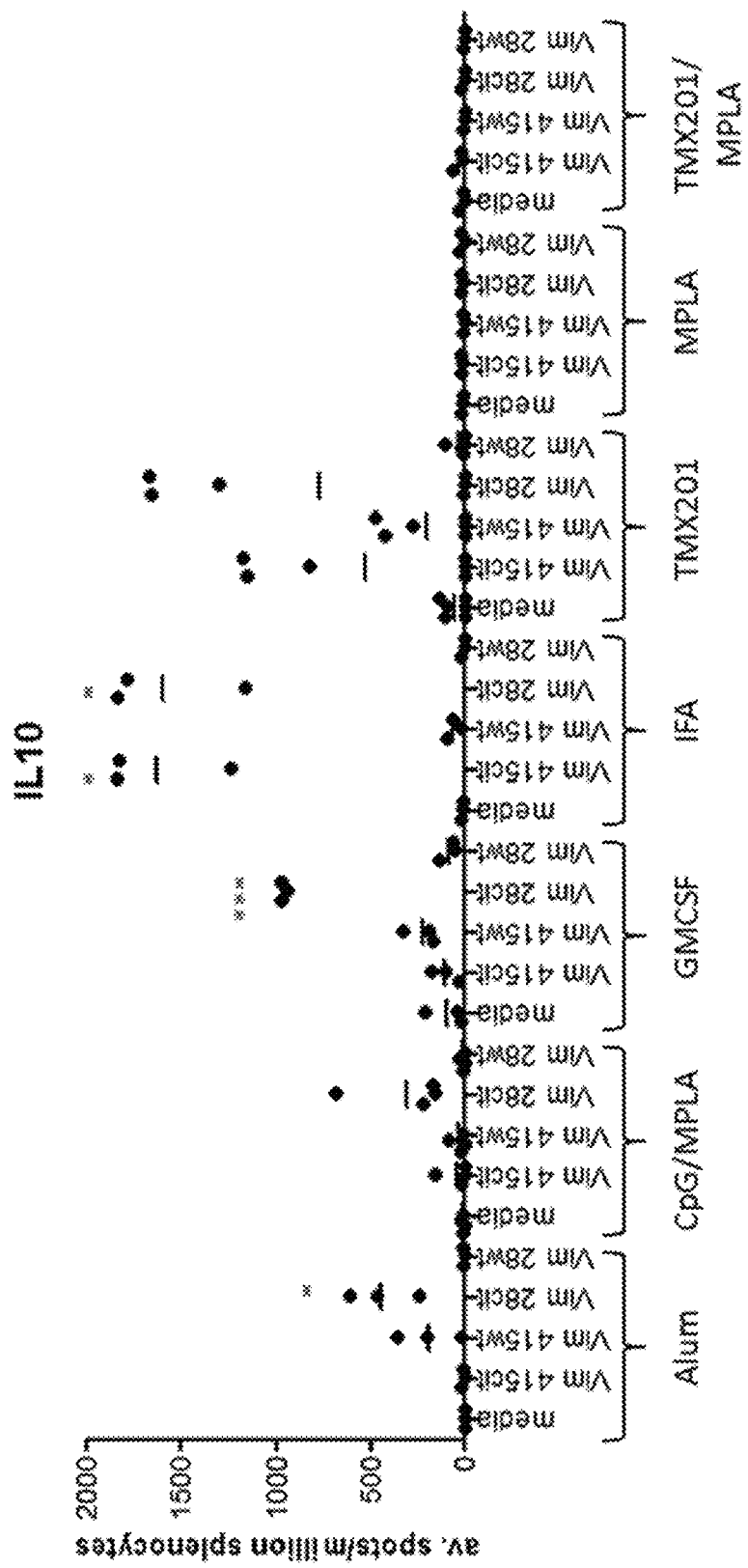
FIG 18 contd (iii)

FIG 19
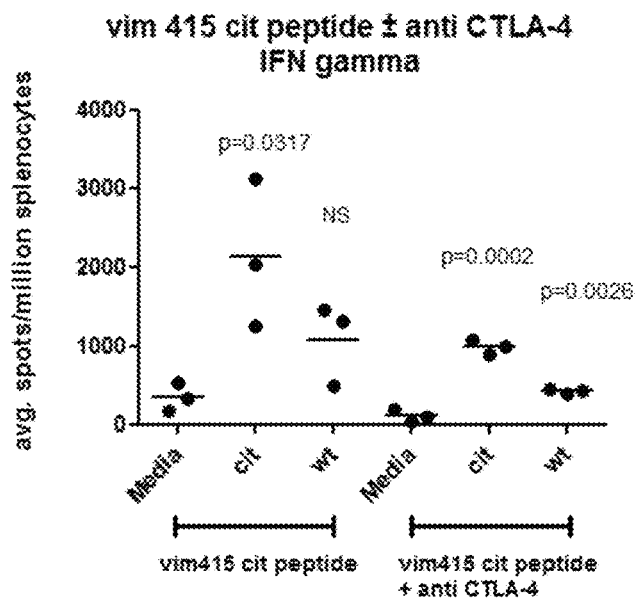
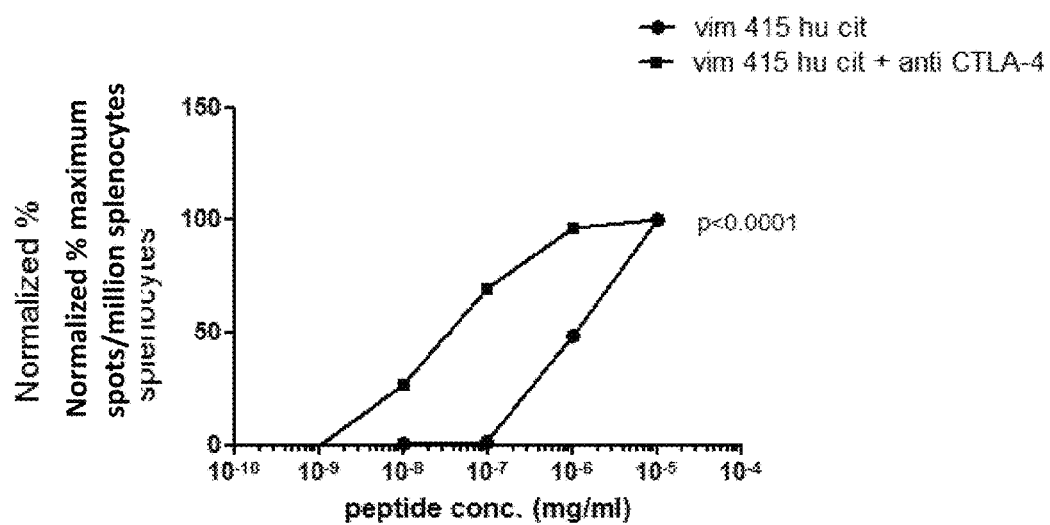

Figure 20:
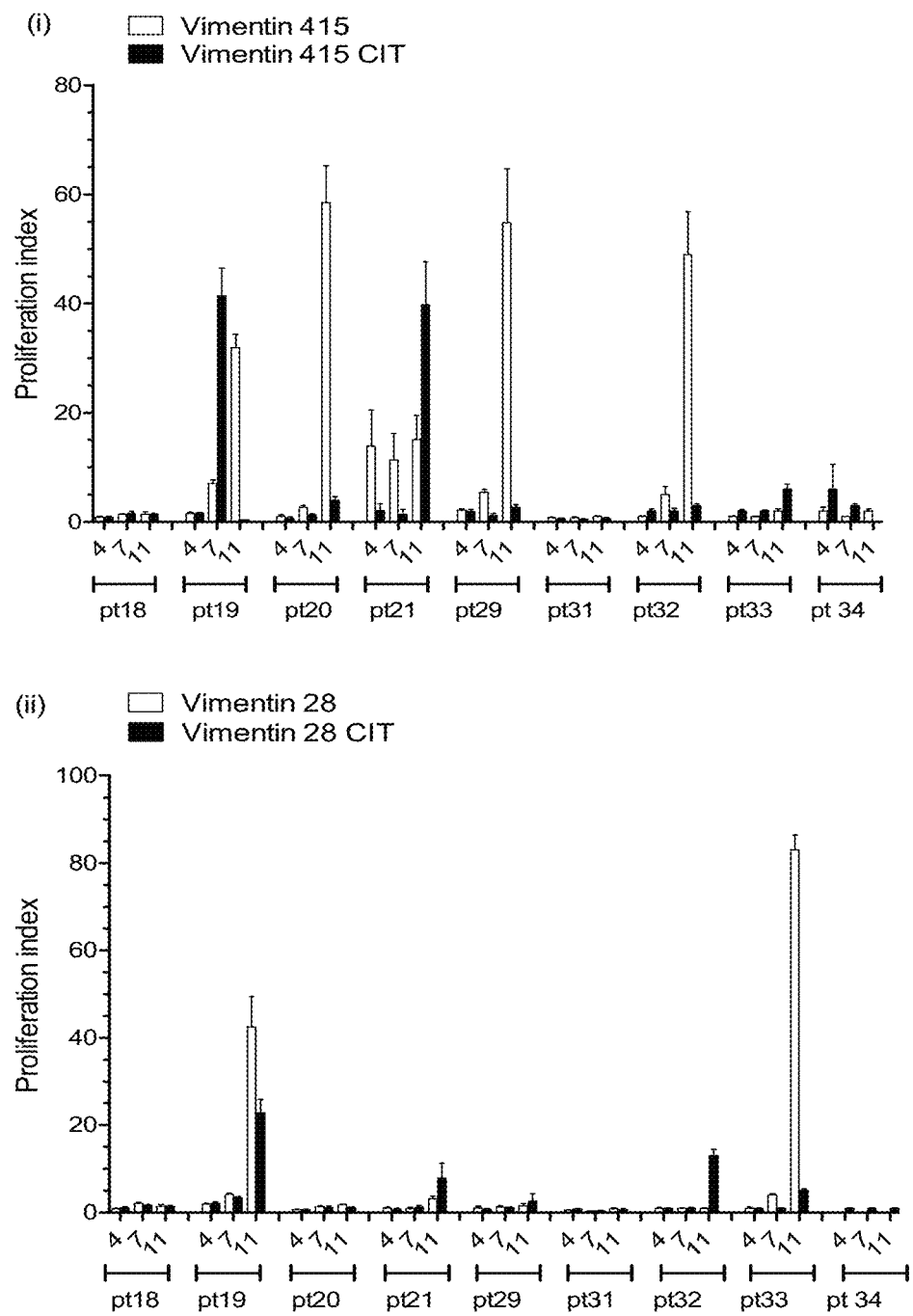

FIG 20 cont
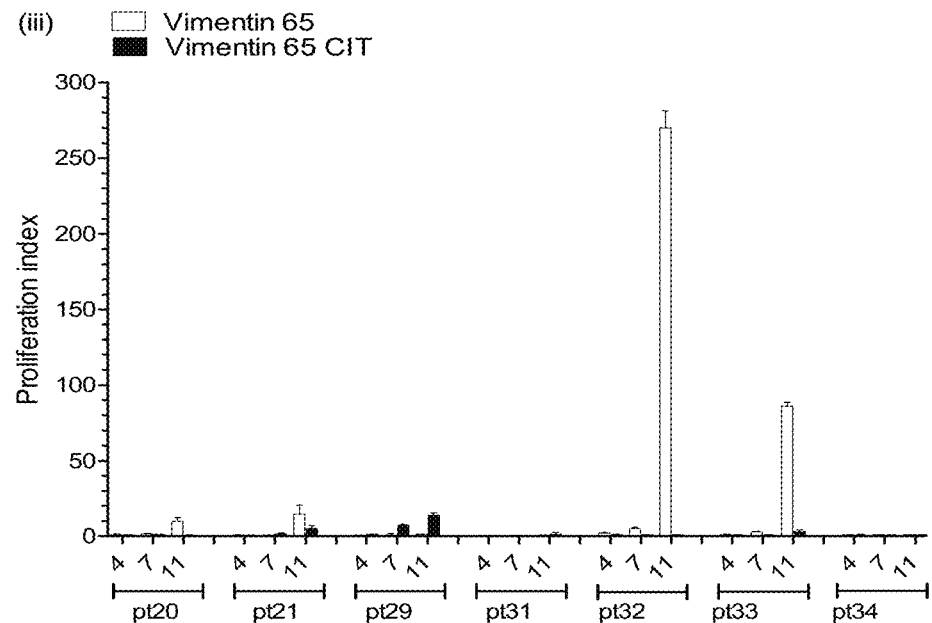
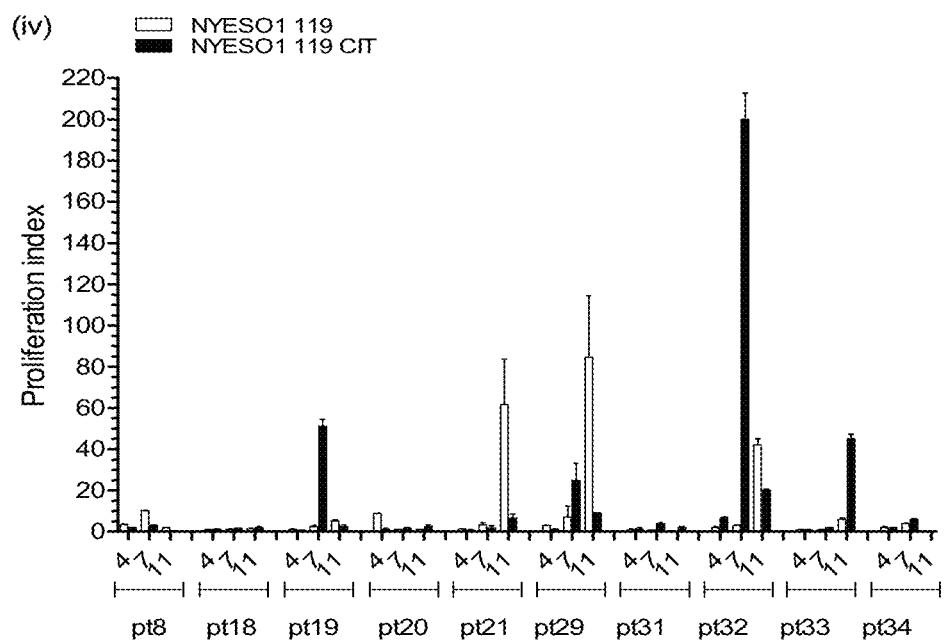

kaplan Meier Survival of patients whose tumours express PAD or HMGB1 a) Ovarian tumours expressing PAD2

Figure 21:
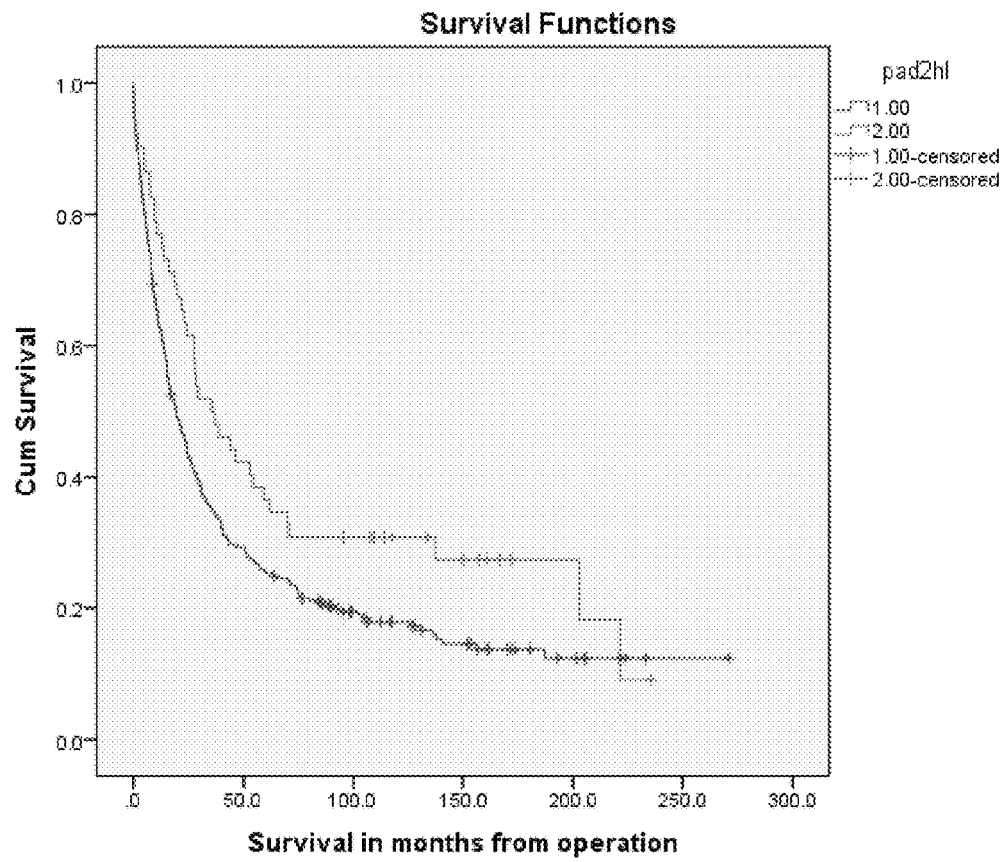

FIG 21 contd
b) Ovarian tumours expressing HMGB1
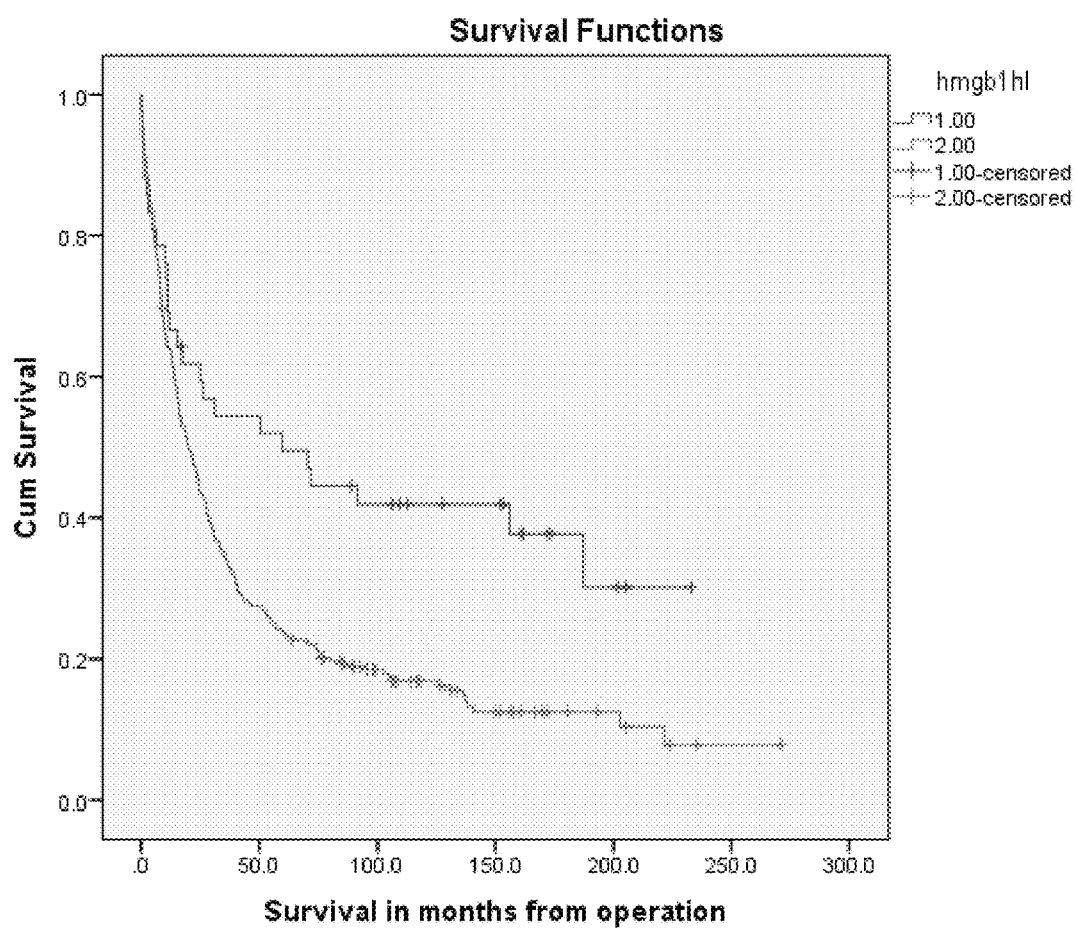

FIG 21 contd
c) ovarian tumours expressing PAD2 and HMGB1 ( 0 denotes no expression, 1 only HMGB1, 2-only PAD2 and 3 both.
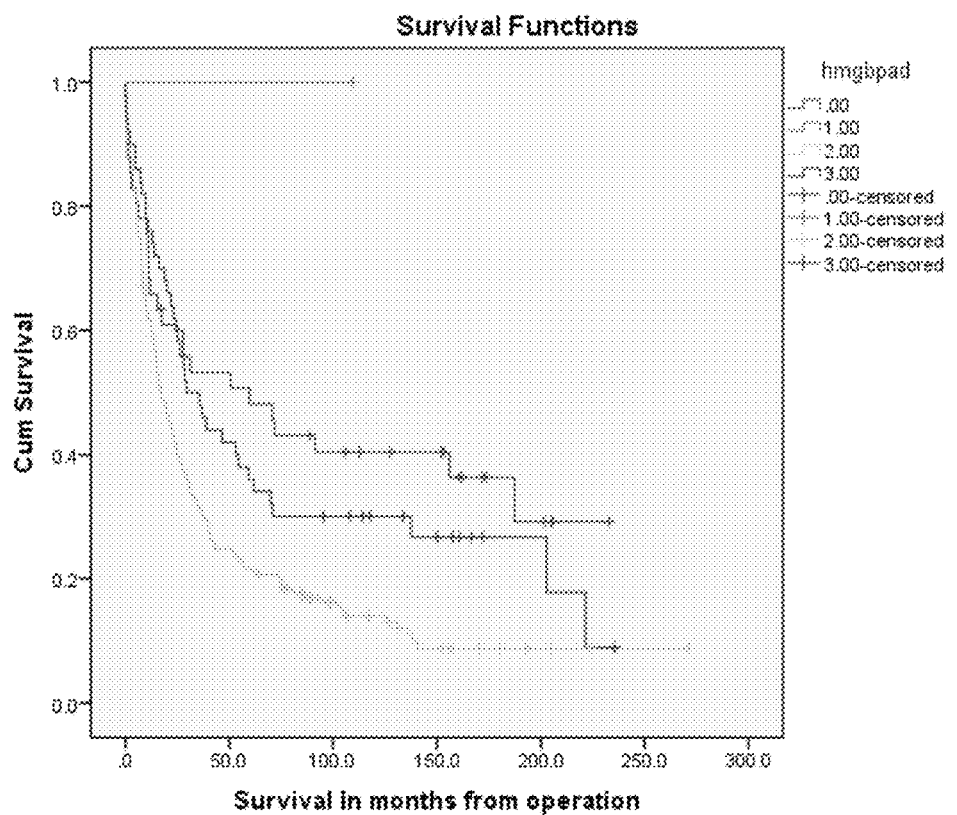
Overall Comparisons
|  | Chi-Square | df | Sig. |
|---|---|---|---|
| Log Rank (Mantel-Cox) | 17.217 | 3 | .001 |
Test of equality of survival distributions for the different levels of hmgbpad.

FIG 21 contd
d) colorectal cancer patients expressing PAD4
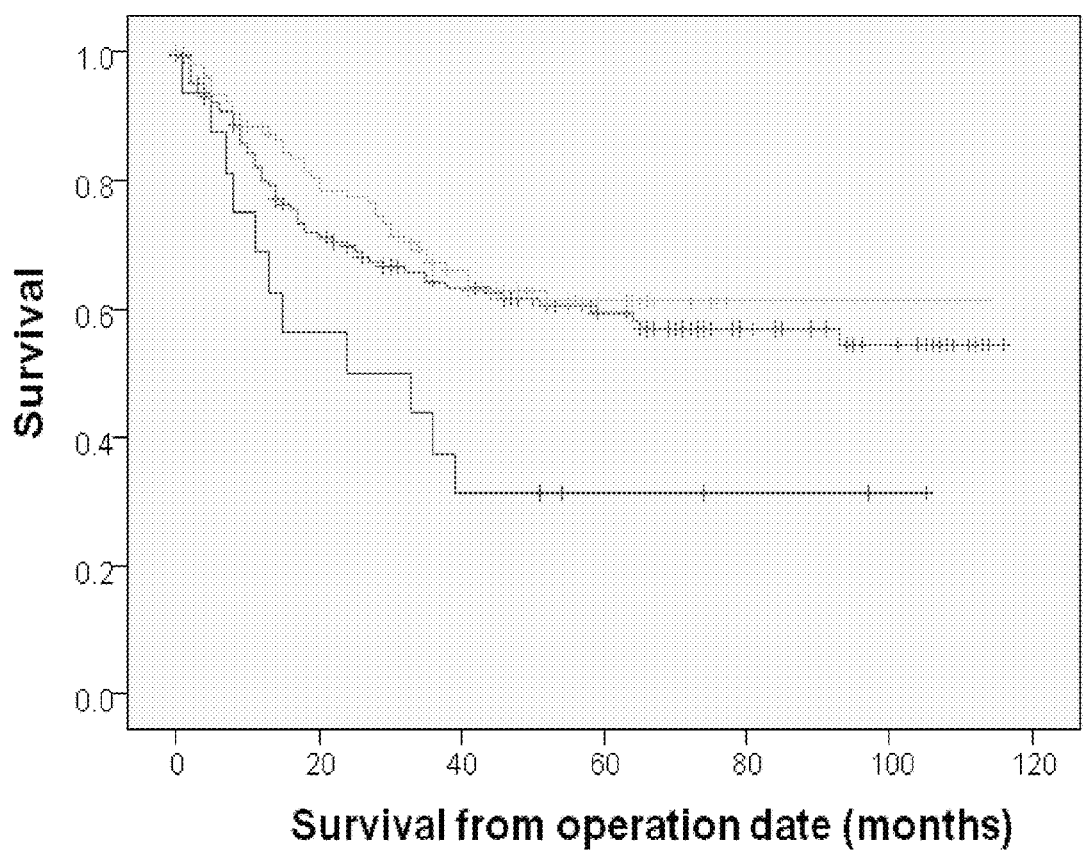
| | Chi-Square | df | Sig. |
|---|---|---|---|
| Log Rank (Mantel-Cox) | 6.871 | 2 | .032 |

Figure 22:
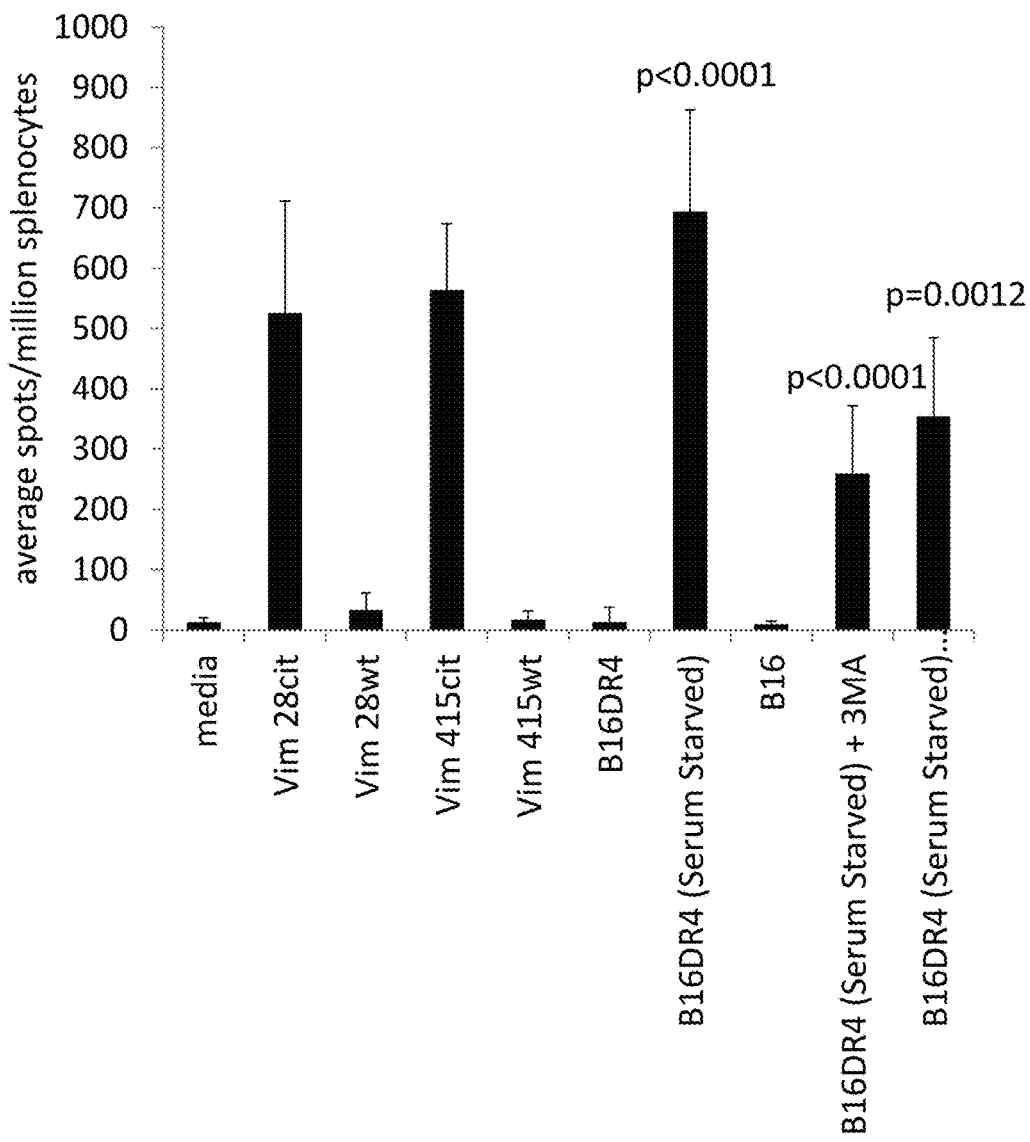

FIG 22 contd (b)
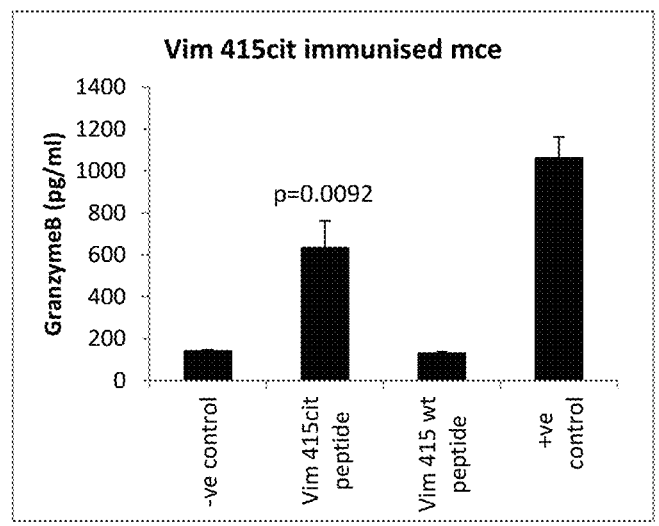

FIG 22 contd
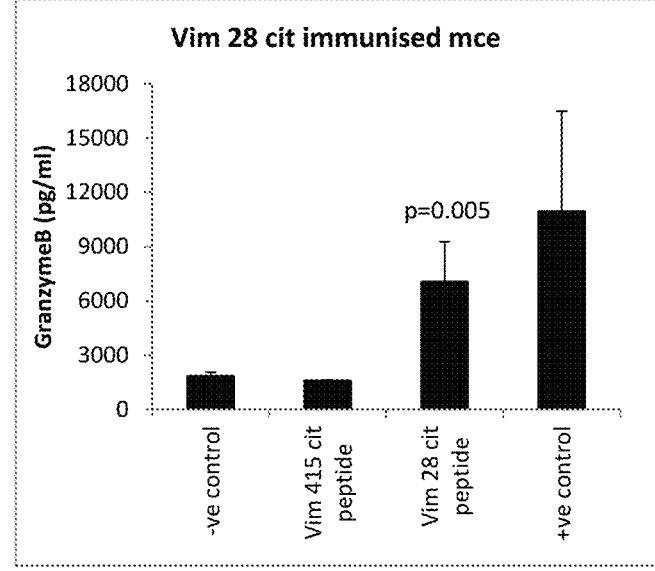
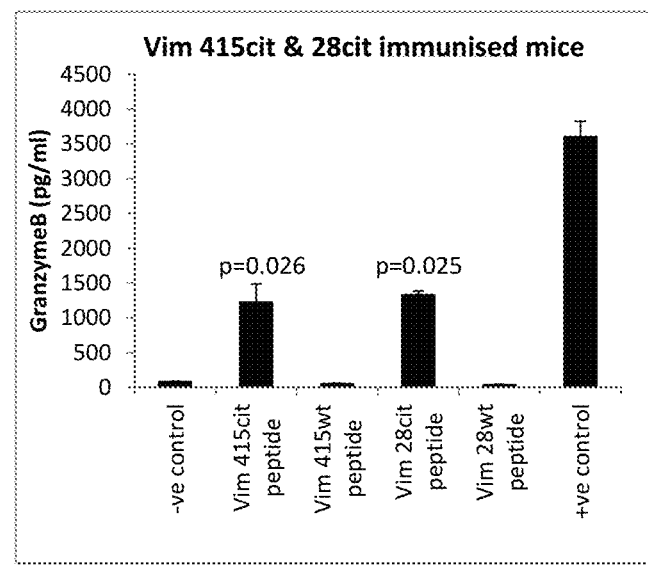

FIG 22 contd
(e)
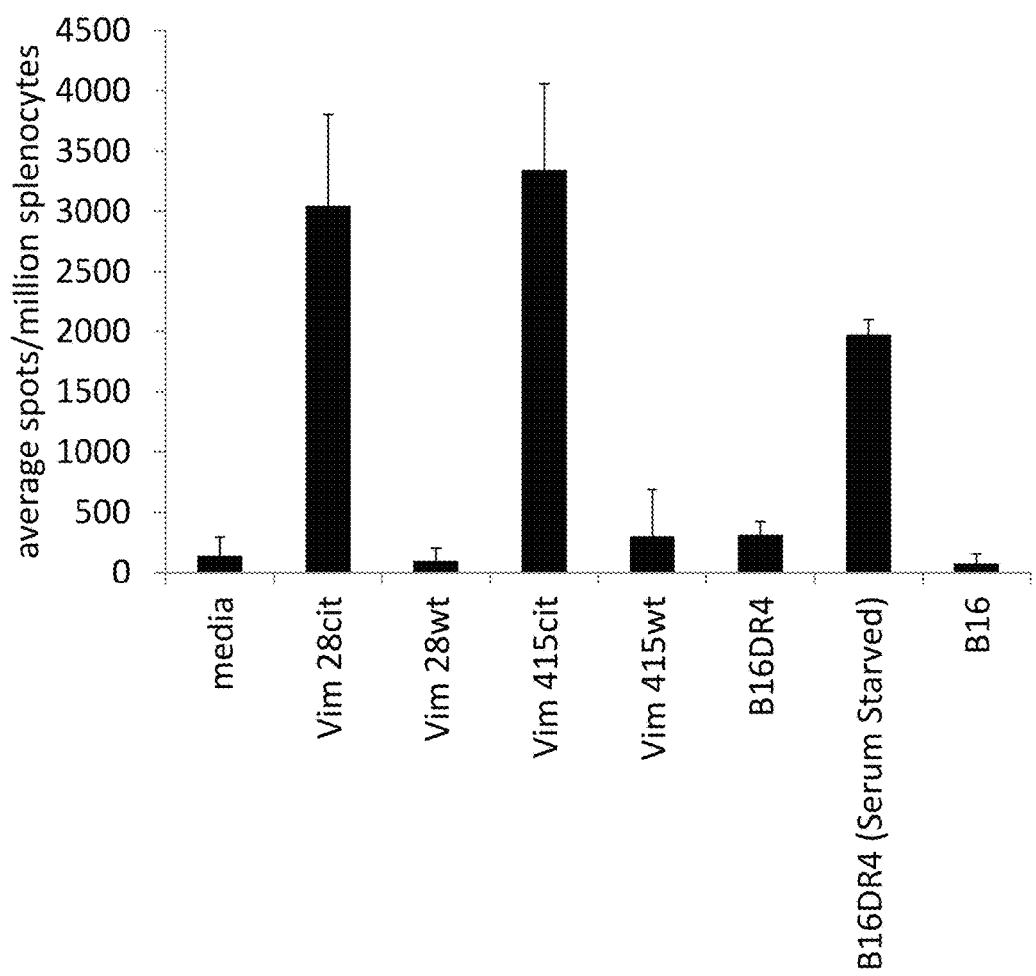

FIG 23
(a)
(i) Vim 415 cit
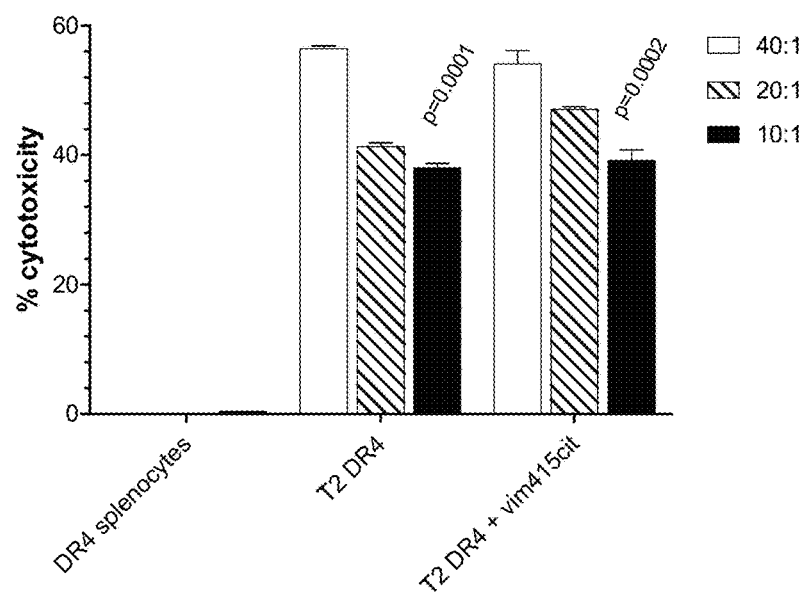
(ii) Vim 28 cit
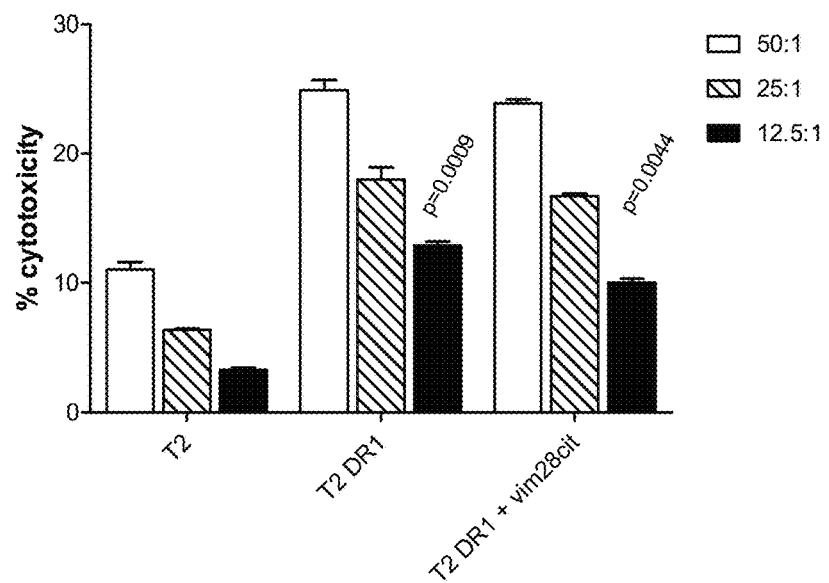

Figure 24:
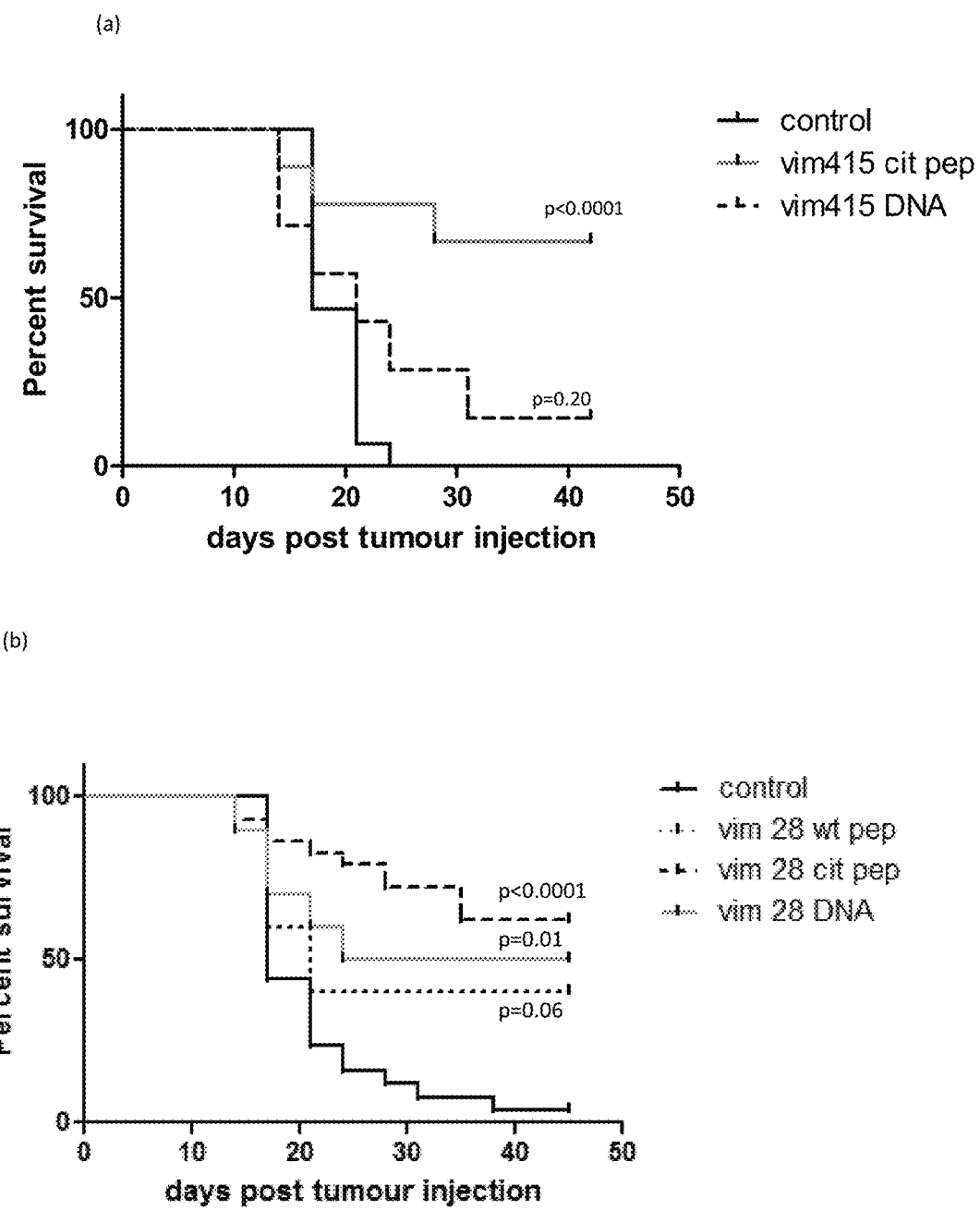

FIG 24 contd
(c)
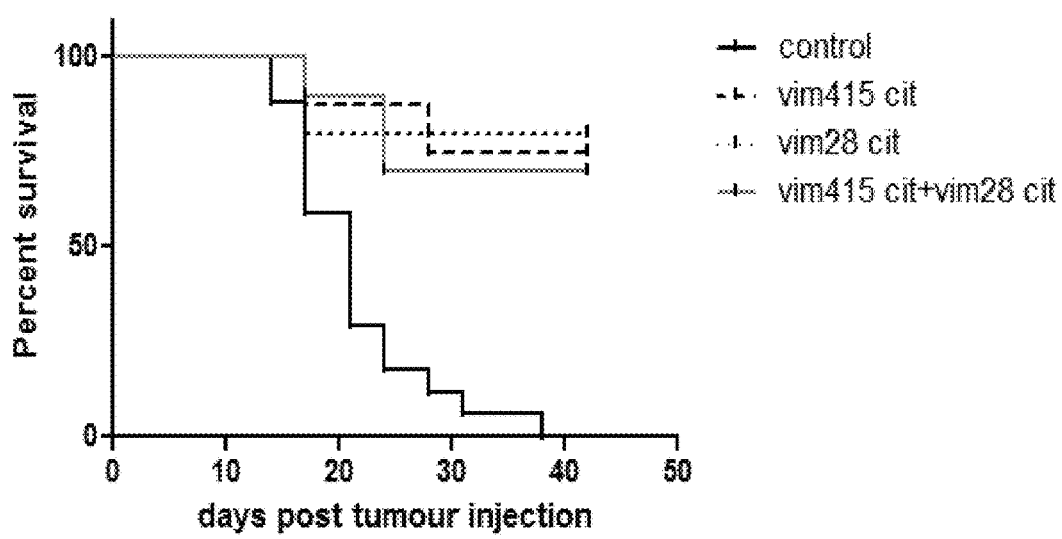
(d)
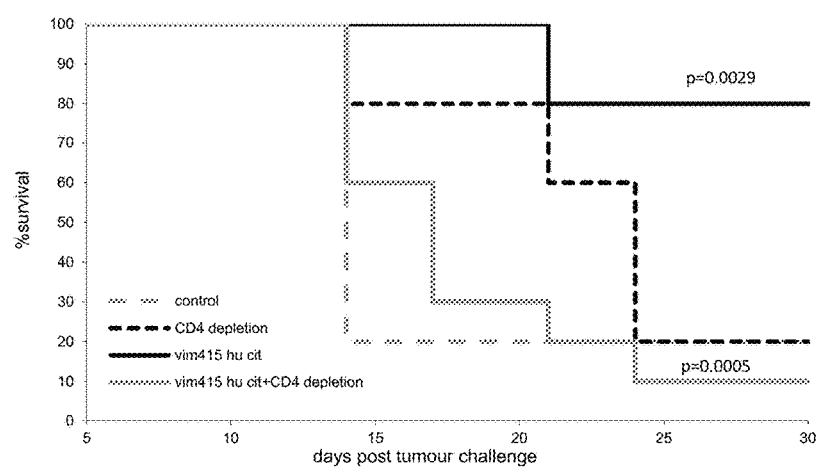

FIG 24 contd
(e)
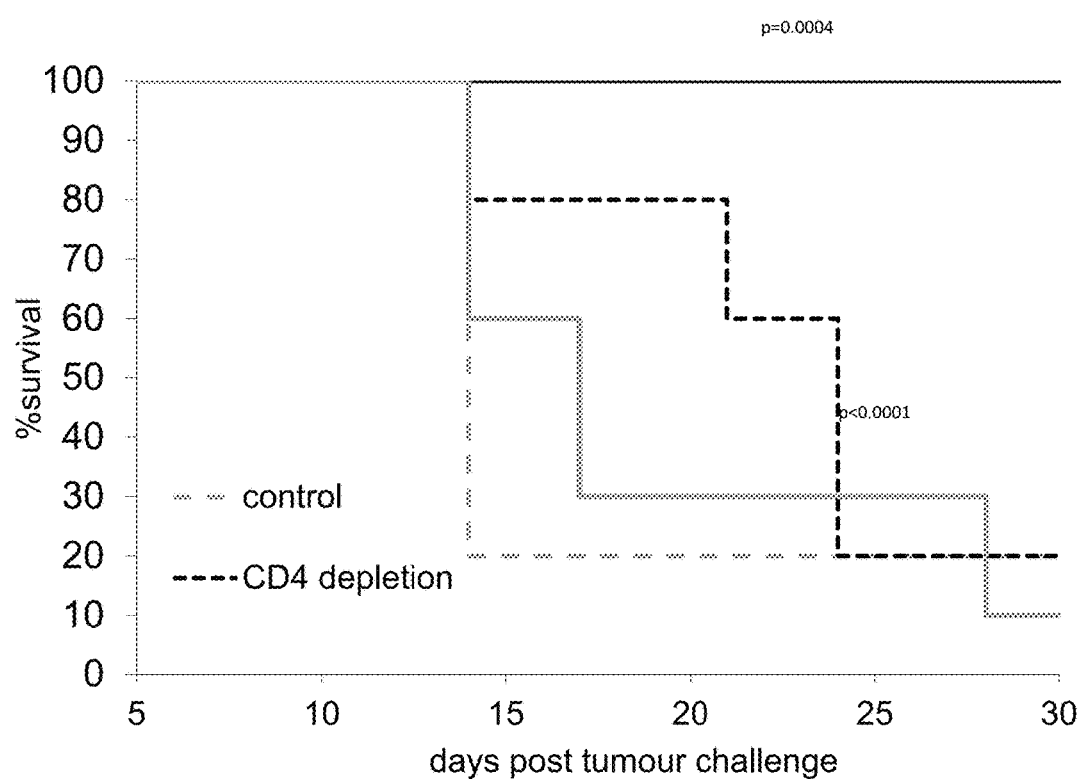

FIG 25
a)
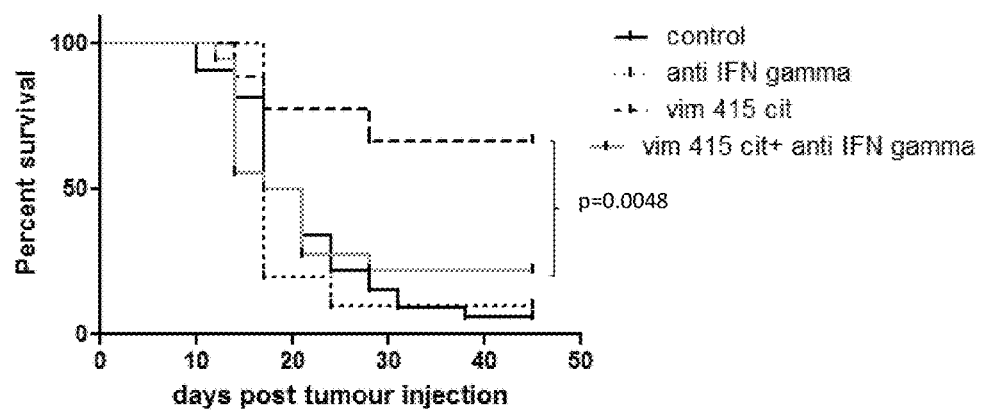
b)
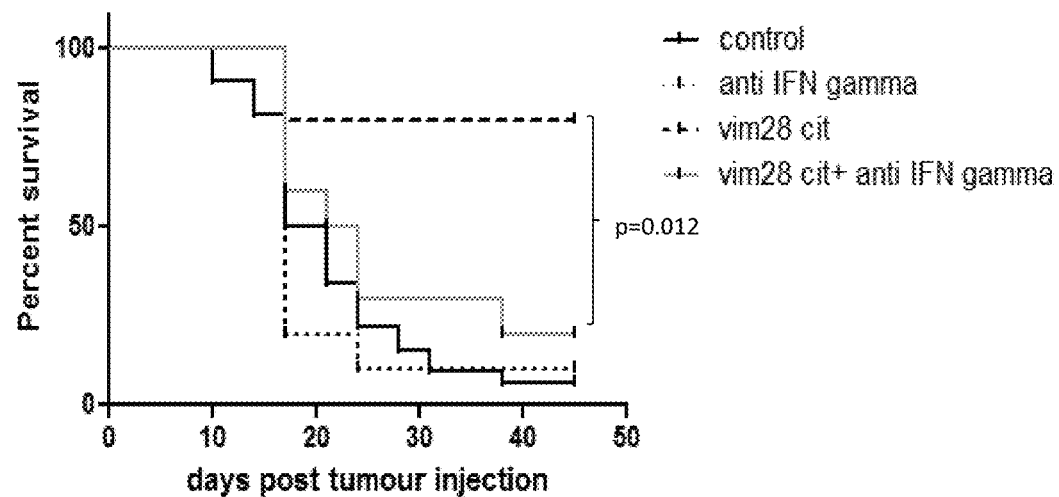

FIG 25 contd
c)
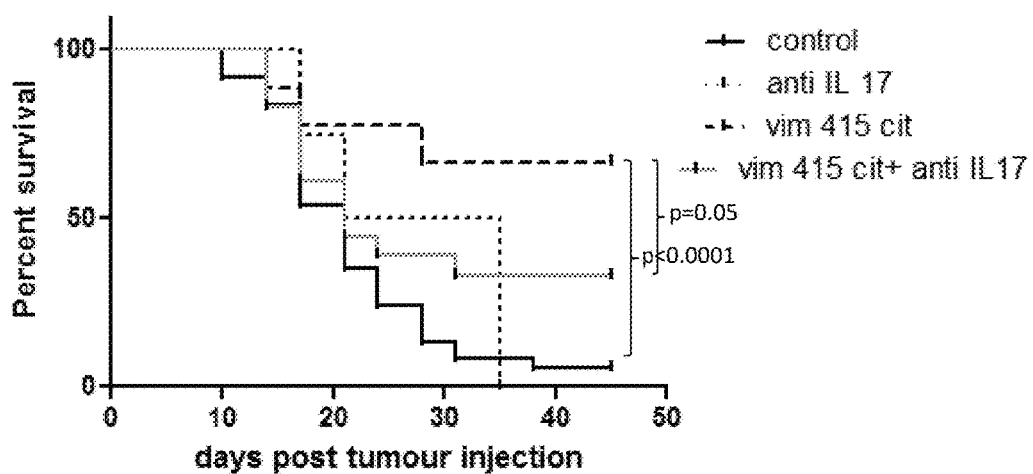
d)
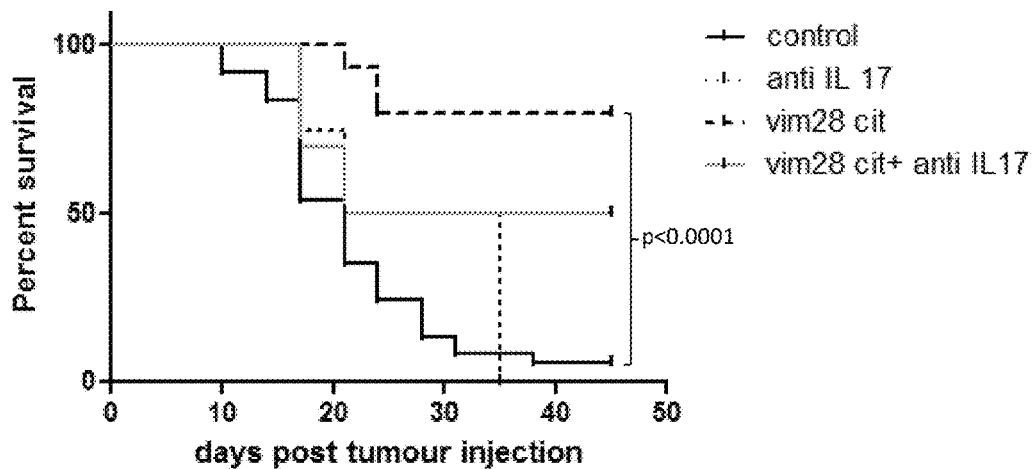

FIG 26
a)
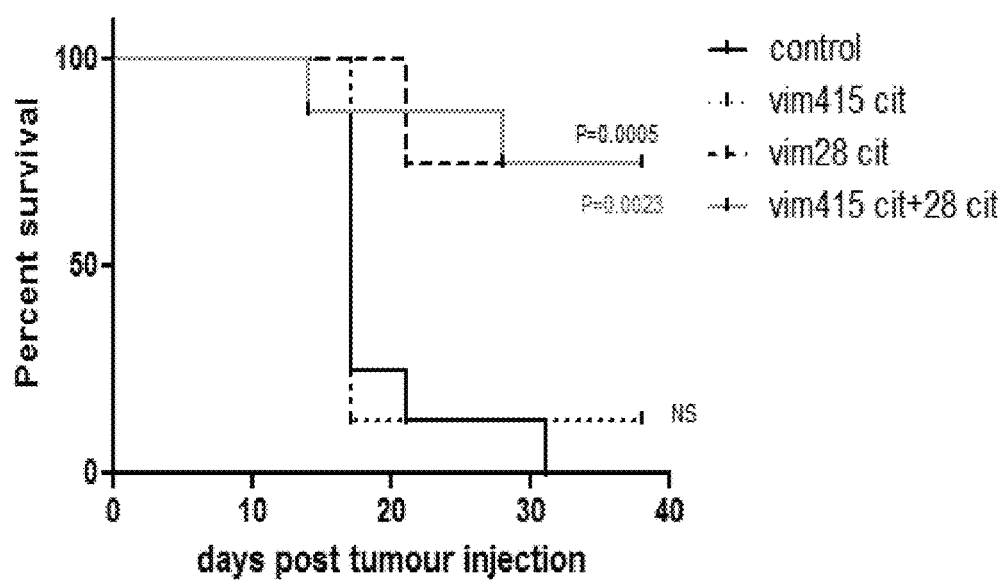
b)
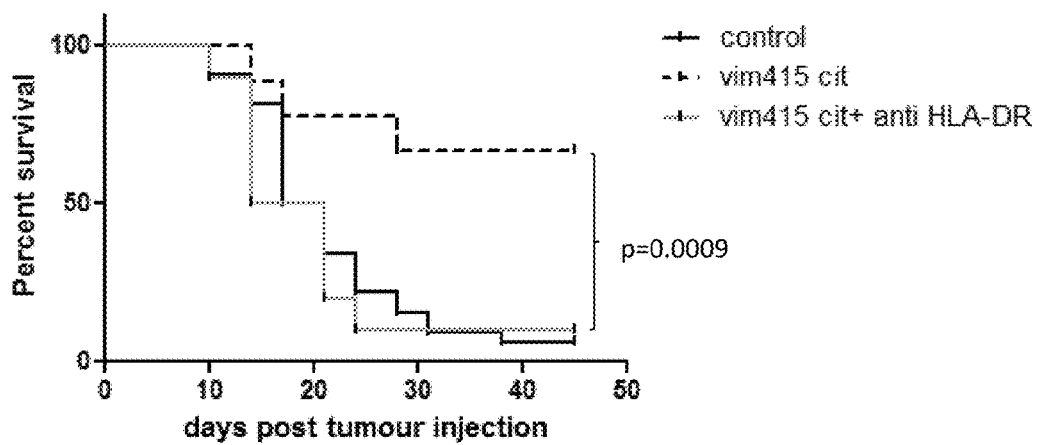

FIG 27

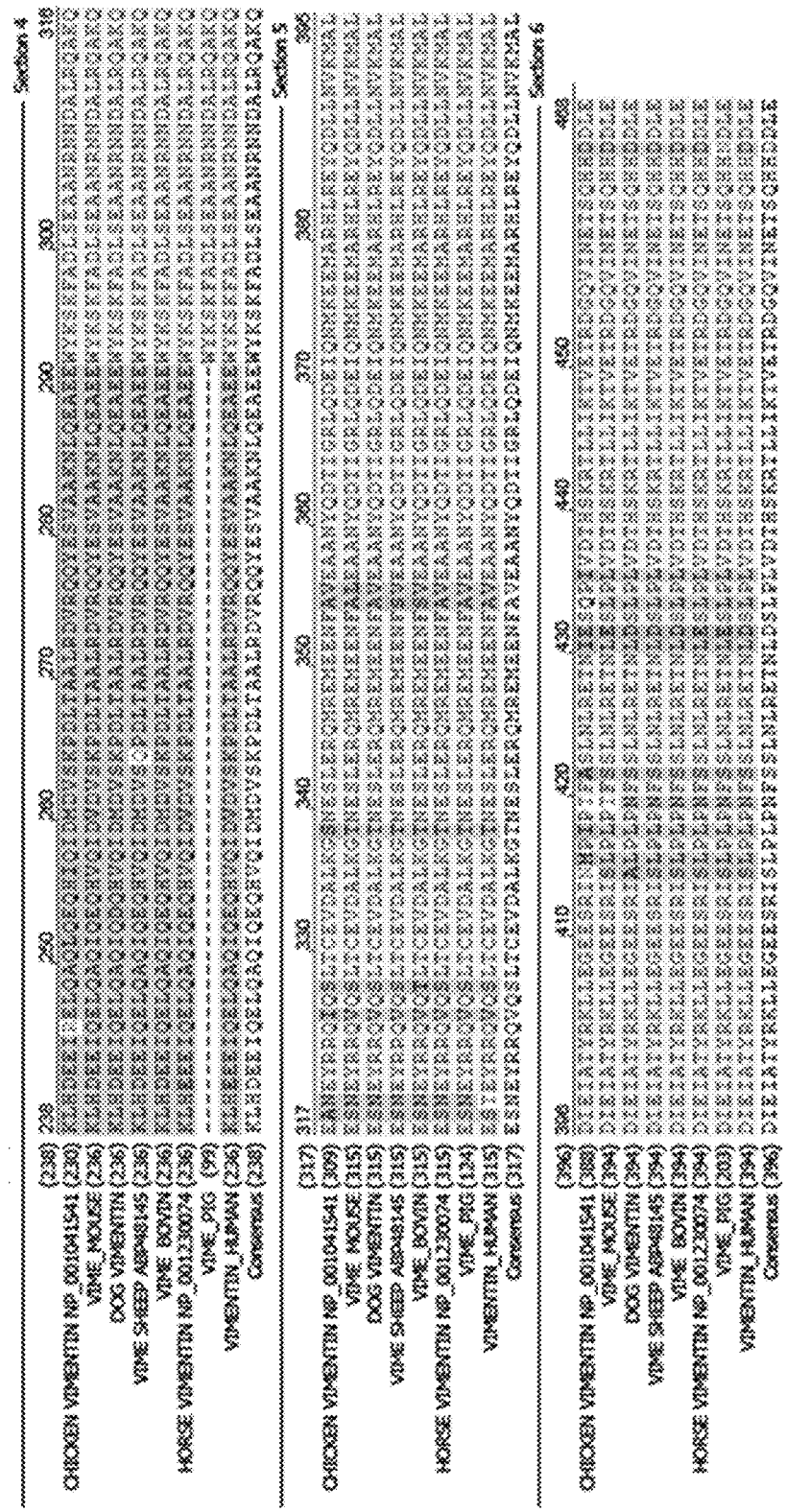
FIG 27 contd

FIG 28
Vimentin
a) HLA-DR1
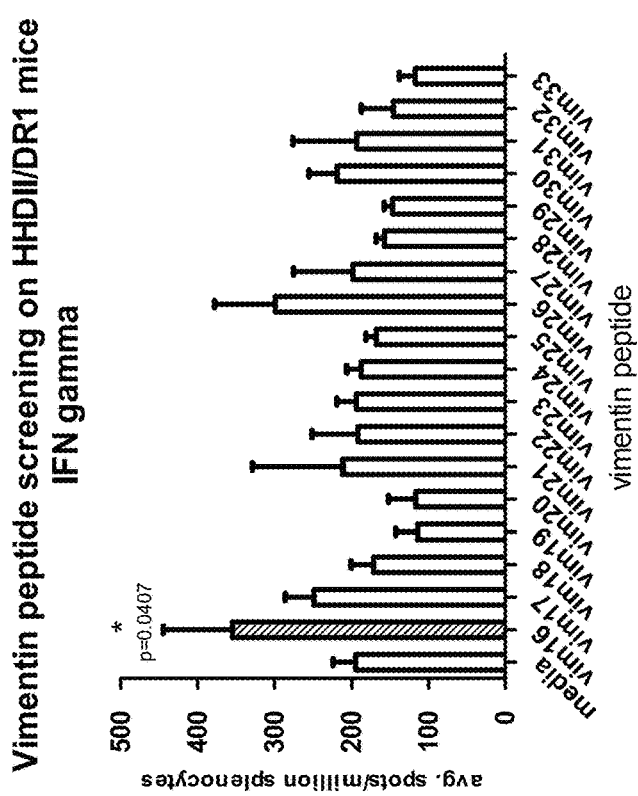
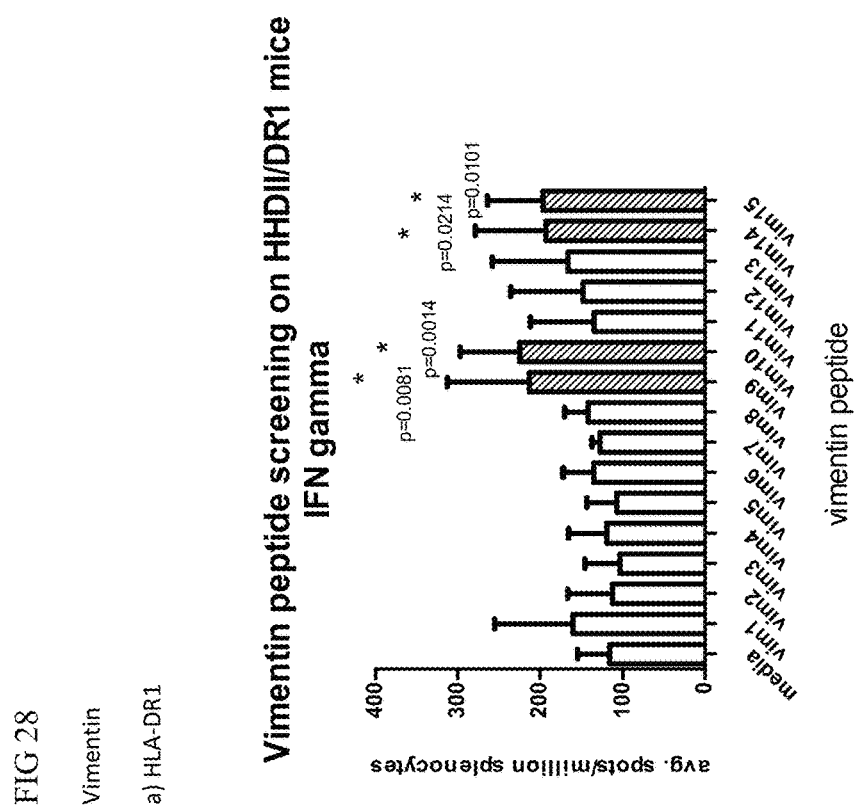

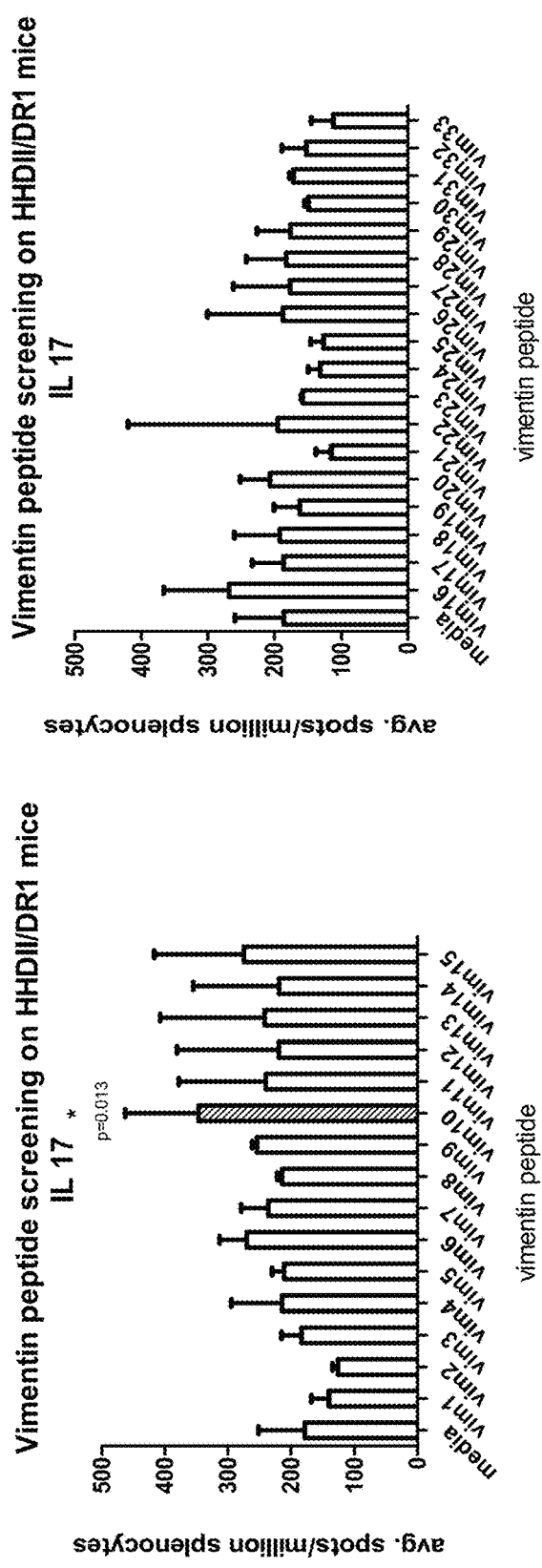
FIG 28 contd

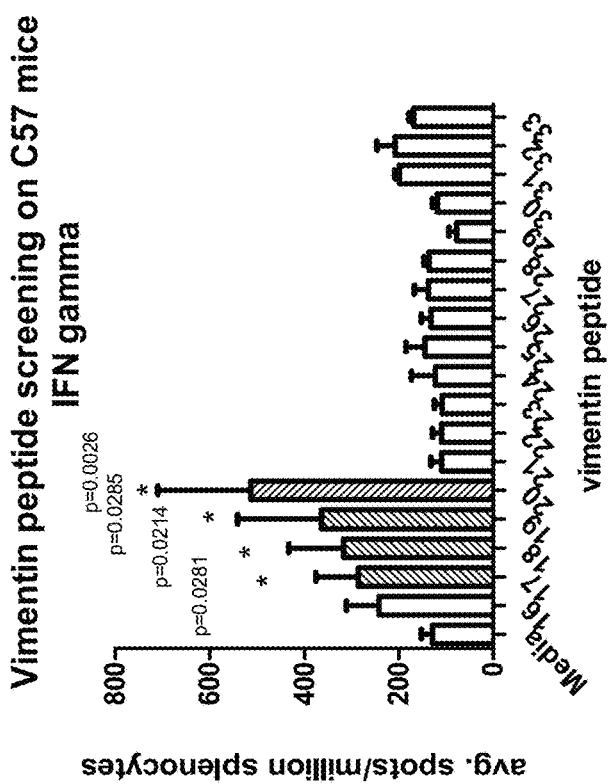
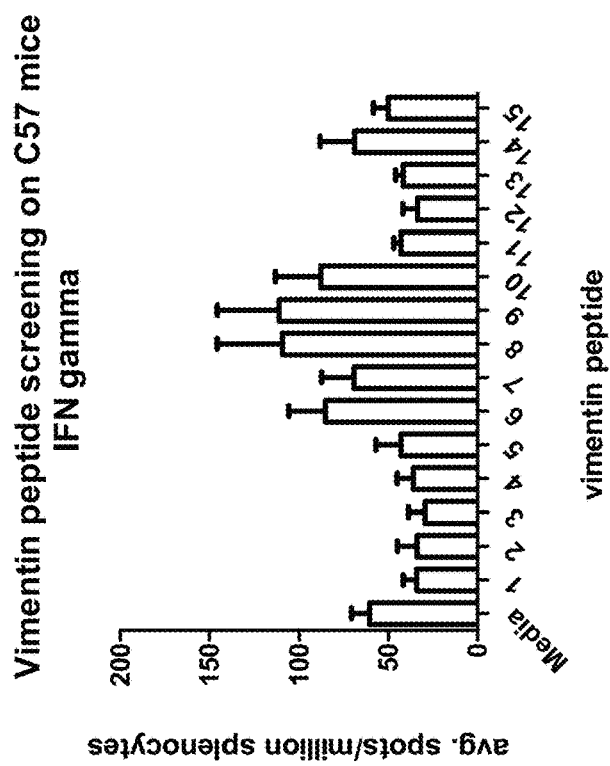
FIG 28 contd
b) C57Bl

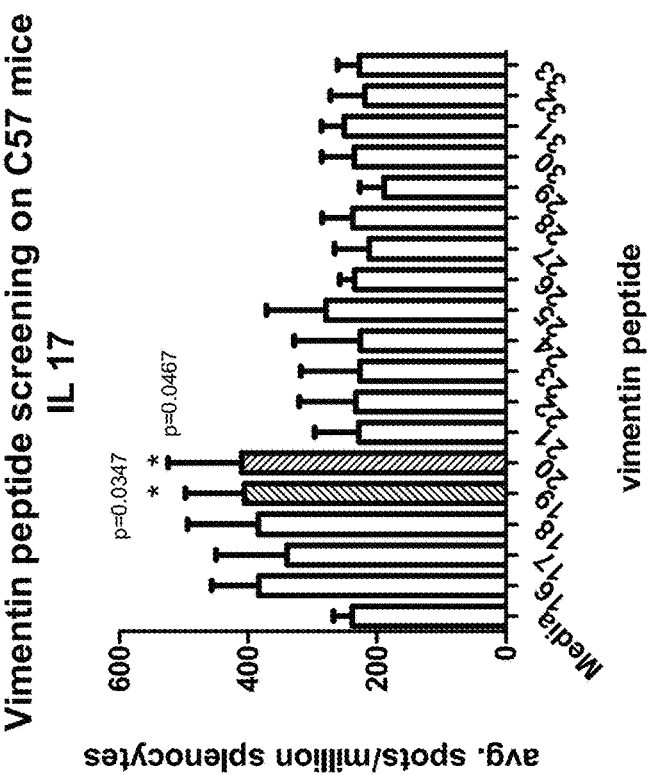
FIG 28 contd

FIG 28 contd
c)
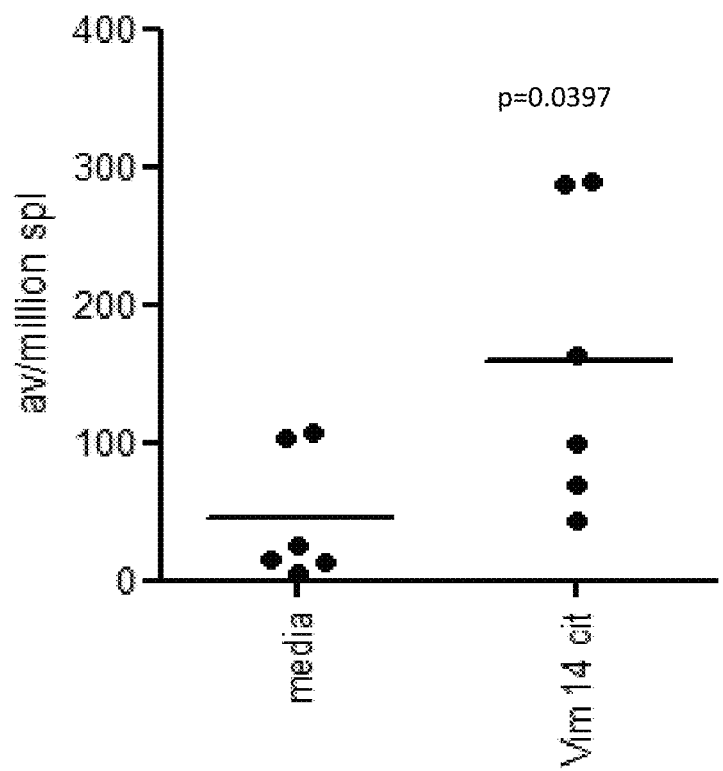

a) HLA-DR1 mice.

Figure 29:
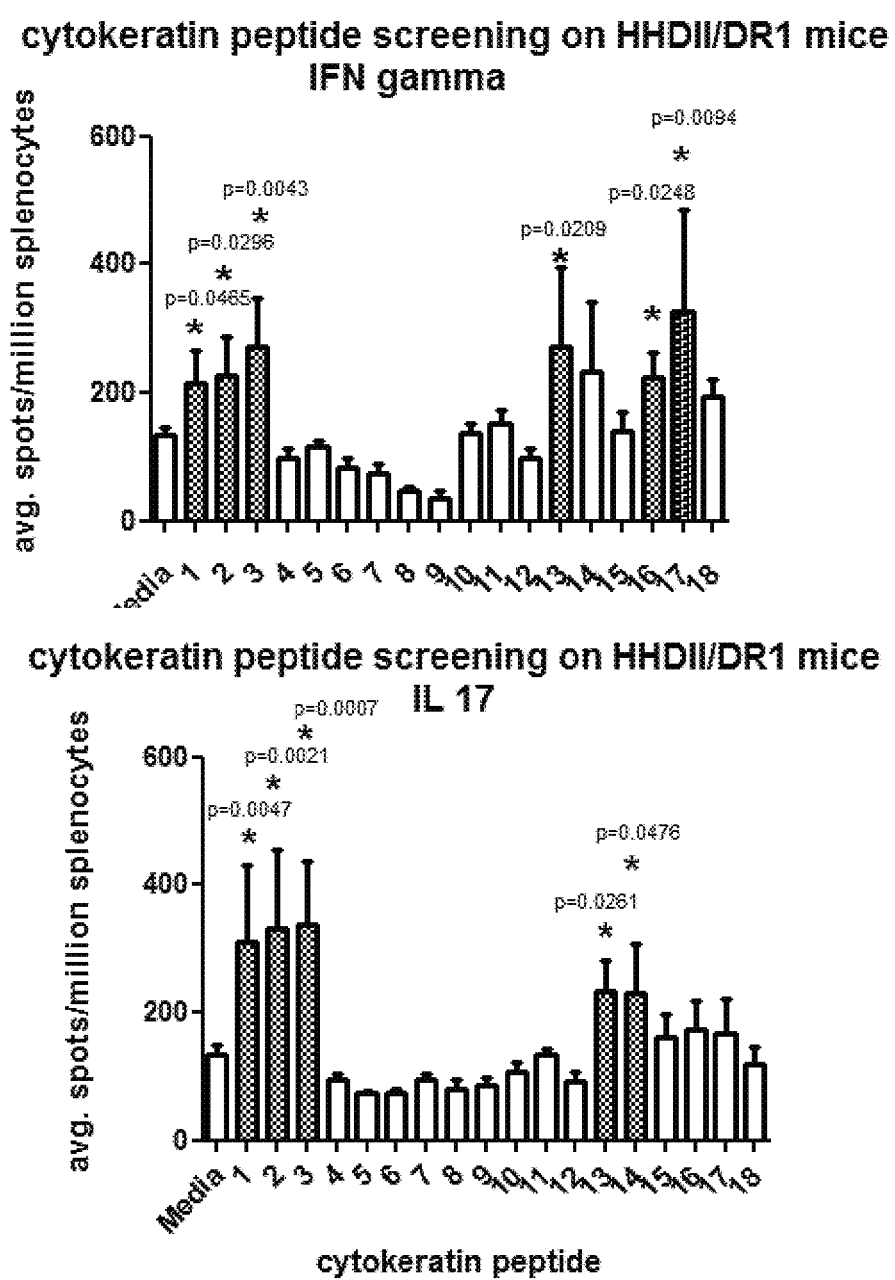

FIG 29 contd
b) C57Bl mice
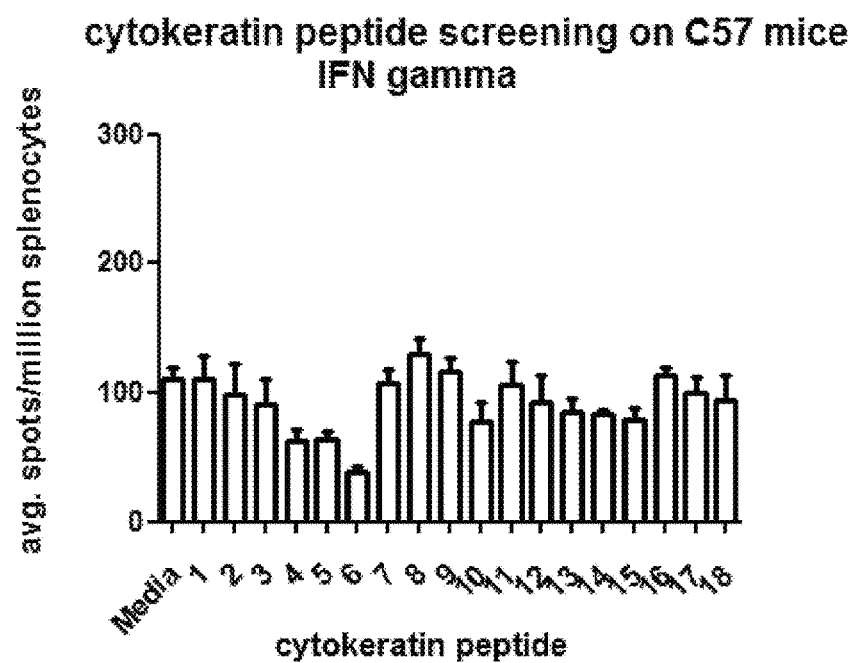
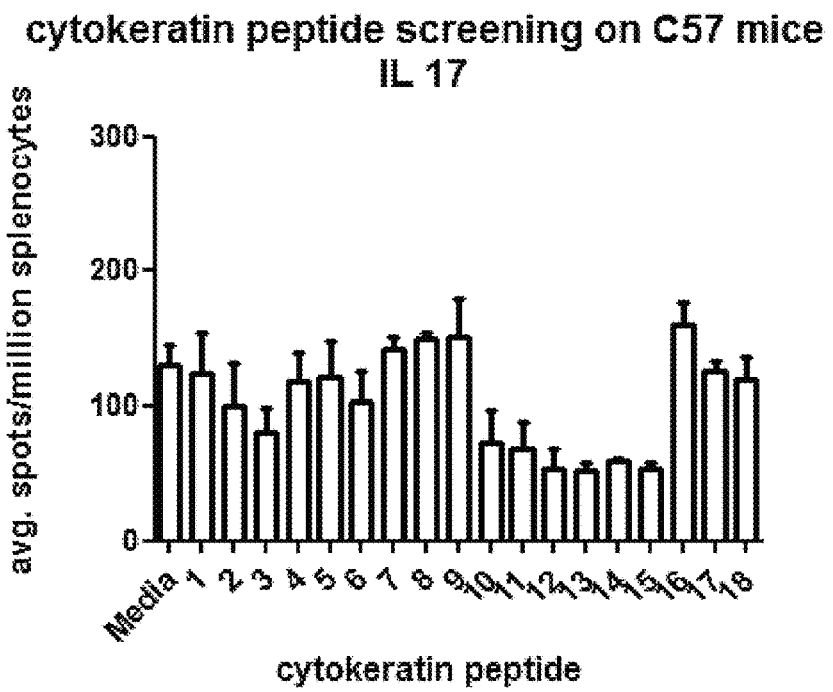

a)

FIG 32

|  | Uniprot accession number |
|---|---|
| NYESO-1 | P78358 |
| MMP7 | P09237 |
| Cytokeratin 18 | P05783 |
| Cytokeratin 8 | P05787 |
| Cytokeratin 19 | P08727 |
| Cartilage intermediate layer protein (CILP) 1<br><br>2 | O75339<br>Q8IUL8 |
| ING4 | Q9UNL4 |
| P53 | P04637 |
| PAD4 | Q9UM07 |
| Vimentin | P08670 |
| Adolase  B<br>        C<br>        A | P05062<br>P09972<br>P04075 |
| PGK1 | P00558 |
| BiP | P11021 |
| Calreticulin | P27797 |
| HSP90α | P07900 |
| HSP80β | P08238 |
| Hsp60 | P10809 |
| GSK3β | P49841 |
| Far upstream element binding protein 1<br><br>3 | Q96AE4<br>Q96I24 |
| Asporin | Q9BXN1 |
| Cathepsin D | P07339 |
| Human Beta actin | P60709 |
| Albumin | P02768 |
| G Histamine H3 receptor | Q9Y5N1 |

FIG 32   contd

|  | Uniprot accession number |
|---|---|
| H1 | P35367 |
| H2 | P25021 |
| ALDH2 | P05091 |
| Protein disulphide isomerase ER60 precursor (PDIA3) | P30101 |
| F- actin capping protein alpha 1 subunit | P52907 |
| Heparin binding protein | P20160 |
| Nucleophosmin B23 | P06748 |
| P300 coactivator? | Q09472 |
| Aggrecan | P16112 |
| Glucose related protein | Q9Y4L1 |
| CXCL-12 | P48061 |
| CXCL-8 | P10145 |
| CXCL-10 | P02778 |
| alpha-enolase | P06733 |
| myelin basic protein | P02686 |
| Antithrombin | P01008 |
| Elongation factor 1alpha | P68104 |
| Adenylcyclase associated protein | Q01518 |
| Histone H1- H1.0 | P07305 |
| Histone H1- H1.1 | Q02539 |
| Histone H1- H1.2 | P16403 |
| Histone H1- H1.3 | P16402 |
| Histone H1- H1.4 | P10412 |
| Histone H1- H1.5 | P16401 |
| Histone H1-H1t | P22492 |
| Histone H1- H1FNT | Q75WM6 |
| Histone H1-H1oo | Q8IZA3 |
| Histone H1-H1x | Q92522 |
| Histone H2A- type 1 | P0C0S8 |
| Histone H2A -type 3 | Q7L7L0 |
| Histone H2A- type 2-A | Q6FI13 |

FIG 32 contd

|  | Uniprot accession number |
|---|---|
| Histone H2A- type 2-B | Q8IUE6 |
| Histone H2A -type 2-C | Q16777 |
| Histone H2B -type 1-A | Q96A08 |
| Histone H2B -type 1-B | P33778 |
| Histone H2B -type 1-C/E/F/G/I | P62807 |
| Histone H2B -type 1-H | Q93079 |
| Histone H2B -type 1-M | Q99879 |
| Histone H2B -type 1-L | Q99880 |
| Histone H2B -type 1-N | Q99877 |
| Histone H2B -type 1-O | P23527 |
| Histone H2B -type 1-J | P06899 |
| Histone H2B -type 1-D | P58876 |
| Histone H2B -type 1-K | O60814 |
| Putative histone H2B type 2-C | Q6DN03 |
| Putative histone H2B type 2-D | Q6DRA6 |
| Histone H2B -type 2-E | Q16778 |
| Histone H2B -type 2-F | Q5QNW6 |
| Histone H2B type 3-B | Q8N257 |
| Histone H2B type F-S | P57053 |
| Histone H2B type F-M | P0C1H6 |
| Histone H2B type W-T | Q7Z2G1 |
| Histone H3-H3.1 | P68431 |
| Histone H3-H3.2 | Q71DI3 |
| Histone H3-H3.3 | P84243 |
| Histone H4 | P62805 |

Figure 33:
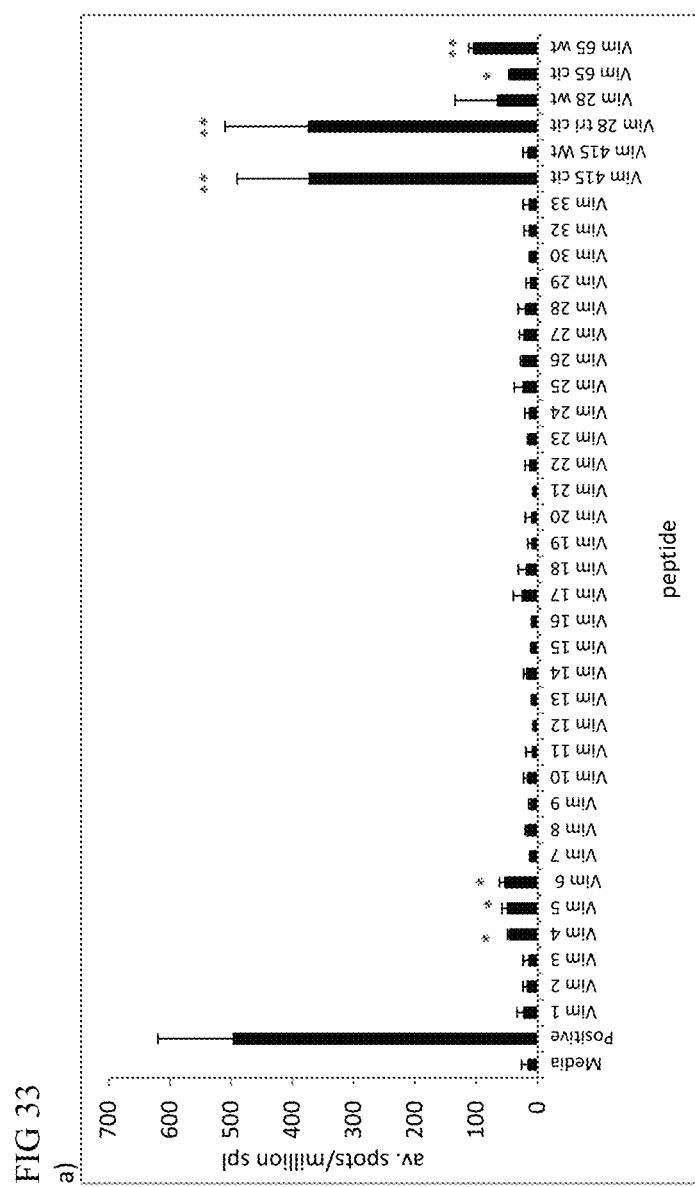

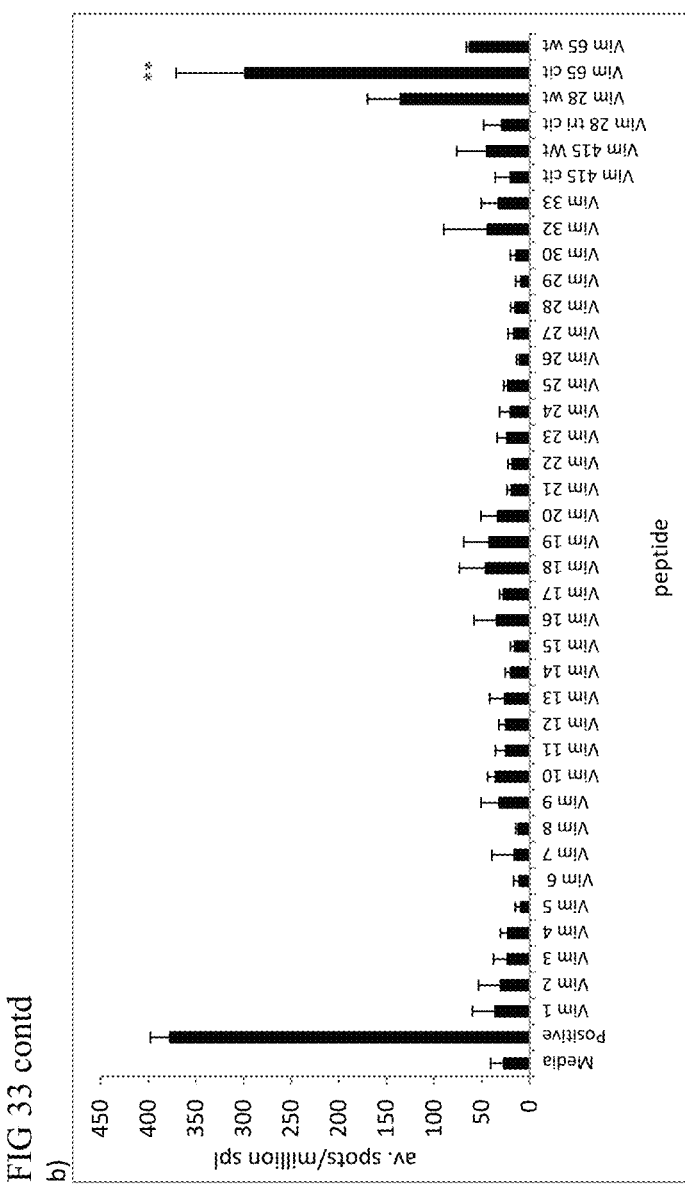
FIG 33 contd
*p<0.05,  p<0.005, * p<0.0001

ANTI-TUMOUR RESPONSE TO MODIFIED SELF-EPITOPES

RELATED APPLICATIONS

This application is a continuation of International Application No. PCT/GB2013/052109, which designated the United States and was filed on Aug. 7, 2013, published in English.

This application claims priority under 35 U.S.C. § 119 or 365 to Great Britain, Application No. 1214007.5, filed Aug. 7, 2012. The entire teachings of the above applications are incorporated herein by reference.

The present invention relates generally to modified peptides that can be used as targets for cancer immunotherapy. These modified peptides can be used as vaccines or as targets for monoclonal antibody (mAb) therapy. Such vaccines or mAbs may be used in the treatment of cancer.

The focus of anti-tumour immune responses has largely been directed at the generation of tumour-specific CD8 responses due, in part, to lack of MHC class II expression by most solid tumours. These tumours therefore constitute better targets for CD8 T cells than CD4 T cells. However, therapies involving CD8 T cells have elicited only modest and short-lived responses in patients. It has been known for many years that CD4 helper cells play a pivotal role in the induction of epitope-specific immune responses, whether antibody or CD8 mediated. It has been reported that memory CD8 responses are impaired if induced in the absence of CD4 help [1, 2]. This was initially believed to be due to their secretion of IL-2 [3] but is more recently believed to also be due to modification/activation of dendritic cells (DCs) which in turn activate CD8 cells [4-7]. In most cases, this help is provided by foreign CD4 epitopes originating from pathogens or inserted in vaccines. However, tumour-specific CD4 responses are also required at the tumour site to enhance inflammation, resulting in enhanced recruitment and retention of CD8 cells, NK cells and other inflammatory mediators of anti-tumour immunity [8-11]. The involvement of CD4 helper T cells in cancer immunity is further construed from studies using CD4 or MHC class II deficient mice where tumour progression ensues, indicating the importance of CD4 T cells in the eradication of tumours. More recent reports in the literature suggest the importance of tumour-reactive CD4 T cells which play a direct role in tumour eradication as well as the superior action of tumour specific Th17 cells at mediating tumour destruction in vivo [12-15]. High frequency and avidity CD4 responses to tumour-specific epitopes can be generated if the repertoire is not subject to tolerance [16-18]. When the repertoire is subject to self-tolerance the induction of epitope specific CD4 responses is much more limited and resulting responses are of lower frequency and avidity.

There are several types of tumour epitope that can be targeted within tumours. These include tumour-specific epitopes and tumour-associated epitopes. The former arise due to mutations or duplications or deletions of larger segments of DNA which are acquired during the generation and pathogenesis of the tumour. The point mutations are difficult to target by the immune system as they must create new epitopes either because they create new anchor residues which can binding to MHC or new amino acids which interacting more strongly with T or B cell receptors (TCR or BCRs). Even if mutations do generate new epitopes, they are frequently only recognised by a small portion of individuals with the appropriate MHC haplotype. Gene duplications and deletions are difficult to target as they are usually unique to individual cancers. In contrast, tumour-associated epitopes are over-expressed normal epitopes. Such normal epitopes are usually expressed within the thymus either directly or via AIRE enzyme, and T cells recognising these epitopes with high affinity are deleted or differentiated into natural T regulatory cells. Although CD8 responses to tumour-associated epitopes have been reported, there are very few CD4 responses to tumour-associated epitopes, suggesting that the repertoire to these epitopes is more heavily regulated for CD4 cells than CD8 cells. The only reported CD4 responses are to cancer testes antigens that are expressed during embryogenesis but only remain active in the gametes in adults and may not be subjected to thymic tolerance, although recent evidence is that AIRE can also present these epitopes in the thymus. The challenge is therefore to find a repertoire of T cells that can recognise self-epitopes and attack tumours.

The inventors have unexpectedly found that certain modifications to T or B cell epitopes result in the epitopes raising a stronger immune response compared to unmodified epitopes. Surprisingly, the inventors have found that certain modified epitopes are associated with tumours and consequently can be used to raise an immune response against such tumours.

According to a first aspect of the invention, there is provided a tumour-associated epitope which stimulates an immune reaction against the tumour for use in medicine, the epitope having a modification selected from deimination of arginine, nitration of tyrosine, oxidation of tryptophan and deamination of glutamine or asparagine.

The invention also provides a tumour-associated epitope which stimulates an immune reaction against the tumour, and/or a nucleic acid comprising a sequence that encodes such an epitope, for use in a method for treating cancer, the epitope having a modification selected from deimination of arginine, nitration of tyrosine, oxidation of tryptophan and deamination of glutamine or asparagine such an epitope, as well as the use of such an epitope and/or nucleic acid in the manufacture of a medicament for the treatment of cancer. The invention also provides a method of treating cancer, comprising administering an epitope or nucleic acid of the invention to a subject in need of such treatment.

The epitope may be a T or B cell epitope. Epitopes in accordance with the present invention may be used alone or in combination. In addition, they may be used in combination with other therapeutic agents, such as anti-cancer agents including but not limited to checkpoint blockade drugs such as ipilimumab.

A preferred modification is deimination of arginine to form citrulline. Free arginine can be converted to free citrulline by nitric oxide synthetase in eukaryotes or by arginine deiminase in bacteria. Citrulline is a modified amino acid but, as it has no tRNA, it cannot be incorporated directly into proteins and results from post-translational modification of arginine by the action of peptidylarginine deiminase (PAD), a family of enzymes found in a variety of tissues. The term "citrullination" or "deimination" refers to modification of arginine to citrulline, which may be a post-translational modification by the enzyme PAD within a peptide sequence. This is shown in more detail in FIG. 1 of the accompanying drawings. In the reaction from arginine to citrulline, one of the terminal nitrogen atoms of the arginine side chain is replaced by an oxygen. The reaction uses one $H_2O$ molecule and yields ammonia as a side-product. This conversion of arginine into citrulline can have important consequences for the structure and function of proteins, since arginine is positively charged at neutral pH, whereas citrulline is uncharged. With the increased hydrophobicity of a protein, there can be changes in protein folding. There are five PAD enzymes, namely PAD1, 2, 3, 4 and 6. Although they are highly homologous with 5-60% sequence identity at the amino acid level, they have different locations (PAD1— epidermis and uterus; PAD2—brain, female reproductive tract, skeletal muscle and haematopoietic cells; PAD3—hair follicle and epithelium; PAD 4—hematopoietic cells, lung, oesophagus, breast and ovary carcinomas; PAD 6—oocytes and pre-implantation embryos [19]. Although there is some overlap with respect to target proteins, each family member also appears to target a unique set of cellular proteins. This is determined by the surface exposure and clustering of arginines which make them good targets and preferred amino acid flanking sequences. For PAD4, small non polar amino acids are preferred in positions −2 and +2 and prolines flanking the arginine prevent citrullination [20, 21]. Thus not all arginines within a protein are citrullinated and not all are presented on MHC antigens for T cell recognition.

Citrullinated epitopes derived from BiP, NY-ESO-1, MMP7, cytokeratins, MUC1, CEA.CAM5, CD59, bcl2, β-catenin, CXCL8, CXCL10, CXC112, α enolase, myelin basic protein, histone, nucleophosmin, B23, co-activator complex, anti-thrombin, aggregan, elongation factor 1α, adenylcyclase associated protein (CAP1), glucose regulated protein, ALDH2, cartilage intermediate layer protein (CLIP), aldolase, phosphoglycerate kinase 1 (PGK1), calreticulin, HSP60, HSP90, far upstream element-binding proteins 1 and 2 (FUSE-BPs), asporin, cathepsin D, heparin binding protein, β-actin, F-actin, capping protein α-1 subunit (CapZα-1), albumin, ghistamine receptor, protein disulphide-isomerase ER60 precursor, mitochondrial aldehyde dehydrogenase (ALDH2) and glycogen synthase kinase-3β (GSK3β) can be used to stimulate anti-cancer immunity in accordance with the present invention. The Uniprot references for these proteins are set out in FIG. 32 of the accompanying drawings.

Antibodies to a variety of citrullinated proteins, including filaggrin, collagen, α-enolase, fibrinogen and vimentin are found in rheumatoid arthritis (RA) patients and are used as specific markers to diagnose the disease [22-24]. More recently, a number of other citrullinated proteins including histone, nucleophosmin, B23, co-activator complex, anti-thrombin, aggregan, elongation factor 1α, adenylcyclase associated protein (CAP1), glucose regulated protein, ALDH2, cartilage intermediate layer protein (CLIP), aldolase, phosphoglycerate kinase 1 (PGK1), calreticulin, HSP60, HSP90, BiP, far upstream element-binding proteins 1 and 2 (FUSE-BPs), asporin, cathepsin D, heparin binding protein, β-actin, F-actin, capping protein α-1 subunit (CapZα-1), albumin, histamine receptor, protein disulphide-isomerase ER60 precursor, mitochondrial aldehyde dehydrogenase (ALDH2) have been described as targets for antibodies in RA patients [49]. Moreover, it has been postulated that citrulline on its own is not sufficient for the generation of an immune response; rather the amino acids surrounding citrulline are essential in determining the antigenicity of the epitope [25-27].

In addition to citrullination, several other post-translational modifications are in accordance with the invention and have been observed within MHC bound peptides. These include nitration of tyrosine residues [28] and oxidation of tryptophan residues [29]. The activation of macrophages and dendritic cells includes production of nitric oxide and other reactive oxygen species. Exposure of proteins can lead to the nitration of tyrosines and to a lesser extent tryptophan. CD4 cells have been shown to specifically recognise these modifications in hen egg lysozyme-derived epitopes [29]. However, the role of nitrated epitopes in any disease has yet to be established. The presence of high levels of nitrotyrosines in prostatic tumour infiltrating lymphocytes suggests the local production of peroxynitrites. Inhibiting the activity of arginase and nitric oxide synthetase, key enzymes in arginine metabolism that are highly expressed in malignant but not in normal prostates, reduced tyrosine nitration and restoration of tumour infiltrating lymphocytes [30]. The deamination of glutamine or asparagine can result from ageing but a significant proportion of this modification is generated by enzymatic mechanisms. Deamination creates predominantly negatively charged side chains (glutamate or aspartate) and alters the capacity of glutamine and asparagine to form hydrogen bonds. Asparagines can be converted to aspartate by N-glycanase and therefore this modification is intimately linked to N-glycosylation. Glutamine residues can be deaminated by tissue transglutamate. The deamination of glutamine in gliadins from dietary wheat glutens is a central to coeliac disease, an autoimmune disorder associated with gluten intolerance in genetically predisposed individuals. The HLA haplotypes, DQ2 and DQ8 have strong affinity for deaminated gliadin peptides and stimulate T cell responses against the gastrointestinal lining [31].

The epitope of the present invention may comprise, consist essentially of or consist of a sequence selected from:

```
                                           (SEQ ID NO: 1)
IQKLYGKRS, preferably (SEQ ID NO: 2)
SQDDIKGIQKLYGKRS (MMP7-247), (SEQ ID NO: 3)
NILTIRLTAA, preferably (SEQ ID NO: 4)
PGVLLKEFTVSGNILTIRLTAADHR (NYESO-1-119), (SEQ ID NO: 5)
ILTIRLTAA, preferably (SEQ ID NO: 4)
PGVLLKEFTVSGNILTIRLTAADHR (NYESO-1-119), (SEQ ID NO: 6)
EIRELQSQ, preferably (SEQ ID NO: 7)
EEEIRELQSQISDTSVVLS (cytokeratin 8 229-247), (SEQ ID NO: 8)
AKQDMARQLREYQEL, preferably (SEQ ID NO: 9)
AKQDMARQLREYQELMNVKL (cytokeratin 8: 363-382), (SEQ ID NO: 10)
AKQDMARQ, preferably (SEQ ID NO: 11)
LQRAKQDMARQLREYQELM (cytokeratin 8: 360-378), (SEQ ID NO: 12)
ISSSSFSRV, preferably (SEQ ID NO: 13)
PGSRISSSSFSRVGSS (cytokeratin 8: 29-44), (SEQ ID NO: 14)
PRAFSSRS, preferably (SEQ ID NO: 15)
STSGPRAFSSRSYTSGPG (cytokeratin 8: 13-30),
```

-continued

EAALQRAKQ, preferably (SEQ ID NO: 16)

ELE<u>AALQRAKQ</u>DMARQL (cytokeratin 8: 355-371), (SEQ ID NO: 17)

LEVDPNIQAVRTQE, preferably (SEQ ID NO: 18)

<u>LEVDPNIQAVRTQE</u>KEQI (cytokeratin 8: 78-95), and (SEQ ID NO: 19)

QKKLKLVRT, preferably (SEQ ID NO: 20)

A<u>QKKLKLVRT</u>SPEYGMP (ING 4158-174) (SEQ ID NO: 21)

LKLVRTSPE, preferably (SEQ ID NO: 22)

AQK<u>LKLVRTSPE</u>YGMP (ING 4158-174) (SEQ ID NO: 21)

KKLKLVRTS, preferably (SEQ ID NO: 23)

A<u>QKKLKLVRTS</u>PEYGMP (ING 4158-174) (SEQ ID NO: 21)

YMSSARSLS, (SEQ ID NO: 24)

MSSARSLSS or (SEQ ID NO: 25)

TEYMSSARS, preferably (SEQ ID NO: 26)

KLA<u>TEYMSSARS</u>LSSEEK (ING4 44-58) (SEQ ID NO: 27)

FDLFENRKK, preferably (SEQ ID NO: 28)

RAP<u>FDLFENRKK</u>KNN (HSP90-346-360) (SEQ ID NO: 29)

YLNFIRGVV or (SEQ ID NO: 30)

FIRGVVDSE, preferably (SEQ ID NO: 31)

IPEY<u>LNFIRGVVDSE</u> (HSP90-378-392), (SEQ ID NO: 32)

LRYYTSASG, (SEQ ID NO: 33)

LLRYYTSAS or (SEQ ID NO: 34)

LSELLRYYT, preferably (SEQ ID NO: 35)

RKK<u>LSELLRYYTSASG</u>DEMVSL (HSP90-456-477) (SEQ ID NO: 36)

RRRLSELLRYHTSQS (HSP90 beta 456-460), (SEQ ID NO: 37)

VGVFKNGRV or (SEQ ID NO: 38)

FKNGRVEII, preferably (SEQ ID NO: 39)

YSCV<u>GVFKNGRVEII</u> (BiP39-53), (SEQ ID NO: 40)

YFNDAQRQA, preferably (SEQ ID NO: 41)

VPA<u>YFNDAQRQA</u>TKDA (BiP172-186), (SEQ ID NO: 42)

VTFEIDVNG, preferably (SEQ ID NO: 43)

E<u>VTFEIDVNG</u>ILRVT (BiP 497-511), (SEQ ID NO: 44)

ITNDQNRLT, preferably (SEQ ID NO: 45)

KITI<u>TNDQNRLT</u>PEE (BiP 522-536), (SEQ ID NO: 46)

LQIVARLKN or (SEQ ID NO: 47)

VARLKNNNR, preferably (SEQ ID NO: 48)

NCA<u>LQIVARLKNNNR</u> (CXCL12-54-68) (SEQ ID NO: 49)

VEIIATMKK or (SEQ ID NO: 50)

RVEIIATMK, preferably (SEQ ID NO: 51)

CP<u>RVEIIATMK</u>KKGE (CXCL10 57-71), (SEQ ID NO: 52)

wherein one or more of the R residues is substituted for citrulline. In NYESO-1-119, it is preferred if the first R residue (at position 136) is substituted for citrulline. In cytokeratin 8: 360-378, it is preferred if the second R residue (at position 369) is substituted for citrulline. In cytokeratin 8: 29-44, it is preferred if the second R residue (at position 40) is substituted for citrulline. In HSP90, BiP, ING4, CXCL10 and CXCL12 it preferred if all R residues within the sequences are substituted for citrulline. The invention also provides these epitopes as further aspects. In particular, the invention provides a peptide comprising, consisting essentially of or consisting of the amino acid sequence YVTTSTcitTYSLGSALcit (SEQ ID NO: 53), optionally comprising, consisting essentially of or consisting of the amino acid s the sequence citS <u>YVTTSTcitTYSLGSALcitPSTS</u> (SEQ ID NO: 54) (vim28-49), wherein cit represents citrulline.

A preferred epitope of the present invention is derived from vimentin and is citrullinated. The inventors have unexpectedly found that citrullinated epitopes derived from vimentin can be used to raise an immune response against tumours including, but not restricted to, melanoma, breast, endometrial, colorectal and ovarian tumours.

A preferred epitope from vimentin comprises, consists essentially of or consists of YVTTSTRTYSLGSALR (SEQ ID NO: 55) (vimentin 30-45), which optionally can be citrullinated. Either or both arginines may be citrullinated. The epitope may comprise, consist essentially of or consist of <u>RSYVTTSTRTYSLGSALRPSTS</u> (SEQ ID NO: 56) (vimentin 28-49), which optionally can be citrullinated. Any one or two, or all, of the three arginines present may be citrullinated. It is preferred that all three R residues are citrullinated. The second R residue (at position 36) may be substituted for citrulline.

Alternative epitopes from vimentin comprise, consist essentially of or consist of at least one of the following sequences:

```
                                      (SEQ ID NO: 57)
VRLRSSVPG
or
                                      (SEQ ID NO: 58)
RLRSSVPGV, preferably (SEQ ID NO: 59)
SAVRLRSSVPGVR (vim65-77),
and
                                      (SEQ ID NO: 60)
FSSLNLRET, preferably (SEQ ID NO: 61)
LPNFSSLNLRETNLDSLPL (vim415-433),
``` wherein one or more of the R residues is substituted for citrulline. In vim65-77, it is preferred if the second R residue (at position 70) is substituted for citrulline.

Further alternative epitopes from vimentin comprise, consist essentially of or consist of at least one of the following sequences:

```
                                      (SEQ ID NO: 62)
RSSVPGVRL, (SEQ ID NO: 63)
SAVRLRSSV, (SEQ ID NO: 64)
ATRSSAVRL, (SEQ ID NO: 65)
YATRSSAVRLRSSVPGVRL (vim 61-79), (SEQ ID NO: 66)
RSSVPGVRL, (SEQ ID NO: 67)
GVRLLQDSV, (SEQ ID NO: 68)
RLRSSVPGVRLLQDSVDFS (vim 69-87), (SEQ ID NO: 69)
QLKGQGKSR, (SEQ ID NO: 70)
KSRLGDLYE, (SEQ ID NO: 71)
EQLKGQGKSRLGDLYEEEM (vim125-154), (SEQ ID NO: 72)
ELRRQVDQL, (SEQ ID NO: 73)
EMRELRRQV, (SEQ ID NO: 74)
DLYEEEMRELRRQVDQLTN (vim 148-166), (SEQ ID NO: 75)
QLTNDKARV, (SEQ ID NO: 76)
VEVERDNLA, (SEQ ID NO: 77)
LTNDKARVE, (SEQ ID NO: 78)
VDQLTNDKARVEVERDNLA (vim 161-179), (SEQ ID NO: 79)
EVERDNLAE, (SEQ ID NO: 80)
NDKARVEVERDNLAEDIMR (vim 166-184), (SEQ ID NO: 81)
IMRLREKLQ, (SEQ ID NO: 82)
DNLAEDIMRLREKLQEEML (vim 176-194), (SEQ ID NO: 83)
QREEAENTL, (SEQ ID NO: 84)
KLQEEMLQR, (SEQ ID NO: 85)
EKLQEEMLQREEAENTLQS (vim 187-205),
and/or (SEQ ID NO: 86)
FRQDVDNAS, (SEQ ID NO: 87)
ENTLQSFRQ, (SEQ ID NO: 88)
EAENTLQSFRQDVDNASLA (vim 198-216),
``` wherein one or more of the R residues may be substituted for citrulline. In the above, preferred R residues for substitution to citrulline are underlined. The core sequence(s) is/are shown prior to the epitope.

In one aspect, the present invention provides an epitope comprising, consisting essentially of or consisting of the sequence YVTTSTRTYSLGSALR (SEQ ID NO: 55) and optionally comprising the sequence RSYVTTSTRTYSLGSALRPSTS (SEQ ID NO: 56) (vim28-49), and/or a nucleic acid encoding such an epitope, for use in a method of treating cancer.

In another aspect, the present invention provides an epitope comprising, consisting essentially of or consisting of the sequence FSSLNLRET (SEQ ID NO: 60), preferably LPNFSSLNLRETNLDSLPL (SEQ ID NO: 61) (vim415-433), and/or a nucleic acid encoding such an epitope, for use in a method of treating autoimmune disease. The inventors have found that this epitope stimulates an IL10 response that suppresses the overall immune response.

Unless otherwise indicated, the underlined residues in the above sequences indicate the core sequences. Amino acids outside these core sequences may be conservatively substituted for other amino acids, preferably for amino acids that have a similar size and/or charge to the native amino acid they are replacing, or may be deleted. Additionally or alternatively, 1, 2, 3, 4, 5 or all non-core amino acids may be substituted or deleted. Epitopes useful in the present invention may have a length, hydrophobicity and/or charge that is optimal for recognition by CD4+ T cells in the context of HLA class II molecules. Epitopes of the invention may comprise at least 13, 14, 15, 16 or more amino acids. Those skilled in the art will appreciate that additional epitopes useful in the invention can be identified using the various techniques set out in Example 10 herein.

The inventors have also found that administration of nucleic acid, such as DNA or RNA, encoding full length vimentin (see FIG. 2 for the sequence of human vimentin. The N-terminal methionine residue can be included for excluded), gives rise to strong immune responses. This forms a further embodiment of the invention.

Vimentin (vim) is highly conserved between those species in which the gene has been cloned (chicken, mouse, dog, sheep, cow, horse, pig and human). Accordingly, vimentin and epitopes derived from vimentin, such as those discussed above, as well as nucleic acids encoding these, can be used for treating cancer in non-human mammals.

The applicant has previously shown that incorporation of T cell epitopes within an antibody DNA construct enhances both the frequency and avidity of the T cell response [32, 33]. As discussed in more detail in the examples below, the inventors cloned a variety of foreign and self-epitopes into antibody-DNA constructs and screened for T cell responses in HLA transgenic mice. All the foreign epitopes stimulated strong T cell responses but the only self-epitope that stimulated a significant response was vimentin 28-49. Even the human gp100 epitope, that only differed by one conservative amino acid change from the native mouse epitope, stimulated a strong response in mice whereas, the completely conserved mouse epitope failed to stimulate a response in mice. This suggests that there is complete tolerance/deletion of T cells recognising the mouse epitope but not the very similar human epitope. The implication is that the human epitope will not stimulate T cell responses in humans and, although the mouse epitope might, the T cells will not be able to recognise the naturally processed human epitope within the tumour. In contrast, the self vimentin 28-49 epitope stimulated an IFNγ response in HLA-DR4 transgenic mice. Previous studies had shown that the vim 28-49 epitope failed to stimulate an immune response in normal donors or patients with rheumatoid arthritis (RA) [34]. In contrast, the inventors have shown that cancer patients make an immune response to vim 28-49. This suggests, unexpectedly, that this epitope is not subject to self-tolerance and there is a repertoire of T cells both in mice and humans that can recognise and respond to this epitope.

Vimentin (gi/4507895) is a homodimeric intracellular protein found in intermediate filaments (IFs), specifically class III IFs, in mesenchymal and other non-epithelial cells. IFs are a major component of the cytoskeleton of higher eukaryotic cells and are composed of a number of different structurally related proteins. Different IF protein genes are expressed in different tissues. Both the human and murine vimentin genes have been characterised (see, e.g., [35, 36]).

Vimentin, along with other IF proteins, has been used in the histological classification of human tumours (for reviews see [37, 38]) and as a marker for de-differentiation in several types of tumours. Vimentin directed diagnostics and therapeutics for multi-drug resistant neoplastic disease have been described (US patent application number 20100260667), as have tumour markers that co-localise with vimentin and other IFs, see e.g. WO0127269. The latter describes a novel marker for neuroblastomas called VIP54 and its use in the detection and cellular imaging of IF as a marker of tumour development and progression. Several other examples are known that show changes in the expressed level and intracellular distribution of vimentin in different types of human solid tumours and solid tumour cell lines [39, 40]. However, hitherto there has been no demonstration of T cell responses to unmodified vimentin.

Human vimentin is a 57 kDa protein, comprising 466 amino acids (see FIG. 2 of the accompanying drawings) and is one of the most widely expressed and highly conserved proteins of the type III IF protein family. It is absent in the cytosol but is expressed in the nucleus and as an extracellular protein. It is involved in the dynamic organisation of the cytoskeleton, with a vital function in organelle transport, cell migration and proliferation.

Epithelial mesenchymal transition (EMT); Vimentin is also over-expressed in various epithelial cancers, including prostate cancer, gastrointestinal cancer, breast cancer, lung cancer, malignant melanoma and tumours of the central nervous system. It is also found in cervical cancer [41], clear-cell renal cell carcinoma [42], certain types of lymphomas [43], papillary thyroid carcinoma [44] and endometrial carcinomas [45]. Its over-expression in cancer correlates with accelerated tumour growth, invasion, and poor prognosis. In gastric cancers, vimentin expression has been most often associated with the invasive phenotype of gastric carcinoma and is suggested to play an important role in the metastasis of gastric carcinomas as well as serving as a prognostic marker [46, 47]. Soft tissue sarcomas and some epithelial cancers exhibiting epithelial to mesenchymal transition (EMT) phenotypes express vimentin. The switch of carcinoma cells from an epithelial to mesenchymal-like phenotype via an EMT is recognised as a relevant step in the metastasis of solid tumours (see FIG. 3 of the accompanying drawings). Additionally, this phenotypic switch of carcinoma cells is associated with the acquisition of tumour resistance mechanisms that reduce the anti-tumour effects of radiation, chemotherapy and some small-molecule-targeted therapies. Although vimentin is recognised as a marker for EMT, its role in tumourgenesis remains unclear. One of the most studied inducers of EMT is TGFβ, which has been shown in multiple tumour types to cooperate with RTK-signalling pathways or other pathways to drive tumour cells towards a more mesenchymal, metastatic phenotype. Ivaska [48] has demonstrated that vimentin contributes to EMT by up-regulating gene expression of several EMT-linked genes, especially expression of the pro-migratory receptor tyrosine kinase Axl. A number of studies support the notion that vimentin functions as a positive regulator of EMT and its up-regulation is a prerequisite for EMT induction [48, 49]. All of the cancers mentioned above may be treated in accordance with the invention, regardless of the epitope, as well as ovarian and gastrointestinal cancer. The invention may also relate, but not be limited, to the treatment of prostate cancer, breast cancer, lung cancer, malignant melanoma, tumours of the central nervous system, cervical cancer, clear-cell renal cell carcinoma, lymphomas, papillary thyroid carcinoma and endometrial carcinomas.

Vimentin 28-49 and other epitopes in accordance with the invention may be delivered in vivo as a peptide, optionally in the form of a peptide as disclosed in WO02/058728. The inventors have surprisingly found that epitopes useful in the invention give rise to strong immune responses when administered as a peptide. Such epitopes may be administered as just the sequence of the epitope, or as a polypeptide containing the epitope, or even as the full length protein. Alternatively, epitopes in accordance with the invention may be administered in vivo as a nucleic acid encoding the epitope, encoding a polypeptide containing the epitope or even encoding the full length protein. Such nucleic acids may be in the form of a mini gene, i.e. encoding a leader sequence and the epitope or a leader sequence and full length protein. Alternatively, they may be in the form of nucleic acids as disclosed in WO2008/116937. In a further aspect, the present invention provides a nucleic acid which comprises at least one sequence that encodes a recombinant heavy chain of an immunoglobulin molecule, the heavy chain having at least one heterologous T cell epitope therein, wherein the T cell epitope is an epitope of the first aspect of the invention, preferably vimentin 28-49. Preferably the nucleic acid further comprises a non-specific promoter, and may be DNA. The immunoglobulin molecule may be an antibody. The epitope may be inserted into a CDR of the heavy chain, preferably CDR3 of the heavy chain. Nucleic acids encoding epitopes useful in the present invention may be targeted to antigen presenting cells and other cells that express PAD enzymes, preferably PAD4 enzymes. Nucleic acids of the present invention may be targeted by including a nucleic acid encoding a targeting agent, such as Fc or a monoclonal antibody targeting a different antigen on APCs, e.g. anti-DEC205 mAb or by means of intradermal injection as skin has a large number of APCs.

Previous studies had shown that vim 26-44 citrullinated at positions 28 and 36, vim 36-54 citrullinated at positions 36 and 45 and vim 415-433 citrullinated at position 424 can stimulate T cells responses in HLA-DR4 mice and/or RA patients [34]. As described in detail in the Examples, to test whether the vim epitopes within a DNA construct were stimulating immune responses against citrullinated vimentin, mice were immunised with DNA encoding the vimentin epitopes and screened for responses against the unmodified and citrullinated epitopes. The mice immunised with vim 28-49 DNA or DNA encoding the whole vimentin sequence responded more strongly to the citrullinated 28-49 epitope than the wild type epitopes. This suggests that, when the DNA is translated, the vim epitopes are citrullinated, the citrullinated epitope binds with higher affinity to MHC or that the T cells stimulated with unmodified vim epitopes recognise the citrullinated epitopes more avidly.

In contrast to vim 28-49, vim 415-433 DNA or DNA encoding the whole vimentin sequence only stimulated responses that recognised the citrullinated epitope vim415-433 but not wild type vim415-433, confirming that the DNA within epitope presenting cells (APCs) was being translated into a peptide that was being citrullinated. In this context, it has recently been shown that dendritic cells express the citrullinating enzymes PAD2 and PAD4 [51]. Of further interest was that vim 415-433 encoding DNA gave a strong Th17 response. DNA vaccines encoding epitopes from MMP7 and NY-ESO-1 also stimulated T cells that could recognise citrullinated and unmodified epitopes. The MMP-7 response was predominantly Th17 whereas the NYESO-1 response was predominantly Th1. Similarly, cancer patients show responses to these MMP7 and NYESO-1 modified and unmodified peptides.

There have been several reports indicating that monocytes express PAD enzymes [27, 52, 53]. More recently, both bone marrow derived dendritic cells and peritoneal macrophages have been shown to express PAD2 and PAD4 [51]. Citrullination as part of the inflammatory process is only just beginning to be explored. Stimulation of peripheral blood mononuclear cells with IFNγ and double stranded RNA, causes citrullination of the chemokines CXCL8 and CXCL10, with a fundamental effect on their receptor usage, proteolytic processing and biological activities [54-56]. This may imply that mediators of cell stress via TOLL receptors, DAMP receptors or heat shock proteins may allow physiological activation of PAD enzymes both within APCs and within target cells, such as infected cells or tumour cells, to allow breaking of tolerance to modified self-epitopes and induction of immune responses. Citrullination within dendritic cells appears to be related to autophagy [57] but this has only been demonstrated with hen egg lysozyme. As disclosed herein, DNA encoding unmodified epitopes can stimulate T cell responses that are specific to the citrullinated epitope. This implies that the DNA must be translated and post-translationally citrullinated within APCs to stimulate T cells that are specific to the citrullinated epitope. This is the first time nucleic acid vaccines have been shown to stimulate citrullination. There are no reports of tumours citrullinating any epitopes presented on MHC molecules.

In addition to showing that that encoding epitopes within antibody-DNA gives higher frequency and higher avidity responses, the inventors have also shown herein that citrullinated peptides can stimulate T cell responses. Citrullinated vim 28-49 peptides stimulated predominantly Th1 responses which recognised modified epitopes although there was some cross reaction against wild type peptides. Wild type vim 28-49 peptide stimulated Th1 responses against both wild type and modified epitopes. When cancer patients were stimulated with either peptide, 2/11 responded to the unmodified epitopes and 5/11 to citrullinated vim 28-49. Hill et al. [50] have previously shown that a modified citrullinated vim 65-77 epitope that substitutes A for L at position 33 binds more strongly to HLA-DR4 than the unmodified epitope. However, this is a synthetic antigen and it has been shown in DR4 transgenic mice that the natural vim 65-77 epitope even if it is citrullinated does not induce immune responses [34]. In contrast we have shown in HLA-DR4 mice, the citrullinated vim 28-49 and vim 65-77 peptides stimulated Th1 responses that predominantly recognised the modified epitope, whereas the wild type epitope was a poor immunogen. Further analysis confirmed that these responses were mediated by CD4 T cells. Citrullinated vim65-77 also stimulated responses in HLA-A2.DR1 transgenic mice. However further analysis revealed that this was a CD8 response and the specific epitope was RLcitSSVPGV. This is the first citrullinated CD8 epitope described.

Unexpectedly, we have shown in cancer patients, 4/9 patients responded to vim 65-77 and 4/9 to citrullinated vim 65-77 but only two of these patients responded to both peptides. As with DNA immunisation, mice immunised with citrullinated vim 415-433 peptide stimulated responses that were specific to the modified epitopes whereas the wild type epitope failed to stimulate a response. Furthermore, citrullinated vim 415-433 peptide stimulated a very strong IL-17 response. In contrast, in cancer patients, 8/11 responded to the wild type epitope whereas only 5/11 responded to citrullinated vim 415-433. This suggests that both the unmodified and the modified epitopes can stimulate T cell responses in patients and that these T cells responses do not always cross react. This is also the first demonstration that cancer patients can respond to citrullinated epitopes, which was previously thought to be restricted to RA patients.

Modified peptides and DNA encoding such peptides can stimulate immune responses to modified epitopes, and these modified epitopes are expressed by target tumour cells. Citrullinated vimentin is present in inflammatory macrophages [58, 59] and is observed during calcium-ionophore induced apoptosis of human and mouse macrophages. Macrophages express PAD both at the RNA and the protein level [60] and citrullinated vimentin is expressed in vitro in macrophage-like cells after ionophore-induced $Ca^{2+}$ influx [27, 58]. However, normally the cytosolic $Ca^{2+}$ concentration (approximately $10^{-7}$ M) is too low for activity of the PAD enzyme. The minimum $Ca^{2+}$ concentration required for PAD activity is approximately 100-fold higher than the normal cytosolic $Ca^{2+}$ concentration. As these ionophores and the concomitant $Ca^{2+}$ influx cause apoptosis, it was suggested that citrullination of vimentin is associated with apoptosis. Indeed, citrulline plays an important role in preparing intracellular proteins for degradation during apoptosis. Vimentin has been shown to be citrullinated in macrophages undergoing apoptosis, and antibodies to citrullinated vimentin shown to be generated in the event of improper disposal of apoptotic material [27]. Such studies suggest an important role for post-translational modifications in regulating vimentin's function especially given modifications appear cell and tissue-specific. However, if PADs are only activated in apoptotic tumour cells, then citrullinated proteins would be poor targets as these cells are already dying. However, the inventors have shown that T cells recognising modified epitopes make potent anti-tumour responses, suggesting that viable tumour cells like APCs can release locally high intracellular calcium levels resulting in citrullination of target proteins. Furthermore, the T cells induced by citrullinated vim 415-433 and vim 28-49 induce CD4 T cells that can recognise and kill tumour cells in the context of MHC class II and epitope expression but not normal cells.

Although citrullinated vim 415-433 was shown to stimulate T cell responses whereas the unmodified epitope did not, this could have been related to the two amino acids difference between human and mouse vim 415-433. Mice were therefore screened for responses against the mouse epitope. Mice immunised with citrullinated human vimentin recognised mouse vimentin. Furthermore, like the human epitope this was a Th1/Th17 response. Previously, the induction of Th1 or Th17 responses has been shown to be heavily influenced by immune adjuvants that create the correct cytokine milieu for the appropriate responses. IFNγ and IL-12 trigger the differentiation of Th1 cells. Th1 cells produce IFNγ, IL-2, TNF and GM-CSF and stimulate, for instance, the activation of CD8+ T cells. In contrast, Th2 cells are differentiated by IL-4. They secrete IL-4, IL-5 and IL-13 and assist B cells in antibody production and down-regulate pro-inflammatory responses induced by Th1 cells. TGFβ, IL-1, IL-6, IL-21 and IL-23 trigger the differentiation of Th17 cells. They produce IL-17 and IL-6. CD4+ T cells differentiate into iTreg in the absence of pro-inflammatory cytokines but high concentrations of TGFβ (see FIG. 4 of the accompanying drawings). These cells secrete TGFβ and IL-10, and are characterised by the transcription factor forkhead box p3 (Foxp3). They control and counteract immune responses by other effector T cells, and are involved in the prevention of autoimmunity[61].

Citrullinated vim 415-433 peptide was therefore immunised with a variety of adjuvants or indeed with no adjuvant. Immunostimulatory adjuvants such as CpG/MPLA and GMCSF both stimulated Th1/Th17 responses and were required, as there was no response in the absence of adjuvant. Inert adjuvants such as Alum and Incomplete Freund's adjuvant caused induction of predominantly IL-10 responses similar to immunisation with wild type vim 415-433 peptide which also induced an IL-10 response, suggesting the induction of an iTreg response. In contrast, combination of citrullinated vim 415-433 peptide with an optimal adjuvant induced an IFNγ/IL-17 response, suggesting a Th17 response. This is the first illustration that T cell epitopes can determine T helper cell differentiation.

As mice responded with a strong Th1/Th17 response to a single immunisation with citrullinated vim 415-433 peptide, this may have reflected a boost to a natural Treg response. However, depletion of natural Tregs failed to influence the frequency or avidity of the citrullinated vim 415-433 immune response, suggesting that this was unlikely. It may have been that the wild type vim 415-433 epitope presented in situ had stimulated an iTreg response, characterised by production of IL-10. Indeed, mice immunised with citrullinated vim 415-433 peptide made IFNγ, IL-17 and IL-10 responses whereas mice immunised with unmodified epitope only stimulated an IL-10 response. Unmodified vim 415-433 peptide also stimulated IL-10 responses in cancer patients. Anti-CTLA-4 mabs can block the interaction of CTLA-4 with its cognate receptor CD80/86, thus preventing the inhibition of T cells induced by this ligand. Immunisation of mice with citrullinated vim 415-433 peptide in the presence of an anti-CTLA-4 mab significantly increased the avidity of the T cell response from $10^{-6}$ M to $10^{-8}$ M.

According to a further aspect of the present invention, there is provided a modified epitope which stimulates an IL-10 immune reaction against self-antigens, and/or a nucleic acid encoding such an epitope, for use in medicine, the epitope having a modification selected from deimination of arginine to citrulline, nitration of tyrosine, oxidation of tryptophan and deamination of glutamine or asparagine. According to a further aspect of the present invention, there is provided a method for modulating T helper cell differentiation, comprising contacting a T helper cell with an epitope and/or nucleic acid as defined herein and optionally an adjuvant. A yet further aspect of the invention provides an epitope and/or nucleic acid as defined herein and optionally an adjuvant for use in a method of modulating T helper cell differentiation. A yet further aspect of the invention provides the use of an epitope and/or nucleic acid as defined herein and optionally an adjuvant in the manufacture of a medicament for modulating T helper cell differentiation. Epitopes useful in these aspects of the invention may be an epitope as defined in the first aspect of the invention, and/or may be a modified epitope which stimulates an IL-10 immune reaction against self-antigens, the epitope having a modification selected from deimination of arginine to citrulline, nitration of tyrosine, oxidation of tryptophan and deamination of glutamine or asparagine. The adjuvant may be incomplete Freund's adjuvant, CpG, MPLA, GMCSF and complete Freund's adjuvant.

Epitopes and/or nucleic acids useful in the invention can be used to direct T helper cell differentiation to stimulate an immune response. As such, they can be used in conjunction with vaccines to increase the efficacy of such vaccines. As demonstrated by the inventors, citrullinated vim 415-433 peptide induced an IFNγ/IL-17 response, suggesting a Th17 response. This is in contrast to the normal response for vim 415-433 and other self-epitopes, which cause T helper cell differentiation into iTreg cells.

Alternatively, epitopes and/or nucleic acids useful in the invention can be used to direct T helper cell differentiation to suppress an immune response. Citrullinated ING4 gives rise to an IL-10 response, suggesting an iTreg response and suppression of an immune response. Such epitopes can be used in the treatment of diseases where immune suppression is desirable, such as autoimmune diseases and graft-versus-host disease (GVHD). Examples of autoimmune diseases include Alopecia Areata, Anklosing Spondylitis, Antiphospholipid Syndrome, Autoimmune Addison's Disease, Autoimmune Hemolytic Anemia, Autoimmune Hepatitis, Autoimmune Inner Ear Disease, Autoimmune Lymphoproliferative Syndrome (ALPS), Autoimmune Thrombocytopenic Purpura (ATP), Behcet's Disease, Bullous Pemphigoid, Cardiomyopathy, Celiac Sprue-Dermatitis, Chronic Fatigue Syndrome Immune, Deficiency Syndrome (CFIDS), Chronic Inflammatory Demyelinating Polyneuropathy, Cicatricial Pemphigoid, Cold Agglutinin Disease, CREST Syndrome, Crohn's Disease, Dego's Disease, Dermatomyositis, Dermatomyositis—Juvenile, Discoid Lupus, Essential Mixed Cryoglobulinemia, Fibromyalgia—Fibromyositis, Grave's Disease, Guillain-Barre, Hashimoto's Thyroiditis, Idiopathic Pulmonary Fibrosis, Idiopathic Thrombocytopenia Purpura (ITP), IgA Nephropathy, Insulin Dependent Diabetes (Type I), Juvenile Arthritis, Lupus, Meniere's Disease, Mixed connective Tissue Disease, Multiple Sclerosis, Myasthenia Gravis, Pemphigus Vulgaris, Pernicious Anemia, Polyarteritis Nodosa, Polychondritis, Polyglancular Syndromes, Polymyalgia Rheumatica, Polymyositis and Dermatomyositis, Primary Agammaglobulinemia, Primary Biliary Cirrhosis, Psoriasis, Raynaud's Phenomenon, Reiter's Syndrome, Rheumatic Fever, Rheumatoid Arthritis, Sarcoidosis, Scleroderma, Sjogren's Syndrome, Stiff-Man Syndrome, Takayasu Arteritis, Temporal Arteritis/Giant Cell Arteritis, Ulcerative Colitis, Uveitis, Vasculitis, Vitiligo and Wegener's Granulomatosis.

According to a further aspect of the present invention, there is provided a method of predicting survival in colorectal cancer, comprising determining the level of peptidylarginine deiminase 4 (PAD4) in a colorectal cancer cell. 94% of tumours express PAD4. Tumour cells that lose expression of PAD4 indicate a poor prognosis and suggest a reduced survival. Thus, if a colorectal cancer shows little or no expression of PAD4, then the patient has a poor prognosis. Without wishing to be bound by theory, this may be related to lack of citrullinated epitopes which can be recognised and by killed by T cells. Thus, the tumour evades immune monitoring. Conversely, if the tumour expresses PAD4, then targets are deiminated, tumour growth is controlled by the immune response and the patient has a better prognosis.

The level of PAD4 can be determined by using an antibody or other immunoassay to measure the amount of the PAD4 protein in the cell. Alternatively, the level of PAD4 mRNA can be measured by in situ hybridisation. Those of skill in the art are aware of suitable alternative techniques for determining the level of mRNA, as well as alternative techniques for determining the level of a protein.

90% of colorectal tumours expressed vimentin, it being mainly found in stromal and infiltrating cells. In 15% of cells, some epithelial cells were also stained and in 12% of tumours greater than 75% of all cells were stained. Only 6% of colorectal tumours failed to stain with a PAD4 specific mAb. Kaplan Meier survival analysis showed there was a correlation with PAD4 intensity and survival. In a multivariate model, TNM stage ($p=<0.0001$), vascular invasion ($p=<0.0001$) and PAD4 expression ($p=0.004$) were independent predictors of patient survival, suggesting that PAD4 could be a useful prognostic marker in colorectal cancer. There was a correlation between expression of PAD4 and BCL2 ($p=0.01$), β-catenin ($p=0.001$), number of CD8 T cells ($p=0.006$), MUC1 ($p=0.000$), CEA ($p=0.000$), CD59 ($p=0.038$) and vimentin ($p=0.000$) suggesting that all these may be targets for modified proteins.

In experiments carried out by the inventors, 89% of ovarian tumours stained strongly for vimentin and only 4% failed to stain with an anti-PAD4 antibody. Furthermore, 82% also expressed citrulline, suggesting that the enzyme was active. Expression of PAD4 correlated with the stress related proteins RAET1E and ULBP1, suggesting activation of this enzyme when cells are stressed. There was also a strong correlation with vimentin, suggesting that citrullinated vimentin is a good target in ovarian cancer. HMGB1 was expressed by 87% of tumours and also correlated with expression of vimentin.

According to a further aspect of the present invention, there is provided a method of predicting survival in ovarian cancer, comprising determining the level of peptidylarginine deiminase 2 (PAD2) and/or High-mobility group protein B1 (HMGB1) in an ovarian cancer cell. 91% of tumours express PAD2. Tumour cells that lose expression of PAD2 indicate a poor prognosis and suggest a reduced survival. Thus, if an ovarian cancer shows little or no expression of PAD2, then the patient has a poor prognosis. Without wishing to be bound by theory, this may be related to lack of citrullinated epitopes which can be recognised and by killed by T cells. Thus, the tumour evades immune monitoring. Conversely, if the tumour expresses PAD2, then targets are deiminated, tumour growth is controlled by the immune response and the patient has a better prognosis.

In experiments carried out by the inventors 16% of ovarian tumours stained strongly for PAD2. Furthermore 91% also express citrulline. Expression of PAD2 correlated with HMGB1 expression suggesting an association with autophagy and with MHC expression suggesting a link with immune responses.

87% of tumours express HMGB1. Tumour cells that lose expression of HMGB1 indicate a better prognosis and suggest an increased survival. Tumours with high levels of HMGB1 had strong autophagy which is a powerful survival mechanism and correlated with a poor prognosis. Thus, if an ovarian cancer shows little or no expression of HMGB1, then the patient has a good prognosis, low levels a better prognosis and high expression a bad prognosis.

The level of HMGB1 can be determined by using an antibody or other immunoassay to measure the amount of the HMGB1 protein in the cell. Alternatively, the level of HMGB1 mRNA can be measured by in situ hybridisation. Those of skill in the art are aware of suitable alternative techniques for determining the level of mRNA, as well as alternative techniques for determining the level of a protein. 87% of ovarian tumours expressed HMGB1, it being mainly found in nuclei and cytoplasm. Kaplan Meier survival analysis showed there was a correlation with HMBG1 levels and survival ($p=0.001$). In a multivariate model, TNM stage ($p=<0.0001$), tumour type ($p=0.031$) response to chemotherapy ($p=<0.001$) and loss of HMGB1 ($p=0.002$) were independent predictors of patient survival, suggesting that HMGB1 could be a useful prognostic marker in ovarian cancer.

In patients who showed high HMGB1 and low PAD2 expression, 219 of 310 patients (70%) had the worst median survival of 50 months, and patients with low HMGB1 and low PAD2 displayed the better survival, with 41 of 310 patients (13%) having a median survival time of 101 months. Without wishing to be bound by theory, this may be related to lack of citrullinated epitopes and lack of autophagy the tumour evades immune monitoring and has a poor survival ability.

In mammals, five PAD isotypes, each encoded by a distinct gene, have been identified [60]. All these enzymes rely strongly on the presence of $Ca^{2+}$ for activity. All isotypes of PAD display extensive mutual sequence homologies. The most noticeable difference between the isotypes is their tissue-specific expression. All isotypes can citrullinate most proteins with accessible arginines in vitro [62], although certain proteins are citrullinated more rapidly than others by individual PADs [63]. Peptide studies indicate that certain amino acids flanking arginine residues influence its susceptibility to citrullination [20].

All these enzymes rely strongly on the presence of $Ca^{2+}$ for activity. All isotypes of PAD display extensive mutual sequence homologies. The most noticeable difference between the isotypes is their tissue-specific expression. All isotypes can citrullinate most proteins with accessible arginines in vitro [62], although certain proteins are citrullinated more rapidly than others by individual PADs [63]. Peptide studies indicate that certain amino acids flanking arginine residues influence its susceptibility to citrullination [20].

The most widely expressed PAD isotype, PAD2, is present in many different tissues, like skeletal muscle, brain, spleen, secretory glands and macrophages. Despite this broad expression pattern, only myelin binding protein (MBP) in the central nervous system, where physiological citrullination is important in ensuring electrical insulation of the myelin sheaths, and vimentin have been identified as natural substrates. In multiple sclerosis (MS), a chronic inflammatory disorder of the CNS, the myelin sheath is destroyed and patients make autoimmune responses to citrullinated MBP. In healthy adults, 18% of MBP is citrullinated whereas in MS over 45% is citrullinated, leading to increased unfolding and degradation.

PAD1 is mainly expressed in epidermis and uterus and, during terminal differentiation of keratinocytes, keratins (K1 and K10) and the keratin associated protein filaggrin are citrullinated. In general citrullination decreases the charge on proteins, leading to atrial unfolding, reduced flexibility and cornification of the epidermis. Psorasis is caused by aberrant citrullination in psoratic epidermis by PAD1. PAD3 is restricted to hair/wool follicles where its natural substrate is trichohyalin which is a major structural protein of inner root sheath cells of hair follicles. PAD6 is expressed by egg cells and the embryo.

Inflammatory leukocytes including synovial T and B cells, macrophages, neutrophils, as well as fibroblast-like synoviocytes express two PAD isoforms, 2 and 4 [27, 64]. Unlike other PADs, which are all mainly localised in the cytoplasm of cells, PAD4 is localised in the nucleus. The nuclear localisation signal of PAD4 was found in the N-terminal region of the protein. PAD4 is mainly expressed in peripheral blood granulocytes and monocytes. PAD4 is also expressed by many tumour tissues including adenocarcinomas [65]. Immunohistochemistry also detected co-localisation of PAD4 with cytokeratin and Western blotting detected citrulline signals in cytokeratin extracted from tumours. In addition, cytokeratin 8, cytokeratin 18, cytokeratin 19 following in vitro citrullination resisted digestion by caspases. This could confer a growth advantage to the tumours. Citrulline-containing protein was not detectable in peripheral leucocytes even through these cells exhibited strong expression of PAD4. It has been suggested that the concentration of calcium is a key factor in activation of PAD4 and consequent citrullination. In addition, citrullination of rheumatoid arthritis (RA) synovium mainly occurred in its extracellular deposits, whilst citrullinated protein has been located inside tumour cells. Citrullination of histones can alter gene expression within tumours and citrullination of ING4 inhibits its association with p53 leading to inactivation of this potent tumour suppressor gene [66].

The invention also includes within its scope polypeptides having the amino acid sequence as set out above and/or in Table 3, 8, 9 or 10 and sequences having substantial identity thereto, for example, 70%, 80%, 85%, 90%, 95% or 99% identity thereto, as well as their use in medicine and in particular in a method for treating cancer. The percent identity of two amino acid sequences or of two nucleic acid sequences is generally determined by aligning the sequences for optimal comparison purposes (e.g., gaps can be introduced in the first sequence for best alignment with the second sequence) and comparing the amino acid residues or nucleotides at corresponding positions. The "best alignment" is an alignment of two sequences that results in the highest percent identity. The percent identity is determined by comparing the number of identical amino acid residues or nucleotides within the sequences (i.e., % identity=number of identical positions/total number of positions×100).

The determination of percent identity between two sequences can be accomplished using a mathematical algorithm known to those of skill in the art. An example of a mathematical algorithm for comparing two sequences is the algorithm of Karlin and Altschul modified as in [67]. The NBLAST and XBLAST programs of Altschul, et al. have incorporated such an algorithm [68]. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, Gapped BLAST can be utilized as described in [69]. Alternatively, PSI-Blast can be used to perform an iterated search that detects distant relationships between molecules. When utilizing BLAST, Gapped BLAST, and PSI-Blast programs, the default parameters of the respective programs (e.g., XBLAST and NBLAST) can be used. See http://www.ncbi.nlm.nih.gov. Another example of a mathematical algorithm utilized for the comparison of sequences is the algorithm of Myers and Miller [70]. The ALIGN program (version 2.0) which is part of the GCG sequence alignment software package has incorporated such an algorithm. Other algorithms for sequence analysis known in the art include ADVANCE and ADAM as described in [71] and FASTA described in [72]. Within FASTA, ktup is a control option that sets the sensitivity and speed of the search.

As used herein, the term "treatment" includes any regime that can benefit a human or non-human animal. The polypeptide or nucleic acid may be employed in combination with a pharmaceutically acceptable carrier or carriers. Such carriers may include, but are not limited to, saline, buffered saline, dextrose, liposomes, water, glycerol, ethanol and combinations thereof.

Peptides useful in the invention may be synthesised using Fmoc chemistry or other standard techniques known to those skilled in the art.

It is envisaged that injections will be the primary route for therapeutic administration of the compositions of the invention although delivery through a catheter or other surgical tubing may also be used. Some suitable routes of administration include intravenous, subcutaneous, intradermal, intraperitoneal and intramuscular administration. Liquid formulations may be utilised after reconstitution from powder formulations.

For intravenous injection, or injection at the site of affliction, the active ingredient will be in the form of a parentally acceptable aqueous solution which is pyrogen-free, has suitable pH, is isotonic and maintains stability. Those of relevant skill in the art are well able to prepare suitable solutions using, for example, isotonic vehicles such as sodium chloride injection, Ringer's Injection or Lactated Ringer's Injection. Preservatives, stabilisers, buffers, antioxidants and/or other additives may be included, as required.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. Where the formulation is a liquid it may be, for example, a physiologic salt solution containing non-phosphate buffer at pH 6.8-7.6, or a lyophilised powder.

The composition may be administered in a localised manner to a tumour site or other desired site or may be delivered in a manner in which it targets tumour or other cells.

The compositions are preferably administered to an individual in a "therapeutically effective amount", this being sufficient to show benefit to the individual. The actual amount administered, and rate and time-course of administration, will depend on the nature and severity of what is being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. The compositions of the invention are particularly relevant to the treatment of cancer, and in the prevention of the recurrence of such conditions after initial treatment or surgery. Examples of the techniques and protocols mentioned above can be found in Remington's Pharmaceutical Sciences [73]. A composition may be administered alone or in combination with other treatments, either simultaneously or sequentially dependent upon the condition to be treated. Other cancer treatments include other monoclonal antibodies, other chemotherapeutic agents, other radiotherapy techniques or other immuno therapy known in the art. One particular application of the compositions of the invention is as an adjunct to surgery, i.e. to help to reduce the risk of cancer reoccurring after a tumour is removed. The compositions of the present invention may be generated wholly or partly by chemical synthesis. The composition can be readily prepared according to well-established, standard liquid or, preferably, solid-phase peptide synthesis methods, general descriptions of which are broadly available (see, for example, in Solid Phase Peptide Synthesis, $2^{nd}$ edition [74], in The Practice of Peptide Synthesis [75] and Applied Biosystems 430A Users Manual, ABI Inc.,) or they may be prepared in solution, by the liquid phase method or by any combination of solid-phase, liquid phase and solution chemistry, e.g. by first completing the respective peptide portion and then, if desired and appropriate, after removal of any protecting groups being present, by introduction of the residue X by reaction of the respective carbonic or sulfonic acid or a reactive derivative thereof.

Another convenient way of producing a composition according to the present invention is to express the nucleic acid encoding it, by use of nucleic acid in an expression system.

The present invention further provides an isolated nucleic acid encoding a composition of the present invention. In a preferred aspect, the present invention provides a nucleic acid which codes for a composition of the invention as defined above. The skilled person will be able to determine substitutions, deletions and/or additions to such nucleic acids which will still provide a composition of the present invention. The nucleic acid may be DNA, cDNA, or RNA such as mRNA obtained by cloning or produced by chemical synthesis. For therapeutic use, the nucleic acid is preferably in a form capable of being expressed in the subject to be treated. The polypeptide useful in the present invention or the nucleic acid of the present invention may be provided as an isolate, in isolated and/or purified form, or free or substantially free of material with which it is naturally associated. In the case of a nucleic acid, it may be free or substantially free of nucleic acid flanking the gene in the human genome, except possibly one or more regulatory sequence(s) for expression. Nucleic acid may be wholly or partially synthetic and may include genomic DNA, cDNA or RNA. Where nucleic acid according to the invention includes RNA, reference to the sequence shown should be construed as reference to the RNA equivalent, with U substituted for T.

Nucleic acid sequences encoding a polypeptide useful in the present invention can be readily prepared by the skilled person, for example using the information and references contained herein and techniques known in the art (for example, see [76, 77]), given the nucleic acid sequences and clones available. These techniques include (i) the use of the polymerase chain reaction (PCR) to amplify samples of such nucleic acid, e.g. from genomic sources, (ii) chemical synthesis, or (iii) preparing cDNA sequences. DNA encoding the polypeptide may be generated and used in any suitable way known to those of skill in the art, including by taking encoding DNA, identifying suitable restriction enzyme recognition sites either side of the portion to be expressed, and cutting out said portion from the DNA. The portion may then be operably linked to a suitable promoter in a standard commercially-available expression system. Another recombinant approach is to amplify the relevant portion of the DNA with suitable PCR primers. Modifications to the sequences can be made, e.g. using site directed mutagenesis, to lead to the expression of modified peptide or to take account of codon preferences in the host cells used to express the nucleic acid.

The present invention also provides constructs in the form of plasmids, vectors, transcription or expression cassettes which comprise at least one nucleic acid as described above. The present invention also provides a recombinant host cell which comprises one or more constructs as above. As mentioned, a nucleic acid encoding a composition of the invention forms an aspect of the present invention, as does a method of production of the composition which method comprises expression from encoding nucleic acid. Expression may conveniently be achieved by culturing under appropriate conditions recombinant host cells containing the nucleic acid. Following production by expression, a composition may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is *E. coli*. The expression of antibodies and antibody fragments in prokaryotic cells such as *E. coli* is well established in the art. For a review, see for example [78]. Expression in eukaryotic cells in culture is also available to those skilled in the art as an option for production of a specific binding member, see for recent review, for example [79, 80].

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: A Laboratory Manual [76]. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology [77].

Thus, a further aspect of the present invention provides a host cell, which may be isolated, containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene.

In one embodiment, the nucleic acid of the invention is integrated into the genome (e.g. chromosome) of the host cell. Integration may be promoted by inclusion of sequences which promote recombination with the genome, in accordance with standard techniques.

The present invention also provides a method which comprises using a construct as stated above in an expression system in order to express a polypeptide as described above. Preferred features of each aspect of the invention are as for each of the other aspects mutatis mutandis. The prior art documents mentioned herein are incorporated to the fullest extent permitted by law.

EXAMPLES

The present invention will now be described further with reference to the following examples and the accompanying drawings.

Figure 1:
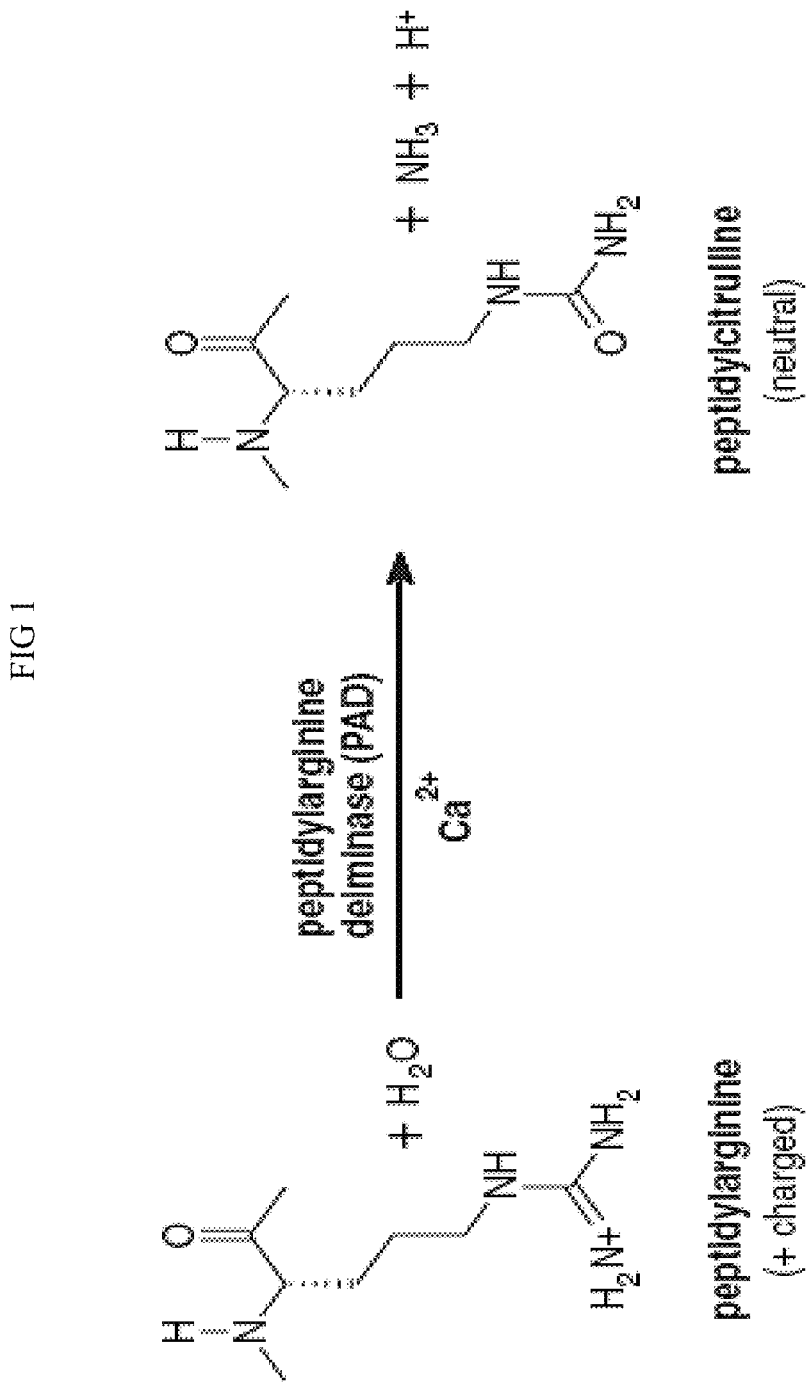

FIG. 1: Enzymatic conversion of arginine to citrulline within proteins is catalyzed by PAD.

FIG. 2: Amino acid sequence of human vimentin.

Figure 3:
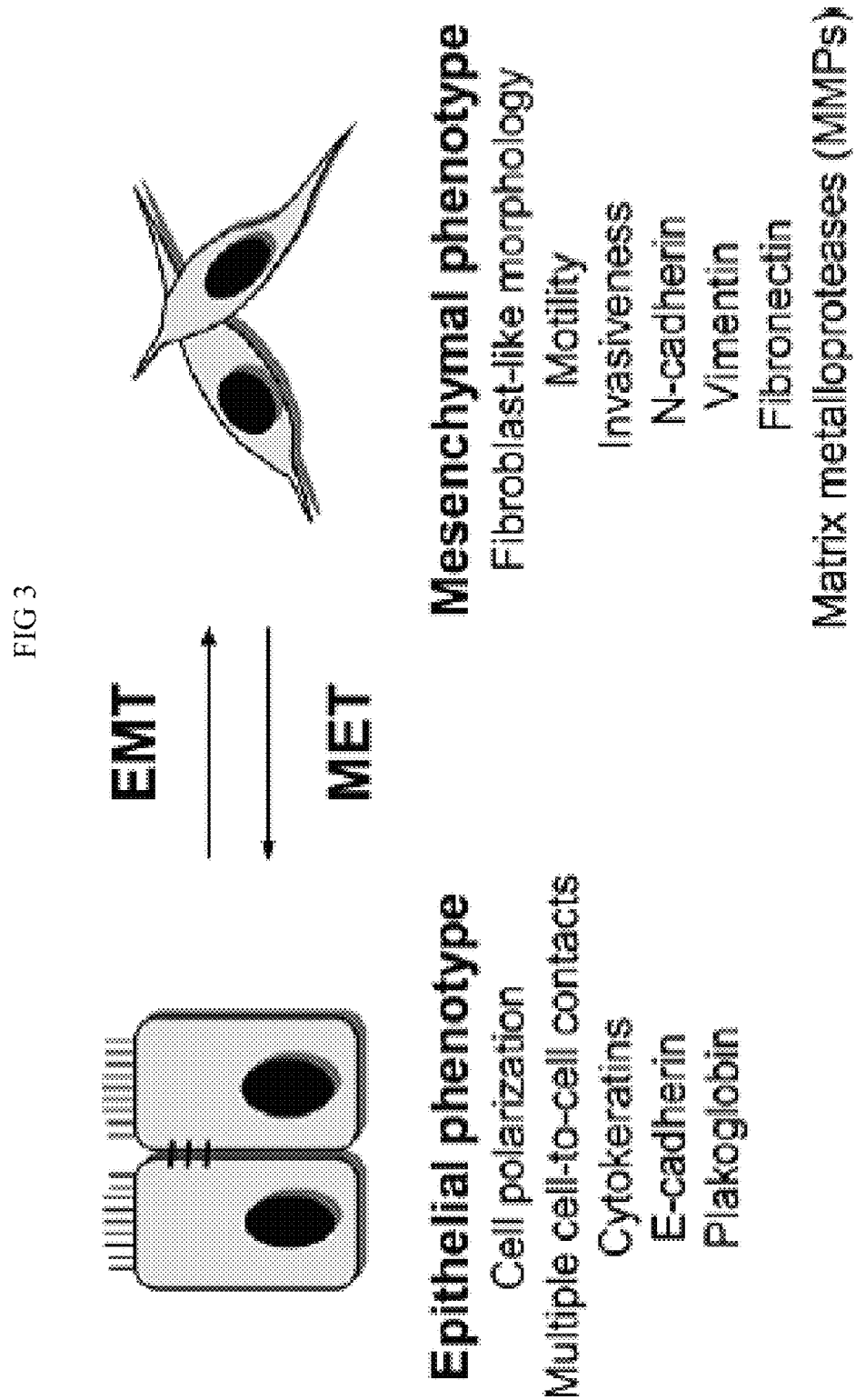

FIG. 3: Relevant phenotypic changes defining the epithelial-to-mesenchymal transition (EMT) and its reverse process, the mesenchymal-to-epithelial transition (MET). Figure taken from [81].

Figure 4:
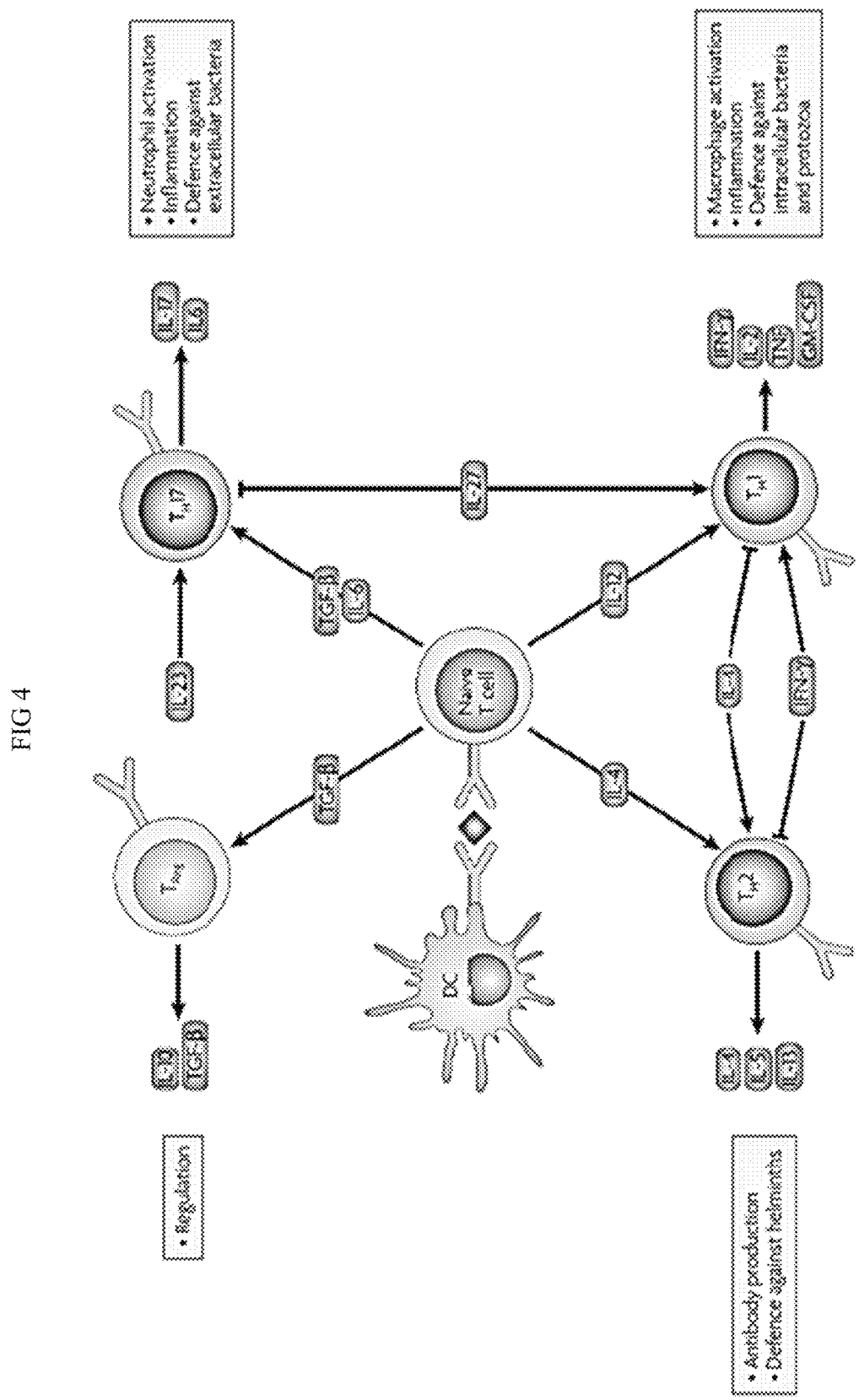

FIG. 4: Subpopulations of CD4$^+$ T cells. The main populations of CD4$^+$ T cells being Th1, Th2 and Th17 as well as iTregs. Treg control the responses of immune effector cells. Figure taken from Kaufmann [61].

Figure 5:
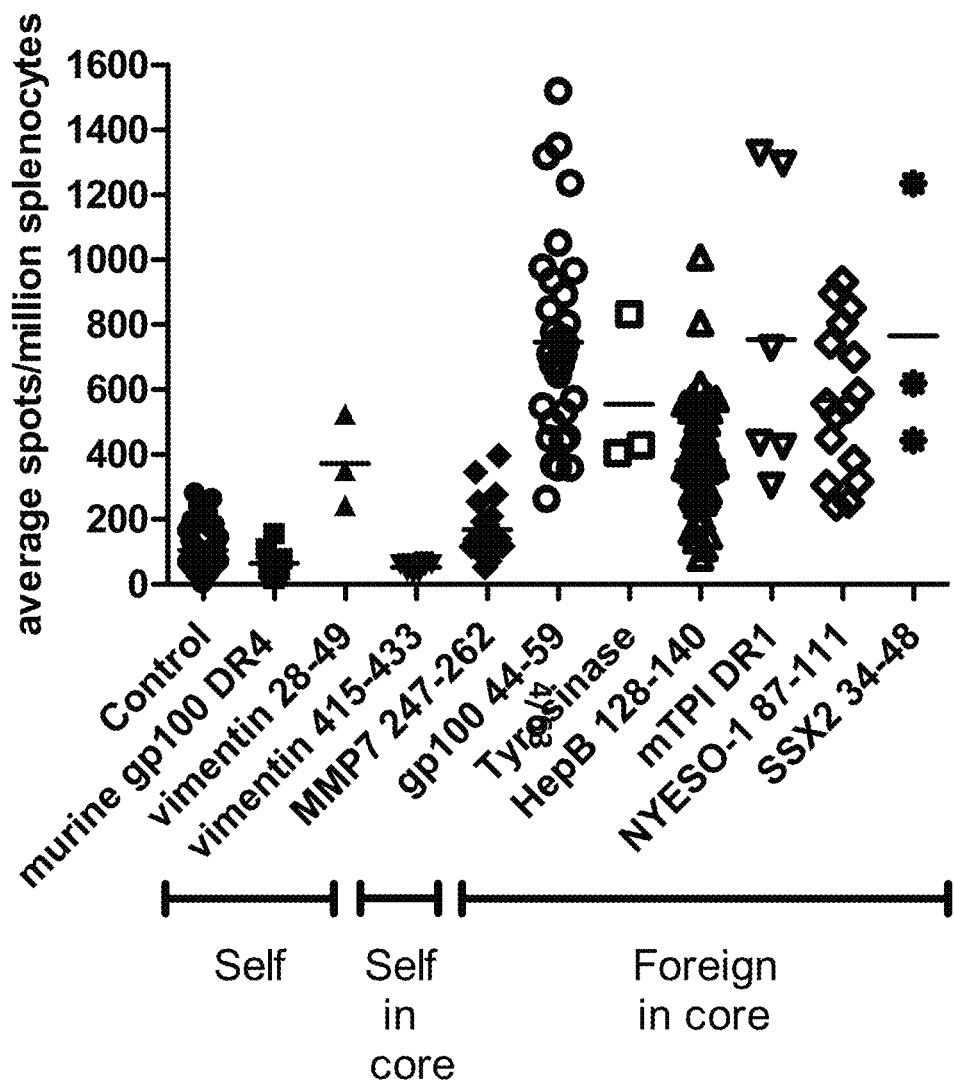

FIG. 5: CD4 T cell responses to helper epitopes encoded within Antibody DNA.HLA-DR4 or HLA-DR1 transgenic mice were immunised with an antibody DNA construct containing the helper epitopes in CDRL1 or CDRH3 via gene gun. All mice were immunised three times on days 0, 7 and 14. Responses specific for the helper epitope were analysed ex vivo at day 20 by IFNγ Elispot assay against relevant helper peptide and an irrelevant control. Responses are measured as spots/million splenocytes.

Figure 6:
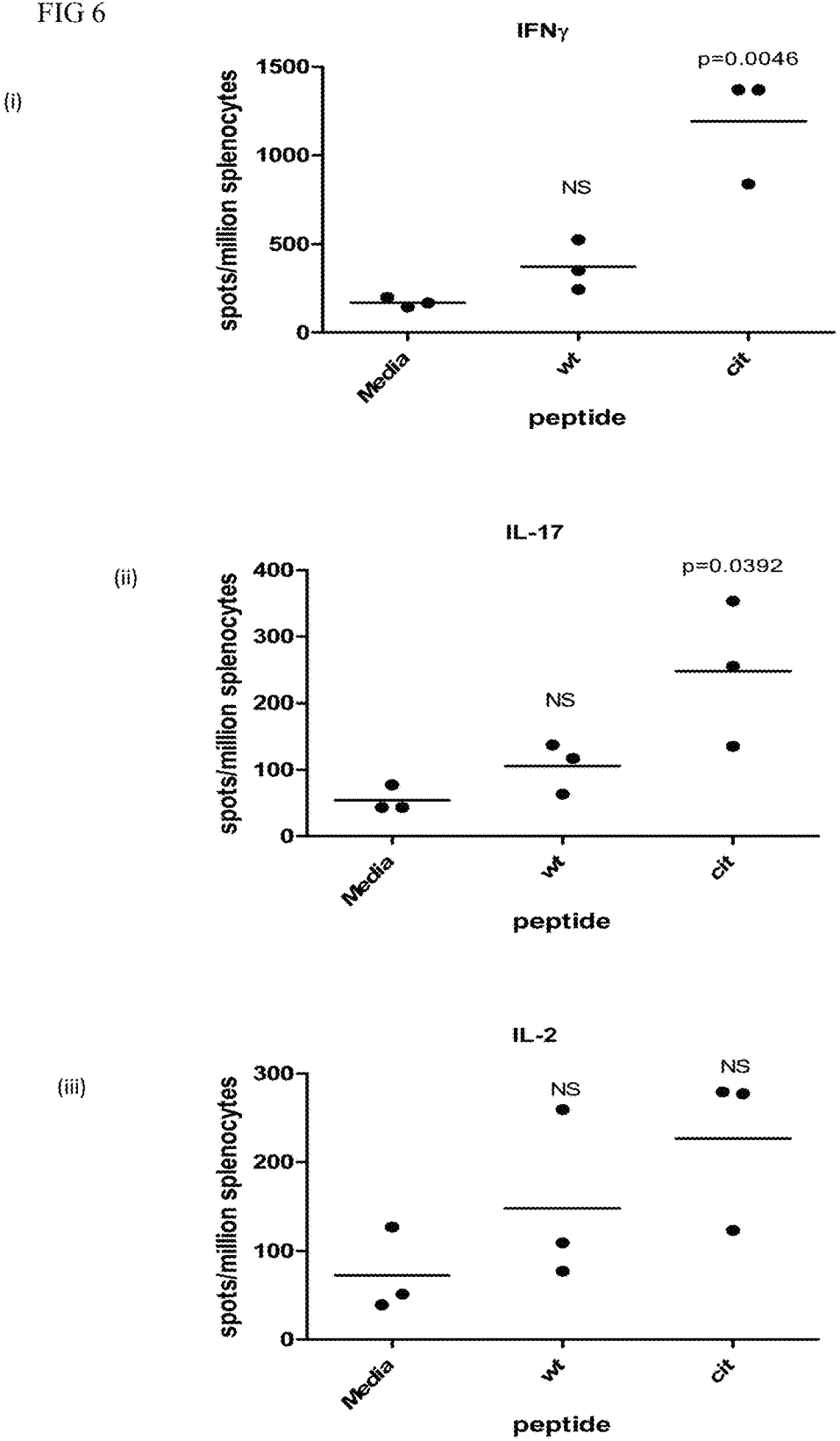

FIG. 6: Vimentin 28-49 helper epitope inserted into the CDRH3 site of the huIgG1 antibody DNA double expression vector is processed, citrullinated and presented in vivo. HLA-DR4 transgenic mice were immunised with the antibody DNA construct via gene gun once a week for 3 consecutive weeks. On day 19, splenocytes were analysed in vitro against vimentin 28-49 wild type and citrullinated peptides at 5 μM concentration by (i) IFN gamma (ii) IL-17 and (iii) IL-2 elispot.

Figure 7:
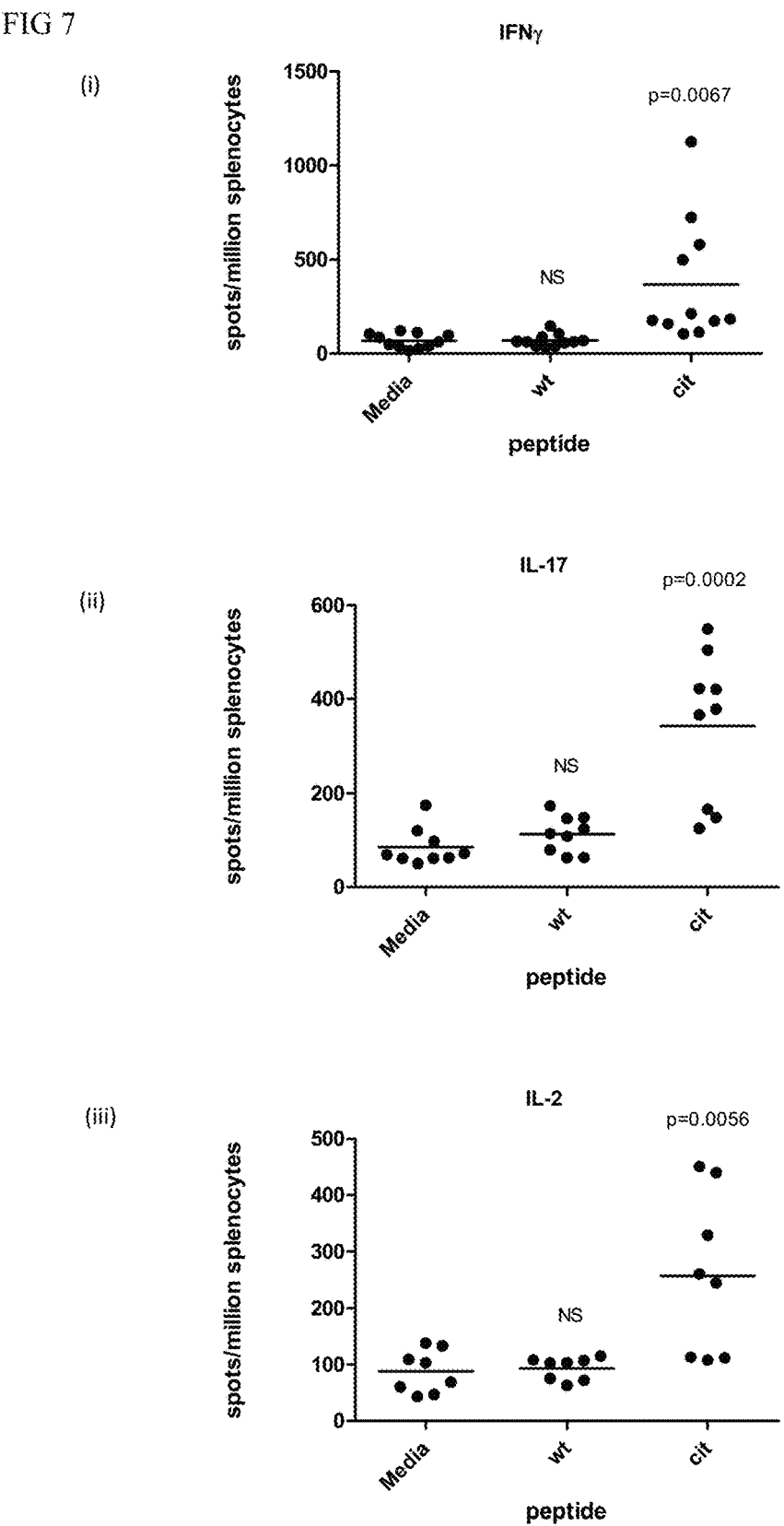

FIG. 7: Vimentin 415-433 helper epitope inserted into the CDRH3 site of the huIgG1 antibody DNA double expression vector is processed, citrullinated and presented in vivo. HLA-DR4 transgenic mice were immunised with the antibody DNA construct via gene gun once a week for 3 consecutive weeks. On day 19, splenocytes were analysed in vitro against vimentin human 415-433 wild type and citrullinated peptides at 5 μM concentration by (i) IFN gamma (ii) IL-17 and (iii) IL-2 elispot.

FIG. 8: CD4 responses in DR1 mice elicited by immunisation with an antibody DNA construct encoding the MMP-7 helper epitope.

HLA-DR1 transgenic mice were immunised with an antibody DNA huIgG1 construct containing the MMP-7 247 helper epitope in CDRL1 via gene gun. All mice were immunised three times on days 0, 7 and 14. Responses specific for the helper epitope were analysed ex vivo at day 20 against both MMP7 human 247 wild type and citrullinated peptides by (i) IFNγ (n=14) (ii) IL-17 (n=14) elispot assays. Responses are measured as spots/million splenocytes.

FIG. 9: NYESO1 119-143 CD4 epitope encoded within an antibody DNA stimulates CD4 responses that are accompanied by an anti-tumour response.

HHDII/DR1 transgenic mice were injected on day 0 with $2.5 \times 10^4$ B16 HHDII NYESO-1 cells. Mice were immunised at day 3, 10 and 17 with antibody DNA huIgG1 DNA containing the helper epitope NYESO-1 119-143 in the CDRL1 site via gene gun. (i) Responses specific for the helper epitope were analysed ex vivo at day 20 by IFNγ Elispot assay against the wild type, citrullinated NYESO-1 119-143 helper peptides and an irrelevant control. Responses are measured as spots/million splenocytes. (ii) Survival of animals immunised with NYESO-1 antibody DNA alone or with homspera adjuvant or with homspera alone.

Figure 10:
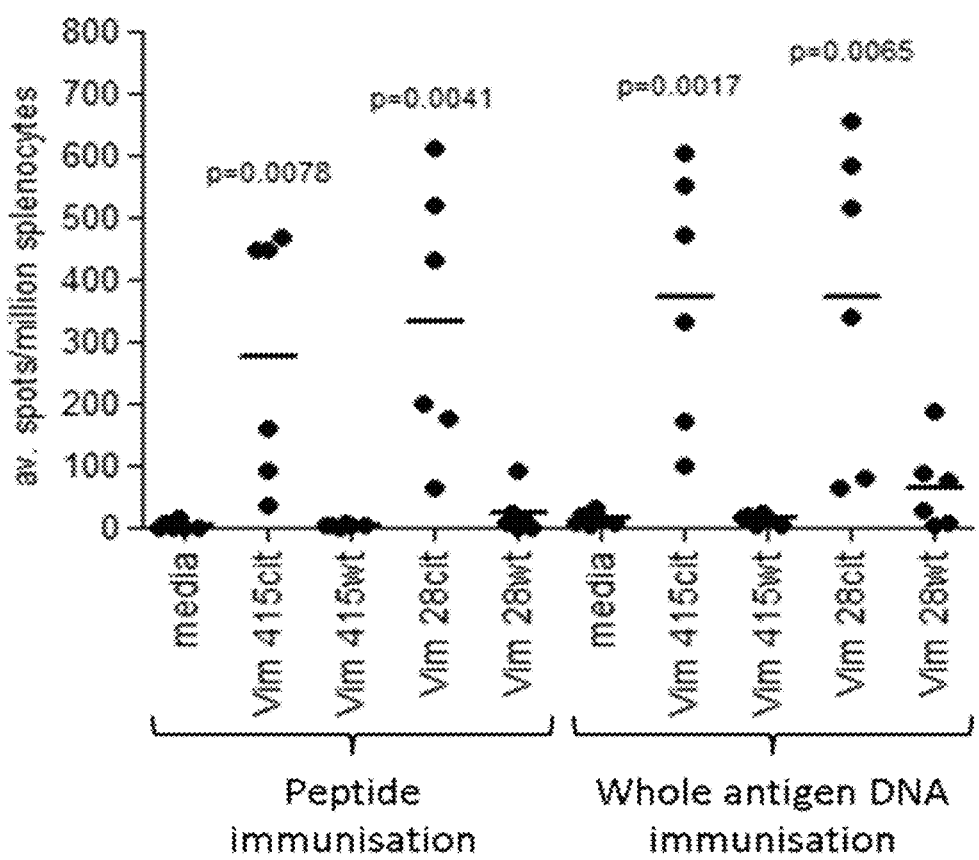

FIG. 10: Vimentin 28-49 and 415-433 epitopes are processed, citrullinated and presented in vivo from a whole antigen DNA construct.

HLA-DR4 transgenic mice were immunised with a DNA construct encoding murine vimentin via gene gun or Vim 28-49 and 415-433 citrullinated peptides in CpG/MPLA s.c. once a week for 3 consecutive weeks. On day 19, splenocytes were analysed in vitro against vimentin 28-49 and 415-433 wild type and citrullinated peptides at 5 μM concentration by IFN gamma elispot assay.

FIG. 11: Comparison of CD4 responses in HLA-DR4 transgenic mice elicited from immunisation with the human wild type and citrullinated vimentin 28-49 peptides. HLA-DR4 transgenic mice were immunised with 25 μg of vimentin 28-49 human wild type or citrullinated peptides at day 0. On day 14, splenocytes were analysed in vitro against (a) vimentin human 28-49 wild type and citrullinated peptides at 5 μM concentration by (i) IFNγ (ii)IL-17 (iii)IL-2 (iv) IL-10 elispot assays, (b) Avidity of cit epitope specific responses by measuring responses to increasing peptide concentration in IFNγ and IL-17 elispot assays, (c) vimentin 28-49 triple, double and single citrullinated peptides at 5 μM concentration by IFNγ elispot assay. Responses are measured as average spots/million splenocytes.

Figure 12:
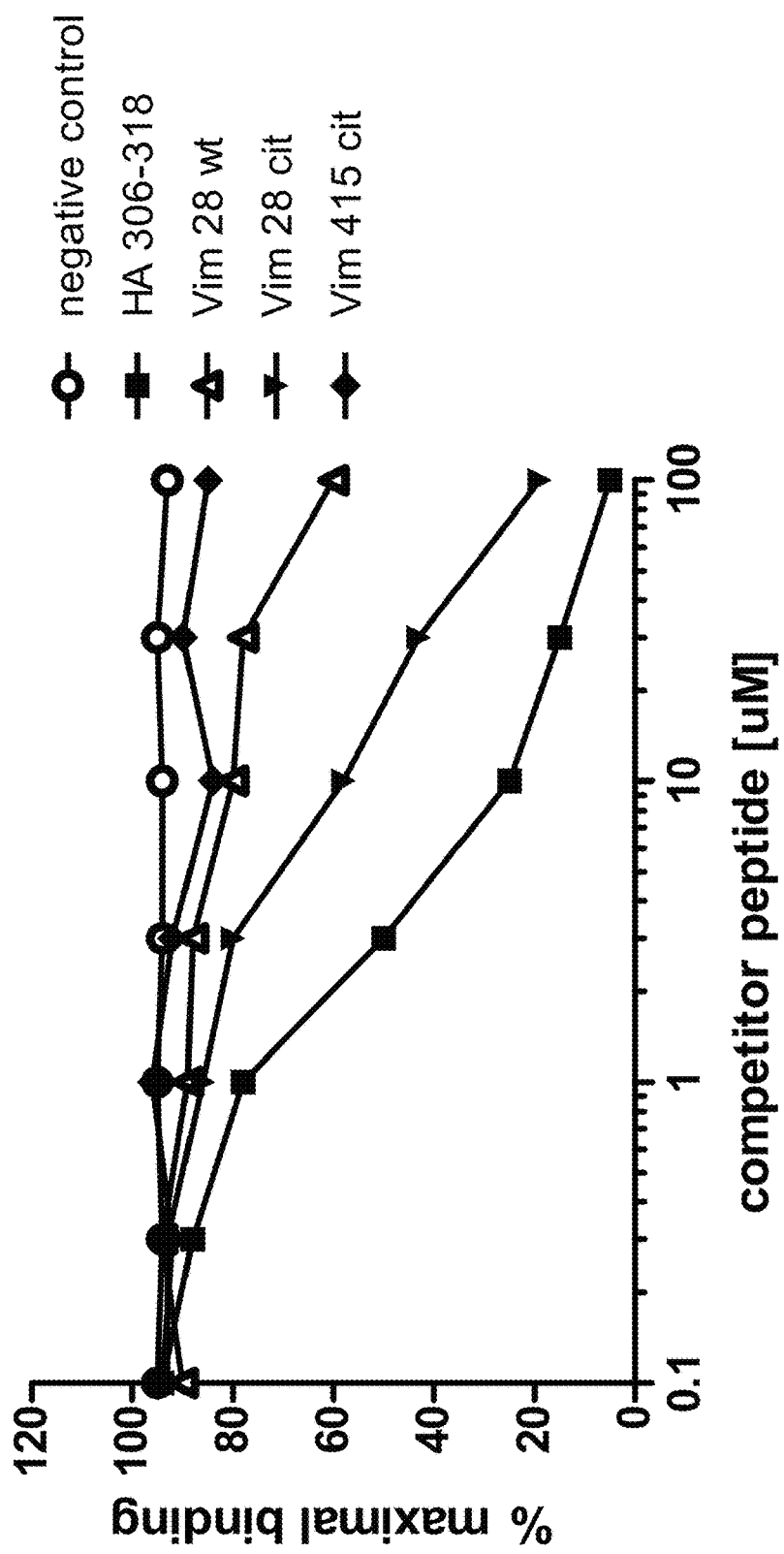

FIG. 12: Binding of vim 28-49, 415-433, vim 415-433 cit and vim 28-49 cit peptides to HLA-DR0401 in a competitive binding assay. Peptides were mixed with a predetermined concentration of biotinylated peptide from Influenza ($HA_{306-318}$) and then assayed for binding to purified HLA-DR0401. Unlabelled $HA_{306-318}$ peptide was used as positive control.

FIG. 13: Comparison of CD4 responses in HLA-DR4 transgenic mice elicited from immunisation with the human wild type and citrullinated vimentin 415 peptides. HLA-DR4 transgenic mice were immunised with 25 µg of vimentin 415 human wild type or citrullinated peptides at day 0. On day 14, splenocytes were analysed in vitro (a) against vimentin human 415 wild type and citrullinated peptides at 5 µM concentration by (i) IFNγ (ii) IL-17 (iii) IL-2 (iv) IL-10 elispot assays. (b) Avidity of epitope specific responses by measuring responses to increasing peptide concentration in IFNγ and IL-17 elispot assays. Responses are measured as average spots/million splenocytes.

FIG. 14: CD4 responses in HLA-DR4 transgenic mice elicited from immunisation with the human citrullinated vimentin 415 peptide and cross reactivity with the murine citrullinated peptide equivalent.

HLA-DR4 transgenic mice were immunised with 25 µg of vimentin 415-433 human citrullinated peptide at day 0. On day 14, splenocytes were analysed in vitro against human and murine vimentin citrullinated 415 peptides at 5 µM concentration by (i) IFNγ (ii) IL-17 elispot assays. Responses are measured as average spots/million splenocytes.

FIG. 15: Confirming that the T cell responses elicited in HLA-DR4 transgenic mice from immunisation with the human citrullinated vimentin 415 peptide (a) and citrullinated vimentin 28 peptide (b) are CD4 responses. HLA-DR4 transgenic mice were immunised with 25 µg of vimentin 415-433 human citrullinated peptide at day 0. On day 14, either whole splenocytes or CD4 depleted splenocytes were analysed in vitro against human vimentin citrullinated 415 or 28 peptides at 5 µM concentration in the presence or absence of L243 HLA-DR blocking antibody by IFNγ elispot assays. Responses are measured as average spots/million splenocytes.

FIG. 16: CD4 responses in HLA-DR4 and HLA-A2/DR1 transgenic mice elicited from immunisation with citrullinated vimentin 65 peptide.

HLA-DR4 (a) or HLA-A2/DR1 (b) transgenic mice were immunised with 25 µg of vimentin 65 citrullinated peptides at day 0. On day 14, splenocytes were analysed in vitro against vimentin human 65 wild type and citrullinated peptides at 5 µM concentration by IFNγ, IL-17 or IL-10 elispot assays. c) on day 14, whole splenocytes were analysed in vitro against human vimentin citrullinated 65 peptides at 5 µM concentration in the presence or absence of L243 HLA-DR blocking antibody by IFNγ elispot assays. Responses are measured as average spots/million splenocytes. d) Immunofluorescent staining and FACS analysis of splenocytes costained for CD8, IFNγ and TNFα. e) On day 14, splenocytes were stimulated in vitro with human citrullinated Vimentin 65 peptide pulsed LPS blasts. Six days post stimulation CTL lines were assessed by chromium release assay for ability to lyse T2 or B16HHD tumour cells pulsed with citrullinated human vimentin 65 peptide and T2 cells or B16HHD alone. Responses are measured as % cytotoxicity. P values indicated on graph are for the target to effector ratio 100:1) splenocytes from immunised mice were analysed in vitro against minimal predicted wild type and citrullinated HLA-A2 binding peptides vimentin 68 and 65 short as well as vimentin human 65 wild type and citrullinated peptides at 5 µM concentration by IFNγ elispot assay. g) splenocytes from immunised mice were assayed for responses to Vim 65 and Vim 68 cit and wild type peptides and EL4 HHD and B16 tumour target cells by IFNg elispot assay.

FIG. 17: Helper responses generated to murine vimentin 415-433 citrullinated peptide in the presence or absence of natural T regulatory cells.

HLA-DR4 transgenic mice were immunised with 25 µg murine vimentin 415-433 citrullinated peptide at day 0. T regulatory cell depletion was carried out using an anti-CD25 monoclonal antibody (PC61) three days prior to the immunisation. On day 14, splenocytes were analysed by IFNγ elispot assay against titrating concentrations of citrullinated murine vimentin 415 peptide.

FIG. 18: Adjuvants influence the Th1/Th17 balance in response to citrullinated vimentin 415 and 28 epitopes.

Human citrullinated vimentin 415-433 and 28-49 peptides (25 µg) in Alum, IFA, GMCSF, MPLA and CpG or TMX201 adjuvant was administered s.c. Fourteen days after immunisation splenocytes were analysed for specific responses to the helper epitope by (i) IFNγ, (ii) IL-17 and (iii) IL-10 elispot assays against wild type and citrullinated peptides and an irrelevant control. Responses are measured as spots/million splenocytes.

FIG. 19: Anti-CTLA-4 mab increases the avidity of the response to citrullinated vimentin 415 peptide.

HLA-DR4 transgenic mice were immunised with 25 µg of human citrullinated vimentin 415 peptide at day 0, 7 and 14. Half of the mice also received anti-CTLA-4 mab at days 7 and 14. On day 21, splenocytes were analysed in vitro against (i) citrullinated vimentin 415 at 5 µM concentration by IFNγ elispot assay. (ii) Avidity of epitope specific responses were measured to increasing peptide concentration in IFNγ elispot assay. Responses are measured as spots/million splenocytes.

FIG. 20: Proliferative responses of peripheral blood mononuclear cells (PBMC's) isolated from patients with cancer to wild type and citrullinated peptides.

PBMC's of patients were stimulated with 10 µg/ml of (i) wild type and citrullinated human vimentin 415-433 peptides (ii) wild type and citrullinated human vimentin 28-49 (iii) wild type and citrullinated human vimentin 65-77 wild type and citrullinated (iv) NYESO-1 119-143 peptides cultured for 4, 7 and 11 days. Lymphocyte proliferation was assessed by $^3$[H]-thymidine incorporation. Proliferative responses are depicted as stimulation index (SI). SI was calculated as the ratio of the mean cpm of peptide stimulated to the mean cpm of unstimulated cultures.

FIG. 21: a) Kaplan Meier survival of ovarian patients whose tumour express PAD2. b) Kaplan Meier survival of ovarian patients whose tumours express HMGB1 c) Kaplan Meier survival of ovarian patients whose tumours express PAD2 and HMGB1 d) Kaplan Meier survival of colorectal patients whose tumours express PAD4.

FIG. 22: HLA-DR4 transgenic mice were immunised on days 0, 7 and 14 with citrullinated human vimentin 415-433 peptide (b) or citrullinated vim 28-48 peptide (c) or both (a, d & e) in CPG and MPLA. A, On day 14, splenocytes were analysed in vitro against human vimentin citrullinated and non citrullinated 415 and 28 peptides at 5 µM concentration and B16DR4 tumour target cells induced into autophagy by serum starvation in presence or absence of 3-MA or CI-amidine by IFNγ elispot assay. B-E, Supernatant from ex vivo IFNγ elispot assay was analysed for presence of GranzymeB by elisa.

FIG. 23: In Vitro Killing of Tumour Cells (ai) HLA-DR4 transgenic mice were immunised on days 0, 7 and 14 with citrullinated human vimentin 415-433 peptide in CPG and MPLA. On day 19, splenocytes were stimulated in vitro with human citrullinated Vimentin 415-433 peptide pulsed blasts. Six days post stimulation CTL lines were assessed by chromium release assay for ability to lyse DR4 splenocytes pulsed with citrullinated human Vimentin 415-433 peptide, T2 DR4 tumour cells pulsed with citrullinated human vimentin 415-433 peptide and T2 DR4 cells alone. Responses are measured as % cytotoxicity. P values indicated on graph are for the target to effector ratio 10:1. P values for 20:1 and 40:1 are all highly significant P<0.0001. (aii) HHD/DR1 transgenic mice were immunised on days 0, 7 and 14 with citrullinated human vimentin 28-49 peptide in CPG and MPLA. On day 19, splenocytes were stimulated in vitro with human citrullinated vimentin 28-49 peptide pulsed blasts. Six days post stimulation CTL lines were assessed by chromium release assay for ability to lyse T2 DR1 tumour cells pulsed with citrullinated human vimentin 28-49 peptide, T2 DR1 cells alone and T2 cells alone. Responses are measured as % cytotoxicity. P values indicated on the graph are significant and for the target to effector ratio 12.5:1.

P values for 25:1 (T2DR1 P=0.0017, T2 DR1+vim28 cit P<0.0001) and 50:1 (T2DR1 P=0.0008, T2 DR1+vim28 cit P=0.0005) are all highly significant.

FIG. 24: Citrullinated Vimentin 415-433 and vim 28-49 CD4 responses influences anti-tumour immune responses.

HLA-DR4 transgenic mice were injected on day 0 with $2.5 \times 10^4$ B16F1-DR4 cells. (a) Mice were immunised via gene gun at days 4, 11 and 18 with control antibody DNA or the antibody DNA vaccine encoding the HLA-DR4 restricted vim415 helper epitope in CDRH3 or With murine citrullinated vimentin 415-433 peptide (25 µg) in CpG and MPLA adjuvant administered s.c. (i) (b) Mice were immunised via gene gun at days 4, 11 and 18 with control antibody DNA or the antibody DNA vaccine encoding the HLA-DR4 restricted vim28 helper epitope in CDRH3 or with citrullinated or wildtype vimentin 28-49 peptide (25 µg) in CpG and MPLA adjuvant administered s.c. (c) Mice were immunised with citrullinated vimentin 415-433 peptide (25 µg) or vimentin 28-49 peptide (25 µg) or both in CpG and MPLA adjuvant administered s.c. (d) Mice were immunised with citrullinated vimentin 415-433 peptide (25 µg) in CpG and MPLA adjuvant administered s.c. in combination with anti-CD4 antibody (clone GK1.5). (e) Mice were immunised with citrullinated vimentin 28-49 peptide (25 µg) in CpG and MPLA adjuvant administered s.c. in combination with anti-CD4 antibody (clone GK1.5).

FIG. 25: Citrullinated Vimentin 415-433 and vimentin 28-49 anti-tumour immune responses are mediated in part by IFNγ and IL-17.

HLA-DR4 transgenic mice were injected on day 0 with $2.5 \times 10^4$ B16F1-DR4 cells. Mice were immunised sc with (a and c) citrullinated vimentin 415-433 peptide (25 µg) or (b and d) citrullinated vimentin 28-49 peptide (25 µg) in CpG and MPLA adjuvant in the presence or absence of IFNγ neutralising monoclonal antibody (a and b) or IL-17 neutralising antibody (c and d).

FIG. 26: Citrullinated Vimentin 415-433 but not vimentin 28-49 anti-tumour immune responses are mediated in part by direct recognition of HLA-DR0401 on the tumour cells.

HLA-DR4 transgenic mice were injected on day 0 with $2.5 \times 10^4$ B16F1 cells (a) or B16F1-DR4 cells (b). Mice were immunised sc with (a) citrullinated vimentin 415-433 peptide (25 µg) or vimentin 28-49 peptide (25 µg) or both in CpG and MPLA adjuvant. (b) vimentin 415-433 peptide (25 µg) in CpG and MPLA adjuvant in the presence or absence of HLA-DR0401 neutralising monoclonal antibody.

FIG. 27: Homology of Vimentin within different species.

FIG. 28: Screening vimentin for novel epitopes that stimulate T cells responses. Human citrullinated vimentin peptides (3×10 µg) in MPLA and CPG adjuvant were administered s.c. Fourteen days after immunisation splenocytes were analysed for specific responses to the helper epitopes by (i) IFNγ and (ii) IL-17 elispot assays against helper peptide and an irrelevant control in a) HLA-A2/DR1 and b) C57/B1 mice. C) citrullinated vim 14 peptide in MPLA and CpG adjuvant was administered s.c. Fourteen days after immunisation splenocytes were analysed for specific responses to the helper epitope by IFNγ elispot. Responses are measured as spots/million splenocytes.

FIG. 29: Screening cytokeratin 8 for novel epitopes that stimulate T cells responses. Human citrullinated cytokeratin peptides (3×10 µg) in MPLA and CPG adjuvant were administered s.c. Fourteen days after immunisation splenocytes were analysed for specific responses to the helper epitopes by (i) IFNγ and (ii) IL-17 elispot assays against helper peptide and an irrelevant control in a) HLA-A2/DR1 and b) C57/B1 mice. Responses are measured as spots/million splenocytes.

Figure 30:
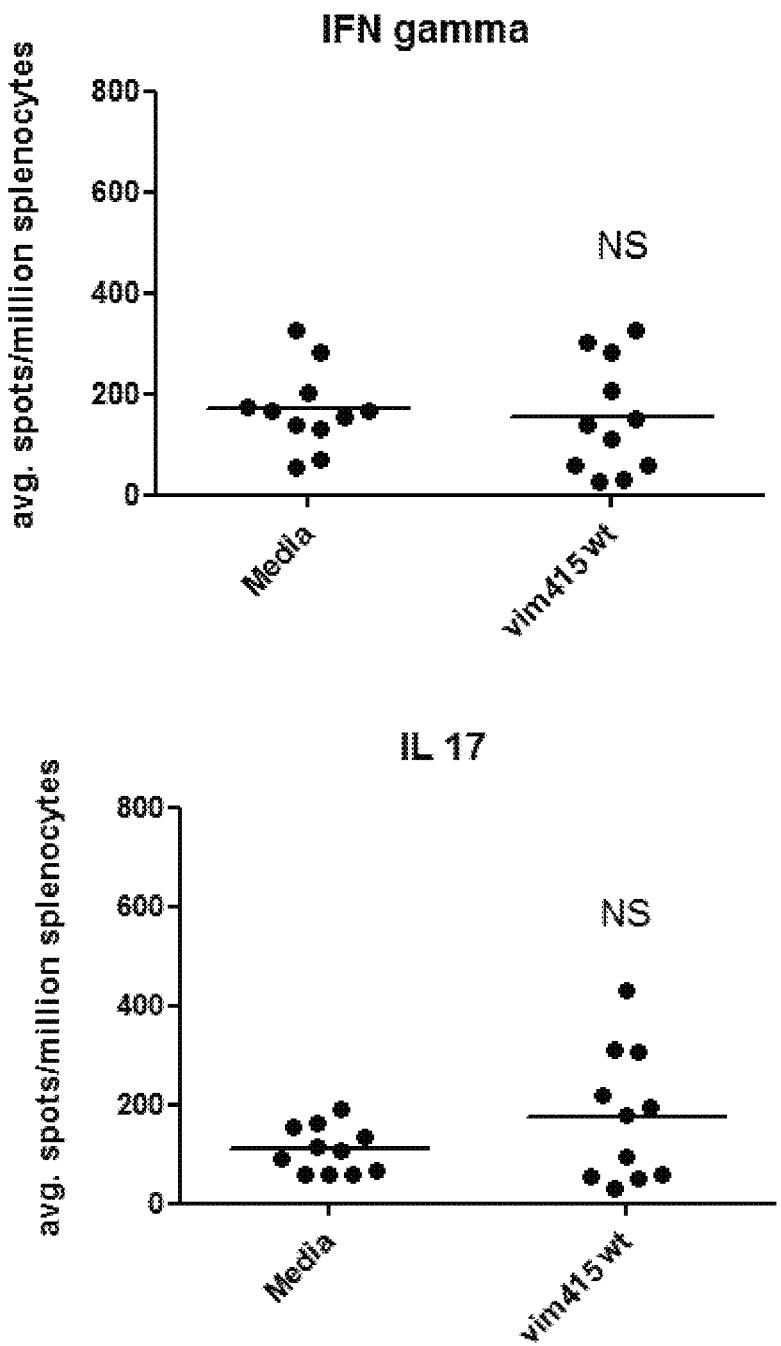
Figure 30:
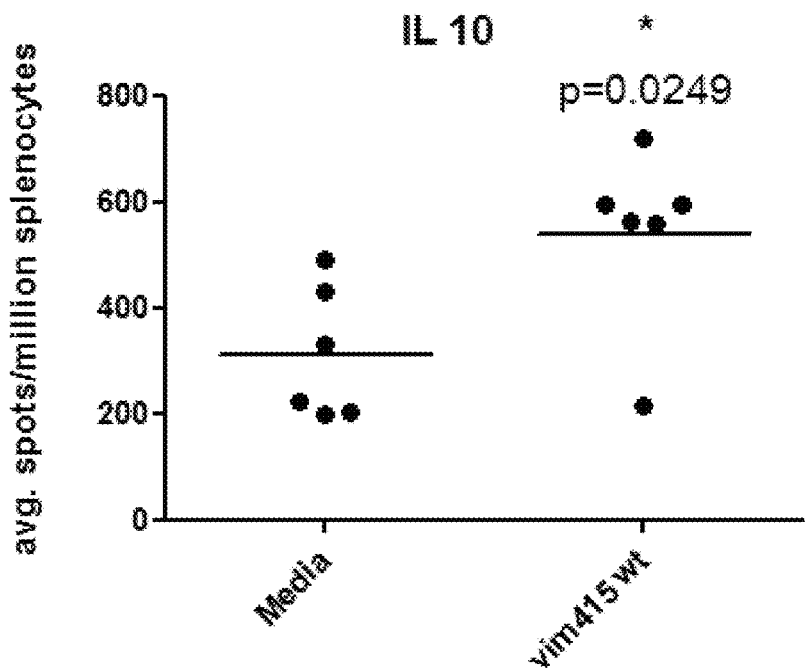

FIG. 30: Wild type vimentin stimulates iTreg cells responses that secrete IL-10. Human 415 vimentin peptide (25 µg) in MPLA and CPG adjuvant was administered s.c. Fourteen days after immunisation splenocytes were analysed for specific responses to the helper epitopes by (i) IFNγ, (ii) IL-17 and (iii) IL-10 elispot assays against helper peptide and an irrelevant control in HLA-DR4 mice. Responses are measured as spots/million splenocytes.

Figure 31:
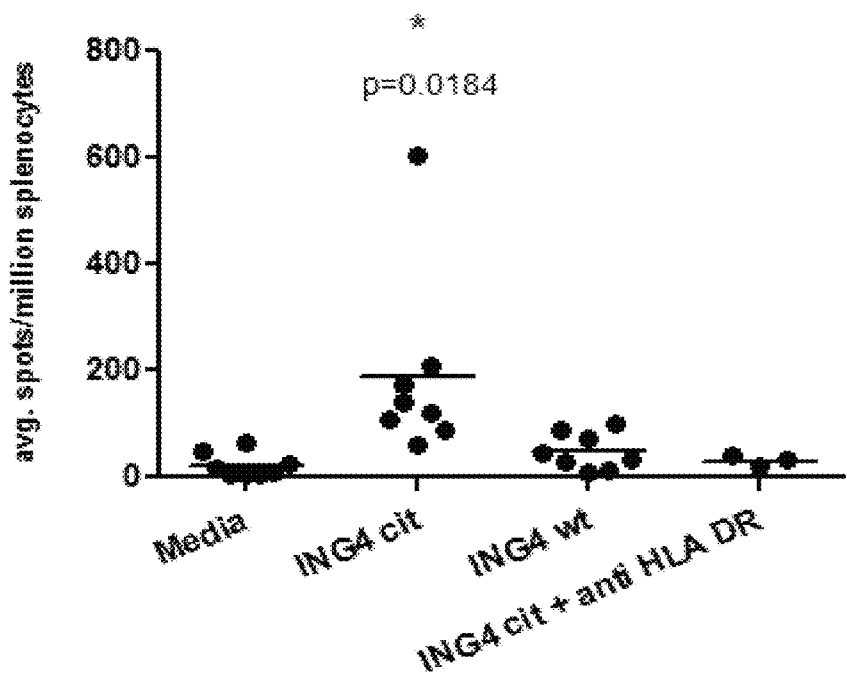

FIG. 31: Citrullinated ING4 stimulates CD4 responses.

Citrullinated ING4 peptide 158-174 peptide (25 µg) in MPLA and CPG adjuvant was administered s.c on days 0, 7 and 14. Seven days after the last immunisation splenocytes were analysed for specific responses to the helper epitopes by IFNγ elispot assays against helper peptide in the presence or absence of an HLA-DR blocking monoclonal antibody in HLA-A2/DR1 mice. Responses are measured as spots/million splenocytes.

FIG. 32: Uniprot references for proteins from which epitopes useful in the present invention can be derived.

FIG. 33: Whole antigen vimentin DNA induces citrullinated vimentin specific T cell responses. HLA-DR4 transgenic mice (a) or HLA-A2/DR1 transgenic mice (b) were immunised with 1 µg DNA encoding whole murine vimentin sequence via gene gun on days 0, 7 and 14. On day 20 splenocytes were analysed for IFNγ responses to a panel of citrullinated vimentin peptides spanning the whole protein by elispot assay. Responses are measured as spots/million splenocytes.

Figure 34:
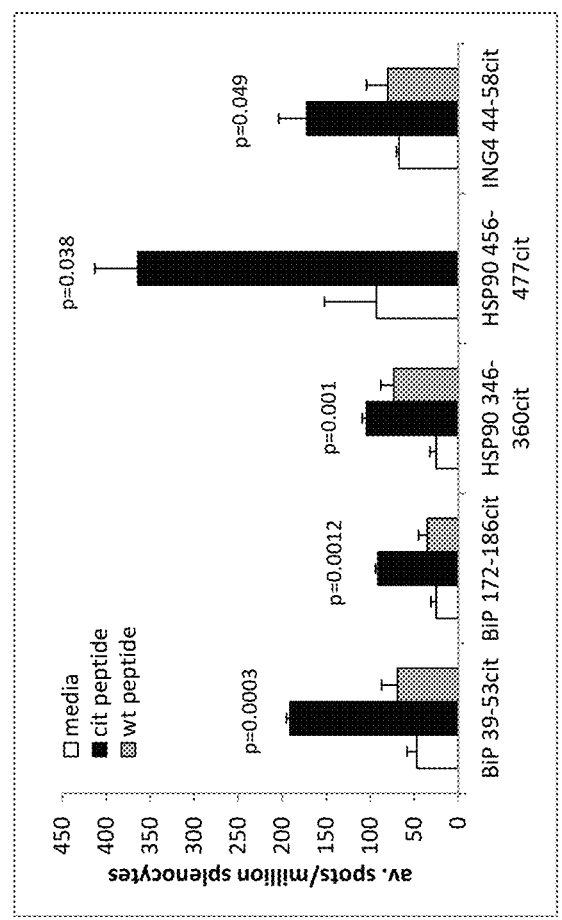

FIG. 34: Screening of predicted peptides for citrulline specific immune responses. Predicted citrullinated peptides (25 µg) from BiP, HSP90 and ING4 were administered s.c. in CpG and MPLA adjuvant at days 0 or 0, 7 and 14 into HLA-DR4 transgenic mice. Splenocytes were analysed for immune responses at day 14 or 20 by IFNg elispot assay against relevant citrullinated and unmodified peptides (5 uM) and background control. Responses are measured as average spots/million splenocytes.

METHODS 2.1. Commercial mAbs

The primary rabbit anti-human Vimentin (clone EPR3776), rabbit anti-human PAD2 (clone pab0197), rabbit anti-human citrulline (clone ab6464) were all purchased from Abcam. The primary rabbit anti-human PAD-4 (clone pab 0199) was obtained from Covalab and the anti-human HLA-DR PE-Cy7 conjugated antibody (clone L243) from eBioscience. Anti-CD25 antibody (clone PC61), anti-IFNγ antibody (clone XMG1.2), anti-IL-17 (clone 17F3) antibody and anti-CD4 (clone GK1.5) antibody were purchased from BioXcell. Anti-CTLA4 antibody was purified from HB304 hybridoma cells culture supernant (ATCC, USA) by sephorose protein G affinity chromatography. Anti-HLA-DR antibody (clone L243) was purified from HB-55 hybridoma cells (ATCC, USA) culture supernatant by sepharose protein G affinity chromatography. Rabbit mAb anti HMGB1 (clone D3E5) was purchased from Cell Signaling Technology.

2.2. Cell Lines

The T cell/B cell hybrid cell line T2 [80] stably transfected with functional class II DR4 (DRB1*0401; T2 DR4) or DR1 (DRB1*0101; T2DR1) have been described [82, 83] and was kindly provided by Dr. Janice Blum and Professor Lawrence Stern. The murine melanoma B16F1 and B16F10 cell lines were obtained from the ATCC. All cell lines were cultured in RPMI medium 1640 (GIBCO/BRL) supplemented with 10% FCS, L-glutamine (2 mM) and sodium bicarbonate buffered unless otherwise stated. HB304 hybridoma cells were cultured in Hybridoma SFM (Invitrogen, UK).

To generate tumour targets presenting citrullinated epitopes for in vitro assays cells were treated with 0.1M citric acid (pH3.0) containing 1% BSA at 4° C. for 2 mins. Cells were subsequently washed with media and cultured in absence of serum for 20 hrs at 37° C. Autophagy and PAD inhibitors, 3-methyladenine (Sigma) and Cl-amidine (Calbiochem), were added for the 20 hr culture in serum free media at final concentrations of 10 mM and 50 µg/ml respectively.

2.3. Immunogens 2.3.1. Peptides

Peptides >90% purity were synthesized by Peptide Synthetics (Fareham, UK). Stored lyophilized in 0.2 mg aliquots at −80° C. On day of use they were reconstituted to the appropriate concentration in 10% dimethyl formamide.

2.4. Plasmids

Generation of antibody DNA constructs have been described in detail elsewhere [84]. In brief to generate the antibody DNA constructs, epitopes were incorporated into complementary determining regions of the heavy and light variable regions of the antibody chains using standard molecular biological techniques. The HLA-DR4 restricted helper CD4 epitopes from the epitopes tyrosinase 448-462 (DYSYLQDSDPDSFQD) (SEQ ID NO: 89), the murine and human gp100 44-59 epitope (WNRQLYPEWTEVQGSN (SEQ ID NO: 90)/WNRQLYPEWTEAQRLD) (SEQ ID NO: 91) and the I-Ab restricted epitope from HepB nucleoprotein 128-140 (TPPAYRPPNAPIL) (SEQ ID NO: 92) were inserted in replacement of CDRL1 of the kappa chain. Similarly the HLA-DR1 restricted helper CD4 epitopes from the epitopes MMPI 247-262 (SQDDIKGQKLYGKRS) (SEQ ID NO: 93), SSX2 33-48 (KEEWEKMKASEKIFY) (SEQ ID NO: 94), NYESO-1 87-111 (LLEFYLAMPFATPMEAELARRSLAQ) (SEQ ID NO: 95) and 119-143 (PGVLLKEFTVSGNILTIRLTAADHR) (SEQ ID NO: 4) were incorporated into CDRL1 while the modified epitope from epitope triosephosphate isomerise 23-37 (GELIGILNAAKVPAD) (SEQ ID NO: 96) was inserted in replacement of CDRL3 of the kappa chain. The HLA-DR4 restricted CD4 vimentin 415-433 (LPNFSSLNLRETNLDSLPL) (SEQ ID NO: 97) and HLA-DR1 28-49 (RSYVTTSTRTYSLGSALRPSTS) (SEQ ID NO: 98) restricted epitopes were both incorporated into CDRH3. The DR1 CD4 NYESO-1 87-111(LLEFYLAMPFATPMEAELARRSLAQ) (SEQ ID NO: 95) was also encoded within the extended sequence 83-111 cloned into the CDRH3 site of the antibody DNA double expression vector. The human IgG1 and murine IgG2a ImmunoBody vectors containing all three vimentin epitopes were also generated. The HLA-DR1 28-49(RSYVTTSTRTYSLGSALRPSTS) (SEQ ID NO: 98), 65-77 (SAVRLRSSVPGVR) (SEQ ID NO: 59) and the HLA-DR4 restricted human CD4 vimentin 415-433(LPNFSSLNLRETNLDSLPL) (SEQ ID NO: 97) epitopes were incorporated into the CDRH1, CDRH2 and CDRH3 sites respectively.

The plasmid pVax1 Murine Vimentin full length was generated by amplification of the full length sequence using as a template cDNA from mRNA that had been isolated from the B16F1 cell line. Forward and reverse primers utilised were designed to incorporate a HindIII and BamHI site respectively. On amplification and confirmation of wild type sequence full length murine vimentin was incorporated into the HindIII/BamHI sites of the multiple cloning site within the mammalian expression vector pVaxI (Invitrogen).

To generate the plasmid pVitro 2 Chimeric HLA-DR401 cDNA was generated from mRNA isolated from the splenocytes of transgenic HLA-DR4 mice. This was used as a template to amplify the chimeric alpha and beta chains separately using forward and reverse primers that incorporated a fspI/EcoRI and BamHI/SalI sites respectively. On sequence confirmation full length chimeric alpha chain comprising of murine H2-Ea with human HLA-DRA alpha 1 domain was ligated into the fspI/EcoRI mcs2 of the vector pVITRO2-hygro-mcs (Invivogen). The beta chain comprising of murine H2-Eb with human DRB1*0401 Beta 1 domain was then inserted into the BamHI/SalI mcs1 of the vector alongside the chimeric alpha chain.

To generate the HHD plasmid cDNA was synthesized from total RNA isolated from EL4-HHD cells. This was used as a template to amplify HHD using the forward and reverse primers and subcloned into pCR2.1. The HHD chain, comprising of a human HLA-A2 leader, the human B2 microglobulin molecule covalently linked via a glycine serine linker to the the α 1 and 2 domains of human HLA-0201 MHC class 1 molecule and the α3, transmembrane and cytoplasmic domains of the murine H-2Db class 1 molecule, was then inserted into the EcoRV/HindIII sites of the mammalian expression vector pCDNA3.1 obtained from invitrogen.

To construct the mammalian double expression plasmid that encodes murine Tap2 and NYESO-1 full length chains, NYESO-1 was amplified from the IMAGE clones 40146393 obtained from geneservice with forward and reverse primers that incorporated a BamH1/XhoI site respectively. On sequence confirmation full length NYESO-1 was ligated into the BamHI/XhoI multiple cloning site of the antibody DNA double expression vector in replacement of the light chain. Murine Tap2 was amplified from the image clone 6530488 after removal of a HindIII site from encoding sequence and incorporation of this site before the start codon, and cloned into the expression vector pOrigHIB using HindIII/EcoRV. Murine Tap2 was then transferred in replacement of the heavy chain using HindIII/AvrII into the double expression vector alongside full length NYESO-1.

In order to knockdown expression of murine B2 microglobulin and murine MHC class II in the cell line B16F10 RNA interference was utilized. Complimentary oligos that target sequence 266 of murineB2 microglobulin and 159 of murine MHC class II were annealed and inserted separately into pCDNA6.2 GW miR (Invitrogen). The pre-miRNA expression cassette containing miRNA 266 was excised using BamHI/XhoI and ligated into the XhoI/BglII site of pCDNA6.2 GW miR 159 in order to chain the two miRNA's and express them in one primary transcript within the same vector.

Endotoxin free plasmid DNA was generated using the endofree Qiagen maxiprep kit (Qiagen, Crawley).

2.5. Transfection

B16F10 cells were transfected successively using Lipofectamine transfection reagent with expression vectors encoding full length NY-ESO-1and Murine Tap2, HHDII and a siRNA to knockdown expression of murine MHC class II and murine β2 microglobulin. Transfected cells were selected by growth in the presence of Zeocin (300 µg/ml), G418 (500 µg/ml) and Blasticidin (4 µg/ml) respectively. Lines were cloned by limiting dilution and expression was confirmed by flow cytometry.

B16F1 cells were transfected using the Lipofectamine transfection reagent (Invitrogen) with 4 µg of the plasmid pVitro 2 Chimeric HLA-DR401 that encodes both full length chimeric alpha and beta chains according to the manufacturer's instructions. Transfected cells were selected by growth in the presence of Hygromycin B (200 µg/ml). Lines were cloned by limiting dilution and expression was confirmed by flow cytometry using the anti-human HLA-DR PE-Cy7 conjugated antibody (clone L243) from eBioscience.

2.6 HLADR0401 Binding Studies

In brief, peptides of interest were mixed with a predetermined concentration biotinylated $HA_{306-318}$ reference peptide at increasing concentrations and added to plate bound HLA DR0401. Amounts of biotinylated reference peptide binding to HLA DR0401 was quantified using streptavidin linked enzyme step followed by detection with chromogenic substrate. Maximal binding is taken as the value achieved by biotinylated $HA_{306-318}$ peptide alone. As a positive control unlabelled $HA_{306-318}$ peptide was used to compete with the biotinylated version.

2.7. Immunisations 2.7.1. Immunisation protocol

C57BL/6 mice (Charles River, UK), HLA-DR4 mice (Taconic, USA), HHDII mice (Pasteur institute, France) and HHDII/DR1 mice (Pasteur institute, France) were used, aged between 8 and 12 weeks, and cared for by the staff at Nottingham Trent University. All work was carried out under a Home Office project licence. Peptides were dissolved in 10% Dimethylformamide to 1 mg/ml and then emulsified (a series of dilutions) with different adjuvants: CpG and MPLA 6 µg/mouse of each (Invivogen, UK), Incomplete Freund's 50 µl/mouse (Sigma, UK), and GMCSF 10 µg/mouse (Peprotech, UK). Peptides (25 µg/mouse) were injected subcutaneously at the base of the tail. DNA (1 µg/mouse) was coated onto 1.0 µm gold particles (BioRad, Hemel Hempstead, UK) using the manufacturer's instructions and administered intradermally by genegun (BioRad). Homspera (10 nM/mouse) (PeptideSynthetics, UK) was injected intradermally with genegun immunisation. Mice were immunized at either day 0 for peptide immunisation or days, 0, 7, and 14 for peptide and genegun immunisation. Spleens were removed for analysis at day 14 for peptide and day 20 for peptide or genegun immunisation unless stated otherwise. 400 µg Anti-CD25 antibody (PC61) was administered i.p. in saline 3 days prior to the immunisation. 200 µg Anti-CTLA-4 antibody (UC10-4F10-11) was administered i.p. in saline at day 7 and 14 with either genegun or peptide immunisation.

For tumour challenge experiments mice were challenged with $2.5\times10^4$ B16 HHDII NYESO/TAP2 siβ2m 1F10 cells or B16 DR4 2E7 cells subcutaneously on the right flank 3 days prior to primary immunisation and then were immunised as above. Anti-IFNγ antibody (300 µg/dose), anti-IL-17 antibody (200 µg/dose) and anti-HLA-DR antibody (300 µg/dose) were administered i.p. in saline at days 2, 7, 11 and 14 post tumour implant. Anti-CD4 antibody (500 µg/dose) was administered i.p.in saline at days 2 and 8 post tumour implant. Tumour growth was monitored at 3-4 days intervals and mice were humanely euthanized once tumour reached ≥10 mm in diameter.

2.8. Analysis of Immune Response 2.8.1. Ex Vivo Elispot Assay

Elispot assays were performed using murine IFNγ, IL-17 and IL-10 capture and detection reagents according to the manufacturer's instructions (Mabtech, Sweden). In brief, anti-IFNγ, IL-17 and IL-10 antibodies were coated onto wells of 96-well Immobilin-P plate. Synthetic peptides (at a variety of concentrations) and $5\times10^5$ per well splenocytes were added to the wells of the plate in triplicate. Tumour target cells were added where relevant at $5\times10^4$/well in triplicate and plates incubated for 40 hrs at 37° C. After incubation, captured IFNγ, IL-2, IL-17 and IL-10 were detected by biotinylated anti-IFNγ, IL-17 and IL-10 antibodies and developed with a strepatavidin alkaline phosphatase and chromogenic substrate. Spots were analysed and counted using an automated plate reader (Cellular Technologies Ltd). Functional avidity was calculated as the concentration mediating 50% maximal effector function using a graph of effector function versus peptide concentration.

2.8.2 Ex Vivo Depletion of CD8 and CD4 Cells from Splenocyte Cultures

Splenocytes were subject to positive isolation of CD4 or CD8 cells using antibody coated magnetic beads (Miltenyi Biotech) according to manufacturer's instructions. For MHC class II blocking studies 20 µg/ml anti-HLA-DR (clone L243) antibody was added to elispot assays.

2.8.3 Granzyme B Elisa

Supernatant from ex vivo IFNγ elispot assays on splenocytes was removed after 40 hrs and assessed for Granzyme B by elisa assay (R&D systems) according to manufacturer's instructions.

2.8.4 Luminex Multiplexed Assay

A three-step indirect procedure was used for the multiplexed Luminex assay (Invitrogen) for IgG antibodies to IL-10, IL-17, IFNγ, TNFα, IL-2 & IL-4. Standard, control, and unknown sera were diluted 1:2 in 50% assay diluent buffer (Invitrogen) & 50% serum free RPMI. Serial standard dilutions were included in each assay. Each dilution of standard, control, and unknown sera was mixed with a set of coupled Luminex microspheres in 96-well filtration plates (Millipore Multiscreen; Millipore Corporation, Bedford, Mass.) and incubated for 2 hours at room temperature with shaking. Microspheres were collected by vacuum filtration and washed with PBST. Biotinylated detector antibody was added to each well for 1 hour at room temperature with shaking. Microspheres were collected by vacuum filtration and washed with PBST. Streptavidin conjugated R-phycoerythrin-was added to each well. Following a 30 min incubation and a wash step, microspheres were resuspended in PBST, and read in a Biorad BioPlex Luminex analyzer equipped with an XY platform. Data acquisition and analysis performed with Luminex software (BioPlex Systems).

2.8.5 Proliferation Assay

PBMC were isolated from freshly drawn heparinised blood by Ficol-Hypaque (Sigma) gradient centrifugation. PBMC ($1.5\times10^6$ cells/well) were stimulated with single peptides (final concentration 10 µg/ml) in RPMI containing 5% pooled autologous human serum, 2 mM glutamine, 20 mM HEPES and Penicillin-streptomycin (1%) in a final volume of 2 ml. Stimulation with purified protein derivative, PPD (final concentration 10 μg/ml) served as a positive control for the proliferative capacity of PBMC. As a negative control PBMC were incubated with medium alone. The PBMC were cultured at 37° C. in an atmosphere of 5% $CO_2$ for 4, 7 and 11 days. To assess proliferation at these times points 100 μl in triplicate from each culture was aliquoted into a round bottom well of a 96 well plate and $^3$H-thymidine added (0.0185 MBq/well) and incubated at 37° C. for a further 8 hours. The cultures were harvested onto unifilter plates and incorporation of $^3$H-thymidine was determined by n-scintillation counting. The results were assessed by calculating the stimulation index (SI) as the ratio of the mean of counts per minute (cpm) of epitope-stimulated to the mean of unstimulated cultures. The proliferative assay was considered positive when SI>2.5.

2.8.6 $^{51}$Cr-Release Assay

Target cells were labelled for 1 hr with 1.85 MBq sodium ($^{51}$Cr) chromate (Amersham, Essex, UK) with or without 10 μg/ml peptide. Post incubation they were washed 3 times in RPMI. Targets $5\times10^3$/well of a 96-well V-bottomed plates were set up and co incubated with different densities of effector cells in a final volume of 200 μl of RPMI, 10% FCS (Sigma), 20 mM HEPES buffer, 2 mM L-glutamine, 100 units/ml penicillin and 100 μg/ml streptomycin. After 20 hrs at 37° C., 50 μl of supernatants were removed from each well and transferred to a Lumaplate (Packard, Rigaweg, the Netherlands). Plates were read on a Topcount Microplate Scintillation Counter (Packard). Percentage specific lysis was calculated using the following formula: specific lysis=100× [(experimental release-spontaneous release)/(maximum release-spontaneous release)]

2.9 Immunohistochemical Analysis

Tissue array sections were first deparaffinised with xylene, rehydrated through graded alcohol and immersed in methanol containing 0.3% hydrogen peroxide for 20 mins to block endogenous peroxidase activity. In order to retrieve antigenicity, sections were immersed in 500 ml of pH6.0 citrate buffer and heated for 20 mins on the 6$^{th}$ sense setting of a microwave. Endogenous avidin/biotin binding was blocked using an avidin/biotin blocking kit (Vector Labs). In order to block non-specific binding of the primary antibody, all sections were then treated with 100 μl of ⅕ normal horse serum (NHS) in PBS for 15 mins. Test sections were incubated with 100 μl of primary antibody diluted in PBS for 1 hr at 22° C. or overnight at 4° C. Positive control tissue comprised whole sections of colorectal cancer tissue stained with β2-microglobulin at 1/1000 dilution (in PBS; Dako). The primary antibody was omitted from the negative control, which was left incubating in NHS. After washing with PBS, all sections were incubated with 100 μl of biotinylated goat anti-mouse/rabbit immunoglobulin (Dako) diluted 1:100 in NHS, for 30 mins. Sections were washed again in PBS and incubated with 100 μl of pre-formed streptavidin-biotin/HRP complex (Dako) for 60 mins at room temperature (RT). Subsequently, visualisation of epitope expression was achieved using DAB. Finally, sections were lightly counterstained with haematoxylin (Dako), dehydrated in alcohol, cleared in xylene (GentaMedica, York, UK) and mounted with distyrene, plasticizer and xylene (DPX; BDH).

Evaluation of staining: In order to allow permanent storage of the slides, they were imaged at ×20 using a NanoZoomer 2.0 slide imaging system (Hamamatsu, Higashi-ku, Japan). Expression of markers on the tissue was analysed using the images in the NanoZoomer Digital Pathology Virtual Slide Viewer (Hamamatsu). Screening of marker expression was performed concurrently by two investigators with previous experience of scoring, blinded to the clinical information. For H score, cores were briefly analysed and representative cores of negative, weak, moderate and strong cores were used as guides for the whole tissue micro-array (TMA). As well as the intensity of the staining, the percentage of positively stained tumour cells was estimated. The two scores were then combined to form the H score, where H=percentage cells stained X intensity (range=0-300). Using the NanoZoomer Slide Viewer, the area of both tumour and stroma were measured and number of positive cells in each area counted. A value of positive cells per $mm^2$ was then calculated.

2.9.1. Colorectal Tumour TMA

Antisera were screened for tumour binding on a gastric cancer TMA. Patient study and design: The study population comprised a series of 462 consecutive patients undergoing elective surgical resection of a histologically proven sporadic primary colorectal cancer at the University Hospital, Nottingham, UK (Table 1). These patients were treated between 1 Jan. 1994 and 31 Dec. 2000; this time period allowed meaningful assessment of the prognostic markers studied. All patients treated during this time-frame were considered eligible for inclusion in the study. Tumours were classified as mucinous carcinoma, when more than 50% of tumour volume consisted of mucin.

TABLE 1

Clinicopathological variables for colorectal TMA patient cohort (n = 462)

| Variable | Categories | Frequency of total cohort (%) |
|---|---|---|
| Gender | Male | 266 (58) |
|  | Female | 199 (42) |
| Age (years) | Median | 72 |
|  | Range | 58-93 |
| Status | Alive | 169 (37) |
|  | Dead | 293 (63) |
| Tumour Grade | Well differentiated | 29 (6) |
|  | Moderately differentiated | 353 (77) |
|  | Poorly differentiated | 71 (15) |
|  | Unknown | 8 (2) |
| Tumour Site | Colon | 238 (52) |
|  | Rectum | 181 (39) |
|  | Unknown | 43 (9) |
| TNM Stage | 0 ($T_{is}$) | 3 (1) |
|  | 1 | 69 (15) |
|  | 2 | 174 (28) |
|  | 3 | 155 (33) |
|  | 4 | 54 (12) |
|  | Unknown | 7 (2) |
| Extramural Vascular Invasion | Negative | 224 (48) |
|  | Positive | 128 (28) |
|  | Unknown | 110 (24) |
| Histological Type | Adenocarcinoma | 392 (85) |
|  | Mucinous carcinoma | 51 (11) |
|  | Columnar carcinoma | 4 (1) |
|  | Signet ring carcinoma | 7 (1) |
|  | Unknown | 8 (2) |

Clinicopathology: Only cases where the relevant pathological material was unavailable were excluded from the study. Follow-up was calculated from time of resection of the original tumour with all surviving cases being censored for data analysis at 31 Dec. 2003, this produced a median follow up of 37 months (range 0-116) for all patients and 75 months (range 36-116) for survivors.

A prospectively maintained database was used to record relevant clinicopathological data, with data provided from the UK Office for National Statistics; this was available in more than 99% of cases. The information collected was independently validated through case note review of deceased patients. Disease specific survival was used as the primary end point; however, data was also collected on the various other relevant clinical and histopathological parameters these are summarised in Table 2.3. Adjuvant chemotherapy consisting of FOLFOX was reserved for those patients with positive lymph nodes, although, surgical and adjuvant treatment was at the discretion of the supervising physician. Prior ethical review of the study was conducted by the Nottingham Local Research and Ethics Committee, who granted approval for the study.

Construction of the array blocks incorporated a wide spectrum of electively resected colorectal tumours and was found to be broadly representative of the colorectal cancer population in the UK. 266 (58%) patients were male and 196 (42%) female. The median age at the time of surgery was 72 years, consistent with a median age at diagnosis of colorectal cancer of 70-74 years in the UK [85]. 69 (15%) tumours arrayed were tumour, node metastasis (TNM) stage 1, 174 (38%) stage 2, 155 (34%) stage 3 and 54 (11%) stage 4; there were 3 cases of in-situ disease. These figures are comparable with national figures for distribution of stage 1-4 at diagnosis of 11, 35, 26 and 29% respectively [85]. The majority of tumours (392, 85%) were adenocarcinomas, and were most frequently of a moderate histological grade (353, 77%). 128 (28%) tumours were noted to have histological evidence of extramural vascular invasion, 224 (48%) had no evidence of vascular invasion, and this information was not available in 110 (24%) cases. At the time of censoring for data analysis 228 (49%) patients had died from their disease, 64 (14%) were deceased from all other causes, and 169 (37%) were alive. The median five-year disease-specific survival for the cohort was 58 months, comparable with the national average of approximately 45% five-year survival for colorectal cancer in the UK [86].

2.9.2. Ovarian Cancer TMA

Antisera were screened for tumour binding on an ovarian cancer TMA. The ovarian cancer TMA represents a cohort of 362 patients with primary ovarian cancer treated at Nottingham University Hospitals between 2000 and 2007. Staging of the cancers was performed using the International Federation of Obstetrics and Gynaecology (FIGO) criteria. All patients included in this study were treated according to the current standard chemotherapy regimens with either single agent carboplatin in 65 patients (41.4%) or platinum-based combination chemotherapy in 89 patients (56.7%), with 3 patients refusing chemotherapy. Platinum-resistant cases were defined as patients who progressed on first-line platinum chemotherapy during treatment or who relapsed within 6 months after treatment. All patients underwent surgery; over 44% of cases (n=69) were deemed to be sub optimally debulked (tumour remaining <1 cm) after initial surgery. Patients were followed-up by physical examination, computed tomography, and CA-125 levels. Haematoxylin and eosin-stained sections from the tumours of these patients were reviewed by a gynaepathologist blinded to the clinical data and pathological diagnosis. For each tumour, a review of its type and differentiation was also carried out by SD. Clinical data associated with each case was collected and recorded from the patients' notes or via the hospital's electronic records (NotIS). Such information included: patients' age at diagnosis, FIGO stage, extent of surgical cyto-reduction, and the type, duration and response to chemotherapy. Details of adjuvant treatment, disease-specific survival (DSS) and overall survival (OS) were documented for all patients. Survival was calculated from the operation date until 30th of May 2008 when any remaining survivors were censored. Median follow up was 36 months. Ethical approval to collect the samples and relevant data for the study was granted by the Nottinghamshire Local Research Ethics Committee.

2.9.3. Normal Tissue TMA

The normal tissue TMA contained 59 cores representing 38 normal organs. Each core was categorised according to the origin of the sample; normal tissue from a non-cancer patient, normal tissue from a cancer patient, but the cancer involves an unrelated organ, normal tissue adjacent to the cancer. The tissue type and category is detailed in Table 2.

TABLE 2

Details of normal tissue TMA and tissue type

| Tissue type | Age | Gender |
|---|---|---|
| Placenta | 29 | F |
| Esophagus | 23 | M |
| Rectum | 24 | F |
| Gallbladder | 24 | M |
| Skin | 83 | F |
| Adipose | 26 | M |
| Heart | 27 | M |
| Skeletal | 26 | M |
| Bladder | 36 | F |
| Ileum | 62 | M |
| Spleen | 30 | M |
| Brain | 68 | M |
| Jejunum | 56 | M |
| Stomach | 66 | M |
| Breast | 27 | F |
| Kidney | 56 | M |
| Testis | 32 | M |
| Cerebellum | 73 | F |
| Liver | 30 | M |
| Thymus | 28 | M |
| Cervix | 30 | F |
| Lung | 24 | M |
| Smooth Muscle | 23 | M |
| Colon | 28 | M |
| Ovary | 50 | F |
| Tonsil | 28 | F |
| Diaphram | 26 | M |
| Pancreas | 50 | M |
| Uterus | 40 | F |
| Duodenum | 24 | M |
| Thyroid | 26 | M |

Example 1. CD4 Responses in Wild Type Mice to Self and Foreign Epitopes

T cell responses to tumour associated epitopes are often weak or non-existent due to tolerance and T cell deletion within the thymus. Nonetheless we screened a variety of self and foreign CD4 epitopes for their ability to stimulate helper responses. As previous studies have shown that antibody DNA constructs gave the strongest immune responses [84], a variety of CD4 foreign and self-epitopes were incorporated into separate constructs and screened in wild type mice. Table 3 lists the sequences of all the epitopes and their mouse homologs where appropriate.

TABLE 3

| | CD4 epitopes | | | | |
|---|---|---|---|---|---|
| | SEQUENCE | COORDINATE | CORE | SYMPATHEI SCORE | HLA |
| | | Self | | | |
| Murine gp100 | WNRQLYPEWTEVQGSN (SEQ ID NO: 90) | 44-59 | LYPEWTEVQ (SEQ ID NO: 99) | 26 | DR4 |
| Vimentin 65-77 | SAVRLRSSVPGVR (SEQ ID NO: 59) | 65-77 | VRLRSSVPG (SEQ ID NO: 57) | 23 | DR1 |
| Vimentin 28-49 | RSYVTTSTRTYSLGSALRPSTS (SEQ ID NO: 98) | 28-49 | TYSLGSALR (SEQ ID NO: 100) YVTTSTRTY (SEQ ID NO: 101) | 27/20 | DR1 DR4 |
| | | Self in core regions | | | |
| Vimentin 415-433 | LPNFSSLNLRETNLDSLPL (SEQ ID NO: 61) | 415-433 | FSSLNLRET (SEQ ID NO: 60) | 26 | DR4 |
| ING4 158-174 | AQKKLKLVRTSPEYGMP (SEQ ID NO: 21) | 158-174 | QKKLKLVRT (SEQ ID NO: 20) LKLVRTSPE (SEQ ID NO: 22) KKLKLVRTS (SEQ ID NO: 23) | 22 20 | DR1 DR4 |
| | | Foreign in core regions | | | |
| Human gp100 | WNRQLYPEWTEAQRLD (SEQ ID NO: 91) | 44-59 | LYPEWTEAQ (SEQ ID NO: 102) | 26 | DR4 |
| MMP-7 247-262 | SQDDIKGIQKLYGKRS (SEQ ID NO: 2) | 247-262 | IQKLYGKRS (SEQ ID NO: 1) | 35 | DR1 |
| Tyrosinase | DYSYLQDSDPDSFQD (SEQ ID NO: 89) | 448-462 | YLQDSDPDS (SEQ ID NO: 103) | 22 | DR4 |
| mTPI | GELIGILNAAKVPAD (SEQ ID NO: 96) | 23-37 | IGILNAAKV (SEQ ID NO: 104) | 36 | DR1 |
| NYESO-1 87-111 | LLEFYLAMPFATPMEAELARRSLAQ (SEQ ID NO: 95) | 87-111 | FYLAMPFAT (SEQ ID NO: 105) | 26/22 | DR1 |
| NYESO-1 119-143 | PGVLLKEFTVSGNILTIRLTAADHR (SEQ ID NO: 4) | 119-143 | ILTIRLTAA (SEQ ID NO: 5) NILTIRLTA (SEQ ID NO: 106) | 23/22 | DR1 DR4 |
| SSX2 34-48 | KEEWEKMKASEKIFY (SEQ ID NO: 94) | 34-48 | WEKMKASEK (SEQ ID NO: 107) | 26 | DR1 |
| Hepatitis B Nucleoprotein | TPPAYRPPNAPIL (SEQ ID NO: 92) | 128-140 | YRPPNAPIL (SEQ ID NO: 108) | | I-Ab (helper) |

Arginine residues are underlined
Non homologous residues are in italics

FIG. 5 shows good CD4 responses to most of the foreign CD4 epitopes but not to self-epitopes. The Hepatitis B nucleoprotein 128-140, CD4 I-Ab helper epitope showed a response by ELISPOT of 50-1,000/million splenocytes (mean 382/million splenocytes) in C57B1 mice. The cancer testes epitope NYESO-1 and SSX2 are foreign epitopes in mice and the DR1 epitopes NYESO-1 (87-111) and SSX2 (34-48) stimulated good responses in HLA-DR1 transgenic mice; NYESO-1 (87-111) 250-900/million splenocytes (mean 567/million splenocytes) and SSX2 (34-48) 500-1200/million splenocytes (mean 765/million splenocytes). The HLA-DR1 mutated TPI epitopes which only differs from the wild type by one amino acid shows a response of 300-1300/million splenocytes. The human gp100 HLA-DR4 epitope 44-59 has one amino acid change from the homologous mouse epitope and shows responses of 263-1521/million splenocytes (median 745/million splenocytes). In contrast, the homologous mouse self-epitope failed to stimulate a response in HLA-DR4 transgenic mice. The human HLA-DR4 tyrosinase epitope has 6 amino acid changes from the homologous mouse epitope and shows responses of 405-832/million splenocytes (median 555/million splenocytes). The HLA-DR1 MMP7 247-262 epitope has 4 amino acid changes between mice and human, one of which is predicted to be in the core MHC binding/TCR recognition region (Table 3). This epitope failed to stimulate a response above background in HLA-DR1 transgenic mice. The HLA-DR4 vimentin 415-433 epitope has two amino acid differences between human and mouse but these are not predicted to be in the core MHC binding/TCR recognition region (Table 3). It failed to stimulate a response in wild type HLA-DR4 transgenic mice. In contrast, vimentin 28-49, is homologous in mice and humans and is a true self epitope which stimulates a response of 200-500/million splenocytes (mean 390/million splenocytes) in HLA-DR4 transgenic mice. This response was intriguing and led us to try and explain why there was no deletion/tolerance to this epitope.

Example 2. DNA Immunisation Result in Responses to Citrullinated Vim 28, Vim 915, MMP7, and NY-ESO-1

RA patients have been shown to make T cell responses to citrullinated vimentin epitopes. As APCs can constitutively citrullinate epitopes it was possible that the antibody DNA constructs were being citrullinated and this was stimulating the response. HLA-DR4 transgenic mice were therefore immunised with an antibody-DNA construct encoding the self-vim 28 epitope. Stimulated T cells from these mice were screened in vitro for IFNγ, IL-17 and IL-2 responses to both citrullinated and uncitrullinated vim 28 peptide. FIG. 6 shows that although mice responded as assayed by ELISPOT to the wild type peptide by production of all three cytokines (mean: IFNγ 400, IL-17 120 and IL-2 150/million splenocytes) responses to the citrullinated peptide were significantly higher for IFNγ and IL-17 (mean: IFNγ 1250/million splenocytes; p=0.0046, IL-17 250/million splenocytes; p=0.0392 but not for IL-2 250/million splenocytes. To see if similar responses were generated to the vim 415 epitope antibody, DNA constructs were used to immunise mice (FIG. 7). In contrast to vim 28-49 and in agreement with our original observation, there were no responses to wild type vim 415-433 but strong responses to the citrullinated peptide and the responses to IL-17 were as strong as the IFNγ responses (mean: IFNγ 400/million splenocytes; p=0.0067, IL-17 350/million splenocytes; p=0.002 and IL-2 250/million splenocytes; p=0.0056). This confirms that when the antibody DNA is translated it is citrullinated.

In contrast, when MMPI 247-262 was incorporated into a DNA vaccine (FIG. 8), no IFNγ responses were seen to either the wild type or citrullinated peptide but significant IL-17 responses where seen to both wild type (mean: 312/million splenocytes; p=0.0061) and citrullinated peptides (mean: 309/million splenocytes; p=0.0267).

When mice were injected with B16 HHDII NYESO-1 tumour cells and then immunised with NYESO-1 119 incorporated into an antibody-DNA vaccine (FIG. 9) with or without the homspera adjuvant, IFNγ responses were only seen to the citrullinated but not the wild type peptide and this was accompanied by an anti-tumour response.

As antigen presenting cells can constitutively citrullinate epitopes it was interesting to see if citrullinated self-epitope specific responses could be induced using full length antigen delivered as a DNA vaccine. HLA-DR4 transgenic mice were therefore immunised with DNA construct encoding the whole murine vimentin antigen. Stimulated T cells from these mice were screened in vitro for IFNγ responses to both citrullinated and uncitrullinated vim 28-49 and 415-433 peptides. FIG. 10 shows that mice immunised with the DNA construct demonstrate IFNγ responses to both citrullinated peptides but not the wild type versions. This confirms that when the DNA is translated it is citrullinated.

These results suggest that epitopes from the antibody-DNA constructs are being citrullinated and that the T cells recognising these modified peptides have not been deleted/anergised.

Example 3. Peptide Immunisation Results in Responses to Citrullinated Vim 28, Vim 415 and Vim 65

To determine if this was restricted to DNA vaccines or whether the citrullinated peptides could also stimulate this repertoire, mice were immunised with wild type and citrullinated vim 28-49 and citrullinated vim 415-433 peptides in combination with CpG and MPLA adjuvants. FIG. 11 shows that citrullinated vim 28-49 stimulated strong IFNγ responses (mean 600/million splenocytes; p=0.0037) against the citrullinated peptide and weaker responses to the wild type peptide (mean 250/million splenocytes; p=0.0175). The wild type peptide stimulated similar IFNγ responses to uncitrullinated (mean 700/million splenocytes; p=0.003) and citrullinated peptide (mean 1,100/million splenocytes; p=0.0182) and weak IL-17 and IL-2 responses. No significant IL-10 responses are observed. The avidity of the responses to both IFNγ and IL-17 were $10^{-6}$ M. The responses in mice to vim 28-49 is to self as the amino acid sequence is identical in mice and humans suggesting that the T cell repertoire to this epitope has not been deleted. The response to citrullinated vim 28-49 is to modified self but the mice can also recognise wild type peptide. Previous studies have shown that peptide 30-49 citrullinated at positions 36 and 45 can stimulate T cell responses in HLA-DR4 transgenic mice. We noticed that there was a further arginine at position 28 so we extended this peptide to give 28-49 and citrullinated positions 28, 36 and 45 (FIG. 11c). The triple citrullinated vim 28-49 peptides gave us a significantly stronger response than the vim28-49 peptide citrullinated at positions 36, 45 peptide (p=0.02 and p=0.0007 respectively). Vim 28-49 only citrullinated at position 28 gave a response to the tri-citrullinated peptide and the Vim 45 citrullinated peptide. The vim 28 and 36 citrullinated peptide also responded to the triple. This data demonstrates that the position of the citrulline makes a difference in the magnitude of the immune response generated for this sequence and suggests that it is the 28 position that is most important. However the triple cit peptide induces responses with higher cross reactivity to other citrullinated versions. Vim 28-49 tri-citrullinated peptide shows better binding to HLA-DR0401 compared to the wild type version as indicated by better competition with the HA 306-318 reference peptide in HLA-DR0401 binding assay (FIG. 12).

FIG. 13 shows that citrullinated vim 415 stimulated strong IFNγ responses (mean 1000/million splenocytes; p=<0.0001) against the citrullinated peptide and no responses to the wild type peptide. It also stimulated strong IL-17 responses (mean 530/million splenocytes; p=<0.0001) against the citrullinated peptide and a weak responses to the wild type peptide (mean 140/million splenocytes; p=0.04). The avidity of the responses to both IFNγ and IL-17 were $10^{-6}$M. The IL-2 responses to the citrullinated epitope were more variable (mean 350/million splenocytes; p=0.046) but there was no response to wild type peptide. The wild type vim 415-433 peptide stimulated a weak IL-2 response to the citrullinated peptides. No significant IL-10 responses were observed. The human vim 415-433 epitope differs from the homologous mouse epitope by two amino acids which are not predicted to be in the core MHC binding/TCR recognition region. To test this hypothesis, mice were immunised with human vim 415 cit peptide and then screened against mouse vim 415 cit. The T cells showed equal responses to both peptides (FIG. 14). Vim 415-433 cit and 28-49 cit responses were shown to be CD4 mediated by depletion of CD4 cells prior to ex vivo elispot assay or addition of MHC class II blocking antibody into the elispot culture (FIG. 15). Both vim 28 cit and vim 415 cit were used to immunise C57B1 mice and HHD1/DR1 mice but they failed to raise a response in either of these stains suggesting that the epitopes are not presented on either I-Ab or HLA-DR0101.

FIG. 16a shows that citrullinated vim 65 peptide stimulated IFNγ responses (mean 550/million splenocytes; p=0.0046) in HLA-DR4 mice against the citrullinated peptide and no responses to the wild type peptide. It also stimulated IL-17 responses (mean 550/million splenocytes) against the citrullinated peptide and no responses to the wild type peptide. The wild type vim 65-77 peptide stimulated a weak IFNγ and IL-17 response to the wild type and citrullinated peptides. The vim 65-77 peptide was also tested in HLA-A2/DR1 mice and showed high frequency IFNγ responses to the citrullinated peptide which demonstrated some cross reactivity to the wild type peptide (FIG. 16b). Low frequency IL-10 responses were also observed to the citrullinated peptide. Blockade of MHC class II does not eliminate the citrullinated peptide specific response thus indicating that vim 65-77 specific response is MHC class I restricted (FIG. 16c). This is further confirmed by intracellular cytokine staining which demonstrate that cells producing IFNγ and TNFa in response to stimulation with the vim 65-77 citrullinated peptide are CD8 positive (FIG. 16d). Vim 65-77 cit specific response also demonstrates cytotoxicity of peptide pulsed HLA-A2 positive target cells (FIG. 16e) indicating restriction through HLA-A2. Attempts at mapping the minimal HLA-A2 restricted epitope within the vim 65-77 sequence using two 9mer peptides with high predicted HLA-A2 binding reveals the optimal sequence to be in the region of vim 68-76 (FIG. 16f). Responses specific for the citrullinated 9mer peptide do not cross react with wild type versions. Analysis of responses to tumour target cells reveals good recognition of transgenic HLA-A2 engineered EL4 cell line (EL4 HHD) over that of HLA mismatched B16 cells by Vim 65-77 cit peptide induced responses ex vivo (FIG. 16g).

Example 4. Determination of Whether CD4 Responses to Self-Epitopes are a Naïve, Memory or Treg Response The mice made a potent IFNγ and IL-17 response to a single immunisation of human vim 415 cit suggesting that it was boosting a memory or a Treg response. To determine if this was a natural Treg response that was being converted to an IFNγ/IL-17 response, mice were depleted of natural Tregs with anti-CD25 mAb and immunised with mouse vim 415 cit. Natural Treg depletion had no influence on the frequency or the avidity of the response suggesting that natural Tregs were not the responding population (FIG. 17). To determine if this response was also induced with other adjuvants mice were immunised with vim 415-433 cit and 28-49 cit in either alum, incomplete Freund's adjuvant (IFA), GMCSF, MPLA, TMX201, MPLA/TMX201 or CpG/MPLA and screened for the production of IFNγ, IL-17 or IL-10 (FIG. 18). Potent IFNγ/IL-17 responses to vim 415-433 cit and 28-49 cit epitopes were induced with CpG/MPLA, GMCSF and TMX201 adjuvants, however, no response was seen when the peptides were administered in alum or IFA. Immunisation with peptide in IFA induced high frequency IL-10 responses to the citrullinated peptides.

Anti-CTLA-4 mabs can block the interaction of CTLA-4 with its cognate receptor CD80/86 thus preventing the inhibition of T cells induced by this ligand. Immunisation of mice with vim 415 cit peptide in the presence of an anti-CTLA-4 mab significantly increased the avidity of the T cell response from $10^{-6}$ M to $10^{-8}$ M (FIG. 19).

Example 5. Cancer Patients Response to Self-Peptides

Nine melanoma patients were screened for their responses to a series of self-peptides (FIG. 20). Five of eight patients showed a response to vim 415 cit at day 4 (1), day 7 (1) or >day 11 (3). Six of eleven patients responded to the unmodified vim 415 at >day 10. Only four of these patients responded to both modified and unmodified peptide. Two of eight patients showed a response to vim 28 at day 11 whereas, five patients responded to vim 28 cit. The two patients responding to unmodified peptide also recognised modified peptide. Four out of eight patients responded to vim 65 and three of eight to vim 65 cit. Only two of these patients responded to both modified and unmodified peptide. Eight patients also showed a response to citrullinated NYESO-1 119-143; six of these responses peaked at day 4-7 suggesting a strong or memory responses. Eight patients showed a response to unmodified NYESO-1 119-143. These patients had a range of HLA types (Table 4). Only one was HLA-DR4 which suggests that other HLA haplotypes can respond to these peptides.

TABLE 4

Haplotypes of cancer patients

| Pt019 | A2 | A3  | B7  | B55 | DR7  | DR16 |
|-------|----|-----|-----|-----|------|------|
| Pt020 | A2 |     | B27 | B40 | DR3  | DR13 |
| Pt021 | A3 | A25 | B44 | B35 | DR1  | DR13 |
| Pt023 | A2 | A3  | B7  | B35 | DR1  | DR15 |
| Pt028 | A2 | A24 | B7  | B35 | DR1  | DR13 |
| Pt029 | A2 | A25 | B15 |     | DR15 |      |

TABLE 4-continued

| Haplotypes of cancer patients | | | | | | |
|---|---|---|---|---|---|---|
| Pt032 | A1 | A11 | B51 | B18 | DR15 | |
| Pt033 | | | B7 | | DR11 | DR15 |
| Pt034 | A11 | | B7 | B35 | DR1 | DR4 |
| Pt035 | A29 | A30 | B50 | | DR1 | DR7 |

Example 6. Expression of PAD Enzymes, Vimentin and Citrulline

Citrullination is carried out by PAD enzymes and in particular the PAD2 and PAD4 enzymes. These require high levels of calcium and are usually activated in dead or dying cells. It therefore seemed unlikely that healthy tumours cells would express citrullinated proteins. Colorectal and ovarian tumours and normal tissues were therefore stained for vimentin, citrullination and expression of the PAD2 and PAD4 enzymes.

Normal Tissues

Expression of vimentin, PAD2, PAD4 and citrulline is shown for normal tissues in Table 5.

Mesenchymal cells such as connective tissue cells, blood cells and neuronal cells all express vimentin as a cytoskeletal protein. Most of the cells within spleen, thyroid, testes, cervix, ovary, tonsils, uterus, lung, thymus and breast stained strongly for vimentin. Weak staining of less than 50% of cells was seen in placenta, rectum, colon, pancreas and the duodenum skeletal and smooth muscle, gall bladder, oesophagus, kidney, liver, bladder, ileum, jejunum, stomach. No staining was observed in skin, adipose tissue, skeletal muscle, rectum, brain, cerebellum, diaphragm or heart.

The majority of liver cells stained strongly with anti-PAD2 mAb. The majority of smooth muscle cells and brain cells stained weakly. Over half of the cells within the cerebellum, pancreas and testes stained strongly with PAD2. Less than 50% of the cells within gall bladder, ileum, jejunum, stomach, and colon stained strongly for PAD2. Whereas oesophagus, rectum, skeletal muscle, bladder, breast, kidney, placenta, heart, diaphragm, duodenum thyroid and lung cells stained less than 50% of their cells weakly. Skin, adipose tissue, spleen, tonsils, thymus, ovary and uterus were negative.

TABLE 5

Expression of Vimentin, PAD2, PAD4 and citrullinated proteins in normal tissues

| | Vimentin | | PAD-2 | | PAD-4 | | Anti-citrulline | | HMGB1 | |
|---|---|---|---|---|---|---|---|---|---|---|
| | Intensity | Area | Intensity | Area | Intensity | Area | Intensity | Area | Intensity | Area |
| Placenta | + | 25-50% | + | 25-50% | + | 25-50% | − | 0% | + | 75-100% |
| Oesophagus | + | 1-25% | + | 25-50% | + | 25-50% | +/− | 1-25% | + | 50-75% |
| Rectum | − | − | + | 25-50% | − | − | +/− | 1-25% | −/+ | 25-50% |
| Gallbladder | + | 1-25% | ++ | 1-25% | + | 1-25% | +/− | 1-25% | + | 75-100% |
| Skin | − | − | − | − | − | − | +/− | 75-100% | −/+ | 1-25% |
| Adipose | − | − | − | − | − | − | − | 0% | − | 0% |
| Heart | − | − | + | 25-50% | + | 50-75% | +/− | 75-100% | −/+ | 1-25% |
| Skeletal Muscle | + | 1-25% | + | 1-25% | − | − | +/− | 1-25% | + | 75-100% |
| Bladder | + | 1-25% | + | 1-25% | − | − | +/− | 1-25% | + | 50-75% |
| Ileum | + | 25-50% | ++ | 1-25% | + | 1-25% | +/− | 1-25% | + | 50-75% |
| Spleen | ++ | 75-100% | − | − | − | − | − | − | + | 75-100% |
| Brain | − | − | + | 75-100% | + | 75-100% | +/− | 75-100% | −/+ | 25-50% |
| Jejunum | + | 1-25% | ++ | 1-25% | − | − | +/− | 25-50% | −/+ | 25-50% |
| Stomach | + | 1-25% | ++ | 25-50% | ++ | 1-25% | − | − | −/+ | 0-25% |
| Breast | ++ | 50-75% | + | 1-25% | + | 25-50% | + | 50-75% | + | 25-50% |
| Kidney | + | 1-25% | + | 1-25% | − | − | +/− | 75-100% | −/+ | 1-25% |
| Testis | ++ | 75-100% | ++ | 50-75% | + | 50-75% | + | 75-100% | −/+ | 25-50% |
| Cerebellum | − | 0% | ++ | 50-75% | ++ | 75-100% | ++ | 75-100% | ++ | 75-100% |
| Liver | + | 1-25% | ++ | 75-100% | ++ | 75-100% | ++ | 75-100% | + | 75-100% |
| Thymus | ++ | 50-75% | − | − | − | − | + | 1-25% | + | 50-75% |
| Cervix | + | 75-100% | + | 1-25% | − | − | − | − | −/+ | 0-25% |
| Lung | + | 50-75% | + | 25-50% | − | − | + | 75-100% | + | 25-50% |
| Smooth Muscle | + | 1-25% | + | 75-100% | − | − | + | 75-100% | −/+ | 0-25% |

TABLE 5-continued

Expression of Vimentin, PAD2, PAD4 and citrullinated proteins in normal tissues

|  | Vimentin | | PAD-2 | | PAD-4 | | Anti-citrulline | | HMGB1 | |
|---|---|---|---|---|---|---|---|---|---|---|
|  | Intensity | Area | Intensity | Area | Intensity | Area | Intensity | Area | Intensity | Area |
| Colon | ++ | 25-50% | ++ | 50-75% | ++ | 25-50% | + | 25-50% | + | 50-75% |
| Ovary | + | 75-100% | − | − | − | − | − | − | −/+ | 0-25% |
| Tonsil | ++ | 75-100% | − | − | − | − | − | − | + | 50-75% |
| Diaphragm | − | − | + | 1-25% | + | 1-25% | + | 1-25% | −/+ | 0-25% |
| Pancreas | + | 1-25% | ++ | 50-75% | − | − | + | 75-100% | + | 50-75% |
| Uterus | ++ | 75-100% | − | − | − | − | + | 1-25% | −/+ | 0-25% |
| Duodenum | ++ | 25-50% | + | 25-50% | + | 25-50% | ++ | 50-75% | + | 50-75% |
| Thyroid | ++ | 75-100% | + | 25-50% | + | 1-25% | ++ | 25-50% | −/+ | 25-50% |

The majority of liver and cerebellum cells stained strongly with anti-PAD4 mab. The majority of brain and heart cells stained weakly. Less than 50% of the cells within colon and stomach stained strongly for PAD4 whereas less than 50% of the cells within ileum, diaphragm, duodenum, thyroid, testes, breast, gallbladder, oesophagus stained weakly. Skin, skeletal and smooth muscle, bladder, spleen, jejunum, kidney, liver, cervix, lung, ovary, tonsils, pancreas, uterus, rectum, adipose tissue, thymus and uterus were negative.

Cerebellum and liver stained strongly with anti-citrulline mab. The majority of skin, heart, kidney lung, pancreas and brain cells stained weakly. Greater than 50% of duodenum stained strongly and greater than 50% of breast and testes cells stained weakly. Less than 50% of the cells within the thymus and colon and jejunum stained weakly. Less than 25% of cells within the thymus stained strongly and greater than 25% within oesophagus, rectum, gallbladder, skeletal muscle, bladder, ileum, thymus, tonsil, diaphragm, and uterus stained weakly. Spleen, skin, stomach, ovary, tonsil, adipose tissue, placenta and cervix were negative for citrulline.

Ovarian Tumours

Ovarian tumours are of mesenchymal origin and would therefore be expected to express vimentin. PAD4 is expressed weakly by normal ovary. 219 ovarian tumours were stained with a vimentin specific mAb. Only 9/219 (4%) of tumours failed to stain, a further 16/219 (7%) stained weakly, whereas 194/219 (89%) stained strongly. Kaplan Meier survival analysis showed there was no correlation with vimentin expression and survival. There was a weak correlation between expression of vimentin and the stress related protein ULBP1 ($p=0.017$), PAD4 ($p=0.018$) and CEA-CAM4 ($p=0.033$).

219 ovarian tumours were stained with a PAD4 specific mAb (FIG. 23). Only 9/219 (4%) of tumours failed to stain, a further 126/219 (58%) stained weakly whereas 84/219 (38%) stained strongly. Kaplan Meier survival analysis showed there was no correlation with PAD4 expression and survival. There was a weak correlation between expression of PAD4 and the stress related proteins RAETIE ($p=0.036$) and ULBP1 ($p=0.016$) and a strong correlation with expression of vimentin ($p=0.001$) and Lewis$^y$ ($p=0.006$).

Although tumours express PAD4 it should only be activated in dying cells. To assess if this is true ovarian tumours were stained with an anti-citrulline peptide specific mAb. Only 7/228 (3%) of tumours failed to stain, a further 34/228 (15%) stained weakly whereas 187/228 (82%) stained strongly. However, not all of the cells within a tumour stained. In 69/228 (30%) less than 25% of cells stained. 83/228 (36%) stained between 25-50% of cells and, as previously, these were mainly of stromal origin. In 53/228 (23%) 50-75% of the cells stained including some epithelial cells and in 16/228 (7%) of tumours greater than 75% of cells stained. Kaplan Meier survival analysis showed there was no correlation with citrulline expression and survival. There was a correlation between intensity of expression of citrulline and CEA-CAMS ($p=0.037$), BCL2 ($p=0.011$) and Lewis$^y$ ($p=0.053$). There was a correlation between percentage of cells expressing citrulline and grade ($p=0.034$), BCL2 ($p=0.035$), CD59 ($p=0.049$) and ULBP1 ($p=0.044$).

360 ovarian tumours were stained for PAD2. 9% could not be evaluated due to the absence of enough tissue core or no evaluable tumour cells (i.e. all stroma) in the core. Of the 329 evaluable ovarian tumours stained with a PAD2 specific mAb, all tumours expressed PAD2. A further 277/329 (84%) stained weakly, 52/329 (16%) stained strongly. Kaplan Meier (FIG. 21a) analysis showed there was a correlation with PAD2 expression and survival with high expression of PAD2 being protective ($p=0.033$), There was a correlation between expression of PAD2 with MHC ($p=0.038$) expression and HMGB1 ($P=0.008$) expression. After multivariate analysis PAD2 remained an independent prognostic factor ($p=0.002$).

360 ovarian tumours were stained for HMGB1. 10% could not be evaluated due to the absence of enough tissue core or no evaluable tumour cells (i.e. all stroma) in the core. Of the 316 evaluable Ovarian tumours stained with a HMGB-1 specific mAb, only 23/360 (7%) tumours failed to stain. A further 42/316 (13%) stained weakly, 52/329 (87%) stained strongly. Kaplan Meier (FIG. 21b) analysis showed there was a correlation of HMGB1 expression and survival with low expression of HMGB1 being protective (v0.002). There was a weak correlation between expression of HMGB1 and vimentin ($p=0.034$). After multivariate analysis HMGB I remained an independent prognostic factor ($p=0.02$). Tumour stage, tumour type and response to chemotherapy also correlate with patient survival. In a multivariate model TNM stage ($p=<0.0001$), tumour type (p=<0.031), response to chemotherapy (p=<0.0001), and HMGB1 expression (p=0.002) where independent predictors of patient survival.

When tumour cell expression of high and low PAD2 was compared with high and low HMGB1 expression (FIG. 21c), in patients who showed high HMGB1 and low PAD2 expression, 219 of 310 patients (70%) had the worst median survival of 50 months, and patients with low HMGB1 and low PAD2 displayed the better survival, with 41 of 310 patients (13%) having a median survival time of 101 months.

Colorectal Tumours

Colorectal tumours are of epithelial origin and are not expected to express vimentin unless they are undergoing epithelial to mesenchymal transition. Expression of PAD2 and PAD4 was seen in normal colon.

282 colorectal tumours were stained with a vimentin specific mAb. Only 25/282 (9%) of tumours failed to stain, a further 4/282 (1%) stained weakly whereas 253/282 (90%) stained strongly. However not all of the cells within a tumour stained. 114/282 (40%) less than 25% of cells stained and these were all stromal cells. 68/282 (24%) between 25-50% of cells stained and again these were mainly of stromal origin. 42/282 (15%) 50-75% of the cells stained including some epithelial cells and in 33/282 (12%) of tumours greater than 75% of cells stained. Kaplan Meier survival analysis showed that there was no correlation with vimentin intensity or percentage of cells stained and survival. There was a correlation between expression of vimentin and TRAIL R2 (p=0.003), IL-17 in tumours (p=0.021), MUC1 p=0.001), PAD2 (p=0.025) and PAD4 (p=<0.0001).

296 colorectal tumours were stained with a PAD2 specific mAb (FIG. 26). Only 45/296 (15%) of tumours failed to stain, a further 60/296 (20%) stained weakly whereas 191/296 (65%) stained strongly. However, not all of the cells within a tumour stained. 99/296 (33%) less than 25% of cells stained. 82/296 (28%) between 25-50% of cells stained and again these were mainly of stromal origin. 55/296 (19%) 50-75% of the cells stained and in 15/296 (5%) of tumours greater than 75% of cells stained. Kaplan Meier survival analysis showed there was no correlation with PAD2 intensity, or percentage of cells stained and survival. There was a correlation between expression of PAD2 and CD59 (p=0.006) β-catenin (p=0.005), number of CD8 T cells (p=0.009), MUC1 (p=0.012), vimentin (p=0.038) and PAD4 (p=0.000).

291 colorectal tumours were stained with a PAD4 specific mAb (FIG. 26). Only 18/291 (6%) of tumours failed to stain, a further 158/291 (54%) stained weakly whereas 115/291 (40%) stained strongly. However not all of the cells within a tumour stained. 65/291 (22%) less than 25% of cells stained. 68/291 (23%) between 25-50% of cells stained and again these were mainly of stromal origin. 98/291 (34%) 50-75% of the cells stained and in 42/291 (14%) of tumours greater than 75% of cells stained. Kaplan Meier survival analysis showed there was a correlation with PAD4 intensity and survival (FIG. 21d, Table 6; p=0.032).

TABLE 6

Means for Survival Time of colorectal cancer patients expressing PAD4.

| Intensity of staining for PAD4 | Mean(a) | | | |
|---|---|---|---|---|
| | Estimate | Std. Error | 95% Confidence Interval | |
| | | | Lower Bound | Upper Bound |
| .00 | 44.813 | 10.483 | 24.267 | 65.358 |
| 1.00 | 74.140 | 4.262 | 65.786 | 82.494 |
| 2.00 | 78.125 | 4.632 | 69.047 | 87.203 |
| Overall | 74.391 | 3.104 | 68.307 | 80.475 |

(a)Estimation is limited to the largest survival time if it is censored.

Tumour stage and vascular invasion also correlate with patient survival. In a multivariate model TNM stage (p=<0.0001), vascular invasion (p=<0.0001) and PAD4 expression (p=0.017) where independent predictors of patient survival.

There was a correlation between expression of PAD4 and BCL2 (p=0.01), β-catenin (p=0.001), number of CD8 T cells (p=0.006), MUC1 (p=0.000), CEA.CAM5 (p=0.000), CD59 (p=0.038) vimentin (p=0.000) and PAD2 (p=0.000).

Although tumours express PAD4, it should only be activated in dying cells. To assess if this is true colorectal tumours were stained with an anti-citrulline peptide specific mAb. All of the tumours stained 41/316 (13%) stained weakly whereas 275/316 (87%) stained strongly. Kaplan Meier survival analysis showed there was a weak correlation with citrulline expression and survival (p=0.078). There was a correlation between expression of citrulline and radiation therapy (p>0.001).

Example 7. Anti-Tumour Responses to Citrullinated Peptides

Both mice and humans show responses to citrullinated self-peptides and DNA vaccines. However if these epitopes are not citrullinated in tumours then T cells will have no anti-tumour activity.

As human tumours express vimentin, PAD2/4 and citrulline the anti-tumour response of citrullinated vimentin was assessed in a mouse model. Splenocytes from mice immunised with both citrullinated vimentin 415-433 and 28-49 peptides were assessed for ability to respond to B16 tumour cells in vitro. FIG. 22a shows IFNγ release specific for B16 tumour cells expressing HLA-DR4 (B16DR4) that have been induced to undergo autophagy by serum starvation compared to untreated cells or HLA-mismatched cells indicating recognition of tumour cells (p<0.0001). Recognition of the autophagy induced B16DR4 cells significantly decreases when treated in the presence of autophagy inhibitor 3-methyl adenine (3-MA) (p<0.0001) or PAD inhibitor Cl amidine (p=0.0012). Thus, indicating that this recognition is autophagy and citrullination dependent. Splenocytes from mice immunised with either citrullinated vim 28-49 or vim 415-433 peptides or both demonstrate release of Granzyme B, a marker of cytotoxicity, upon stimulation with Vim 415-433 (p<0.0001) and vim 28-49 (p<0.0001) citrullinated peptides but not the wildtype versions (FIG. 22b-d). Granzyme B is also released upon response to serum starved B16DR4 tumour target cells suggesting cytotoxicity of tumour targets presenting the citrullinated epitopes (p=0.014) (FIG. 22e).

Mice immunised with either vim 415 cit or vim 28 cit were assessed for their ability to kill T2 tumour cells transfected with human DR4 in vitro. FIG. 23a shows that both citrullinated peptides could induce CD4 cells that killed transfected targets whether they were pulsed with the appropriate peptide or not. As T2 cells express vimentin this implies that these peptides are presented endogenously by the T2 cells. In contrast, there was no killing of normal splenocytes which also express vimentin but no PAD enzymes.

HLA/DR4 transgenic mice were implanted with B16 tumours transfected with DR4. They were immunised with vim 415-433 citrullinated peptide or DNA vaccine encoding vim 415-433 sequence and tumour growth was monitored. Mice immunised with either vim 415-433 cit peptide or vim 415-433 encoded within a DNA vaccine stimulate strong anti-tumour responses (FIG. 24a). In unimmunised mice the tumour grew rapidly and all mice had to be sacrificed by day 23. In contrast, 50% of mice immunised with vim 415 cit peptide had no tumour at day 35 and 30% were cured of their tumour. Immunisation of mice with vim 28-49 citrullinated peptide or a DNA vaccine encoding vim 28-49 sequence show significantly enhanced survival over unimmunised control or those immunised with vim 28-49 wild type peptide (FIG. 24b). Mice immunised with wild type vim 28-49 peptide showed an anti-tumour response that almost reached significance. Immunisation with vim 415-433 and 28-49 citrullinated peptides in combination show even better tumour protection and overall survival compared to control (p<0.0001) (FIG. 24c). These studies show that tumours express citrullinated vimentin which is then a target for cytotoxic CD4 killer T cells. To demonstrate that these anti-tumour responses are mediated by CD4 T cells mice were treated with anti-CD4 antibody to deplete CD4 cells in vivo. Vaccination in combination with CD4 T cell depletion totally abrogates the anti-tumour response mediated by both Vim 415 cit (p=0.0005) and Vim 28 cit peptides (p=0.0001, FIGS. 24d and e).

Both vim 415-433 and vim 28-49 citrullinated peptides induce high frequency IFNγ responses. Blockade of IFNγ in vivo abrogates both vim 415-433 and vim 28-49 citrullinated peptide specific anti-tumour responses (FIGS. 25a and b). Vim 415-433 cit specific responses also show IL-17 responses. Blockade of these in vivo have a low significant influence upon in vivo anti-tumour effects (FIG. 25c). Blockade of IL-17 also had a small effect significant influence on the vim 28-49 cit specific anti-tumour response in vivo (FIG. 25d).

To determine the importance of direct tumour recognition by vim 415-433 and vim 28-49 cit specific responses mice were challenged with the B16 tumour lacking expression of HLA-DR0401 and subsequently immunised with Vim 415-433 or vim 28-49 citrullinated peptides. Mice immunised with vim 28-49 citrullinated peptides show delayed tumour growth and enhanced survival compared to control (FIG. 26a) suggesting that direct recognition of HLA-DR4 and cognate peptide on tumour cells was not necessary for the anti-tumour response, but that bystander release of IFNγ in response to antigen presenting cells expressing cognate peptide and HLA-DR4 within the tumour environment were responsible for the anti-tumour response. In contrast mice immunised with citrullinated vim 415-433 failed to show any tumour response in this model suggesting that direct recognition of tumour cells expressing HLA-DR4 and cognate peptide was essential for the anti-tumour response of this epitope. To confirm vim 415-433 specific responses are dependent upon direct tumour recognition, mice challenged with B16 tumour expressing HLA-DR0401, were immunised with vim 415-433 citrullinated peptide in combination with an anti-HLA-DR blocking antibody. Blockade of HLA-DR prevents the anti-tumour response (FIG. 26b).

Example 8. Homology of Vimentin Between Different Species

Vimentin is highly conserved between chicken, mouse, dog sheep, cows, horse, pig and humans (FIG. 27). As the vaccine induces T cell responses in humans and mice and anti-tumour responses in mice, it can be assumed similar responses will be seen in other species.

Example 9. Vimentin Responses Restricted Through Other HLA Haplotypes

HLA-DR4 mice made a potent IFNγ and 1L-17 response to a single immunisation of human vim 415 cit peptide. To determine if this or other citrullinated vimentin epitopes could induce immune responses in other haplotypes a range of 20 mer peptides (table 8) covering the whole span of vimentin and incorporating every arginine replaced with citrulline residues was screened for IFNγ/IL-17 responses in HLA-DR1 and C57/B1 mice (FIG. 28). Mice were immunised with a combination of 3 citrullinated vim peptides in combination with CpG and MPLA adjuvants and then screened for IFNγ and IL-17 responses against each individual peptide in the combination. FIG. 28a shows that citrullinated vim peptides 9, 10, 14, 15 and 16 showed significant IFNγ responses (200-350 spots/million splenocytes p<0.02) and peptide 10 showed an IL-17 response (350 spots/million splenocytes) in HLA-DR1 transgenic mice. FIG. 28b shows that citrullinated vim peptides 16, 17, 18, 19 and 20 showed significant IFNγ responses (300-500 spots/million splenocytes p<0.02) and peptides 19 and 20 showed an IL-17 response (~400 spots/million splenocytes, p<0.05) in C57B1/6 mice. Table 7 shows the sequences of these peptides, the position of the citrulline amino acids and the position within the vimentin protein.

FIG. 28c shows responses in HLA-A2/DR1 mice immunised with vim 14 citrullinated peptide.

TABLE 7

Citrullinated vimentin IFNγ/IL-17 responses

| Antigen | Amino acid position within sequence | Peptide | Core regions | Significant response in HLA-DR1 mice | Significant response in C57B1 mice |
|---|---|---|---|---|---|
| Vimentin 1 | 1-19 | MST<u>R</u>SVSSSSY<u>R</u><u>R</u>MFGGPG (SEQ ID NO: 109) | | − | − |
| Vimentin 2 | 3-22 | <u>R</u>SVSSSSY<u>R</u><u>R</u>MFGGPGTAS (SEQ ID NO: 110) | | − | − |

TABLE 7-continued

Citrullinated vimentin IFNγ/IL-17 responses

| Antigen | Amino acid position within sequence | Peptide | Core regions | Significant response in HLA-DR1 mice | Significant response in C57B1 mice |
|---|---|---|---|---|---|
| Vimentin 3 | 14-32 | MFGGPGTASRPSSSRSYVT (SEQ ID NO: 111) | | − | − |
| Vimentin 4 | 19-33 | GTASRPSSSRSYVTTSTRT (SEQ ID NO: 112) | | − | − |
| Vimentin 5 | 26-44 | SSRSYVTTSTRTYSLGSAL (SEQ ID NO: 113) | | − | − |
| Vimentin 6 | 36-54 | RTYSLGSALRPSTSRSLYA (SEQ ID NO: 114) | | − | − |
| Vimentin 7 | 41-59 | GSALRPSTSRSLYASSPGG (SEQ ID NO: 115) | | − | − |
| Vimentin 8 | 55-66 | SSPGGVYATRSSAVRLRSS (SEQ ID NO: 116) | | − | − |
| Vimentin 9 | 61-79 | YATRSSAVRLRSSVPGVRL (SEQ ID NO: 65) | RSSVPGVRL (SEQ ID NO: 62) SAVRLRSSV (SEQ ID NO: 63) ATRSSAVRL (SEQ ID NO: 64) | + | − |
| Vimentin 10 | 69-87 | RLRSSVPGVRLLQDSVDFS (SEQ ID NO: 68) | RSSVPGVRL (SEQ ID NO: 62) GVRLLQDSV (SEQ ID NO: 67) | + | − |
| Vimentin 11 | 91-109 | AINTEFKNTRTNEKVELQE (SEQ ID NO: 117) | | − | − |
| Vimentin 12 | 103-121 | EKVELQELNDRFANYIDKV (SEQ ID NO: 118) | | − | − |
| Vimentin 13 | 113-131 | RFANYIDKVRFLEQQNKIL (SEQ ID NO: 119) | | − | − |
| Vimentin 14 | 125-154 | EQLKGQGKSRLGDLYEEEM (SEQ ID NO: 71) | QLKGQGKSR (SEQ ID NO: 69) KSRLGDLYE (SEQ ID NO: 70) | + | − |
| Vimentin 15 | 148-166 | DLYEEEMRELRRQVDQLTN (SEQ ID NO: 74) | ELRRQVDQL (SEQ ID NO: 72) EMRELRRQV (SEQ ID NO: 73) | + | − |
| Vimentin 16 | 161-179 | VDQLTNDKARVEVERDNLA (SEQ ID NO: 78) | QLTNDKARV (SEQ ID NO: 75) VEVERDNLA (SEQ ID NO: 76) LTNDKARVE (SEQ ID NO: 77) | + | + |
| Vimentin 17 | 166-184 | NDKARVEVERDNLAEDIMR (SEQ ID NO: 80) | EVERDNLAE (SEQ ID NO: 79) | − | + |

TABLE 7-continued

Citrullinated vimentin IFNγ/IL-17 responses

| Antigen | Amino acid position within sequence | Peptide | Core regions | Significant response in HLA-DR1 mice | Significant response in C57B1 mice |
|---|---|---|---|---|---|
| Vimentin 18 | 176-194 | DNLAEDIM<u>R</u>L<u>R</u>EKLQEEML (SEQ ID NO: 82) | IM<u>R</u>L<u>R</u>EKLQ (SEQ ID NO: 81) | - | + |
| Vimentin 19 | 187-205 | EKLQEEMLQ<u>R</u>EEAENTLQS (SEQ ID NO: 85) | Q<u>R</u>EEAENTL (SEQ ID NO: 83) KLQEEMLQ<u>R</u> (SEQ ID NO: 84) | - | + |
| Vimentin 20 | 198-216 | EAENTLQSF<u>R</u>QDVDNASLA (SEQ ID NO: 88) | F<u>R</u>QDVDNAS (SEQ ID NO: 86) ENTLQSF<u>R</u>Q (SEQ ID NO: 87) | - | + |
| Vimentin 21 | 211-229 | DNASLA<u>R</u>LDLE<u>R</u>KVESLQE (SEQ ID NO: 120) | | - | - |
| Vimentin 22 | 262-280 | KPDLTAAL<u>R</u>DV<u>R</u>QQYESVA (SEQ ID NO: 121) | | - | - |
| Vimentin 23 | 295-312 | FADLSEAAN<u>R</u>NNDAL<u>R</u>QAK (SEQ ID NO: 122) | | - | - |
| Vimentin 24 | 301-319 | AAN<u>R</u>NNDAL<u>R</u>QAKQESTEY (SEQ ID NO: 123) | | - | - |
| Vimentin 25 | 311-329 | QAKQESTEY<u>RR</u>QVQSLTCE (SEQ ID NO: 124) | | - | - |
| Vimentin 26 | 334-352 | KGTNESLE<u>R</u>QM<u>R</u>EMEENFA (SEQ ID NO: 125) | | - | - |
| Vimentin 27 | 355-373 | AANYQDTIG<u>R</u>LQDEIQNMK (SEQ ID NO: 126) | | - | - |
| Vimentin 28 | 370-388 | QNMKEEMA<u>R</u>HL<u>R</u>EYQDLLN (SEQ ID NO: 127) | | - | - |
| Vimentin 29 | 392-410 | ALDIEIATY<u>R</u>KLLEGEES<u>R</u> (SEQ ID NO: 128) | | - | - |
| Vimentin 30 | 401-419 | <u>R</u>KLLEGEES<u>R</u>ISLPLPNFS (SEQ ID NO: 129) | | - | - |
| Vimentin 31 | 415-433 | LPNFSSLNL<u>R</u>ETNLDSLPL (SEQ ID NO: 61) | | - | - |
| Vimentin 32 | 431-449 | LPLVDTHSK<u>R</u>TLLIKTVET (SEQ ID NO: 130) | | - | - |
| Vimentin 33 | 441-459 | TLLIKTVET<u>R</u>DGQVINETS (SEQ ID NO: 131) | | - | - |

Arginine residues substituted with citrulline are underlined

Example 10. How to Screen for Citrullinated T Cell Epitopes

Any citrullinated protein that has been described in the literature can be a potential target for T cells. However, it must first have the capacity to be presented on MHC class I and/or class II MHC antigens and it must be recognised by a T cell receptor. Antigen presenting cells constitutively undergo autophagy and it is within these double membrane autophagosomes that sufficient intracellular $Ca^{2+}$ can accumulate to active PAD enzymes, citrullinate epitopes which are then presented on MHC antigens. Finally to be an anti-tumour target, tumour cells must also induce citrullination within autophagosomes and present the same modified epitope on MHC antigens. Therefore, to identify citrullinated epitopes that can still stimulate anti-tumour immunity, it is necessary to screen target proteins for induction of T cell responses and for tumour recognition.

a) In vitro T cell proliferation of human peripheral blood by citrullinated peptides. Human peripheral blood can be stimulated in vitro as outlined in Example 5. Citrullinated 20mer peptides spanning the whole protein can be screened for T cell proliferation. Sorting of CD4 and CD8 T cells can identify CD4 and CD8 epitopes and the HLA restriction can be identified by HLA typing the donor.

b) Stimulate cells from conventional or HLA transgenic mice in vitro or in vivo with 20 mer citrullinated peptides which span the whole of a target protein To determine if citrullinated cytokeratin-8 epitopes could induce immune responses, a range of 20 mer peptides (Table 8) covering the whole span of cytokeratin-8 and incorporating arginines in the predicted core binding region replaced with citrulline residues were screened for IFNγ/IL-17 responses in HLA-DR1 and C57 BI mice (FIG. 29). Mice were immunised with a combination of 3 citrullinated cytokeratin 8 peptides in combination with CpG and MPLA adjuvants and then screened for IFNγ and IL-17 responses against each individual peptide in the combination. FIG. 28a shows that citrullinated cytokeratin 8 peptides 1, 2, 3, 13, 16 and 17 showed significant IFNγ responses (200-300 spots/million splenocytes p<0.02) and peptides 1, 2, 3, 13 and 14 showed an IL-17 response (250-350 spots/million splenocytes; p<0.02) in HLA-DR1 transgenic mice. FIG. 29b shows that the cytokeratin 8 peptides did not stimulate a response in C57BI mice.

TABLE 8

Citrullinated cytokeratin IFNγ/IL-17 responses

| Antigen | Coordinates | Peptides | Core regions | Significant response in HLA-DR1 mice | Significant response in C57B1 mice |
|---|---|---|---|---|---|
| Cytokeratin 1 | 229-247 | EEEIRELQSQISDTSVVLS (SEQ ID NO: 7) | EIRELQSQI (SEQ ID NO: 132) | + | − |
| Cytokeratin 2 | 363-382 | AKQDMARQLREYQELMNVKL (SEQ ID NO: 9) | ARQLREYQE (SEQ ID NO: 133) AKQDMARQL (SEQ ID NO: 134) | + | − |
| Cytokeratin 3 | 360-378 | LQRAKQDMARQLREYQELM (SEQ ID NO: 11) | AKQDMARQL (SEQ ID NO: 134) ARQLREYQE (SEQ ID NO: 133) | + | − |
| Cytokeratin 4 | 324-342 | LKGQRASLEAAIADAEQRG (SEQ ID NO: 135) | | − | − |
| Cytokeratin 5 | 239-257 | ISDTSVVLSMDNSRSLDMD (SEQ ID NO: 136) | | − | − |
| Cytokeratin 6 | 137-156 | DNMFESYINNLRRQLETLGQ (SEQ ID NO: 137) | | − | − |
| Cytokeratin 7 | 388-407 | IATYRKLLEGEESRLESGMQ (SEQ ID NO: 138) | | − | − |
| Cytokeratin 8 | 264-281 | KAQYEDIANRSRAEAESM (SEQ ID NO: 139) | | − | − |
| Cytokeratin 9 | 460-478 | AVVVKKIETRDGKLVSESS (SEQ ID NO: 140) | | − | − |
| Cytokeratin 10 | 99-117 | NNKFASFIDKVRFLEQQNK (SEQ ID NO: 141) | | − | − |
| Cytokeratin 11 | 202-221 | EAYMNKVELESRLEGLTDEI (SEQ ID NO: 142) | | − | − |
| Cytokeratin 12 | 208-226 | VELESRLEGLTDEINFLRQ (SEQ ID NO: 143) | | − | − |
| Cytokeratin 13 | 29-44 | PGSRISSSSFSRVGSS (SEQ ID NO: 13) | ISSSSFSRV (SEQ ID NO: 12) | + | − |
| Cytokeratin 14 | 13-30 | STSGPRAFSSRSYTSGPG (SEQ ID NO: 15) | GPRAFSSRS (SEQ ID NO: 144) | + | − |
| Cytokeratin 15 | 174-193 | DFKNKYEDEINKRTEMENEF (SEQ ID NO: 145) | | − | − |

TABLE 8-continued

Citrullinated cytokeratin IFNγ/IL-17 responses

| Antigen | Coordinates | Peptides | Core regions | Significant response in HLA-DR1 mice | Significant response in C57B1 mice |
|---|---|---|---|---|---|
| Cytokeratin 16 | 355-371 | ELEAALQRAKQDMARQL (SEQ ID NO: 17) | EAALQRAKQ (SEQ ID NO: 16) | + | - |
| Cytokeratin 17 | 78-95 | LEVDPNIQAVRTQEKEQI (SEQ ID NO: 19) | NIQAVRTQE (SEQ ID NO: 146) DPNIQAVRT (SEQ ID NO: 147) | + | - |
| Cytokeratin 18 | 297-316 | KHGDDLRRTKTEISEMNRNI (SEQ ID NO: 148) | | - | - |

Arginine residues substituted to citrulline are underlined c) Screen known citrullinated epitopes for T cell responses ING4 protein is citrullinated by PAD4 at position 133 in its NLS region. This prevents its association with p53 which is essential for p53 activation. Citrullinated ING4 protein is rapidly degraded suggesting it may be abundantly expressed on MHC class II. ING4 peptide AQKKLKLVRTSPEYGMP failed to stimulate any immune response in HLA-DR1 transgenic mice but AQKKLKLVcitTSPEYGMP stimulated an IFNγ/IL-17 response (mean 200 spots/million splenocytes) to the citrullinated peptide but no response to the wild type peptide. The response to the citrullinated peptides was blocked with a MHC class II blocking mab (FIG. 31a). This is a further example of a protein that can stimulate citrullinated/tumour specific CD4 responses.

d) Screen any protein for citrullinated T cell epitopes.

As we have shown in example 2, immunising with DNA encoding a whole antigen results in responses to citrullinated peptides. Here we show that if we immunise with DNA encoding whole antigen and screen against all possible citrullinated 20mer peptides only T cell responses to the citrullinated epitopes presented by the HLA molecules stimulate an immune response. The panel of citrullinated peptides is detailed in Table 7. FIG. 33a shows responses generated from vimentin DNA immunisation in HLA-DR4 transgenic mice and FIG. 34b shows responses in HLA-A2/DR1 transgenic mice. HLA-DR4 transgenic mice show high frequency responses specific for the citrullinated vimentin 28-49 and 415-433 peptides as well as lower frequency responses to vimentin 19-33, 26-44 and 36-54 peptides. HLA-A2/DR1 transgenic mice demonstrate high frequency responses specific for the citrullinated vimentin 65-77 peptide. This exemplifies the use of DNA encoding whole antigens to induce citrullinated T cell responses and is an excellent method for screening for further citrullinated T cell epitopes. Similarly proteins can be citrullinated ex vivo by incubating with PAD enzymes in the presence of high levels of calcium. These proteins can be used to immunise mice and the T cells are then screened against all possible citrullinated 20mer peptides.

e) screen predicted peptides selected based on MHC binding score and arginine residues within the core region.

We have shown that responses can be induced to known citrullinated epitopes but here we also demonstrate that peptide epitopes can be selected based on predicted MHC binding scores and presence of arginine residues within the core MHC binding region. For this example peptides were selected from BiP, HSP90, CXCL10, CXCL12 and ING4 that had high predicted binding to HLA-DR4 using the SYFPEITHI prediction algorithm (www.syfpeithi.de) and then further restricted through the presence of arginines in the core binding region (determined using IEDB prediction algorithm (www.iedb.org) (Table 9). Peptides containing all arginines changed to citrulline were tested.

TABLE 9

Predicted HLA-DR4 peptides

| | SEQUENCE | COORDINATE | CORE | SYMPATHEI SCORE | Response in HLA-DR4 mice |
|---|---|---|---|---|---|
| HSP90 346-360 | RAPFDLFENRKKKNN (SEQ ID NO: 29) | 346-360 | FDLFENRK K (SEQ ID NO: 28) | 28 | + |
| HSP90 378-392 | IPEYLNFIRGVVDSE (SEQ ID NO: 32) | 378-392 | YLNFIRGV V, (SEQ ID NO: 30) FIRGVVDS E (SEQ ID NO: 31) | 28 | - |

TABLE 9-continued

Predicted HLA-DR4 peptides

| | SEQUENCE | COORDINATE | CORE | SYMPATHEI SCORE | Response in HLA-DR4 mice |
|---|---|---|---|---|---|
| HSP90 456-477 | RKKLSELLRYYTSASG DEMVSL (SEQ ID NO: 36) | 456-477 | LRYYTSAS G, (SEQ ID NO: 33) LLRYYTSA S, (SEQ ID NO: 34) LSELLRYY T (SEQ ID NO: 35) | 26/22/20 | + |
| HSP90beta 456-470 | RRRLSELLRYHTSQS (SEQ ID NO: 37) | 546-470 | | 26 | |
| BiP 39-53 | YSCVGVFKNGRVEII (SEQ ID NO: 40) | 39-53 | VGVFKNG R (SEQ ID NO: 150) FKNGRVEI I (SEQ ID NO: 151) | 26 | + |
| BiP 172-186 | VPAYFNDAQRQATKD A (SEQ ID NO: 42) | 172-186 | YFNDAQR QA (SEQ ID NO: 41) | 28 | + |
| BiP 522-536 | KITITNDQNRLTPEE (SEQ ID NO: 46) | 522-536 | ITNDQNRL T (SEQ ID NO: 45) | 26 | − |
| ING4 44-58 | KLATEYMSSARSLSSE EK (SEQ ID NO: 27) | 44-58 | YMSSARSL S, (SEQ ID NO: 24) MSSARSLS S, (SEQ ID NO: 25) TEYMSSAR S (SEQ ID NO: 26) | 26/22 | + |
| CXCL10 57-71 | CPRVEIIATMKKKGE (SEQ ID NO: 52) | 57-71 | VEIIATMK K, (SEQ ID NO: 50) RVEIIATM K (SEQ ID NO: 51) | 26 | − |
| CXCL12 54-68 | NCALQIVARLKNNNR (SEQ ID NO: 49) | 54-68 | LQIVARLK N, (SEQ ID NO: 47) VARLKNN NR (SEQ ID NO: 48) | 26 | − |

HLA-DR4 transgenic mice were immunised on up to three occasions with citrullinated peptides and responses assessed ex vivo by IFNg elispot against relevant citrullinated and unmodified peptides. FIG. 34 shows significant responses to citrullinated BiP 39-53, BiP 172-186, HSP90 346-360, HSP90 456-477 and ING4 44-58 over that to unmodified peptide or background control. This provides another efficient method for the selection of citrullinated T cell epitopes.

To prove that the T cells recognise tumours, they can be screened for recognition of tumour target cells, acid stripped to encourage MHC recycling and serum starved to induce autophagy (FIGS. 22a and e). The role of citrullination and autophagy can be confirmed using PAD and autophagy inhibitors (FIG. 22a). In vivo anti-tumour responses can be measured by initiating tumours, immunising with citrullinated peptides and monitoring tumour growth as shown in FIGS. 24-26).

Example 11

Previous studies have shown that it is possible to determine the differentiation of naïve CD4 cells to different helper phenotypes depending upon their cytokine milieu present when they are stimulated. In contrast, we have shown for the first time in FIG. 15 that certain epitopes can determine T helper cells differentiation despite the cytokine environment. Vim415 cit stimulated a Th1/IL-17 phenotype even when immunised in the presence of the Th2 adjuvant complete Freund's adjuvant. This suggests that the strength of the CD4 T cell receptor engagement with MHC peptide can determine T cell differentiation. In this context we have shown that wild type vim415 stimulates an IL-10 response (FIG. 30; mean 580 spots/million splenocytes p=0.0249) even in the presence of the Th1 adjuvants CpG/MPLA. However, it failed to stimulate a significant IFNγ or IL-17 response.

REFERENCES

1. Gao, F. G., et al., *Antigen-specific CD4+ T-cell help is required to activate a memory CD8+ T cell to a fully functional tumor killer cell.* Cancer Res, 2002. 62(22): p. 6438-41.
2. Janssen, E. M., et al., *CD4+ T cells are required for secondary expansion and memory in CD8+ T lymphocytes.* Nature, 2003. 421(6925): p. 852-6.
3. Fearon, E. R., et al., *Interleukin-2 production by tumor cells bypasses T helper function in the generation of an antitumor response.* Cell, 1990. 60(3): p. 397-403.
4. Baxevanis, C. N., et al., *Tumor-specific CD4+T lymphocytes from cancer patients are required for optimal induction of cytotoxic T cells against the autologous tumor.* J Immunol, 2000. 164(7): p. 3902-12.
5. Cella, M., et al., *Ligation of CD40 on dendritic cells triggers production of high levels of interleukin-12 and enhances T cell stimulatory capacity. T-T help via APC activation.* J Exp Med, 1996. 184(2): p. 747-52.
6. Ridge, J. P., F. Di Rosa, and P. Matzinger, *A conditioned dendritic cell can be a temporal bridge between a CD4+ T-helper and a T-killer cell.* Nature, 1998. 393(6684): p. 474-8.
7. Schoenberger, S. P., et al., *T-cell help for cytotoxic T lymphocytes is mediated by CD40-CD40L interactions.* Nature, 1998. 393(6684): p. 480-3.
8. Ayyoub, M., et al., *An immunodominant SSX-2-derived epitope recognized by CD4+ T cells in association with HLA-DR.* J Clin Invest, 2004. 113(8): p. 1225-33.
9. Halder, T., et al., *Isolation of novel HLA-DR restricted potential tumor-associated antigens from the melanoma cell line FM3.* Cancer Res, 1997. 57(15): p. 3238-44.
10. Pardoll, D. M. and S. L. Topalian, *The role of CD4+ T cell responses in antitumor immunity.* Curr Opin Immunol, 1998. 10(5): p. 588-94.
11. Topalian, S. L., *MHC class II restricted tumor antigens and the role of CD4+ T cells in cancer immunotherapy.* Curr Opin Immunol, 1994. 6(5): p. 741-5.
12. Muranski, P., et al., *Tumor-specific Th17-polarized cells eradicate large established melanoma.* Blood, 2008. 112(2): p. 362-73.
13. Paludan, C., et al., *Epstein-Barr nuclear antigen 1-specific CD4(+) Th1 cells kill Burkitt's lymphoma cells.* J Immunol, 2002. 169(3): p. 1593-603.
14. Quezada, S. A., et al., *Tumor-reactive CD4(+) T cells develop cytotoxic activity and eradicate large established melanoma after transfer into lymphopenic hosts.* J Exp Med, 2010. 207(3): p. 637-50.
15. Xie, Y., et al., *Naive tumor-specific CD4(+) T cells differentiated in vivo eradicate established melanoma.* Journal of Experimental Medicine, 2010. 207(3): p. 651-667.
16. Brandmaier, A. G., et al., *High-avidity autoreactive CD4+ T cells induce host CTL, overcome T(regs) and mediate tumor destruction.* J Immunother, 2009. 32(7): p. 677-88.
17. Lauwen, M. M., et al., *Self-tolerance does not restrict the CD4+ T-helper response against the p53 tumor antigen.* Cancer Res, 2008. 68(3): p. 893-900.
18. Touloukian, C. E., et al., *Identification of a MHC class II-restricted human gp100 epitope using DR4-IE transgenic mice.* J Immunol, 2000. 164(7): p. 3535-42.
19. Mohanan, S., et al., *Potential role of peptidylarginine deiminase enzymes and protein citrullination in cancer pathogenesis.* Biochem Res Int, 2012. 2012: p. 895343.
20. Nomura, K., *Specificity and mode of action of the muscle-type protein-arginine deiminase.* Arch Biochem Biophys, 1992. 293(2): p. 362-9.
21. Stensland, M. E., et al., *Primary sequence, together with other factors, influence peptide deimination by peptidylarginine deiminase-4.* Biol Chem, 2009. 390(2): p. 99-107.
22. Klareskog, L., et al., *Immunity to citrullinated proteins in rheumatoid arthritis.* Annual Review of Immunology, 2008. 26: p. 651-675.
23. Migliorini, P., et al., *The immune response to citrullinated antigens in autoimmune diseases.* Autoimmunity Reviews, 2005. 4(8): p. 561-564.
24. Nijenhuis, S., et al., *Autoantibodies to citrullinated proteins in rheumatoid arthritis: clinical performance and biochemical aspects of an RA-specific marker.* Clinica Chimica Acta, 2004. 350(1-2): p. 17-34.
25. Sebbag, M., et al., *Epitopes of human fibrin recognized by the rheumatoid arthritis-specific autoantibodies to citrullinated proteins.* European Journal of Immunology, 2006. 36(8): p. 2250-2263.
26. Vossenaar, E. R., et al., *Rheumatoid arthritis specific anti-Sa antibodies target citrullinated vimentin.* Arthritis Res Ther, 2004. 6(2): p. R142-50.
27. Vossenaar, E. R., et al., *Expression and activity of citrullinating peptidylarginine deiminase enzymes in monocytes and macrophages.* Annals of the Rheumatic Diseases, 2004. 63(4): p. 373-381.
28. Birnboim, H. C., et al., *Cutting edge: MHC class II-restricted peptides containing the inflammation-associated marker 3-nitrotyrosine evade central tolerance and elicit a robust cell-mediated immune response.* J Immunol, 2003. 171(2): p. 528-532.
29. Herzog, J., et al., *Activated antigen presenting cells select and present chemically modified peptides recognized by unique CD4 T cells.* Proceedings of the National Academy of Sciences of the United States of America, 2005. 102(22): p. 7928-7933.
30. Bronte, V., et al., *Boosting antitumor responses of T lymphocytes infiltrating human prostate cancers.* Journal of Experimental Medicine, 2005. 201(8): p. 1257-1268.
31. Arentz-Hansen, H., et al., *The intestinal T cell response to alpha-gliadin in adult celiac disease is focused on a single deamidated glutamine targeted by tissue transglutaminase.* J Exp Med, 2000. 191(4): p. 603-12.
32. Pudney, V. A., et al., *DNA vaccination with T-cell epitopes encoded within Ab molecules induces high-avidity anti-tumor CD8(+) T cells.* European Journal of Immunology, 2010. 40(3): p. 899-910.
33. DURRANT, L. G. M., Rachael Louise; PUDNEY, Victoria Anne; *NUCLEIC ACIDS,* 2008.
34. Feitsma, A. L., et al., *Identification of Citrullinated Vimentin Peptides as T Cell Epitopes in HLA-DR4-Positive Patients With Rheumatoid Arthritis.* Arthritis and Rheumatism, 2010. 62(1): p. 117-125.
35. Kryszke, M. H. and P. Vicart, *Regulation of the expression of the human vimentin gene: Application to cellular immortalization.* Pathologie Biologie, 1998. 46(1): p. 39-45.

36. Paulin, D., EXPRESSION OF THE GENES-CODING FOR THE HUMAN INTERMEDIATE FILAMENT PROTEINS. Pathologie Biologie, 1989. 37(4): p. 277-282.
37. Ramaekers, F. C., et al., Use of antibodies to intermediate filaments in the characterization of human tumors. Cold Spring Harb Symp Quant Biol, 1982. 46 Pt 1: p. 331-9.
38. Thomas, P. A., et al., Association between keratin and vimentin expression, malignant phenotype, and survival in postmenopausal breast cancer patients. Clinical Cancer Research, 1999. 5(10): p. 2698-2703.
39. Conforti, G., et al., DIFFERENT VIMENTIN EXPRESSION IN 2 CLONES DERIVED FROM A HUMAN COLOCARCINOMA CELL-LINE (LOVO) SHOWING DIFFERENT SENSITIVITY TO DOXORUBICIN. British Journal of Cancer, 1995. 71(3): p. 505-511.
40. Moran, E., et al., Co-expression of MDR-associated markers, including P-170, MRP and LRP and cytoskeletal proteins, in three resistant variants of the human ovarian carcinoma cell line, OAW42. European Journal of Cancer, 1997. 33(4): p. 652-660.
41. Gilles, C., et al., Vimentin expression in cervical carcinomas: association with invasive and migratory potential. J Pathol, 1996. 180(2): p. 175-80.
42. Williams, A. A., et al., CD 9 and vimentin distinguish clear cell from chromophobe renal cell carcinoma. BMC Clin Pathol, 2009. 9: p. 9.
43. Gustmann, C., et al., CYTOKERATIN EXPRESSION AND VIMENTIN CONTENT IN LARGE CELL ANAPLASTIC LYMPHOMAS AND OTHER NON-HODGKINS-LYMPHOMAS. American Journal of Pathology, 1991. 138(6): p. 1413-1422.
44. Yamamoto, Y., K. Izumi, and H. Otsuka, AN IMMUNOHISTOCHEMICAL STUDY OF EPITHELIAL MEMBRANE ANTIGEN, CYTOKERATIN, AND VIMENTIN IN PAPILLARY THYROID-CARCINOMA-RECOGNITION OF LETHAL AND FAVORABLE PROGNOSTIC TYPES. Cancer, 1992. 70(9): p. 2326-2333.
45. Coppola, D., et al., Prognostic significance of p53, bcl-2, vimentin, and S100 protein positive Langerhans cells in endometrial carcinoma. Human Pathology, 1998. 29(5): p. 455-462.
46. Fuyuhiro, Y., et al., Clinical Significance of Vimentin positive Gastric Cancer Cells. Anticancer Research, 2010. 30(12): p. 5239-5243.
47. Takemura, K., et al., EXPRESSION OF VIMENTIN IN GASTRIC-CANCER-A POSSIBLE INDICATOR FOR PROGNOSIS. Pathobiology, 1994. 62(3): p. 149-154.
48. Ivaska, J., Vimentin: Central hub in EMT induction? Small Gtpases, 2011. 2(1): p. 51-53.
49. Vuoriluoto, K., et al., Vimentin regulates EMT induction by Slug and oncogenic H-Ras and migration by governing Axl expression in breast cancer. Oncogene, 2011. 30(12): p. 1436-1448.
50. Hill, J. A., et al., Cutting edge: The conversion of arginine to citrulline allows for a high-affinity peptide interaction with the rheumatoid arthritis-associated HLA-DRB1*0401 MHC class II molecule. J Immunol, 2003. 171(2): p. 538-541.
51. Ireland, J., J. Herzog, and E. R. Unanue, Cutting edge: Unique T cells that recognize citrullinated peptides are a feature of protein immunization. J Immunol, 2006. 177(3): p. 1421-1425.
52. Asaga, H., et al., Immunocytochemical localization of peptidylarginine deiminase in human eosinophils and neutrophils. Journal of Leukocyte Biology, 2001. 70(1): p. 46-51.
53. Nagata, S. and T. Senshu, PEPTIDYLARGININE DEIMINASE IN RAT AND MOUSE HEMATOPOIETIC-CELLS. Experientia, 1990. 46(1): p. 72-74.
54. Loos, T., et al., Citrullination of CXCL10 and CXCL11 by peptidylarginine deiminase: a naturally occurring posttranslational modification of chemokines and new dimension of immunoregulation. Blood, 2008. 112(7): p. 2648-2656.
55. Proost, P., et al., Citrullination of CXCL8 by peptidylarginine deiminase alters receptor usage, prevents proteolysis, and dampens tissue inflammation. Journal of Experimental Medicine, 2008. 205(9): p. 2085-2097.
56. Struyf, S., et al., Citrullination of CXCL12 Differentially Reduces CXCR4 and CXCR7 Binding with Loss of Inflammatory and Anti-HIV-1 Activity via CXCR4. J Immunol, 2009. 182(1): p. 666-674.
57. Ireland, J. M. and E. R. Unanue, Autophagy in antigen presenting cells results in presentation of citrullinated peptides to CD4 T cells. Journal of Experimental Medicine, 2011. 208(13): p. 2625-2632.
58. Asaga, H., M. Yamada, and T. Senshu, Selective deimination of vimentin in calcium ionophore-induced apoptosis of mouse peritoneal macrophages. Biochem Biophys Res Commun, 1998. 243(3): p. 641-6.
59. Mor-Vaknin, N., et al., Vimentin is secreted by activated macrophages. Nature Cell Biology, 2003. 5(1): p. 59-63.
60. Vossenaar, E. R., et al., PAD, a growing family of citrullinating enzymes: genes, features and involvement in disease. Bioessays, 2003. 25(11): p. 1106-18.
61. Kaufmann, S. H. E., The contribution of immunology to the rational design of novel antibacterial vaccines. Nature Reviews Microbiology, 2007. 5(7): p. 491-504.
62. Kubilus, J., R. F. Waitkus, and H. P. Baden, PARTIAL-PURIFICATION AND SPECIFICITY OF AN ARGININE-CONVERTING ENZYME FROM BOVINE EPIDERMIS. Biochimica Et Biophysica Acta, 1980. 615(1): p. 246-251.
63. Senshu, T., et al., Studies on specificity of peptidylarginine deiminase reactions using an immunochemical probe that recognizes an enzymatically deiminated partial sequence of mouse keratin K1. Journal of Dermatological Science, 1999. 21(2): p. 113-126.
64. Chang, X., et al., Localization of peptidylarginine deiminase 4 (PADI4) and citrullinated protein in synovial tissue of rheumatoid arthritis. Rheumatology, 2005. 44(1): p. 40-50.
65. Chang, X. and J. Han, Expression of peptidylarginine deiminase type 4 (PAD4) in various tumors. Mol Carcinog, 2006. 45(3): p. 183-96.
66. Guo, Q. and W. Fast, Citrullination of inhibitor of growth 4 (ING4) by peptidylarginine deiminase 4 (PAD4) disrupts the interaction between ING4 and p. 53. J Biol Chem, 2011. 286(19): p. 17069-78.
67. Karlin, S. and S. F. Altschul, Applications and statistics for multiple high-scoring segments in molecular sequences. Proc Natl Acad Sci USA, 1993. 90(12): p. 5873-7.
68. Altschul, S. F., et al., Basic local alignment search tool. J Mol Biol, 1990. 215(3): p. 403-10.
69. Altschul, S. F., et al., Gapped BLAST and PSI-BLAST: a new generation of protein database search programs. Nucleic Acids Res, 1997. 25(17): p. 3389-402.
70. Myers, E. W. and W. Miller, Approximate matching of regular expressions. Bull Math Biol, 1989. 51(1): p. 5-37.
71. Torelli, A. and C. A. Robotti, ADVANCE and ADAM: two algorithms for the analysis of global similarity between homologous informational sequences. Comput Appl Biosci, 1994. 10(1): p. 3-5.
72. Pearson, W. R. and D. J. Lipman, *Improved tools for biological sequence comparison*. Proc Natl Acad Sci USA, 1988. 85(8): p. 2444-8.
73. Remington, R., *Remington's pharmaceutical sciences*. 16th ed. 1980: Mack Pub. Co.
74. Stewart, *Solid phase peptide synthesis*. 2nd ed. 1984, Rockford: Illinois Pierce Chemical Company.
75. Bodanzsky, B., *The practice of peptide synthesis*. 1984, New York: Springer Verlag.
76. Sambrook, J., Fritsch and Maniatis, *Molecular cloning: A laboratory manual*. 2nd ed. 1989: Cold Spring Harbor Laboratory Press.
77. Ausubel, J., *Short protocols in molecular biology*. 1992: John Wiley & Sons
78. Pluckthun, A., *Antibody engineering: advances from the use of Escherichia coli expression systems*. Biotechnology (N Y), 1991. 9(6): p. 545-51.
79. Reff, M. E., *High-level production of recombinant immunoglobulins in mammalian cells*. Curr Opin Biotechnol, 1993. 4(5): p. 573-6.
80. Trill, J. J., A. R. Shatzman, and S. Ganguly, *Production of monoclonal antibodies in COS and CHO cells*. Curr Opin Biotechnol, 1995. 6(5): p. 553-60.
81. Palena, C., et al., *Strategies to target molecules that control the acquisition of a mesenchymal-like phenotype by carcinoma cells*. Exp Biol Med (Maywood), 2011. 236(5): p. 537-45.
82. Denzin, L. K., et al., *Assembly and intracellular transport of HLA-DM and correction of the class II antigen processing defect in T2 cells*. Immunity, 1994. 1(7): p. 595-606.
83. Kovats, S., et al., *Presentation of abundant endogenous class II DR-restricted antigens by DM-negative B cell lines*. Eur J Immunol, 1997. 27(4): p. 1014-21.
84. Metheringham, R. L., et al., *Antibodies designed as effective cancer vaccines*. MAbs, 2009. 1(1): p. 71-85.
85. Quinn M J B P, B. A., Kirby E A, Jones J, *Cancer trends in england and wales, 1950-1999*, in London: Stationery Office2001. p. 206-207.
86. NICE, *Improving outcomes in colorectal cancers: Manual update*, 2004: London: National Institute for Clinical Excellence.

The invention claimed is:

1. A method of stimulating an immune response to a tumor that expresses a citrullinated tumor-associated MHC Class II CD4+ T-cell epitope in a subject in need thereof comprising administering to said subject a therapeutically effective amount of the citrullinated tumor-associated epitope which stimulates an immune reaction against the tumor, wherein the citrullinated tumor-associated epitope comprises at least one of the following sequences:

```
                                       (SEQ ID NO: 98)
RSYVTTSTRTYSLGSALRPSTS (vim28-49), (SEQ ID NO: 59)
SAVRLRSSVPGVR (vim65-77)

(SEQ ID NO: 61)
LPNFSSLNLRETNLDSLPL (vim415-433).
``` wherein one or more of the R residues is substituted for citrulline.

2. The method of claim 1, wherein the tumor is a melanoma, breast, endometrial, colorectal or ovarian tumor.

3. The method of claim 1, wherein the subject is a human or veterinary subject.

4. The method of claim 1, wherein the epitope comprises citSYVTTSTcitTYSLGSALcitPSTS (SEQ ID NO: 54) (vim28-49).

5. A method of treating cancer in a subject in need thereof comprising administering to said subject a therapeutically effective amount of an epitope comprising the sequence YVTTSTRTYSLGSALR (SEQ ID NO: 55), optionally comprising the sequence RSYVTTSTRTYSLGSALRPSTS (vim28-49) (SEQ ID NO: 56), wherein the sequence of the epitope is less than that of the full length protein.

6. The method of claim 5, wherein the cancer is melanoma, breast cancer, endometrial cancer, colorectal cancer or ovarian cancer.

7. The method of claim 5, wherein the subject is a human or veterinary subject.

8. A method of stimulating an immune response to a tumor that expresses a citrullinated tumor-associated MHC Class II CD4+ T-cell epitope in a subject in need thereof comprising administering to said subject a therapeutically effective amount of the citrullinated tumor-associated epitope which stimulates an immune reaction against the tumor, wherein the citrullinated tumor-associated epitope is:
YVTTSTRTYSLGSALR (SEQ ID NO: 55),
wherein one or more of the R residues is substituted for citrulline.

9. The method of claim 8, wherein the tumor is a melanoma, breast, endometrial, colorectal or ovarian tumor.

10. The method of claim 8, wherein the subject is a human or veterinary subject.

* * * * *

UNITED STATES PATENT AND TRADEMARK OFFICE
CERTIFICATE OF CORRECTION

PATENT NO. : 10,233,220 B2
APPLICATION NO. : 14/614964
DATED : March 19, 2019
INVENTOR(S) : Linda Gillian Durrant, Victoria Anne Brentville and Rachael Louise Metheringham It is certified that error appears in the above-identified patent and that said Letters Patent is hereby corrected as shown below:

In the Claims

In Column 147, Line 12, please delete "(SEQ ID NO: 98)" and replace with -- (SEQ ID NO: 56) --.

Signed and Sealed this
Seventh Day of May, 2019

Andrei Iancu
*Director of the United States Patent and Trademark Office*

```
                              SEQUENCE LISTING

<160> NUMBER OF SEQ ID NOS: 160

<210> SEQ ID NO 1
<211> LENGTH: 9
<212> TYPE: PRT
<213> ORGANISM: Artificial Sequence
<220> FEATURE:
<223> OTHER INFORMATION: Modified epitope wherein one or more of the R
      residues is substituted for citrulline.

<400> SEQUENCE: 1

Ile Gln Lys Leu Tyr Gly Lys Arg Ser
1               5

<210> SEQ ID NO 2
<211> LENGTH: 16
<212> TYPE: PRT
<213> ORGANISM: Artificial Sequence
<220> FEATURE:
<223> OTHER INFORMATION: Modified epitope wherein one or more of the R
      residues is substituted for citrulline.

<400> SEQUENCE: 2

Ser Gln Asp Asp Ile Lys Gly Ile Gln Lys Leu Tyr Gly Lys Arg Ser
1               5                   10                  15

<210> SEQ ID NO 3
<211> LENGTH: 10
<212> TYPE: PRT
<213> ORGANISM: Artificial Sequence
<220> FEATURE:
<223> OTHER INFORMATION: Modified epitope wherein one or more of the R
      residues is substituted for citrulline.

<400> SEQUENCE: 3

Asn Ile Leu Thr Ile Arg Leu Thr Ala Ala
1               5                   10

<210> SEQ ID NO 4
<211> LENGTH: 25
<212> TYPE: PRT
<213> ORGANISM: Artificial Sequence
<220> FEATURE:
<223> OTHER INFORMATION: Modified peptide wherein one or more of the R
``` residues is substituted for citrulline.

<400> SEQUENCE: 4

Pro Gly Val Leu Leu Lys Glu Phe Thr Val Ser Gly Asn Ile Leu Thr
1               5                   10                  15

Ile Arg Leu Thr Ala Ala Asp His Arg
            20                  25

<210> SEQ ID NO 5
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 5

Ile Leu Thr Ile Arg Leu Thr Ala Ala
1               5

<210> SEQ ID NO 6
<211> LENGTH: 8
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 6

Glu Ile Arg Glu Leu Gln Ser Gln
1               5

<210> SEQ ID NO 7
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 7

Glu Glu Glu Ile Arg Glu Leu Gln Ser Gln Ile Ser Asp Thr Ser Val
1               5                   10                  15

Val Leu Ser

<210> SEQ ID NO 8
<211> LENGTH: 15
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 8

Ala Lys Gln Asp Met Ala Arg Gln Leu Arg Glu Tyr Gln Glu Leu
1               5                   10                  15

<210> SEQ ID NO 9
<211> LENGTH: 20
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 9

Ala Lys Gln Asp Met Ala Arg Gln Leu Arg Glu Tyr Gln Glu Leu Met
1               5                   10                  15

Asn Val Lys Leu
            20

<210> SEQ ID NO 10
<211> LENGTH: 8
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 10

Ala Lys Gln Asp Met Ala Arg Gln
1               5

<210> SEQ ID NO 11
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 11

Leu Gln Arg Ala Lys Gln Asp Met Ala Arg Gln Leu Arg Glu Tyr Gln
1               5                   10                  15

Glu Leu Met

<210> SEQ ID NO 12
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 12

Ile Ser Ser Ser Ser Phe Ser Arg Val
1               5

<210> SEQ ID NO 13
<211> LENGTH: 16
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 13

Pro Gly Ser Arg Ile Ser Ser Ser Ser Phe Ser Arg Val Gly Ser Ser
1               5                   10                  15

<210> SEQ ID NO 14
<211> LENGTH: 8
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 14

Pro Arg Ala Phe Ser Ser Arg Ser
1               5

```
<210> SEQ ID NO 15
<211> LENGTH: 18
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 15

Ser Thr Ser Gly Pro Arg Ala Phe Ser Ser Arg Ser Tyr Thr Ser Gly
1               5                   10                  15

Pro Gly

<210> SEQ ID NO 16
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 16

Glu Ala Ala Leu Gln Arg Ala Lys Gln
1               5

<210> SEQ ID NO 17
<211> LENGTH: 17
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 17

Glu Leu Glu Ala Ala Leu Gln Arg Ala Lys Gln Asp Met Ala Arg Gln
1               5                   10                  15

Leu

<210> SEQ ID NO 18
<211> LENGTH: 14
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 18

Leu Glu Val Asp Pro Asn Ile Gln Ala Val Arg Thr Gln Glu
1               5                   10

<210> SEQ ID NO 19
<211> LENGTH: 18
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 19

Leu Glu Val Asp Pro Asn Ile Gln Ala Val Arg Thr Gln Glu Lys Glu
1               5                   10                  15

Gln Ile

<210> SEQ ID NO 20
<211> LENGTH: 9
<212> TYPE: PRT
```

```
<213> ORGANISM: Artificial Sequence
<220> FEATURE:
<223> OTHER INFORMATION: Modified peptide wherein one or more of the R
      residues is substituted for citrulline.

<400> SEQUENCE: 20

Gln Lys Lys Leu Lys Leu Val Arg Thr
1               5

<210> SEQ ID NO 21
<211> LENGTH: 17
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 21

Ala Gln Lys Lys Leu Lys Leu Val Arg Thr Ser Pro Glu Tyr Gly Met
1               5                   10                  15

Pro

<210> SEQ ID NO 22
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 22

Leu Lys Leu Val Arg Thr Ser Pro Glu
1               5

<210> SEQ ID NO 23
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 23

Lys Lys Leu Lys Leu Val Arg Thr Ser
1               5

<210> SEQ ID NO 24
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 24

Tyr Met Ser Ser Ala Arg Ser Leu Ser
1               5

<210> SEQ ID NO 25
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 25
```

Met Ser Ser Ala Arg Ser Leu Ser Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 26

Thr Glu Tyr Met Ser Ser Ala Arg Ser
1               5

<210> SEQ ID NO 27
<211> LENGTH: 18
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 27

Lys Leu Ala Thr Glu Tyr Met Ser Ser Ala Arg Ser Leu Ser Ser Glu
1               5                   10                  15

Glu Lys

<210> SEQ ID NO 28
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 28

Phe Asp Leu Phe Glu Asn Arg Lys Lys
1               5

<210> SEQ ID NO 29
<211> LENGTH: 15
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 29

Arg Ala Pro Phe Asp Leu Phe Glu Asn Arg Lys Lys Lys Asn Asn
1               5                   10                  15

<210> SEQ ID NO 30
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 30

Tyr Leu Asn Phe Ile Arg Gly Val Val
1               5

<210> SEQ ID NO 31
<211> LENGTH: 9
<212> TYPE: PRT

```
<213> ORGANISM: Artificial Sequence
<220> FEATURE:
<223> OTHER INFORMATION: Modified peptide wherein one or more of the R
      residues is substituted for citrulline.

<400> SEQUENCE: 31

Phe Ile Arg Gly Val Val Asp Ser Glu
1               5

<210> SEQ ID NO 32
<211> LENGTH: 15
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 32

Ile Pro Glu Tyr Leu Asn Phe Ile Arg Gly Val Val Asp Ser Glu
1               5                   10                  15

<210> SEQ ID NO 33
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 33

Leu Arg Tyr Tyr Thr Ser Ala Ser Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 34

Leu Leu Arg Tyr Tyr Thr Ser Ala Ser
1               5

<210> SEQ ID NO 35
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 35

Leu Ser Glu Leu Leu Arg Tyr Tyr Thr
1               5

<210> SEQ ID NO 36
<211> LENGTH: 22
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 36

Arg Lys Lys Leu Ser Glu Leu Leu Arg Tyr Tyr Thr Ser Ala Ser Gly
1               5                   10                  15
```

-continued

Asp Glu Met Val Ser Leu
          20

<210> SEQ ID NO 37
<211> LENGTH: 15
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 37

Arg Arg Arg Leu Ser Glu Leu Leu Arg Tyr His Thr Ser Gln Ser
1               5                   10                  15

<210> SEQ ID NO 38
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 38

Val Gly Val Phe Lys Asn Gly Arg Val
1               5

<210> SEQ ID NO 39
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 39

Phe Lys Asn Gly Arg Val Glu Ile Ile
1               5

<210> SEQ ID NO 40
<211> LENGTH: 15
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 40

Tyr Ser Cys Val Gly Val Phe Lys Asn Gly Arg Val Glu Ile Ile
1               5                   10                  15

<210> SEQ ID NO 41
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 41

Tyr Phe Asn Asp Ala Gln Arg Gln Ala
1               5

<210> SEQ ID NO 42
<211> LENGTH: 16
<212> TYPE: PRT
<213> ORGANISM: Artificial Sequence

```
<220> FEATURE:
<223> OTHER INFORMATION: Modified peptide wherein one or more of the R
      residues is substituted for citrulline.

<400> SEQUENCE: 42

Val Pro Ala Tyr Phe Asn Asp Ala Gln Arg Gln Ala Thr Lys Asp Ala
1               5                   10                  15

<210> SEQ ID NO 43
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 43

Val Thr Phe Glu Ile Asp Val Asn Gly
1               5

<210> SEQ ID NO 44
<211> LENGTH: 15
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 44

Glu Val Thr Phe Glu Ile Asp Val Asn Gly Ile Leu Arg Val Thr
1               5                   10                  15

<210> SEQ ID NO 45
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 45

Ile Thr Asn Asp Gln Asn Arg Leu Thr
1               5

<210> SEQ ID NO 46
<211> LENGTH: 15
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 46

Lys Ile Thr Ile Thr Asn Asp Gln Asn Arg Leu Thr Pro Glu Glu
1               5                   10                  15

<210> SEQ ID NO 47
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 47

Leu Gln Ile Val Ala Arg Leu Lys Asn
1               5
```

```
<210> SEQ ID NO 48
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 48

Val Ala Arg Leu Lys Asn Asn Asn Arg
1               5

<210> SEQ ID NO 49
<211> LENGTH: 15
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 49

Asn Cys Ala Leu Gln Ile Val Ala Arg Leu Lys Asn Asn Asn Arg
1               5                   10                  15

<210> SEQ ID NO 50
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 50

Val Glu Ile Ile Ala Thr Met Lys Lys
1               5

<210> SEQ ID NO 51
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 51

Arg Val Glu Ile Ile Ala Thr Met Lys
1               5

<210> SEQ ID NO 52
<211> LENGTH: 15
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 52

Cys Pro Arg Val Glu Ile Ile Ala Thr Met Lys Lys Lys Gly Glu
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: Modified peptide wherein Xaa is citrulline
<220> FEATURE:
<221> NAME/KEY: MOD_RES
```

```
<222> LOCATION: (7)..(7)
<223> OTHER INFORMATION: Xaa is citrulline
<220> FEATURE:
<221> NAME/KEY: MOD_RES
<222> LOCATION: (16)..(16)
<223> OTHER INFORMATION: Xaa is citrulline

<400> SEQUENCE: 53

Tyr Val Thr Thr Ser Thr Xaa Thr Tyr Ser Leu Gly Ser Ala Leu Xaa
1               5                   10                  15

<210> SEQ ID NO 54
<211> LENGTH: 22
<212> TYPE: PRT
<213> ORGANISM: Artificial Sequence
<220> FEATURE:
<223> OTHER INFORMATION: Modified peptide wherein Xaa is citrulline
<220> FEATURE:
<221> NAME/KEY: MOD_RES
<222> LOCATION: (1)..(1)
<223> OTHER INFORMATION: Xaa is citrulline
<220> FEATURE:
<221> NAME/KEY: MOD_RES
<222> LOCATION: (9)..(9)
<223> OTHER INFORMATION: Xaa is citrulline
<220> FEATURE:
<221> NAME/KEY: MOD_RES
<222> LOCATION: (18)..(18)
<223> OTHER INFORMATION: Xaa is citrulline

<400> SEQUENCE: 54

Xaa Ser Tyr Val Thr Thr Ser Thr Xaa Thr Tyr Ser Leu Gly Ser Ala
1               5                   10                  15

Leu Xaa Pro Ser Thr Ser
            20

<210> SEQ ID NO 55
<211> LENGTH: 16
<212> TYPE: PRT
<213> ORGANISM: Artificial Sequence
<220> FEATURE:
<223> OTHER INFORMATION: Modified peptide which optionally can be
      citrullinated. Either or both arginines may be citrullinated.

<400> SEQUENCE: 55

Tyr Val Thr Thr Ser Thr Arg Thr Tyr Ser Leu Gly Ser Ala Leu Arg
1               5                   10                  15

<210> SEQ ID NO 56
<211> LENGTH: 22
<212> TYPE: PRT
<213> ORGANISM: Artificial Sequence
<220> FEATURE:
<223> OTHER INFORMATION: Modified peptide which optionally may be
      citrullinated. Any one or two, or all, of the three arginines
      present may be citrullinated.

<400> SEQUENCE: 56

Arg Ser Tyr Val Thr Thr Ser Thr Arg Thr Tyr Ser Leu Gly Ser Ala
1               5                   10                  15

Leu Arg Pro Ser Thr Ser
            20

<210> SEQ ID NO 57
<211> LENGTH: 9
<212> TYPE: PRT
<213> ORGANISM: Artificial Sequence
<220> FEATURE:
<223> OTHER INFORMATION: Modified peptide wherein one or more of the R
``` residues is substituted for citrulline.

<400> SEQUENCE: 57

Val Arg Leu Arg Ser Ser Val Pro Gly
1               5

<210> SEQ ID NO 58
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 58

Arg Leu Arg Ser Ser Val Pro Gly Val
1               5

<210> SEQ ID NO 59
<211> LENGTH: 13
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 59

Ser Ala Val Arg Leu Arg Ser Ser Val Pro Gly Val Arg
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 60

Phe Ser Ser Leu Asn Leu Arg Glu Thr
1               5

<210> SEQ ID NO 61
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 61

Leu Pro Asn Phe Ser Ser Leu Asn Leu Arg Glu Thr Asn Leu Asp Ser
1               5                   10                  15

Leu Pro Leu

<210> SEQ ID NO 62
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 62

Arg Ser Ser Val Pro Gly Val Arg Leu
1               5

```
<210> SEQ ID NO 63
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline

<400> SEQUENCE: 63

Ser Ala Val Arg Leu Arg Ser Ser Val
1               5

<210> SEQ ID NO 64
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 64

Ala Thr Arg Ser Ser Ala Val Arg Leu
1               5

<210> SEQ ID NO 65
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 65

Tyr Ala Thr Arg Ser Ser Ala Val Arg Leu Arg Ser Ser Val Pro Gly
1               5                   10                  15

Val Arg Leu

<210> SEQ ID NO 66
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 66

Arg Ser Ser Val Pro Gly Val Arg Leu
1               5

<210> SEQ ID NO 67
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 67

Gly Val Arg Leu Leu Gln Asp Ser Val
1               5

<210> SEQ ID NO 68
<211> LENGTH: 19
<212> TYPE: PRT
<213> ORGANISM: Artificial Sequence
<220> FEATURE:
<223> OTHER INFORMATION: Modified peptide wherein one or more of the R
``` residues is substituted for citrulline.

<400> SEQUENCE: 68

Arg Leu Arg Ser Ser Val Pro Gly Val Arg Leu Leu Gln Asp Ser Val
1               5                   10                  15

Asp Phe Ser

<210> SEQ ID NO 69
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 69

Gln Leu Lys Gly Gln Gly Lys Ser Arg
1               5

<210> SEQ ID NO 70
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 70

Lys Ser Arg Leu Gly Asp Leu Tyr Glu
1               5

<210> SEQ ID NO 71
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 71

Glu Gln Leu Lys Gly Gln Gly Lys Ser Arg Leu Gly Asp Leu Tyr Glu
1               5                   10                  15

Glu Glu Met

<210> SEQ ID NO 72
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 72

Glu Leu Arg Arg Gln Val Asp Gln Leu
1               5

<210> SEQ ID NO 73
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 73

Glu Met Arg Glu Leu Arg Arg Gln Val

```
1               5
```

<210> SEQ ID NO 74
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 74

```
Asp Leu Tyr Glu Glu Glu Met Arg Glu Leu Arg Arg Gln Val Asp Gln
1               5                  10                  15

Leu Thr Asn
```

<210> SEQ ID NO 75
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 75

```
Gln Leu Thr Asn Asp Lys Ala Arg Val
1               5
```

<210> SEQ ID NO 76
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 76

```
Val Glu Val Glu Arg Asp Asn Leu Ala
1               5
```

<210> SEQ ID NO 77
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 77

```
Leu Thr Asn Asp Lys Ala Arg Val Glu
1               5
```

<210> SEQ ID NO 78
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 78

```
Val Asp Gln Leu Thr Asn Asp Lys Ala Arg Val Glu Val Glu Arg Asp
1               5                  10                  15

Asn Leu Ala
```

<210> SEQ ID NO 79
<211> LENGTH: 9

```
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 79

Glu Val Glu Arg Asp Asn Leu Ala Glu
1               5

<210> SEQ ID NO 80
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 80

Asn Asp Lys Ala Arg Val Glu Val Glu Arg Asp Asn Leu Ala Glu Asp
1               5                   10                  15

Ile Met Arg

<210> SEQ ID NO 81
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 81

Ile Met Arg Leu Arg Glu Lys Leu Gln
1               5

<210> SEQ ID NO 82
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 82

Asp Asn Leu Ala Glu Asp Ile Met Arg Leu Arg Glu Lys Leu Gln Glu
1               5                   10                  15

Glu Met Leu

<210> SEQ ID NO 83
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 83

Gln Arg Glu Glu Ala Glu Asn Thr Leu
1               5

<210> SEQ ID NO 84
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.
```

```
<400> SEQUENCE: 84

Lys Leu Gln Glu Glu Met Leu Gln Arg
1               5

<210> SEQ ID NO 85
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 85

Glu Lys Leu Gln Glu Glu Met Leu Gln Arg Glu Glu Ala Glu Asn Thr
1               5                   10                  15

Leu Gln Ser

<210> SEQ ID NO 86
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 86

Phe Arg Gln Asp Val Asp Asn Ala Ser
1               5

<210> SEQ ID NO 87
<211> LENGTH: 9
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 87

Glu Asn Thr Leu Gln Ser Phe Arg Gln
1               5

<210> SEQ ID NO 88
<211> LENGTH: 19
<212> TYPE: PRT
<213> ORGANISM: Artificial Sequence
<220> FEATURE:
<223> OTHER INFORMATION: Modified peptide wherein one or more of the R
      residues is substituted for citrulline.

<400> SEQUENCE: 88

Glu Ala Glu Asn Thr Leu Gln Ser Phe Arg Gln Asp Val Asp Asn Ala
1               5                   10                  15

Ser Leu Ala

<210> SEQ ID NO 89
<211> LENGTH: 15
<212> TYPE: PRT
<213> ORGANISM: Artificial Sequence
<220> FEATURE:
<223> OTHER INFORMATION: Epitope

<400> SEQUENCE: 89

Asp Tyr Ser Tyr Leu Gln Asp Ser Asp Pro Asp Ser Phe Gln Asp
1               5                   10                  15
```

```
<210> SEQ ID NO 90
<211> LENGTH: 16
<212> TYPE: PRT
<213> ORGANISM: Artificial Sequence
<220> FEATURE:
<223> OTHER INFORMATION: Epitope

<400> SEQUENCE: 90

Trp Asn Arg Gln Leu Tyr Pro Glu Trp Thr Glu Val Gln Gly Ser Asn
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Epitope

<400> SEQUENCE: 91

Trp Asn Arg Gln Leu Tyr Pro Glu Trp Thr Glu Ala Gln Arg Leu Asp
1               5                   10                  15

<210> SEQ ID NO 92
<211> LENGTH: 13
<212> TYPE: PRT
<213> ORGANISM: Artificial Sequence
<220> FEATURE:
<223> OTHER INFORMATION: Epitope

<400> SEQUENCE: 92

Thr Pro Pro Ala Tyr Arg Pro Pro Asn Ala Pro Ile Leu
1               5                   10

<210> SEQ ID NO 93
<211> LENGTH: 15
<212> TYPE: PRT
<213> ORGANISM: Artificial Sequence
<220> FEATURE:
<223> OTHER INFORMATION: Epitope

<400> SEQUENCE: 93

Ser Gln Asp Asp Ile Lys Gly Gln Lys Leu Tyr Gly Lys Arg Ser
1               5                   10                  15

<210> SEQ ID NO 94
<211> LENGTH: 15
<212> TYPE: PRT
<213> ORGANISM: Artificial Sequence
<220> FEATURE:
<223> OTHER INFORMATION: Epitope

<400> SEQUENCE: 94

Lys Glu Glu Trp Glu Lys Met Lys Ala Ser Glu Lys Ile Phe Tyr
1               5                   10                  15

<210> SEQ ID NO 95
<211> LENGTH: 25
<212> TYPE: PRT
<213> ORGANISM: Artificial Sequence
<220> FEATURE:
<223> OTHER INFORMATION: Epitope

<400> SEQUENCE: 95

Leu Leu Glu Phe Tyr Leu Ala Met Pro Phe Ala Thr Pro Met Glu Ala
1               5                   10                  15

Glu Leu Ala Arg Arg Ser Leu Ala Gln
```

```
                   20                  25

<210> SEQ ID NO 96
<211> LENGTH: 15
<212> TYPE: PRT
<213> ORGANISM: Artificial Sequence
<220> FEATURE:
<223> OTHER INFORMATION: Epitope

<400> SEQUENCE: 96

Gly Glu Leu Ile Gly Ile Leu Asn Ala Ala Lys Val Pro Ala Asp
1               5                   10                  15

<210> SEQ ID NO 97
<211> LENGTH: 19
<212> TYPE: PRT
<213> ORGANISM: Artificial Sequence
<220> FEATURE:
<223> OTHER INFORMATION: Epitope

<400> SEQUENCE: 97

Leu Pro Asn Phe Ser Ser Leu Asn Leu Arg Glu Thr Asn Leu Asp Ser
1               5                   10                  15

Leu Pro Leu

<210> SEQ ID NO 98
<211> LENGTH: 22
<212> TYPE: PRT
<213> ORGANISM: Artificial Sequence
<220> FEATURE:
<223> OTHER INFORMATION: Epitope

<400> SEQUENCE: 98

Arg Ser Tyr Val Thr Thr Ser Thr Arg Thr Tyr Ser Leu Gly Ser Ala
1               5                   10                  15

Leu Arg Pro Ser Thr Ser
            20

<210> SEQ ID NO 99
<211> LENGTH: 9
<212> TYPE: PRT
<213> ORGANISM: Artificial Sequence
<220> FEATURE:
<223> OTHER INFORMATION: CD4 epitope

<400> SEQUENCE: 99

Leu Tyr Pro Glu Trp Thr Glu Val Gln
1               5

<210> SEQ ID NO 100
<211> LENGTH: 9
<212> TYPE: PRT
<213> ORGANISM: Artificial Sequence
<220> FEATURE:
<223> OTHER INFORMATION: CD4 epitope

<400> SEQUENCE: 100

Thr Tyr Ser Leu Gly Ser Ala Leu Arg
1               5

<210> SEQ ID NO 101
<211> LENGTH: 9
<212> TYPE: PRT
<213> ORGANISM: Artificial Sequence
<220> FEATURE:
<223> OTHER INFORMATION: CD4 epitope
```

```
<400> SEQUENCE: 101

Tyr Val Thr Thr Ser Thr Arg Thr Tyr
1               5

<210> SEQ ID NO 102
<211> LENGTH: 9
<212> TYPE: PRT
<213> ORGANISM: Artificial Sequence
<220> FEATURE:
<223> OTHER INFORMATION: CD4 epitope

<400> SEQUENCE: 102

Leu Tyr Pro Glu Trp Thr Glu Ala Gln
1               5

<210> SEQ ID NO 103
<211> LENGTH: 9
<212> TYPE: PRT
<213> ORGANISM: Artificial Sequence
<220> FEATURE:
<223> OTHER INFORMATION: CD4 epitope

<400> SEQUENCE: 103

Tyr Leu Gln Asp Ser Asp Pro Asp Ser
1               5

<210> SEQ ID NO 104
<211> LENGTH: 9
<212> TYPE: PRT
<213> ORGANISM: Artificial Sequence
<220> FEATURE:
<223> OTHER INFORMATION: CD4 epitope

<400> SEQUENCE: 104

Ile Gly Ile Leu Asn Ala Ala Lys Val
1               5

<210> SEQ ID NO 105
<211> LENGTH: 9
<212> TYPE: PRT
<213> ORGANISM: Artificial Sequence
<220> FEATURE:
<223> OTHER INFORMATION: CD4 epitope

<400> SEQUENCE: 105

Phe Tyr Leu Ala Met Pro Phe Ala Thr
1               5

<210> SEQ ID NO 106
<211> LENGTH: 9
<212> TYPE: PRT
<213> ORGANISM: Artificial Sequence
<220> FEATURE:
<223> OTHER INFORMATION: CD4 epitope

<400> SEQUENCE: 106

Asn Ile Leu Thr Ile Arg Leu Thr Ala
1               5

<210> SEQ ID NO 107
<211> LENGTH: 9
<212> TYPE: PRT
<213> ORGANISM: Artificial Sequence
<220> FEATURE:
<223> OTHER INFORMATION: CD4 epitope
```

```
<400> SEQUENCE: 107

Trp Glu Lys Met Lys Ala Ser Glu Lys
1               5

<210> SEQ ID NO 108
<211> LENGTH: 9
<212> TYPE: PRT
<213> ORGANISM: Artificial Sequence
<220> FEATURE:
<223> OTHER INFORMATION: CD4 epitope

<400> SEQUENCE: 108

Tyr Arg Pro Pro Asn Ala Pro Ile Leu
1               5

<210> SEQ ID NO 109
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (4)..(4)
<223> OTHER INFORMATION: Arginine residue substituted with citrulline
<220> FEATURE:
<221> NAME/KEY: MOD_RES
<222> LOCATION: (12)..(12)
<223> OTHER INFORMATION: Arginine residue substituted with citrulline
<220> FEATURE:
<221> NAME/KEY: MOD_RES
<222> LOCATION: (13)..(13)
<223> OTHER INFORMATION: Arginine residue substituted with citrulline

<400> SEQUENCE: 109

Met Ser Thr Arg Ser Val Ser Ser Ser Tyr Arg Arg Met Phe Gly
1               5                   10                  15

Gly Pro Gly

<210> SEQ ID NO 110
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (1)..(1)
<223> OTHER INFORMATION: Arginine residue substituted with citrulline
<220> FEATURE:
<221> NAME/KEY: MOD_RES
<222> LOCATION: (9)..(9)
<223> OTHER INFORMATION: Arginine residue substituted with citrulline
<220> FEATURE:
<221> NAME/KEY: MOD_RES
<222> LOCATION: (10)..(10)
<223> OTHER INFORMATION: Arginine residue substituted with citrulline

<400> SEQUENCE: 110

Arg Ser Val Ser Ser Ser Ser Tyr Arg Arg Met Phe Gly Gly Pro Gly
1               5                   10                  15

Thr Ala Ser

<210> SEQ ID NO 111
<211> LENGTH: 19
<212> TYPE: PRT
<213> ORGANISM: Artificial Sequence
<220> FEATURE:
<223> OTHER INFORMATION: Modified peptide
```

```
<220> FEATURE:
<221> NAME/KEY: MOD_RES
<222> LOCATION: (10)..(10)
<223> OTHER INFORMATION: Arginine residue substituted with citrulline
<220> FEATURE:
<221> NAME/KEY: MOD_RES
<222> LOCATION: (15)..(15)
<223> OTHER INFORMATION: Arginine residue substituted with citrulline

<400> SEQUENCE: 111

Met Phe Gly Gly Pro Gly Thr Ala Ser Arg Pro Ser Ser Ser Arg Ser
1               5                   10                  15

Tyr Val Thr

<210> SEQ ID NO 112
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (5)..(5)
<223> OTHER INFORMATION: Arginine residue substituted with citrulline
<220> FEATURE:
<221> NAME/KEY: MOD_RES
<222> LOCATION: (10)..(10)
<223> OTHER INFORMATION: Arginine residue substituted with citrulline
<220> FEATURE:
<221> NAME/KEY: MOD_RES
<222> LOCATION: (18)..(18)
<223> OTHER INFORMATION: Arginine residue substituted with citrulline

<400> SEQUENCE: 112

Gly Thr Ala Ser Arg Pro Ser Ser Ser Arg Ser Tyr Val Thr Thr Ser
1               5                   10                  15

Thr Arg Thr

<210> SEQ ID NO 113
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (3)..(3)
<223> OTHER INFORMATION: Arginine residue substituted with citrulline
<220> FEATURE:
<221> NAME/KEY: MOD_RES
<222> LOCATION: (11)..(11)
<223> OTHER INFORMATION: Arginine residue substituted with citrulline

<400> SEQUENCE: 113

Ser Ser Arg Ser Tyr Val Thr Thr Ser Thr Arg Thr Tyr Ser Leu Gly
1               5                   10                  15

Ser Ala Leu

<210> SEQ ID NO 114
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (1)..(1)
<223> OTHER INFORMATION: Arginine residue substituted with citrulline
<220> FEATURE:
<221> NAME/KEY: MOD_RES
```

```
<222> LOCATION: (10)..(10)
<223> OTHER INFORMATION: Arginine residue substituted with citrulline
<220> FEATURE:
<221> NAME/KEY: MOD_RES
<222> LOCATION: (15)..(15)
<223> OTHER INFORMATION: Arginine residue substituted with citrulline

<400> SEQUENCE: 114

Arg Thr Tyr Ser Leu Gly Ser Ala Leu Arg Pro Ser Thr Ser Arg Ser
1               5                   10                  15

Leu Tyr Ala

<210> SEQ ID NO 115
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (5)..(5)
<223> OTHER INFORMATION: Arginine residue substituted with citrulline
<220> FEATURE:
<221> NAME/KEY: MOD_RES
<222> LOCATION: (10)..(10)
<223> OTHER INFORMATION: Arginine residue substituted with citrulline

<400> SEQUENCE: 115

Gly Ser Ala Leu Arg Pro Ser Thr Ser Arg Ser Leu Tyr Ala Ser Ser
1               5                   10                  15

Pro Gly Gly

<210> SEQ ID NO 116
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)
<223> OTHER INFORMATION: Arginine residue substituted with citrulline
<220> FEATURE:
<221> NAME/KEY: MOD_RES
<222> LOCATION: (15)..(15)
<223> OTHER INFORMATION: Arginine residue substituted with citrulline
<220> FEATURE:
<221> NAME/KEY: MOD_RES
<222> LOCATION: (17)..(17)
<223> OTHER INFORMATION: Arginine residue substituted with citrulline

<400> SEQUENCE: 116

Ser Ser Pro Gly Gly Val Tyr Ala Thr Arg Ser Ser Ala Val Arg Leu
1               5                   10                  15

Arg Ser Ser

<210> SEQ ID NO 117
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)
<223> OTHER INFORMATION: Arginine residue substituted with citrulline

<400> SEQUENCE: 117

Ala Ile Asn Thr Glu Phe Lys Asn Thr Arg Thr Asn Glu Lys Val Glu
```

```
1               5                   10                  15
Leu Gln Glu

<210> SEQ ID NO 118
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (11)..(11)
<223> OTHER INFORMATION: Arginine residue substituted with citrulline

<400> SEQUENCE: 118

Glu Lys Val Glu Leu Gln Glu Leu Asn Asp Arg Phe Ala Asn Tyr Ile
1               5                   10                  15

Asp Lys Val

<210> SEQ ID NO 119
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (1)..(1)
<223> OTHER INFORMATION: Arginine residue substituted with citrulline
<220> FEATURE:
<221> NAME/KEY: MOD_RES
<222> LOCATION: (10)..(10)
<223> OTHER INFORMATION: Arginine residue substituted with citrulline

<400> SEQUENCE: 119

Arg Phe Ala Asn Tyr Ile Asp Lys Val Arg Phe Leu Glu Gln Gln Asn
1               5                   10                  15

Lys Ile Leu

<210> SEQ ID NO 120
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (7)..(7)
<223> OTHER INFORMATION: Arginine residue substituted with citrulline
<220> FEATURE:
<221> NAME/KEY: MOD_RES
<222> LOCATION: (12)..(12)
<223> OTHER INFORMATION: Arginine residue substituted with citrulline

<400> SEQUENCE: 120

Asp Asn Ala Ser Leu Ala Arg Leu Asp Leu Glu Arg Lys Val Glu Ser
1               5                   10                  15

Leu Gln Glu

<210> SEQ ID NO 121
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (9)..(9)
```

```
<223> OTHER INFORMATION: Arginine residue substituted with citrulline
<220> FEATURE:
<221> NAME/KEY: MOD_RES
<222> LOCATION: (12)..(12)
<223> OTHER INFORMATION: Arginine residue substituted with citrulline

<400> SEQUENCE: 121

Lys Pro Asp Leu Thr Ala Ala Leu Arg Asp Val Arg Gln Gln Tyr Glu
1               5                   10                  15

Ser Val Ala

<210> SEQ ID NO 122
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)
<223> OTHER INFORMATION: Arginine residue substituted with citrulline
<220> FEATURE:
<221> NAME/KEY: MOD_RES
<222> LOCATION: (16)..(16)
<223> OTHER INFORMATION: Arginine residue substituted with citrulline

<400> SEQUENCE: 122

Phe Ala Asp Leu Ser Glu Ala Ala Asn Arg Asn Asn Asp Ala Leu Arg
1               5                   10                  15

Gln Ala Lys

<210> SEQ ID NO 123
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (4)..(4)
<223> OTHER INFORMATION: Arginine residue substituted with citrulline
<220> FEATURE:
<221> NAME/KEY: MOD_RES
<222> LOCATION: (10)..(10)
<223> OTHER INFORMATION: Arginine residue substituted with citrulline

<400> SEQUENCE: 123

Ala Ala Asn Arg Asn Asn Asp Ala Leu Arg Gln Ala Lys Gln Glu Ser
1               5                   10                  15

Thr Glu Tyr

<210> SEQ ID NO 124
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)
<223> OTHER INFORMATION: Arginine residue substituted with citrulline
<220> FEATURE:
<221> NAME/KEY: MOD_RES
<222> LOCATION: (11)..(11)
<223> OTHER INFORMATION: Arginine residue substituted with citrulline

<400> SEQUENCE: 124

Gln Ala Lys Gln Glu Ser Thr Glu Tyr Arg Arg Gln Val Gln Ser Leu
1               5                   10                  15
```

Thr Cys Glu

<210> SEQ ID NO 125
<211> LENGTH: 19
<212> TYPE: PRT
<213> ORGANISM: Artificial Sequence
<220> FEATURE:
<223> OTHER INFORMATION: Modified epitope wherein one or more of the R
      residues is substituted for citrulline.
<220> FEATURE:
<221> NAME/KEY: MOD_RES
<222> LOCATION: (9)..(9)
<223> OTHER INFORMATION: Arginine residue substituted with citrulline
<220> FEATURE:
<221> NAME/KEY: MOD_RES
<222> LOCATION: (12)..(12)
<223> OTHER INFORMATION: Arginine residue substituted with citrulline

<400> SEQUENCE: 125

Lys Gly Thr Asn Glu Ser Leu Glu Arg Gln Met Arg Glu Met Glu Glu
1               5                   10                  15

Asn Phe Ala

<210> SEQ ID NO 126
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)
<223> OTHER INFORMATION: Arginine residue substituted with citrulline

<400> SEQUENCE: 126

Ala Ala Asn Tyr Gln Asp Thr Ile Gly Arg Leu Gln Asp Glu Ile Gln
1               5                   10                  15

Asn Met Lys

<210> SEQ ID NO 127
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (9)..(9)
<223> OTHER INFORMATION: Arginine residue substituted with citrulline
<220> FEATURE:
<221> NAME/KEY: MOD_RES
<222> LOCATION: (12)..(12)
<223> OTHER INFORMATION: Arginine residue substituted with citrulline

<400> SEQUENCE: 127

Gln Asn Met Lys Glu Glu Met Ala Arg His Leu Arg Glu Tyr Gln Asp
1               5                   10                  15

Leu Leu Asn

<210> SEQ ID NO 128
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)

<223> OTHER INFORMATION: Arginine residue substituted with citrulline
<220> FEATURE:
<221> NAME/KEY: MOD_RES
<222> LOCATION: (19)..(19)
<223> OTHER INFORMATION: Arginine residue substituted with citrulline

<400> SEQUENCE: 128

Ala Leu Asp Ile Glu Ile Ala Thr Tyr Arg Lys Leu Leu Glu Gly Glu
1               5                   10                  15

Glu Ser Arg

<210> SEQ ID NO 129
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (1)..(1)
<223> OTHER INFORMATION: Arginine residue substituted with citrulline
<220> FEATURE:
<221> NAME/KEY: MOD_RES
<222> LOCATION: (10)..(10)
<223> OTHER INFORMATION: Arginine residue substituted with citrulline

<400> SEQUENCE: 129

Arg Lys Leu Leu Glu Gly Glu Glu Ser Arg Ile Ser Leu Pro Leu Pro
1               5                   10                  15

Asn Phe Ser

<210> SEQ ID NO 130
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)
<223> OTHER INFORMATION: Arginine residue substituted with citrulline

<400> SEQUENCE: 130

Leu Pro Leu Val Asp Thr His Ser Lys Arg Thr Leu Leu Ile Lys Thr
1               5                   10                  15

Val Glu Thr

<210> SEQ ID NO 131
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)
<223> OTHER INFORMATION: Arginine residue substituted with citrulline

<400> SEQUENCE: 131

Thr Leu Leu Ile Lys Thr Val Glu Thr Arg Asp Gly Gln Val Ile Asn
1               5                   10                  15

Glu Thr Ser

<210> SEQ ID NO 132
<211> LENGTH: 9
<212> TYPE: PRT
<213> ORGANISM: Artificial Sequence -continued

```
<220> FEATURE:
<223> OTHER INFORMATION: Modified peptide

<400> SEQUENCE: 132

Glu Ile Arg Glu Leu Gln Ser Gln Ile
1               5

<210> SEQ ID NO 133
<211> LENGTH: 9
<212> TYPE: PRT
<213> ORGANISM: Artificial Sequence
<220> FEATURE:
<223> OTHER INFORMATION: Modified peptide

<400> SEQUENCE: 133

Ala Arg Gln Leu Arg Glu Tyr Gln Glu
1               5

<210> SEQ ID NO 134
<211> LENGTH: 9
<212> TYPE: PRT
<213> ORGANISM: Artificial Sequence
<220> FEATURE:
<223> OTHER INFORMATION: Modified peptide

<400> SEQUENCE: 134

Ala Lys Gln Asp Met Ala Arg Gln Leu
1               5

<210> SEQ ID NO 135
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (5)..(5)
<223> OTHER INFORMATION: Arginine residue subsituted with citrulline

<400> SEQUENCE: 135

Leu Lys Gly Gln Arg Ala Ser Leu Glu Ala Ala Ile Ala Asp Ala Glu
1               5                   10                  15

Gln Arg Gly

<210> SEQ ID NO 136
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (14)..(14)
<223> OTHER INFORMATION: Arginine residue subsituted with citrulline

<400> SEQUENCE: 136

Ile Ser Asp Thr Ser Val Val Leu Ser Met Asp Asn Ser Arg Ser Leu
1               5                   10                  15

Asp Met Asp

<210> SEQ ID NO 137
<211> LENGTH: 20
<212> TYPE: PRT
<213> ORGANISM: Artificial Sequence
<220> FEATURE:
<223> OTHER INFORMATION: Modified peptide
```

```
<220> FEATURE:
<221> NAME/KEY: MOD_RES
<222> LOCATION: (13)..(13)
<223> OTHER INFORMATION: Arginine residue subsituted with citrulline

<400> SEQUENCE: 137

Asp Asn Met Phe Glu Ser Tyr Ile Asn Asn Leu Arg Arg Gln Leu Glu
1               5                   10                  15

Thr Leu Gly Gln
            20

<210> SEQ ID NO 138
<211> LENGTH: 20
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (14)..(14)
<223> OTHER INFORMATION: Arginine residue subsituted with citrulline

<400> SEQUENCE: 138

Ile Ala Thr Tyr Arg Lys Leu Leu Glu Gly Glu Glu Ser Arg Leu Glu
1               5                   10                  15

Ser Gly Met Gln
            20

<210> SEQ ID NO 139
<211> LENGTH: 18
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)
<223> OTHER INFORMATION: Arginine residue subsituted with citrulline

<400> SEQUENCE: 139

Lys Ala Gln Tyr Glu Asp Ile Ala Asn Arg Ser Arg Ala Glu Ala Glu
1               5                   10                  15

Ser Met

<210> SEQ ID NO 140
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (10)..(10)
<223> OTHER INFORMATION: Arginine residue subsituted with citrulline

<400> SEQUENCE: 140

Ala Val Val Val Lys Lys Ile Glu Thr Arg Asp Gly Lys Leu Val Ser
1               5                   10                  15

Glu Ser Ser

<210> SEQ ID NO 141
<211> LENGTH: 19
<212> TYPE: PRT
<213> ORGANISM: Artificial Sequence
<220> FEATURE:
<223> OTHER INFORMATION: Modified peptide
<220> FEATURE:
```

```
<221> NAME/KEY: MOD_RES
<222> LOCATION: (12)..(12)
<223> OTHER INFORMATION: Arginine residue subsituted with citrulline

<400> SEQUENCE: 141

Asn Asn Lys Phe Ala Ser Phe Ile Asp Lys Val Arg Phe Leu Glu Gln
1               5                   10                  15

Gln Asn Lys

<210> SEQ ID NO 142
<211> LENGTH: 20
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (12)..(12)
<223> OTHER INFORMATION: Arginine residue subsituted with citrulline

<400> SEQUENCE: 142

Glu Ala Tyr Met Asn Lys Val Glu Leu Glu Ser Arg Leu Glu Gly Leu
1               5                   10                  15

Thr Asp Glu Ile
            20

<210> SEQ ID NO 143
<211> LENGTH: 19
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (18)..(18)
<223> OTHER INFORMATION: Arginine residue subsituted with citrulline

<400> SEQUENCE: 143

Val Glu Leu Glu Ser Arg Leu Glu Gly Leu Thr Asp Glu Ile Asn Phe
1               5                   10                  15

Leu Arg Gln

<210> SEQ ID NO 144
<211> LENGTH: 9
<212> TYPE: PRT
<213> ORGANISM: Artificial Sequence
<220> FEATURE:
<223> OTHER INFORMATION: Modified peptide

<400> SEQUENCE: 144

Gly Pro Arg Ala Phe Ser Ser Arg Ser
1               5

<210> SEQ ID NO 145
<211> LENGTH: 20
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (13)..(13)
<223> OTHER INFORMATION: Arginine residue subsituted with citrulline

<400> SEQUENCE: 145

Asp Phe Lys Asn Lys Tyr Glu Asp Glu Ile Asn Lys Arg Thr Glu Met
1               5                   10                  15
```

Glu Asn Glu Phe
            20

<210> SEQ ID NO 146
<211> LENGTH: 9
<212> TYPE: PRT
<213> ORGANISM: Artificial Sequence
<220> FEATURE:
<223> OTHER INFORMATION: Modified peptide

<400> SEQUENCE: 146

Asn Ile Gln Ala Val Arg Thr Gln Glu
1               5

<210> SEQ ID NO 147
<211> LENGTH: 9
<212> TYPE: PRT
<213> ORGANISM: Artificial Sequence
<220> FEATURE:
<223> OTHER INFORMATION: Modified peptide

<400> SEQUENCE: 147

Asp Pro Asn Ile Gln Ala Val Arg Thr
1               5

<210> SEQ ID NO 148
<211> LENGTH: 20
<212> TYPE: PRT
<213> ORGANISM: Artificial Sequence
<220> FEATURE:
<223> OTHER INFORMATION: Modified peptide
<220> FEATURE:
<221> NAME/KEY: MOD_RES
<222> LOCATION: (8)..(8)
<223> OTHER INFORMATION: Arginine residue subsituted with citrulline

<400> SEQUENCE: 148

Lys His Gly Asp Asp Leu Arg Arg Thr Lys Thr Glu Ile Ser Glu Met
1               5                   10                  15

Asn Arg Asn Ile
            20

<210> SEQ ID NO 149
<211> LENGTH: 17
<212> TYPE: PRT
<213> ORGANISM: Artificial Sequence
<220> FEATURE:
<223> OTHER INFORMATION: Modified peptide wherein Xaa is citrulline
<220> FEATURE:
<221> NAME/KEY: MOD_RES
<222> LOCATION: (9)..(9)
<223> OTHER INFORMATION: Xaa is citrulline

<400> SEQUENCE: 149

Ala Gln Lys Lys Leu Lys Leu Val Xaa Thr Ser Pro Glu Tyr Gly Met
1               5                   10                  15

Pro

<210> SEQ ID NO 150
<211> LENGTH: 8
<212> TYPE: PRT
<213> ORGANISM: Artificial Sequence
<220> FEATURE:
<223> OTHER INFORMATION: Modified peptide

<400> SEQUENCE: 150

```
Val Gly Val Phe Lys Asn Gly Arg
1               5
```

<210> SEQ ID NO 151
<211> LENGTH: 9
<212> TYPE: PRT
<213> ORGANISM: Artificial Sequence
<220> FEATURE:
<223> OTHER INFORMATION: Modified peptide

<400> SEQUENCE: 151

```
Phe Lys Asn Gly Arg Val Glu Ile Ile
1               5
```

<210> SEQ ID NO 152
<211> LENGTH: 466
<212> TYPE: PRT
<213> ORGANISM: Homo sapiens

<400> SEQUENCE: 152

```
Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
            35                  40                  45

Ser Arg Ser Leu Tyr Ala Ser Ser Pro Gly Gly Val Tyr Ala Thr Arg
        50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
```

290                 295                 300
Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                    325                 330                 335

Asn Glu Ser Leu Glu Arg Gln Met Arg Glu Met Glu Glu Asn Phe Ala
                340                 345                 350

Val Glu Ala Ala Asn Tyr Gln Asp Thr Ile Gly Arg Leu Gln Asp Glu
                355                 360                 365

Ile Gln Asn Met Lys Glu Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                    405                 410                 415

Asn Phe Ser Ser Leu Asn Leu Arg Glu Thr Asn Leu Asp Ser Leu Pro
                420                  425                 430

Leu Val Asp Thr His Ser Lys Arg Thr Leu Leu Ile Lys Thr Val Glu
                435                 440                 445

Thr Arg Asp Gly Gln Val Ile Asn Glu Thr Ser Gln His His Asp Asp
        450                 455                 460

Leu Glu
465

<210> SEQ ID NO 153
<211> LENGTH: 460
<212> TYPE: PRT
<213> ORGANISM: Gallus gallus

<400> SEQUENCE: 153

Met Ser Phe Thr Ser Ser Lys Asn Ser Ser Tyr Arg Arg Met Phe Gly
1               5                   10                  15

Gly Gly Ser Arg Pro Ser Ser Gly Thr Arg Tyr Ile Thr Ser Ser Thr
            20                  25                  30

Arg Tyr Ser Leu Gly Ser Ala Leu Arg Pro Ser Ser Ala Arg Tyr Val
        35                  40                  45

Ser Ala Ser Pro Gly Gly Val Tyr Arg Thr Lys Ala Thr Ser Val Arg
    50                  55                  60

Leu Arg Ser Ser Met Pro Pro Met Arg Met His Asp Ala Val Asp Phe
65                  70                  75                  80

Thr Leu Ala Asp Ala Ile Asn Thr Glu Phe Lys Ala Asn Arg Thr Asn
                85                  90                  95

Glu Lys Val Glu Leu Gln Glu Leu Asn Asp Arg Phe Ala Asn Tyr Ile
            100                 105                 110

Asp Lys Val Arg Phe Leu Glu Gln Gln Asn Lys Ile Leu Leu Ala Glu
        115                 120                 125

Leu Glu Gln Leu Lys Gly Lys Gly Thr Ser Arg Leu Gly Asp Leu Tyr
    130                 135                 140

Glu Glu Glu Met Arg Asp Val Arg Arg Gln Val Asp Gln Leu Thr Asn
145                 150                 155                 160

Asp Lys Ala Arg Val Glu Val Glu Arg Asp Asn Leu Ala Asp Asp Ile
                165                 170                 175

Met Arg Leu Arg Glu Lys Leu Gln Glu Glu Met Leu Gln Arg Glu Glu
            180                 185                 190

```
Ala Glu Ser Thr Leu Gln Ser Phe Arg Gln Asp Val Asp Asn Ala Ser
            195                 200                 205

Leu Ala Gly Leu Asp Leu Glu Arg Pro Val Glu Ser Leu Gln Glu Glu
    210                 215                 220

Ile Val Phe Leu Lys Lys Leu His Asp Glu Glu Ile Arg Glu Leu Gln
225                 230                 235                 240

Ala Gln Leu Gln Glu Gln His Ile Gln Ile Asp Met Asp Val Ser Lys
            245                 250                 255

Pro Asp Leu Thr Ala Ala Leu Arg Asp Val Arg Gln Gln Tyr Glu Ser
            260                 265                 270

Val Ala Ala Lys Asn Leu Gln Glu Ala Glu Glu Trp Tyr Lys Ser Lys
            275                 280                 285

Phe Ala Asp Leu Ser Glu Ala Ala Asn Arg Asn Asn Asp Ala Leu Arg
            290                 295                 300

Gln Ala Lys Gln Glu Ala Asn Glu Tyr Arg Arg Gln Ile Gln Ser Leu
305                 310                 315                 320

Thr Cys Glu Val Asp Ala Leu Lys Gly Ser Asn Glu Ser Leu Glu Arg
                325                 330                 335

Gln Met Arg Glu Met Glu Glu Asn Phe Ala Val Glu Ala Ala Asn Tyr
            340                 345                 350

Gln Asp Thr Ile Gly Arg Leu Gln Asp Glu Ile Gln Asn Met Lys Glu
            355                 360                 365

Glu Met Ala Arg His Leu Arg Glu Tyr Gln Asp Leu Leu Asn Val Lys
            370                 375                 380

Met Ala Leu Asp Ile Glu Ile Ala Thr Tyr Arg Lys Leu Leu Glu Gly
385                 390                 395                 400

Glu Glu Ser Arg Ile Asn Met Pro Ile Pro Thr Phe Ala Ser Leu Asn
                405                 410                 415

Leu Arg Glu Thr Asn Ile Glu Ser Gln Pro Ile Val Asp Thr His Ser
            420                 425                 430

Lys Arg Thr Leu Leu Ile Lys Thr Val Glu Thr Arg Asp Gly Gln Val
            435                 440                 445

Ile Asn Glu Thr Ser Gln His His Asp Asp Leu Glu
            450                 455                 460

<210> SEQ ID NO 154
<211> LENGTH: 466
<212> TYPE: PRT
<213> ORGANISM: Mus musculus

<400> SEQUENCE: 154

Met Ser Thr Arg Ser Val Ser Ser Ser Tyr Arg Arg Met Phe Gly
1               5                   10                  15

Gly Ser Gly Thr Ser Ser Arg Pro Ser Ser Asn Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Ser Leu Tyr Ser Ser Pro Gly Gly Ala Tyr Val Thr Arg
    50                  55                  60

Ser Ser Ala Val Arg Leu Arg Ser Val Pro Gly Val Arg Leu Leu
65                  70                  75                  80

Gln Asp Ser Val Asp Phe Ser Leu Ala Asp Ala Ile Asn Thr Glu Phe
            85                  90                  95

Lys Asn Thr Arg Thr Asn Glu Lys Val Glu Leu Gln Glu Leu Asn Asp
            100                 105                 110
```

```
Arg Phe Ala Asn Tyr Ile Asp Lys Val Arg Phe Leu Glu Gln Gln Asn
        115                 120                 125
Lys Ile Leu Leu Ala Glu Leu Glu Gln Leu Lys Gly Gln Gly Lys Ser
130                 135                 140
Arg Leu Gly Asp Leu Tyr Glu Glu Met Arg Glu Leu Arg Arg Gln
145                 150                 155                 160
Val Asp Gln Leu Thr Asn Asp Lys Ala Arg Val Glu Val Glu Arg Asp
                    165                 170                 175
Asn Leu Ala Glu Asp Ile Met Arg Leu Arg Glu Lys Leu Gln Glu Glu
                180                 185                 190
Met Leu Gln Arg Glu Glu Ala Glu Ser Thr Leu Gln Ser Phe Arg Gln
            195                 200                 205
Asp Val Asp Asn Ala Ser Leu Ala Arg Leu Asp Leu Glu Arg Lys Val
        210                 215                 220
Glu Ser Leu Gln Glu Glu Ile Ala Phe Leu Lys Lys Leu His Asp Glu
225                 230                 235                 240
Glu Ile Gln Glu Leu Gln Ala Gln Ile Gln Glu Gln His Val Gln Ile
                    245                 250                 255
Asp Val Asp Val Ser Lys Pro Asp Leu Thr Ala Ala Leu Arg Asp Val
                260                 265                 270
Arg Gln Gln Tyr Glu Ser Val Ala Ala Lys Asn Leu Gln Glu Ala Glu
            275                 280                 285
Glu Trp Tyr Lys Ser Lys Phe Ala Asp Leu Ser Glu Ala Ala Asn Arg
        290                 295                 300
Asn Asn Asp Ala Leu Arg Gln Ala Lys Gln Glu Ser Asn Glu Tyr Arg
305                 310                 315                 320
Arg Gln Val Gln Ser Leu Thr Cys Glu Val Asp Ala Leu Lys Gly Thr
                    325                 330                 335
Asn Glu Ser Leu Glu Arg Gln Met Arg Glu Met Glu Glu Asn Phe Ala
                340                 345                 350
Leu Glu Ala Ala Asn Tyr Gln Asp Thr Ile Gly Arg Leu Gln Asp Glu
            355                 360                 365
Ile Gln Asn Met Lys Glu Glu Met Ala Arg His Leu Arg Glu Tyr Gln
        370                 375                 380
Asp Leu Leu Asn Val Lys Met Ala Leu Asp Ile Glu Ile Ala Thr Tyr
385                 390                 395                 400
Arg Lys Leu Leu Glu Gly Glu Glu Ser Arg Ile Ser Leu Pro Leu Pro
                    405                 410                 415
Thr Phe Ser Ser Leu Asn Leu Arg Glu Thr Asn Leu Glu Ser Leu Pro
                420                 425                 430
Leu Val Asp Thr His Ser Lys Arg Thr Leu Leu Ile Lys Thr Val Glu
            435                 440                 445
Thr Arg Asp Gly Gln Val Ile Asn Glu Thr Ser Gln His His Asp Asp
        450                 455                 460
Leu Glu
465

<210> SEQ ID NO 155
<211> LENGTH: 466
<212> TYPE: PRT
<213> ORGANISM: Canis familiaris

<400> SEQUENCE: 155

Met Ser Thr Arg Ser Val Ser Ser Ser Ser Tyr Arg Arg Met Phe Gly
```

-continued

```
1               5                   10                  15
Gly Pro Gly Thr Gly Ser Arg Pro Ser Ser Thr Arg Ser Tyr Val Thr
                20                  25                  30
Thr Ser Thr Arg Thr Tyr Ser Leu Gly Ser Ala Leu Arg Pro Ser Thr
                35                  40                  45
Ser Arg Ser Leu Tyr Ala Ser Ser Pro Gly Gly Ala Tyr Ala Thr Arg
 50                  55                  60
Ser Ser Ala Val Arg Leu Arg Ser Ser Val Pro Gly Val Arg Leu Leu
 65                  70                  75                  80
Gln Asp Ser Val Asp Phe Ser Leu Ala Asp Ala Ile Asn Thr Glu Phe
                85                  90                  95
Lys Asn Thr Arg Thr Asn Glu Lys Val Glu Leu Gln Glu Leu Asn Asp
                100                 105                 110
Arg Phe Ala Asn Tyr Ile Asp Lys Val Arg Phe Leu Glu Gln Gln Asn
                115                 120                 125
Lys Ile Leu Leu Ala Glu Leu Glu Gln Leu Lys Gly Gln Gly Lys Ser
                130                 135                 140
Arg Leu Gly Asp Leu Tyr Glu Glu Glu Met Arg Glu Leu Arg Arg Gln
145                 150                 155                 160
Val Asp Gln Leu Thr Asn Asp Lys Ala Arg Val Glu Val Glu Arg Asp
                165                 170                 175
Asn Leu Ala Glu Asp Ile Met Arg Leu Arg Glu Lys Leu Gln Glu Glu
                180                 185                 190
Met Leu Gln Arg Glu Glu Ala Glu Ser Thr Leu Gln Ser Phe Arg Gln
                195                 200                 205
Asp Val Asp Asn Ala Ser Leu Ala Arg Leu Asp Leu Glu Arg Lys Val
                210                 215                 220
Glu Ser Leu Gln Glu Glu Ile Ala Phe Leu Lys Lys Leu His Asp Glu
225                 230                 235                 240
Glu Ile Gln Glu Leu Gln Ala Gln Ile Gln Asp Gln His Val Gln Ile
                245                 250                 255
Asp Met Asp Val Ser Lys Pro Asp Leu Thr Ala Ala Leu Arg Asp Val
                260                 265                 270
Arg Gln Gln Tyr Glu Ser Val Ala Ala Lys Asn Leu Gln Glu Ala Glu
                275                 280                 285
Glu Trp Tyr Lys Ser Lys Phe Ala Asp Leu Ser Glu Ala Ala Asn Arg
                290                 295                 300
Asn Asn Asp Ala Leu Arg Gln Ala Lys Gln Glu Ser Asn Glu Tyr Arg
305                 310                 315                 320
Arg Gln Val Gln Ser Leu Thr Cys Glu Val Asp Ala Leu Lys Gly Thr
                325                 330                 335
Asn Glu Ser Leu Glu Arg Gln Met Arg Glu Met Glu Glu Asn Phe Ala
                340                 345                 350
Val Glu Ala Ala Asn Tyr Gln Asp Thr Ile Gly Arg Leu Gln Asp Glu
                355                 360                 365
Ile Gln Asn Met Lys Glu Glu Met Ala Arg His Leu Arg Glu Tyr Gln
                370                 375                 380
Asp Leu Leu Asn Val Lys Met Ala Leu Asp Ile Glu Ile Ala Thr Tyr
385                 390                 395                 400
Arg Lys Leu Leu Glu Gly Glu Glu Ser Arg Ile Ala Leu Pro Leu Pro
                405                 410                 415
Asn Phe Ser Ser Leu Asn Leu Arg Glu Thr Asn Leu Asp Ser Leu Pro
                420                 425                 430
```

Leu Val Asp Thr His Ser Lys Arg Thr Leu Ile Lys Thr Val Glu
            435                 440                 445

Thr Arg Asp Gly Gln Val Ile Asn Glu Thr Ser Gln His His Asp Asp
        450                 455                 460

Leu Glu
465

<210> SEQ ID NO 156
<211> LENGTH: 466
<212> TYPE: PRT
<213> ORGANISM: Ovis aries

<400> SEQUENCE: 156

Met Ser Thr Arg Ser Val Ser Ser Ser Tyr Arg Arg Met Phe Gly
1               5                   10                  15

Gly Pro Gly Thr Ala Ser Arg Pro Ser Ser Thr Arg Ser Tyr Val Thr
            20                  25                  30

Thr Ser Thr Arg Thr Tyr Ser Leu Gly Ser Ala Leu Arg Pro Ser Thr
        35                  40                  45

Ser Arg Thr Leu Tyr Thr Ser Pro Gly Gly Val Tyr Ala Thr Arg
 50                  55                  60

Ser Ser Ala Val Arg Leu Arg Ser Gly Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
            100                 105                 110

Arg Phe Ala Asn Tyr Ile Asp Lys Val Arg Phe Leu Glu Gln Gln Asn
        115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Ser Thr Leu Gln Ser Phe Arg Gln
        195                 200                 205

Asp Val Asp Asn Ala Ser Leu Ala Arg Leu Asp Leu Glu Arg Lys Val
210                 215                 220

Glu Ser Leu Gln Glu Glu Ile Ala Phe Leu Lys Lys Leu His Asp Glu
225                 230                 235                 240

Glu Ile Gln Glu Leu Gln Ala Gln Ile Gln Glu Gln His Val Gln Ile
                245                 250                 255

Asp Met Asp Val Ser Gln Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
290                 295                 300

Asn Asn Asp Ala Leu Arg Gln Ala Lys Gln Glu Ser Asn Glu Tyr Arg
305                 310                 315                 320

Arg Gln Val Gln Ser Leu Thr Cys Glu Val Asp Ala Leu Lys Gly Thr

```
                    325                 330                 335
Asn Glu Ser Leu Glu Arg Gln Met Arg Glu Met Glu Glu Asn Phe Ser
                340                 345                 350
Val Glu Ala Ala Asn Tyr Gln Asp Thr Ile Gly Arg Leu Gln Asp Glu
                355                 360                 365
Ile Gln Asn Met Lys Glu Glu Met Ala Arg His Leu Arg Glu Tyr Gln
        370                 375                 380
Asp Leu Leu Asn Val Lys Met Ala Leu Asp Ile Glu Ile Ala Thr Tyr
385                 390                 395                 400
Arg Lys Leu Leu Glu Gly Glu Glu Ser Arg Ile Ser Leu Pro Leu Pro
                405                 410                 415
Asn Phe Ser Ser Leu Asn Leu Arg Glu Thr Asn Leu Asp Ser Leu Pro
                420                 425                 430
Leu Val Asp Thr His Ser Lys Arg Thr Leu Leu Ile Lys Thr Val Glu
                435                 440                 445
Thr Arg Asp Gly Gln Val Ile Asn Glu Thr Ser Gln His His Asp Asp
        450                 455                 460
Leu Glu
465

<210> SEQ ID NO 157
<211> LENGTH: 466
<212> TYPE: PRT
<213> ORGANISM: Bos taurus

<400> SEQUENCE: 157

Met Ser Thr Arg Ser Val Ser Ser Ser Tyr Arg Arg Met Phe Gly
1               5                   10                  15

Gly Pro Gly Thr Ala Ser Arg Pro Ser Ser Thr Arg Ser Tyr Val Thr
                20                  25                  30

Thr Ser Thr Arg Thr Tyr Ser Leu Gly Ser Ala Leu Arg Pro Thr Thr
            35                  40                  45

Ser Arg Thr Leu Tyr Thr Ser Ser Pro Gly Gly Val Tyr Ala Thr Arg
    50                  55                  60

Ser Ser Ala Val Arg Leu Arg Ser Gly Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Ser Thr Leu Gln Ser Phe Arg Gln
            195                 200                 205

Asp Val Asp Asn Ala Ser Leu Ala Arg Leu Asp Leu Glu Arg Lys Val
    210                 215                 220
```

```
Glu Ser Leu Gln Glu Glu Ile Ala Phe Leu Lys Lys Leu His Asp Glu
225                 230                 235                 240

Glu Ile Gln Glu Leu Gln Ala Gln Ile Gln Glu Gln His Val Gln Ile
            245                 250                 255

Asp Met Asp Val Ser Lys Pro Asp Leu Thr Ala Ala Leu Arg Asp Val
        260                 265                 270

Arg Gln Gln Tyr Glu Ser Val Ala Ala Lys Asn Leu Gln Glu Ala Glu
    275                 280                 285

Glu Trp Tyr Lys Ser Lys Phe Ala Asp Leu Ser Glu Ala Ala Asn Arg
290                 295                 300

Asn Asn Asp Ala Leu Arg Gln Ala Lys Gln Glu Ser Asn Glu Tyr Arg
305                 310                 315                 320

Arg Gln Val Gln Thr Leu Thr Cys Glu Val Asp Ala Leu Lys Gly Thr
                325                 330                 335

Asn Glu Ser Leu Glu Arg Gln Met Arg Glu Met Glu Glu Asn Phe Ser
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465

<210> SEQ ID NO 158
<211> LENGTH: 466
<212> TYPE: PRT
<213> ORGANISM: Equus caballus

<400> SEQUENCE: 158

Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
            20                  25                  30

Thr Ser Thr Arg Thr Tyr Ser Leu Gly Ser Ala Leu Arg Pro Ser Ser
        35                  40                  45

Ser Arg Thr Leu Tyr Ser Ser Pro Ser Gly Val Tyr Ala Thr Arg
    50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
            85                  90                  95

Lys Asn Thr Arg Thr Asn Glu Lys Val Glu Leu Gln Glu Leu Asn Asp
        100                 105                 110

Arg Phe Ala Ser Tyr Ile Asp Lys Val Arg Phe Leu Glu Gln Gln Asn
    115                 120                 125
```

```
Lys Ile Leu Ala Glu Leu Glu Gln Leu Lys Gly Gln Gly Lys Ser
    130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Val Gln Arg Glu Glu Ala Glu Ser Thr Leu Gln Ser Phe Arg Gln
        195                 200                 205

Asp Val Asp Asn Ala Ser Leu Ala Arg Leu Asp Leu Glu Arg Lys Val
    210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
    290                 295                 300

Asn Asn Asp Ala Leu Arg Gln Ala Lys Gln Glu Ser Asn Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Glu Ser Leu Pro
            420                 425                 430

Leu Val Asp Thr His Ser Lys Arg Thr Leu Leu Ile Lys Thr Val Glu
        435                 440                 445

Thr Arg Asp Gly Gln Val Ile Asn Glu Thr Ser Gln His His Asp Asp
    450                 455                 460

Leu Glu
465

<210> SEQ ID NO 159
<211> LENGTH: 275
<212> TYPE: PRT
<213> ORGANISM: Sus scrofa

<400> SEQUENCE: 159

Ser Thr Arg Thr Val Ser Ser Ser Tyr Arg Arg Met Phe Gly Gly
1               5                   10                  15

Pro Gly Thr Ala Ser Arg Pro Ser Ser Ser Arg Ser Tyr Val Thr Thr
```

```
            20                  25                  30
Ser Thr Arg Thr Tyr Ser Leu Gly Ser Ala Leu Arg Pro Ser Thr Ser
            35                  40                  45

Arg Ser Leu Ser Thr Ser Ser Pro Gly Gly Val Gly Tyr Tyr Ala Thr
 50                  55                  60

Arg Ser Ser Ala Val Arg Leu Arg Ser Ser Val Pro Gly Val Arg Leu
 65                  70                  75                  80

Leu Gln Asp Ala Val Asp Phe Ser Leu Ala Asp Ala Ile Asn Thr Glu
                 85                  90                  95

Phe Lys Trp Tyr Lys Ser Lys Phe Ala Asp Leu Ser Glu Ala Ala Asn
                100                 105                 110

Arg Asn Asn Asp Ala Leu Arg Gln Ala Lys Gln Glu Ser Asn Glu Tyr
            115                 120                 125

Arg Arg Gln Val Gln Ser Leu Thr Cys Glu Val Asp Ala Leu Lys Gly
            130                 135                 140

Thr Asn Glu Ser Leu Glu Arg Gln Met Arg Glu Met Glu Glu Asn Phe
145                 150                 155                 160

Ala Val Glu Ala Ala Asn Tyr Gln Asp Thr Ile Gly Arg Leu Gln Asp
                165                 170                 175

Glu Ile Gln Asn Met Lys Glu Glu Met Ala Arg His Leu Arg Glu Tyr
            180                 185                 190

Gln Asp Leu Leu Asn Val Lys Met Ala Leu Asp Ile Glu Ile Ala Thr
            195                 200                 205

Tyr Arg Lys Leu Leu Glu Gly Glu Ser Arg Ile Ser Leu Pro Leu
            210                 215                 220

Pro Asn Phe Ser Ser Leu Asn Leu Arg Glu Thr Asn Leu Glu Ser Leu
225                 230                 235                 240

Pro Leu Val Asp Thr His Ser Lys Arg Thr Leu Leu Ile Lys Thr Val
                245                 250                 255

Glu Thr Arg Asp Gly Gln Val Ile Asn Glu Thr Ser Gln His His Asn
            260                 265                 270

Asp Leu Glu
        275

<210> SEQ ID NO 160
<211> LENGTH: 466
<212> TYPE: PRT
<213> ORGANISM: Artificial Sequence
<220> FEATURE:
<223> OTHER INFORMATION: Synthetic

<400> SEQUENCE: 160

Met Ser Thr Arg Ser Val Ser Ser Ser Tyr Arg Arg Met Phe Gly
 1               5                  10                  15

Gly Pro Gly Thr Ala Ser Arg Pro Ser Ser Arg Ser Tyr Val Thr
                 20                  25                  30

Thr Ser Thr Arg Thr Tyr Ser Leu Gly Ser Ala Leu Arg Pro Ser Thr
             35                  40                  45

Ser Arg Ser Leu Tyr Ser Ser Pro Gly Gly Val Tyr Ala Thr Arg
         50                  55                  60

Ser Ser Ala Val Arg Leu Arg Ser Ser Val Pro Gly Val Arg Leu Leu
 65                  70                  75                  80

Gln Asp Ser Val Asp Phe Ser Leu Ala Asp Ala Ile Asn Thr Glu Phe
                 85                  90                  95

Lys Asn Thr Arg Thr Asn Glu Lys Val Glu Leu Gln Glu Leu Asn Asp
```

```
                100             105             110
Arg Phe Ala Asn Tyr Ile Asp Lys Val Arg Phe Leu Glu Gln Gln Asn
            115                 120                 125

Lys Ile Leu Leu Ala Glu Leu Glu Gln Leu Lys Gly Gln Gly Lys Ser
130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
            180                 185                 190

Met Leu Gln Arg Glu Glu Ala Glu Ser Thr Leu Gln Ser Phe Arg Gln
            195                 200                 205

Asp Val Asp Asn Ala Ser Leu Ala Arg Leu Asp Leu Glu Arg Lys Val
            210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Met Asp Val Ser Lys Pro Asp Leu Thr Ala Ala Leu Arg Asp Val
            260                 265                 270

Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
            290                 295                 300

Asn Asn Asp Ala Leu Arg Gln Ala Lys Gln Glu Ser Asn Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
            370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
            420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
            450                 455                 460

Leu Glu
465
```